US012595248B2

(12) United States Patent
Machacek et al.

(10) Patent No.: US 12,595,248 B2
(45) Date of Patent: *Apr. 7, 2026

(54) PRMT5 INHIBITORS

(71) Applicant: Merck Sharp & Dohme LLC, Rahway, NJ (US)

(72) Inventors: Michelle Machacek, Belmont, MA (US); Michael D. Altman, Needham, MA (US); Chunghui Huang, Arlington, MA (US); Michael H. Reutershan, Brighton, MA (US); David L. Sloman, Newton, MA (US); Phieng Siliphaivanh, Newton Highlands, MA (US); Sebastian E. Schneider, Cambridge, MA (US); Charles S. Yeung, Dedham, MA (US); David J. Witter, Toronto (CA); Craig R. Gibeau, Northborough, MA (US); Yingchun Ye, Belmont, MA (US)

(73) Assignee: Merck Sharp & Dohme LLC, Rahway, NJ (US)

( * ) Notice: Subject to any disclaimer, the term of this patent is extended or adjusted under 35 U.S.C. 154(b) by 946 days.

This patent is subject to a terminal disclaimer.

(21) Appl. No.: 17/783,975

(22) PCT Filed: Dec. 14, 2020

(86) PCT No.: PCT/US2020/064755

§ 371 (c)(1),
(2) Date: Jun. 9, 2022

(87) PCT Pub. No.: WO2021/126728

PCT Pub. Date: Jun. 24, 2021

(65) Prior Publication Data

US 2023/0108114 A1 Apr. 6, 2023

Related U.S. Application Data

(60) Provisional application No. 63/025,561, filed on May 15, 2020, provisional application No. 62/949,245, filed on Dec. 17, 2019.

(51) Int. Cl.

| | |
|---|---|
| ***C07D 401/14*** | (2006.01) |
| ***C07D 405/14*** | (2006.01) |
| ***C07D 413/14*** | (2006.01) |
| ***C07D 451/04*** | (2006.01) |
| ***C07D 471/04*** | (2006.01) |
| ***C07D 487/04*** | (2006.01) |
| ***C07D 498/08*** | (2006.01) |

(52) U.S. Cl.

CPC ......... *C07D 401/14* (2013.01); *C07D 405/14* (2013.01); *C07D 413/14* (2013.01); *C07D 451/04* (2013.01); *C07D 471/04* (2013.01); *C07D 487/04* (2013.01); *C07D 498/08* (2013.01)

(58) Field of Classification Search

CPC .. C07D 401/00; C07D 405/00; C07D 413/00; C07D 451/00; C07D 471/00; C07D 487/00; C07D 498/00

See application file for complete search history.

(56) References Cited

U.S. PATENT DOCUMENTS

| | | | |
|---|---|---|---|
| 2,789,118 | A | 4/1957 | Seymour |
| 2,990,401 | A | 6/1961 | Seymour |
| 3,048,581 | A | 8/1962 | Josef |
| 3,126,375 | A | 3/1964 | Hensel et al. |
| 3,749,712 | A | 7/1973 | Cavazza |
| 3,928,326 | A | 12/1975 | Brattsand |
| 3,929,768 | A | 12/1975 | Brattsand |
| 3,996,359 | A | 12/1976 | Brattsand |

(Continued)

FOREIGN PATENT DOCUMENTS

| | | | |
|---|---|---|---|
| WO | 1994015932 | A1 | 7/1994 |
| WO | 0050032 | A1 | 8/2000 |

(Continued)

OTHER PUBLICATIONS

WO2015091417A1 (Bayer Pharma) Published Jun. 25, 2014. Retrieved from Google Patents (Year: 2015).*

(Continued)

*Primary Examiner* — Theodore R. Howell

(74) *Attorney, Agent, or Firm* — James T. Corcoran; Catherine D. Fitch

(57) ABSTRACT

The present invention provides a compound of Formula (I) and the pharmaceutically acceptable salts, esters, and prodrugs thereof, which are PRMT5 inhibitors. Also provided are methods of making compounds of Formula I, pharmaceutical compositions comprising compounds of Formula I, and methods of using these compounds to treat cancer, sickle cell, and hereditary persistence of foetal hemoglobin (HPFH) mutations.

(I)

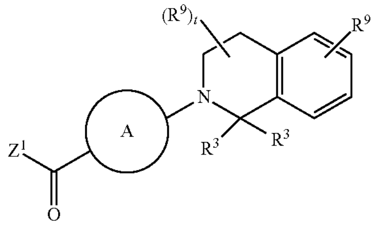

32 Claims, No Drawings

(56) References Cited

U.S. PATENT DOCUMENTS

| | | | |
|---|---|---|---|
| 4,231,938 | A | 11/1980 | Monaghan et al. |
| 4,294,926 | A | 10/1981 | Monaghan et al. |
| 4,319,039 | A | 3/1982 | Albers-Schonberg |
| 4,346,227 | A | 8/1982 | Terahara et al. |
| 4,410,629 | A | 10/1983 | Terahara et al. |
| 4,444,784 | A | 4/1984 | Hoffman et al. |
| 4,537,859 | A | 8/1985 | Terahara et al. |
| 4,681,893 | A | 7/1987 | Roth |
| 4,782,084 | A | 11/1988 | Vyas et al. |
| 4,820,850 | A | 4/1989 | Verhoeven et al. |
| 4,885,314 | A | 12/1989 | Vyas |
| 4,911,165 | A | 3/1990 | Lennard et al. |
| 4,916,239 | A | 4/1990 | Treiber |
| 4,929,437 | A | 5/1990 | Tobert |
| 5,030,447 | A | 7/1991 | Joshi et al. |
| 5,118,853 | A | 6/1992 | Lee et al. |
| 5,134,142 | A | 7/1992 | Matsuo et al. |
| 5,177,080 | A | 1/1993 | Angerbauer et al. |
| 5,180,589 | A | 1/1993 | Joshi et al. |
| 5,189,164 | A | 2/1993 | Kapa et al. |
| 5,273,995 | A | 12/1993 | Roth |
| 5,290,946 | A | 3/1994 | Lee et al. |
| 5,342,952 | A | 8/1994 | Butler et al. |
| 5,344,991 | A | 9/1994 | Reitz et al. |
| 5,354,772 | A | 10/1994 | Kathawala |
| 5,356,896 | A | 10/1994 | Kabadi et al. |
| 5,393,790 | A | 2/1995 | Reitz et al. |
| 5,409,944 | A | 4/1995 | Black et al. |
| 5,436,265 | A | 7/1995 | Black et al. |
| 5,466,823 | A | 11/1995 | Talley et al. |
| 5,474,995 | A | 12/1995 | Ducharme et al. |
| 5,489,691 | A | 2/1996 | Butler et al. |
| 5,536,752 | A | 7/1996 | Ducharme et al. |
| 5,550,142 | A | 8/1996 | Ducharme et al. |
| 5,604,260 | A | 2/1997 | Guay et al. |
| 5,633,272 | A | 5/1997 | Talley et al. |
| 5,698,584 | A | 12/1997 | Black et al. |
| 5,710,140 | A | 1/1998 | Ducharme et al. |
| 5,861,419 | A | 1/1999 | Dube et al. |
| 5,932,598 | A | 8/1999 | Talley et al. |
| 6,001,843 | A | 12/1999 | Dube et al. |
| 6,020,343 | A | 2/2000 | Belley et al. |
| 6,069,134 | A | 5/2000 | Roth et al. |
| RE37,314 | E | 8/2001 | Hirai et al. |
| 6,284,781 | B1 | 9/2001 | Danishefsky et al. |
| 6,288,237 | B1 | 9/2001 | Hoefle et al. |
| 7,454,431 | B2 | 11/2008 | Vo et al. |
| 7,589,068 | B2 | 9/2009 | Cosford et al. |
| 7,655,675 | B2 | 2/2010 | Nadin et al. |
| 2004/0102360 | A1 | 5/2004 | Barnett et al. |
| 2004/0116432 | A1 | 6/2004 | Carling et al. |
| 2005/0176776 | A1 | 8/2005 | Coleman et al. |
| 2005/0222138 | A1 | 10/2005 | Ohhata et al. |
| 2017/0298075 | A1 | 10/2017 | Bergman et al. |
| 2018/0155343 | A1 | 6/2018 | Almansa-Rosales |
| 2019/0343826 | A1 | 11/2019 | Duncan et al. |
| 2023/0108452 | A1 | 4/2023 | Machacek et al. |

FOREIGN PATENT DOCUMENTS

| | | | | |
|---|---|---|---|---|
| WO | 200044777 | A1 | 8/2000 | |
| WO | 200061186 | A1 | 10/2000 | |
| WO | 2001070677 | A1 | 9/2001 | |
| WO | 2001090084 | A1 | 11/2001 | |
| WO | 2002030912 | A1 | 4/2002 | |
| WO | 2002036555 | A1 | 5/2002 | |
| WO | 2002047671 | A2 | 6/2002 | |
| WO | 2002081433 | A1 | 10/2002 | |
| WO | 2002081435 | A1 | 10/2002 | |
| WO | 2002083064 | A2 | 10/2002 | |
| WO | 2002083138 | A1 | 10/2002 | |
| WO | 2002083139 | A1 | 10/2002 | |
| WO | 2002083140 | A1 | 10/2002 | |
| WO | 2003013506 | A1 | 2/2003 | |
| WO | 2003018543 | A1 | 3/2003 | |
| WO | 2003039460 | A2 | 5/2003 | |
| WO | 2003049527 | A2 | 6/2003 | |
| WO | 2003049678 | A2 | 6/2003 | |
| WO | 2003049679 | A2 | 6/2003 | |
| WO | 2003050064 | A2 | 6/2003 | |
| WO | 2003050122 | A2 | 6/2003 | |
| WO | 2003079973 | A2 | 10/2003 | |
| WO | 2003084473 | A2 | 10/2003 | |
| WO | 2003086279 | A2 | 10/2003 | |
| WO | 2003086394 | A1 | 10/2003 | |
| WO | 2003086403 | A1 | 10/2003 | |
| WO | 2003086404 | A1 | 10/2003 | |
| WO | 2003093251 | A1 | 11/2003 | |
| WO | 2003093252 | A1 | 11/2003 | |
| WO | 2003093253 | A1 | 11/2003 | |
| WO | 2003093264 | A1 | 11/2003 | |
| WO | 2003099211 | A2 | 12/2003 | |
| WO | 2003105855 | A1 | 12/2003 | |
| WO | 2003106417 | A1 | 12/2003 | |
| WO | 2004031137 | A1 | 4/2004 | |
| WO | 2004031138 | A1 | 4/2004 | |
| WO | 2004031139 | A1 | 4/2004 | |
| WO | 2004037171 | A2 | 5/2004 | |
| WO | 2004039370 | A1 | 5/2004 | |
| WO | 2004039774 | A2 | 5/2004 | |
| WO | 2004039800 | A1 | 5/2004 | |
| WO | 2004041162 | A2 | 5/2004 | |
| WO | 2004058148 | A2 | 7/2004 | |
| WO | 2004058700 | A2 | 7/2004 | |
| WO | 2004089911 | A1 | 10/2004 | |
| WO | 2004096129 | A2 | 11/2004 | |
| WO | 2004096130 | A2 | 11/2004 | |
| WO | 2004096131 | A2 | 11/2004 | |
| WO | 2004096135 | A2 | 11/2004 | |
| WO | 2004101538 | A1 | 11/2004 | |
| WO | 2004101539 | A1 | 11/2004 | |
| WO | 2005014553 | A1 | 2/2005 | |
| WO | 2005017190 | A2 | 2/2005 | |
| WO | 2005018547 | A2 | 3/2005 | |
| WO | 2005018638 | A1 | 3/2005 | |
| WO | 2005019205 | A1 | 3/2005 | |
| WO | 2005019206 | A1 | 3/2005 | |
| WO | 2005030731 | A1 | 4/2005 | |
| WO | 2005100344 | A1 | 10/2005 | |
| WO | 2005100356 | A1 | 10/2005 | |
| WO | 2012087861 | A1 | 6/2012 | |
| WO | WO-2015091417 | A1 * | 6/2015 | ......... A61K 31/4725 |
| WO | 2018167269 | A1 | 9/2018 | |

OTHER PUBLICATIONS

Huang et al., "Straightforward synthesis of 4,5-bifunctionalized 1,2-oxazinanes via Lewis acid promoted regio- and stereo-selective nucleophilic ring-opening of 3,6-dihydro-1,2-oxazine oxides," Tetrahedron 2019:75(45),130336. (Year: 2019).*

Aggarwal, Priya et al., Nuclear Cyclin D1/CDK4 Kinase Regulates CUL4 Expression and Triggers Neoplastic Growth via Activation of the PRMT5 Methyltransferase, Cancer Cell, 18, 329-340, 2010.

Ben-Av et al., Induction of Vascular Endothielial Growth Factor Expression in Synovial fibroblasts by Prostaglandin E and Interleukin-1: A Potential mechanism for Inflammatory Angiogenesis, FEBS Letters, 372, 83-87, 1995.

Benezra et al., In Vivo Angiogenic Activity of Interleukins, Arch Ophthalmol, 108, 573-576, 1990.

Blume-Jensen, Peter et al., Oncogenic kinase signalling, Nature, 411, 355-365, 2001.

Bouma et al., Thrombin Activable Fibrinolysis Inhibitor (TAFI, Plasma Procarboxypeptidedase B, Procarboxypeptidase R, Procarboxypeptidase U), Thrombosis Research, 101, 329-354, 2001.

Brower, Tumor Angiogenesis New Drugs on the Block, Nature America, 17, 963-968, 1999.

Chakraborty et al., Developmental Expression of the Cyclo-Oxygenase -1 and Cyclo-oxygenase-2 genes in the Peri-implantation Mouse Uterus and their differential regulation by the blastocyst and ovarian steroids, J. Mol Endocrinol, 16, 107-122, 1996.

(56) References Cited

OTHER PUBLICATIONS

Chiang, Kelly et al., PRMT5 Is a Critical Regulator of Breast Cancer Stem Cell Function via Histone Methylation and FOXP1 Expression, Cell Reports, 21, 3498-3513, 2017.
Chiarugi et al., Cox-2, iNOS and p53 as play-makers of tumor angiogenesis (Review), International J. of Molecular Medicine, 2, 715-719, 1998.
Cho, Er-Chieh et al., Arginine methylation controls growth regulation by E2F-1, The EMBO Journal, 31, 1785-1797, 2012.
Clarke, Thomas L. et al., PRMT5-Dependent Methylation of the TIP60 Coactivator RUVBL1 Is a Key Regulator of Homologous Recombination, Molecular Cell, 65, 900-916, e1-e7, 2017.
Diaz-Flores et al., Intense Vascular Sprouting From Rat Femoral Vein Induced by Prostaglandins E1 and E2, The Anatomical Record, 238, 68-76, 1994.
Fathallah-Shaykh et al., Gene Transfer of IFN-y into Established Brain Tumors Represses Grwoth by Antiangiogenesis, J. of Immunology, 164, 217-222, 2000.
Fernandez et al., Neovascularization Produced by Angiotensin II, Clinical Mediicne, 105, 141-145, 1985.
Gerhart, Sarah V. et al., Activation of the p53-MDM4 regulatory axis defines the antitumour response to PRMT5 inhibition through its role in regulating cellular splicing, Scientific Reports, 8:9711, 1-15, 2018.
Gralinkski et al., Effects of Troglitazone and Pioglitazone on Cytokine-Mediated Endothelial Cell Proliferation in Vitro, J. of Cardiovascular Pharmacology, 31, 909-913, 1998.
Gu et al., Effect of Novel CAAX Peptidomimetic Farnesyltransferase Inhibitor on Angiogenesis In Vitro and In Vivo, European J. of Cancer, 35, 1394-1401, 1999.
Gu, Zhongping et al., Protein Arginine Methyltransferase 5 Functions in Opposite Ways in the Cytoplasm and Nucleus of Prostate Cancer Cells, PLOS ONE, Issue 8 | e44033, 1-13, 2012.
Hall et al., The Promise and Reality of Cancer Gene Therapy, Am. J. Hum. Genet, 61, 785-789, 1997.
Hamard, Pierre-Jacques et al., PRMT5 Regulates DNA Repair by Controlling the Alternative Splicing of Histone-Modifying Enzymes, Cell Reports, 24, 2643-2657, 2018.
Harada et al., Expression and Regulation of Vascular Endothelial Growth Factor in Osteoblasts, Clinical Ortho, 313, 76-80, 1995.
Hla et al., Human Cyclooxygenase-2 cDNA, Proc. Natl. Acad. Sci., 89, 7384-7388, 1992.
Kanduri, Meena et al., Differential genome-wide array-based methylation profiles in prognostic subsets of chronic lymphocytic leukemia, Blood, 115(2), 296-305, 2010.
Kim et al., Inhibition of Endothelial Growth Factor-Induced Angiogenesis Suppreses Tumour Growth in Vivo, Nature, 362, 841-844, 1993.
Kim, A. Y. et al., Gastric cancer by multidetector row CT: preoperative staging, Abdom Imaging, 30, 465-472, 2005.
Korte et al., Changes of the Coagulation and Fibrinolysis System n Malignancy: Their possible Impact on Future Diagnostic And Therapeutic Procedures, Clin Chem Lab Med, 38 (8), 679-692, 2000, 38.
Kufe et al., Principles of Gene Therapy, Cancer Medicine, 5th Ed., pp. 876-889, 2000.
Li et al., Adenovirus-Mediated Delivery of a uPA/uPAR Antagonist Suppresses Angiogenesis-Dependent Tumor Growth and Dissemination in Mice, Gene Therapy, 5, 1105-1113, 1998.
Majima et al., Significant Roles of Inducible Cyclooxygenase (COX)-2 in Angiogenesis in Rat Sponge Implants, Jpn. J. Pharmacol., 75, 105-114, 1997.
Miller et al., Histone Deacetylase Inhibitors, J. of Medicinal Chemistry, 46, 5097-5116, 2003.
Murata et al., Peroxisome Proliferator-Activated Receptor-y Ligands Inhibit Choroidal Neovascularization, Inestigative Ophthalmology & visual Science, 41, 2309-2317, 2000.
Murata et al., Response of Experimental Retinal Neovascularization to Thiazolidinediones, Arch Ophthamol, 119, 709-717, 2001.
Nicholas, Courtney et al., PRMT5 is upregulated in malignant and metastatic melanoma, and regulates expression of the MITF transcription factor, Cancer Res, 72 (8 Suppl): LB-254, 4 pages, 2012.
Pal, Sharmistha et al., Low levels of miR-92b/96 induce PRMT5 translation and H3R8/H4R3 methylation in mantle cell lymphoma, The EMBO Journal, 26, 3558-3569, 2007.
Powers, Matthew A. et al., Protein Arginine Methyltransferase 5 Accelerates Tumor Growth by Arginine Methylation of the Tumor Suppressor Programmed Cell Death 4, Cancer Res, 71(16), 5579-5587, 2011.
Pubchem, SID 230731034, Available Date: Feb. 12, 2015 [retrieved on Mar. 2, 2021]. Retrieved from the Internet URL: https://pubchem.ncbi.nlm.nih.gov/substance/230731034entire document (8 pages).
Rank, Gerhard et al., Identification of a PRMT5-dependent repressor complex linked to silencing of human fetal globin gene expression, Blood, 116(9), 1585-1592, 2010.
Seed et al., The Inhibition of Colon-26 Adenocarcinoma Development and Angiogenesis by Topical Diclofenac in 2.5% Hyaluronan, Cancer Research, 57, 1625-1629, 1997.
Tsujii et al., Cyclooxgenase Regulates Angiogenesis Induced by Colon Cancer Cells, Cell, 93, 705-716, 1998.
Wang, Li et al., Protein Arginine Methyltransferase 5 Suppresses the Transcription of the RB Family of Tumor Suppressors in Leukemia and Lymphoma Cells, Molecular and Cellular Biology, vol. 28, No. 20, 6262-6277, 2008.
Xin et al., Peroxisome Proliferator Activated Receptor y Ligands are Potent Inhibitors of Angiogenesis in Vitro and in Vivo, J. Biol Chem,, 13, 9116-9121, 1999.
Yalpani et al., Coronary Heart Disease is the most Serious Threat to life in the Western World, but Progress is Being Made in Finding Ways to Reduce the Risks of Suffering Such a Fate, Chemistry & Industry, 85-89, 1996.
Zacharski et al., Heparin and Cancer, Thromb Haemost, 80, 10-23, 1998.
Ziche et al., Role of Prostaglandin E, and Copper in Angiogenesis, JNCI, 69, 475-482, 1982.
PUBCHEM-SID: 337380882 Deposit Date: Jun. 18, 2017 (Jun. 18, 2017) pp. 1-7; p. 2, structure (7 pages).

* cited by examiner

PRMT5 INHIBITORS

CROSS-REFERENCE TO RELATED APPLICATIONS

This application is a national stage entry under 35 U.S.C. § 371 of PCT/US2020/064755 filed Dec. 14, 2020, which claims priority to U.S. applications 63/025,561 filed May 15, 2020; and 62/949,245 filed Dec. 17, 2019, the contents of which are hereby incorporated by reference in their entireties.

BACKGROUND OF THE INVENTION

PRMT5 (aka JBP1, SKB1, 1BP72, SKB1his and HRMTIL5) is a Type II arginine methyltransferase, and was first identified in a two-hybrid search for proteins interacting with the Janus tyrosine kinase (Jak2) (Pollack et al., 1999). PRMT5 plays a significant role in control and modulation of gene transcription. Inter alia, PRMT5 is known to symmetrically methylate histone H3 at Arg-8 (a site distinct from that methylated by PRMT4) and histone H4 at Arg-3 (the same site methylated by PRMT1). PRMT5 has been reported to perform diverse roles including but not limited to impacting cell viability, stemness, DNA damage repair and RNA splicing (Clarke et al., Mol Cell (2017), Chiang et al., Cell Rep (2017), Gerhart et al., Sci Rep (2018)). Specifically, inhibition of PRMT5 induces alternative splicing of the negative regulator of p53, MDM4 resulting in increased expression of the short isoform of MDM4 (MDM4-S), decreased expression of the full-length isoform (MDM4-FL) and increased p53 activity (Gerhart el al Sci Rep (2018)). Most of the physiological functions of p53 are attributable to its role as a transcriptional activator, responding to agents that damage DNA. p53 status is wild type in approximately half of human cancer cases. These include 94% in cervix, 87% in blood malignancies, 85% in bones and endocrine glands, and 75% of primary breast cancer. Restoration of p53 in cancer cells harboring wild type p53, by way of inhibiting mechanisms that suppress its function leads to growth arrest and apoptosis and is regarded as a potentially effective means of tumor suppression.

In response to DNA damage caused by a variety of agents, including doxorubicin, camptothecin and UV light, and also in response to treatment with Nutlin-3, knockdown of PRMT5 results in an increase in sub-G1 population and concomitant reduction in G1 cells and, in the presence of p53, a significant increase in apoptosis. Knockdown of PRMT5 also resulted in an increased level of p21, a key p53 target gene that regulates cell cycle arrest during the p53 response and MDM2, a p53 E3 ubiquitin ligase, but not PUMA, NOXA, AlP1 & APAF1, p53 target genes linked to apoptosis.

Knockdown of PRMT5 (but not PRMT1 or CARM1/PRMT4) results in decreased p53 stabilization, decreased basal p53 levels, decreased p53 oligomerisation, and also decreased expression of elF4E a major component of translational machinery involved in ribosome binding to mRNA. Indeed, elF4E is a potent oncogene, which has been shown to promote malignant transformation in vitro and human cancer formation.

The role of PRMT5 in the DNA damage response has been explored with groups reporting a role for PRMT5 in regulating high fidelity holomlogous recombination mediated DNA repair in both solid (Clarke et al., Mol Cell (2017)) and hematological tumor models (Hamard et al., Cell Rep (2018)).

PRMT5 is aberrantly expressed in around half of human cancer cases, further linking this mechanism to cancers. PRMT5 overexpression has been observed in patient tissue samples and cell lines of Prostate cancer (Gu et al., 2012), Lung cancer (Zhongping et al., 2012), Melanoma cancer (Nicholas et al., 2012), Breast cancer (Powers et al., 2011), Colorectal cancer (Cho et al., 2012), Gastric cancer (Kim et al., 2005), Esophagus and Lung carcinoma (Aggarwal et al., 2010) and B-Cell lymphomas and leukemia (Wang, 2008). Moreover, elevated expression of PRMT5 in Melanoma, Breast and Colorectal cancers has been demonstrated to correlate with a poor prognosis.

Lymphoid malignancies including chronic lymphocytic leukemia (CLL) are associated with over-expression of PRMT5. PRMT5 is over-expressed (at the protein level) in the nucleus and cytosol in a number of patient derived Burkitt's lymphoma; mantle cell lymphoma (MCL); in vitro EBV-transformed lymphoma; leukemia cell lines; and B-CLL cell lines, relative to normal CD19+B lymphocytes (Pal et al., 2007; Wang et al., 2008). Intriguingly, despite elevated levels of PRMT5 protein in these tumor cells, the levels of PRMT5 mRNA are reduced (by a factor of 2-5). Translation of PRMT5 mRNA is, however, enhanced in lymphoma cells, resulting in increased levels of PRMT5 (Pal et al., 2007; Wang et al., 2008).

In addition to genomic changes, CLL, like almost all cancers, has aberrant epigenetic abnormalities characterised by global hypomethylation and hot-spots of repressive hypermethylation of promoters including tumor suppressor genes. While the role of epigenetics in the origin and progression of CLL remains unclear, epigenetic changes appear to occur early in the disease and specific patterns of DNA methylation are associated with worse prognosis (Chen et al., 2009; Kanduri et al., 2010). Global symmetric methylation of histones H3R8 and H4R3 is increased in transformed lymphoid cell lines and MCL clinical samples (Pal et al., 2007), correlating with the overexpression of PRMT5 observed in a wide variety of lymphoid cancer cell lines and MCL clinical samples.

PRMT5 is therefore a target for the identification of novel cancer therapeutics.

Hemoglobin is a major protein in red blood cells and is essential for the transport of oxygen from the lungs to the tissues. In adult humans, the most common hemoglobin type is a tetramer called hemoglobin A, consisting of two α and two β subunits. In human infants, the hemoglobin molecule is made up of two α and two γ chains. The gamma chains are gradually replaced by β subunits as the infant grows. The developmental switch in human β-like globin gene subtype from foetal (γ) to adult (β) that begins at birth heralds the onset of the hemoglobinopathies β-thalassemia or sickle cell disease (SCD). In β-thalassemia the adult chains are not produced. In SCD, a point mutation in the coding sequence in the β globin gene leads to the production of a protein with altered polymerisation properties. The observation that increased adult γ-globin gene expression (in the setting of hereditary persistence of foetal hemoglobin (HPFH) mutations) significantly ameliorates the clinical severity of β-thalassemia and SCD has prompted the search for therapeutic strategies to reverse γ-globin gene silencing. To date, this has been achieved through pharmacological induction, using compounds that broadly influence epigenetic modifications, including DNA methylation and histone deacetylation. The development of more targeted therapies is dependent on the identification of the molecular mechanisms underpinning foetal globin gene silencing. These mechanisms have remained elusive, despite exhaustive study of the HPFH mutations, and considerable progress in many other aspects of globin gene regulation.

PRMT5 plays a critical role in triggering coordinated repressive epigenetic events that initiate with dimethylation of histone H4 Arginine 3 (H4R3me2s), and culminate in DNA methylation and transcriptional silencing of the γ-genes (Rank et al., 2010). Integral to the synchronous establishment of the repressive markers is the assembly of a PRMT5-dependent complex containing the DNA methyltransferase DNMT3A, and other repressor proteins (Rank et al., 2010). DNMT3A is directly recruited to bind to the PRMT5-induced H4R3me2s mark, and loss of this mark through shRNA-mediated knock-down of PRMT5, or enforced expression of a mutant form of PRMT5 lacking methyltransferase activity leads to marked upregulation of γ-gene expression, and complete abrogation of DNA methylation at the γ-promoter. Treatment of human erythroid progenitors with non-specific methyltransferase inhibitors (Adox and MTA) also resulted in upregulation of γ-gene expression (He Y, 2013). Inhibitors of PRMT5 thus have potential as therapeutics for hemoglobinopathies such as β-thalassemia or Sickle Cell Disease (SCD).

The present inventors have developed compounds that inhibit the activity of PRMT5 and therefore may be of use in treating conditions ameliorated by the inhibition of the activity of PRMT5.

SUMMARY OF THE INVENTION

Invented are compounds of formula I (I)

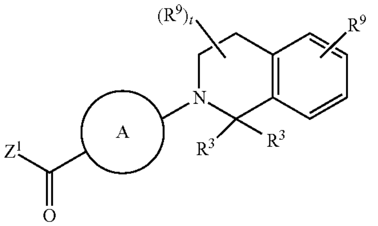

and the pharmaceutically acceptable salts, esters, and prodrugs thereof, which are PRMT5 inhibitors. Also provided are methods of making compounds of Formula I, pharmaceutical compositions comprising compounds of Formula I, and methods of using these compounds to treat cancer, sickle cell, and hereditary persistence of foetal hemoglobin (HPFH) mutations.

The invention does not include:

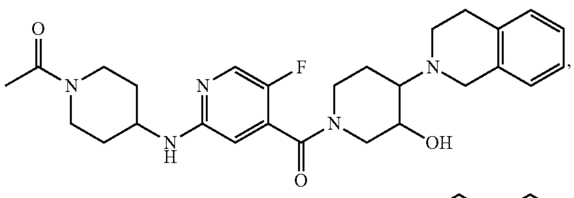

,

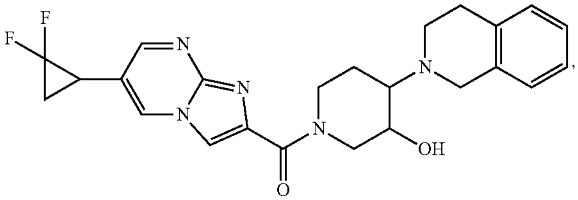

,

-continued

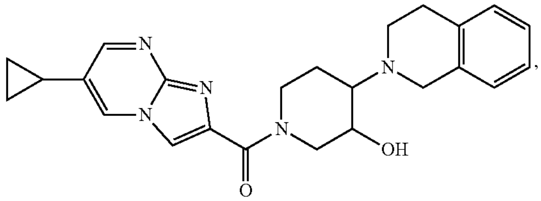

, or

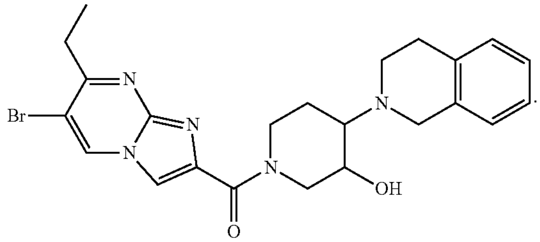

.

DETAILED DESCRIPTION OF THE INVENTION

The invention is a compound of Formula I (I)

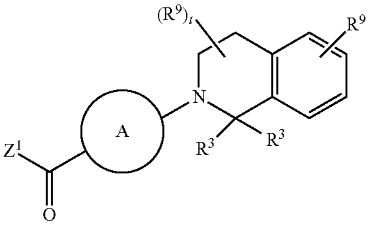

or a pharmaceutically acceptable salt thereof, wherein;

A is a 6 or 7 membered heterocycle containing 1 N atom substituted with OH and optionally substituted with 0-2 $R^2$;

$Z^1$ is

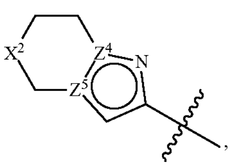

,

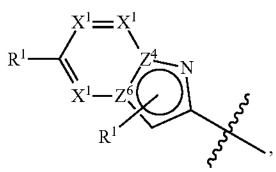

,

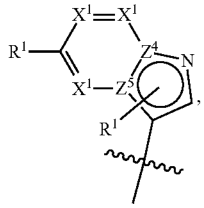

,

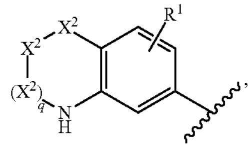

,

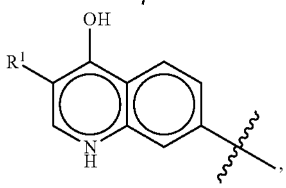

,

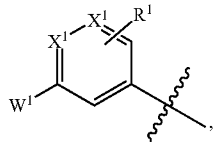

,

-continued

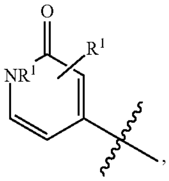

, or

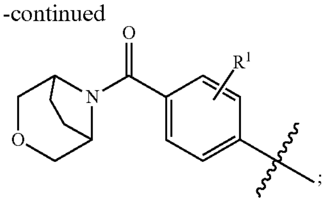

;

when present, $W^1$ is H, $CHF_2$, $NHW^2$, or $OCHF_2$;

when present, $W^2$ is

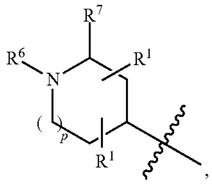

,

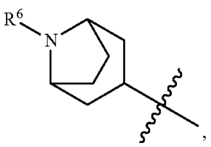

,

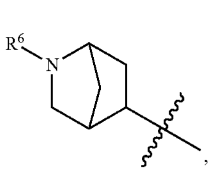

,

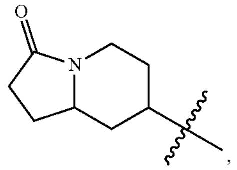

,

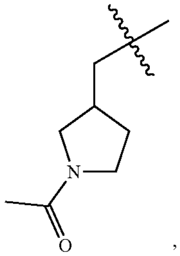

,

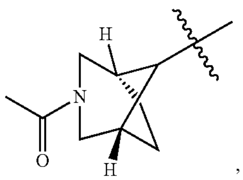

,

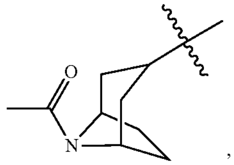

, or

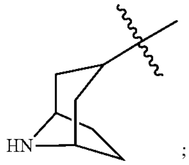

;

when present, each $R^1$ is independently selected from hydrogen, halogen, $C_{1-6}$alkyl, $OC_{0-6}$alkyl, $C_{1-6}$alkyl$OC_{1-6}$alkyl, tetrahydrofuran, cyclopropyl, triazole, thiazole or pyrazole, wherein the $C_{1-6}$alkyl, $OC_{0-6}$alkyl, $C_{1-6}$alkyl$OC_{1-6}$alkyl, tetrahydrofuran, or cyclopropyl are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN, or cyclopropyl;

when present, $R^2$ is independently selected from H or $CH_3$;

each $R^3$ is selected from hydrogen or deuterium;

when present, $R^6$ is H, $C_{1-6}$alkyl, $C(O)C_{1-6}$alkyl, $C(O)OC_{1-6}$alkyl, $C(O)C_{1-6}$cycloalkyl. $C(O)N(C_{1-6}alkyl)_2$, or $S(O)_2C_{1-6}$alkyl;

when present, $R^7$ is H or =O;

when present, $R^9$ is H, halogen, or $CH_3$;

when present, $Z^4$ is N while $Z^5$ is C, or $Z^4$ is C while $Z^5$ is N;

when present, each $X^1$ is selected from N or $CR^1$, provided no more than one $X^1$ is N;

when present, each $X^2$ is independently selected from O, C=O, $CHR^1$, $C(R^1)_2$, or $NR^1$, where two $X^2$ in the same ring cannot both be $NR^1$;

when present, t is 1 or 2;

when present, p is 0 or 1; and when present, q is 1 or 2, wherein formula I does not include:

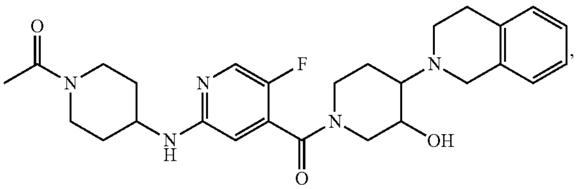

,

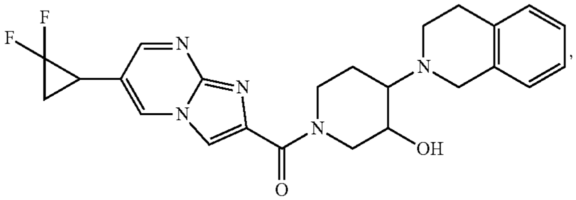

,

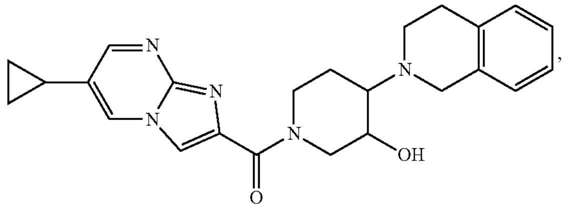

,

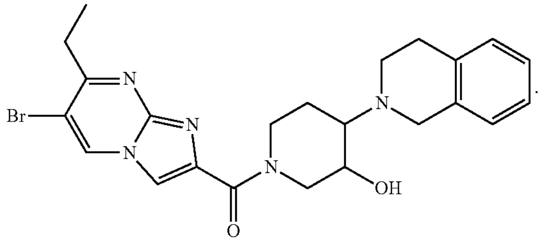

.

In an embodiment of the invention of formula I, each $R^3$ is hydrogen.

In an embodiment of the invention of formula I, A is a 6 membered heterocycle containing 1 N atom substituted with OH and optionally substituted with 0-2 $R^2$.

In an embodiment of the invention of formula I, A is:

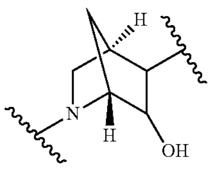 [SMILES: *C1C(O)[C@H]2C[C@@H]1CN2*]

substituted with OH and optionally substituted with 0-2 $R^2$.

(Ii)

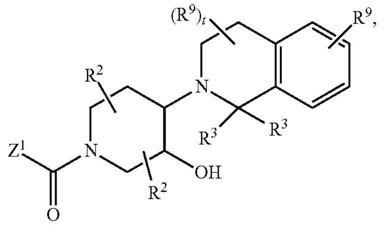

or a pharmaceutically acceptable salt thereof.

An embodiment of the invention is the compound of formula (Ia);

Ia

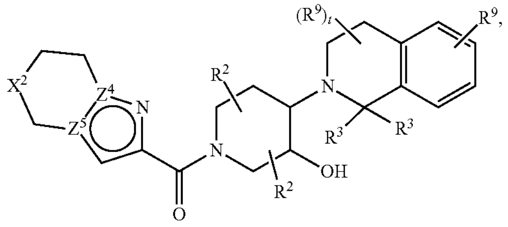

or a pharmaceutically acceptable salt thereof.

An embodiment of the invention is the compound of formula (Ib);

(Ib)

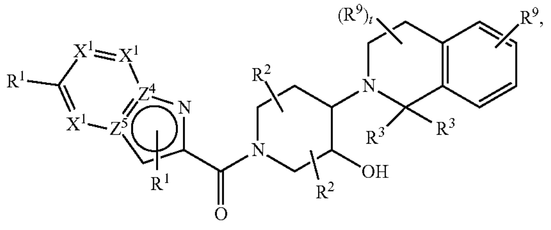

or a pharmaceutically acceptable salt thereof.

An embodiment of the invention is the compound of formula (Ic);

(Ic)

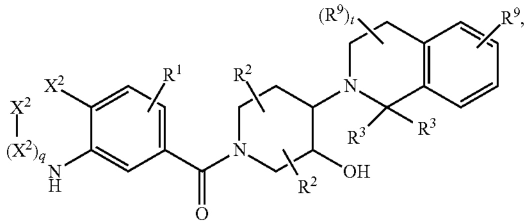

or a pharmaceutically acceptable salt thereof.

An embodiment of the invention is the compound of formula (Id);

(Id)

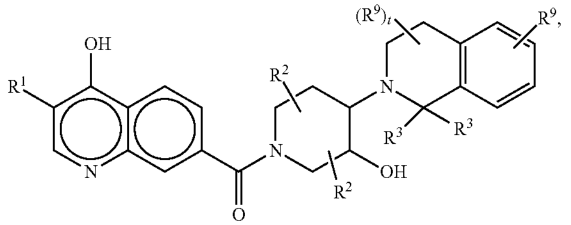

or a pharmaceutically acceptable salt thereof.

An embodiment of the invention is the compound of formula (Ie);

Ie

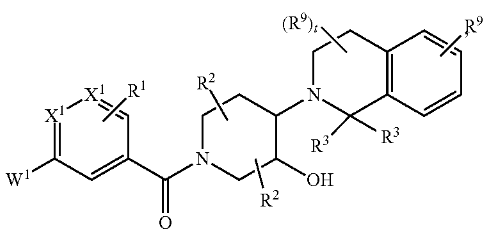

or a pharmaceutically acceptable salt thereof.

An embodiment of the invention is the compound of formula (If);

If

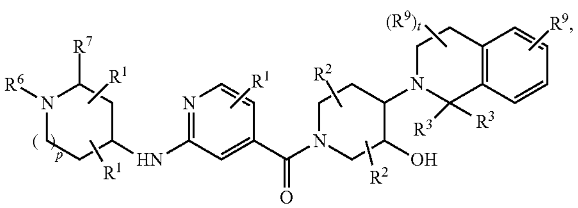

or a pharmaceutically acceptable salt thereof.

An embodiment of the invention is the compound of formula (Ig);

Ig

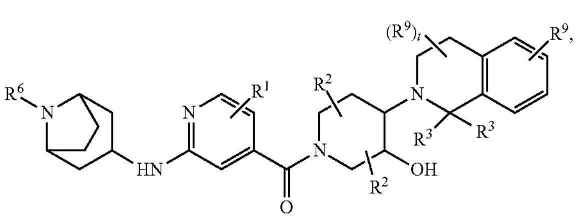

or a pharmaceutically acceptable salt thereof.

An embodiment of the invention is the compound of formula (Ih);

Ih

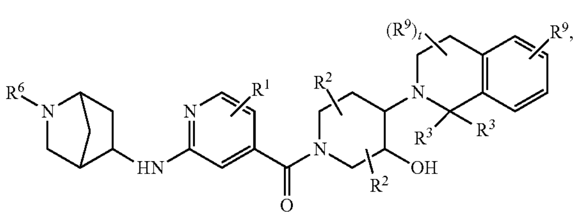

or a pharmaceutically acceptable salt thereof.

An embodiment of the invention is the compound of formula (Ij);

(Ij)

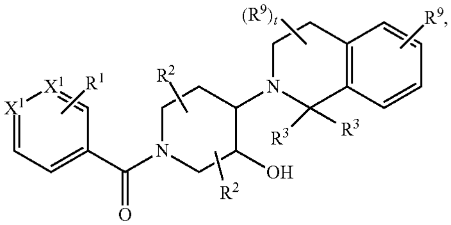

or a pharmaceutically acceptable salt thereof.

An embodiment of the invention is the compound of formula (Ik);

(Ik)

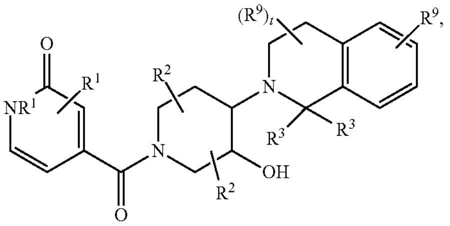

or a pharmaceutically acceptable salt thereof.

An embodiment of the invention is the compound of formula (Im);

(Im)

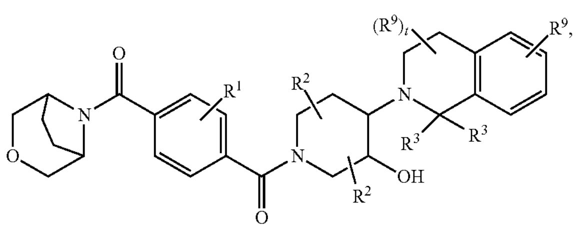

or a pharmaceutically acceptable salt thereof.

An embodiment of the invention is the compound of formula (In);

(In)

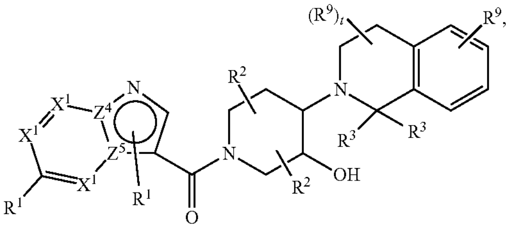

or a pharmaceutically acceptable salt thereof.

In an embodiment of the invention of formula Ii, $Z^1$ is

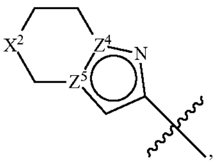
,
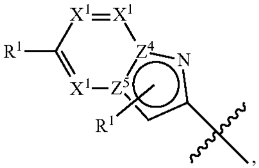
,
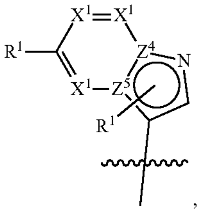
,
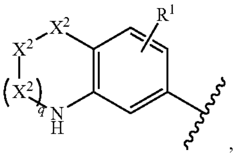
,
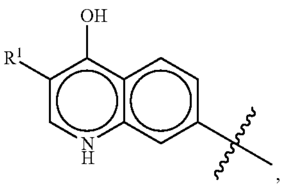
,
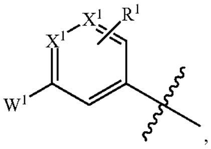
,
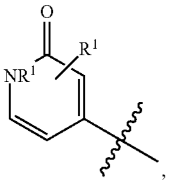
, or
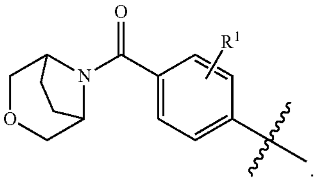
.

In an embodiment of the invention of formula Ii or Ie, when present, $W^1$ is H, $CHF_2$, $NHW^2$, or $OCHF_2$.

In a subembodiment of the present invention of Formula Ie, $W^1$ is H.

In a subembodiment of the present invention of Formula Ie, $W^1$ is $NHW^2$.

In an embodiment of the invention of formula Ii or Ie, when present, $W^2$ is

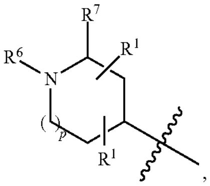
,
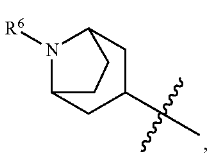
,

-continued

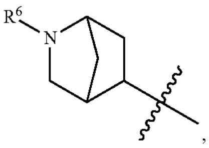,
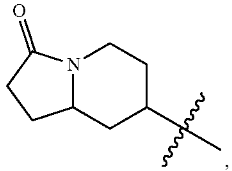,
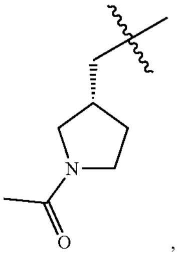,
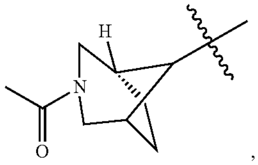,
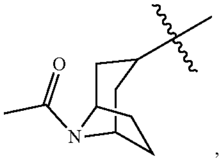, or
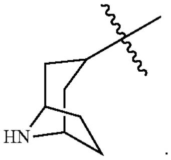.

In a subembodiment of the present invention of Formula Ie, $W^2$ is

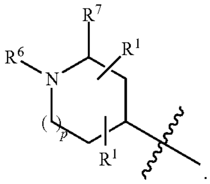.

For the avoidance of doubt, formula I, Ii, Ia, Ib, Ic, Id, Ie, If, Ig, Ih, Ij, Ik, Im, or In, does not include:

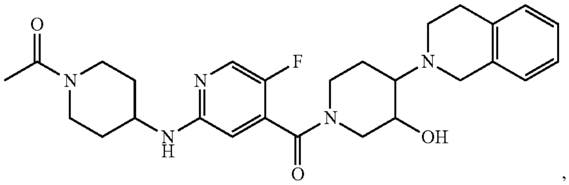,
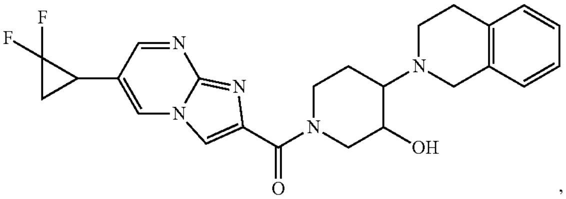,
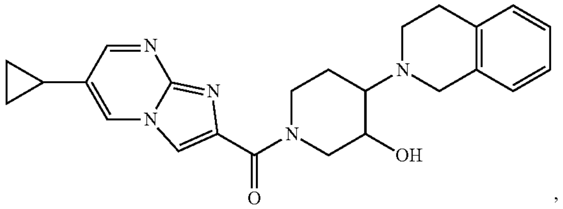,

-continued

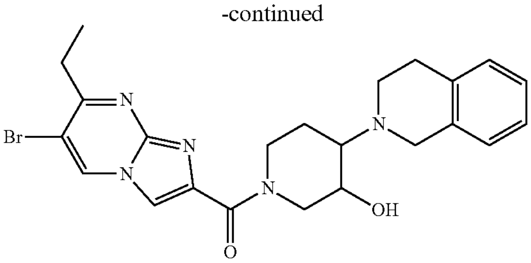, or a pharmaceutically acceptable salt thereof.

For the avoidance of doubt, formula I, Ii, Ia, Ib, Ic, Id, Ie, If, Ig, Ih, Ij, Ik, Im, or In, does not include:

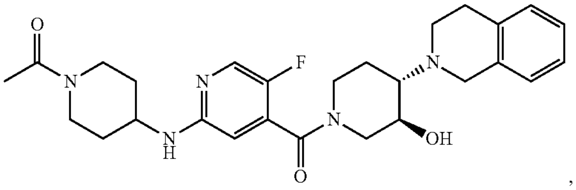,
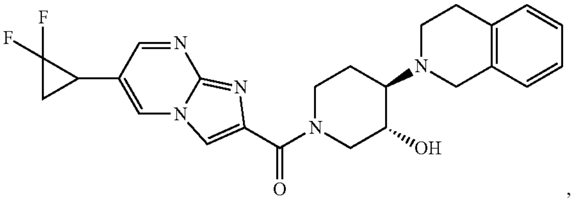,
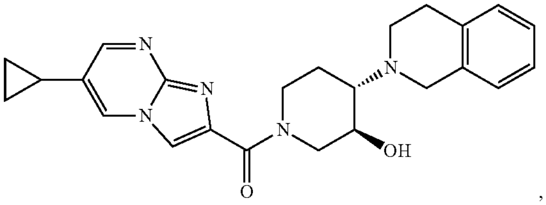, or
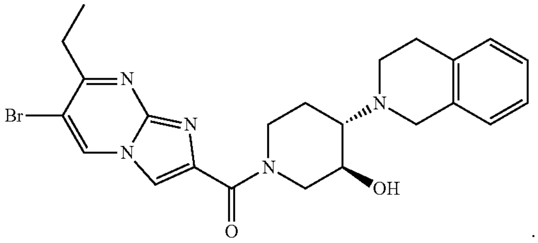.

For the avoidance of doubt, formula I, Ii, Ia, Ib, Ic, Id, Ie, If, Ig, Ih, Ij, Ik, Im, or In, does not include:

1-{4-[(4-{[(3S,4S)-4-(3,4-dihydroisoquinolin-2(1H)-yl)-3-hydroxypiperidin-1-yl]carbonyl}-5-fluoropyridin-2-yl)amino]piperidin-1-yl}ethanone, (6-(2,2-difluorocyclopropyl)imidazo[1,2-a]pyrimidin-2-yl)((3S,4S)-4-(3,4-dihydroisoquinolin-2(1H)-yl)-3-hydroxypiperidin-1-yl)methanone, (6-cyclopropylimidazo[1,2-a]pyrimidin-2-yl)((3S,4S)-4-(3,4-dihydroisoquinolin-2(1H)-yl)-3-hydroxypiperidin-1-yl)methanone, or (6-bromo-7-ethylimidazo[1,2-a]pyrimidin-2-yl)((3S,4S)-4-(3,4-dihydroisoquinolin-2(1H)-yl)-3-hydroxypiperidin-1-yl)methanone.

In an embodiment of the invention of formula I, Ii, Ia, Ib, Ic, Id, Ie, If, Ig, Ih, Ij, Ik, Im, or In, $R^2$ is independently selected from H or $CH_3$. In an embodiment of the invention of formula I, Ii, Ia, Ib, Ic, Id, Ie, If, Ig, Ih, Ij, Ik, Im, or In, each $R^2$ is H. In a subembodiment of the invention of formula Ie or If, each $R^2$ is $CH_3$.

In an embodiment of the invention of formula I, Ii, Ia, Ib, Ic, Id, Ie, If, Ig, Ih, Ij, Ik, Im, or In, $R^3$ is independently selected from hydrogen or deuterium. In an embodiment of the invention of formula Ia, Ib, Ic, Id, Ie, If, Ij, Ik, Im, or In, each $R^3$ is hydrogen. In an embodiment of the invention of formula Ie, If, Ij, Ik, or Im, each $R^3$ is deuterium.

In an embodiment of the invention of formula I, Ii, Ia, Ib, Ic, Id, Ie, If, Ig, Ih, Ij, Ik, Im, or In, t is 1 or 2.

In an embodiment of the invention of formula I, Ii, Ia, Ib, Ic, Id, Ie, If, Ig, Ih, Ij, Ik, Im, or In, $R^9$ is independently selected from hydrogen, halogen or $CH_3$. In an embodiment of the invention of formula I, Ii, Ia, Ib, Ic, Id, Ie, If, Ig, Ih, Ij, Ik, Im, or In, $R^9$ is H. In an embodiment of the invention of formula Ie, If, Ij, Ig, or Im, one $R^9$ is halogen and at least one $R^9$ is hydrogen. In an embodiment of the invention of formula Ie, If, Ij, or Im, two $R^9$'s are halogens. In an embodiment of the invention of formula Ie, If, Ij, or Im, one $R^9$ is halogens and at least one is hydrogen. In an embodiment of the invention of formula Ie, If, Ij, or Im, one $R^9$ is $CH_3$, and at least one $R^9$ is hydrogen. In an embodiment of the invention of formula Im, each $R^9$ is F.

In an embodiment of the invention of formula I, Ii, Ia, Ib, Ic, Id, Ie, If, Ig, Ih, Ij, Ik, Im, or In, when present, each $R^1$ is independently selected from H, halogen, =O, $C_{1-6}$alkyl, $OC_{0-6}$alkyl, $C_{1-6}$alkyl$OC_{1-6}$alkyl, tetrahydrofuran, cyclopropyl, triazole, thiazole or pyrazole, wherein the $C_{1-6}$alkyl, $OC_{0-6}$alkyl, $C_{1-6}$alkyl$OC_{1-6}$alkyl, tetrahydrofuran, or cyclopropyl are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN, or cyclopropyl.

In a subembodiment of the invention of formula I, Ii, Ia, Ib, Ic, Id, Ie, If, Ig, Ih, Ij, Ik, Im, or In, when present, each $R^1$ is independently selected from H, halogen, =O, OH, $CH_3$, $CF_3$, $OCH_3$, $CH_2CH_3$, $CH(CH_3)CN$, $CH_2CF_3$, $OCH_2CF_3$, $OCH_2CH_3$, $OCH_2CF_3$, $CH(CH_3)OCH_3$, $CH(CH_3)_2$, $C(CH_3)_2CN$, cyclopropyl, tetrahydrofuran, triazole, thiazole or pyrazole wherein the tetrahydrofuran, or cyclopropyl are optionally substituted with one to three substituents independently selected from halogen, $CH_3$, CN, cyclopropyl, or =O or wherein the triazole, thiazole or pyrazole are optionally substituted with one to three substituents independently selected from halogen, $CH_3$, CN or cyclopropyl.

In a subembodiment of the invention of formula Ii, Ia, Ib, Ic, Id, Ie, If, Ij, each $R^1$ is independently selected from H, halogen, =O, OH, $CH_3$, $CF_3$, $OCH_3$, $CH_2CH_3$, $CH(CH_3)CN$, $CH_2CF_3$, $OCH_2CF_3$, $OCH_2CH_3$, $OCH_2CF_3$, $CH(CH_3)OCH_3$, $CH(CH_3)_2$, or $C(CH_3)_2CN$.

In a subembodiment of the invention of formula Ii, Ib, Ic, Ie, Ij, each $R^1$ is independently selected from H, cyclopropyl, tetrahydrofuran, triazole, thiazole or pyrazole wherein the cyclopropyl or tetrahydrofuran are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN or cyclopropyl.

In one embodiment of the invention of formula Ib, $R^1$ is H or cyclopropyl optionally substituted with one to three substituents independently selected from CN, $CH_3$, or F. In one embodiment of the invention of formula Ic, $R^1$ is H, $CH_3$, $CF_3$, cyclopropyl, $CH_2CH_3$, $CH_2CF_3$, =O, or $CH(CH_3)_2$. In one embodiment of the invention of formula Ic, $R^1$ is H, $CH(CH_3)_2$, $CH_2CH_3$, $CH_3$ or $CH_2CF_3$. In one embodiment of the invention of formula Ic, $R^1$ is H or tetrahydrofuran optionally substituted with one to three substituents independently selected from $CH_3$. In one embodiment of the invention of formula Ie, $R^1$ is H, F, Cl, =O, $OCH_2CF_3$, $OCH_3$, $OCH_2CH_3$, or $C(CH_3)_2CN$. In one embodiment of the invention of formula Ie, $R^1$ is H or tetrahydrofuran optionally substituted with cyclopropyl. In one embodiment of the invention of formula If, $R^1$ is H, F, Cl, $OCH_3$, or $OCH_2CH_3$. In one embodiment of the invention of formula Ij, $R^1$ is H, F, Cl, =O, $OCH_2CF_3$, $OCH_3$, $OCH_2CH_3$, or $C(CH_3)_2CN$. In one embodiment of the invention of formula Ia, $R^1$ is H, $CF_3$, or $CH_2CF_3$. In one embodiment of the invention of formula I, Ii, Ia, Ib, Ic, Id, Ie, If, Ig, Ih, Ij, Ik, Im, or In, $R^1$ is H. In one embodiment of the invention of formula Ia or Ib, $R^1$ is independently selected from H or $CF_3$. In one embodiment of the invention of formula Ia, Ib, Id, or Ik, $R^1$ is independently selected from H or $CH_2CF_3$. In one embodiment of the invention of formula Ib, Ig, or In, $R^1$ is independently selected from H or halogen. In one embodiment of the invention of formula Ib, Ig, Ih or In, $R^1$ is independently selected from H, F, Br, I or Cl.

In one embodiment of the invention of formula Ib, $R^1$ is independently selected from H or $OCH_3$. In one embodiment of the invention of formula Ib, $R^1$ is independently selected from H or OH. In one embodiment of the invention of formula Ib or Im, $R^1$ is independently selected from H or $OCH_2CH_3$. In one embodiment of the invention of formula Ib, $R^1$ is independently selected from H or $CH(CH_3)OCH_3$. In one embodiment of the invention of formula Ib, $R^1$ is independently selected from H or $CH(CH_3)_2$. In one embodiment of the invention of formula Ib, $R^1$ is independently selected from H or $CH(CH_3)CN$. In one embodiment of the invention of formula Ib, $R^1$ is independently selected from H, cyclopropyl, triazole, thiazole or pyrazole, wherein the cyclopropyl, triazole, thiazole or pyrazole are all optionally substituted with 1-3 of F, CN, $CH_3$, $CH_2CH_3$. In one embodiment of the invention of formula Id, $R^1$ is H or cyclopropyl.

In an embodiment of the invention of formula Ii, Ia, or Ic, when present, $X^2$ is independently selected from O, C=O, $CHR^1$, $C(R^1)_2$, or $NR^1$, where two $X^2$, when present in the same ring cannot both be $NR^1$. In a subembodiment of the invention of formula Ia or Ic, $X^2$ is independently selected from O, C=O, $NR^1$, $CHR^1$, or $C(R)_2$. In an embodiment of the invention of formula Ia, $X^2$ is $NR^1$ or $C(R^1)_2$. In a subembodiment of the invention of formula Ia, $X^2$ is $NR^1$. In a subembodiment of the invention of formula Ia, $X^2$ is $C(R^1)_2$. In an embodiment of the invention of formula Ii, Ia, Ib, Ie, Ij, or In, when present, $X^1$ is independently selected from N or $CR^1$, provided no more than one $X^1$ is N. In a subembodiment of the invention of formula Ie or Ij, one $X^1$ is N and one $X^1$ is $CR^1$. In a subembodiment of the invention of formula Ib or In, one $X^1$ is N and two $X^1$ are $CR^1$. In a subembodiment of the invention of formula Ib, Ie, Ij, or In, all $X^1$ present are $CR^1$.

In an embodiment of the invention of formula Ii, Ie, If, Ig or Ih, when present, $R^6$ is H, $C_{1-6}$alkyl, $C(O)C_{1-6}$alkyl, $C(O)OC_{1-6}$alkyl, $C_{1-6}$cycloalkyl, $C(O)N(C_{1-6}alkyl)_2$, or $S(O)_2C_{1-6}$alkyl. In an embodiment of the invention of formula Ie or If, $R^6$ is H, $CH_3$, $C(O)CH_2CH_3$, $C(O)N(CH_3)_2$, $C(O)CH_3$, $C(O)OC(CH_3)_3$, $S(O)_2CH_3$, $C(O)OCH_2CH_3$, $C(O)OCH_2CH_3$, C(O)cyclopropyl, or $C(O)OCH_3$. In an embodiment of the invention of formula Ie or Ih, $R^6$ is $C(O)CH_3$. In an embodiment of the invention of formula Ie, If, Ig or Ih, $R^6$ is H. In an embodiment of the invention of formula Ig, $R^6$ is $C(O)CH_3$ or $C(O)OC(CH_3)_3$.

In an embodiment of the invention of formula Ii, Ie or If, when present, $R^7$ is H or =O. In an embodiment of the invention of formula Ie or If, when present, $R^7$ is H or =O. In an embodiment of the invention of formula Ie or If, when present, $R^7$ is H. In an embodiment of the invention of formula Ie or If, when present, $R^7$ is =O.

In an embodiment of the invention of formula Ii, Ia, Ib or In, when present, $Z^4$ is N while $Z^5$ is C, or $Z^4$ is C while $Z^5$ is N. In a further subembodiment of the invention of formula Ia, Ib or In, $Z^4$ is C and $Z^5$ is N. In a further subembodiment of the invention of formula Ia, Ib or In, $Z^4$ is N and $Z^5$ is C.

In an embodiment of the invention of formula Ii, le or If, when present, p is 0 or 1. In a subembodiment of the invention of formula Ie or If, when present, p is 0 or 1. In a subembodiment of the invention of formula Ie or If, when present, p is 0. In a subembodiment of the invention of formula Ie or If, when present, p is 1.

In an embodiment of the invention of formula Ii or Ic, when present, q is 1 or 2. In a subembodiment of the invention of formula Ic, q is 1. In a subembodiment of the invention of formula Ic, q is 2.

In an embodiment of the invention, the compound of formula I, or a pharmaceutically acceptable salt thereof, is:

(6-Bromoimidazo[1,2-a]pyridin-2-yl)((3S,4S)-4-(3,4-dihydroisoquinolin-2(1H)-yl)-3-hydroxypiperidin-1-yl)methanone, (6-Bromoimidazo[1,2-a]pyridin-2-yl)((3R,4R)-4-(3,4-dihydroisoquinolin-2(1H)-yl)-3-hydroxypiperidin-1-yl)methanone, ((3S,4S)-3-hydroxy-4-(6-methyl-3,4-dihydroisoquinolin-2(1H)-yl)piperidin-1-yl)(6-(2,2,2-trifluoroethoxy)pyridin-3-yl)methanone, ((3R,4R)-3-hydroxy-4-(6-methyl-3,4-dihydroisoquinolin-2(1H)-yl)piperidin-1-yl)(6-(2,2,2-trifluoroethoxy)pyridin-3-yl)methanone, 1-(-4-((4-((3S,4S)-4-(3,4-dihydroisoquinolin-2(1H)-yl)-3-hydroxypiperidine-1-carbonyl)pyridin-2-yl)amino)-3,3-difluoropiperidin-1-yl)ethan-1-one, 1-(-4-((4-((3S,4S)-4-(3,4-dihydroisoquinolin-2(1H)-yl)-3-hydroxypiperidine-1-carbonyl)pyridin-2-yl)amino)-3,3-difluoropiperidin-1-yl)ethan-1-one, 1-(-4-((4-((3R,4R)-4-(3,4-dihydroisoquinolin-2(1H)-yl)-3-hydroxypiperidine-1-carbonyl)pyridin-2-yl)amino)-3,3-difluoropiperidin-1-yl)ethan-1-one, 1-(-4-((4-((3R,4R)-4-(3,4-dihydroisoquinolin-2(1H)-yl)-3-hydroxypiperidine-1-carbonyl)pyridin-2-yl)amino)-3,3-difluoropiperidin-1-yl)ethan-1-one, 6-((3S,4S)-4-(3,4-dihydroisoquinolin-2(1H)-yl)-3-hydroxypiperidine-1-carbonyl)-2-ethyl-2H-benzo[b][1,4]oxazin-3(4H)-one, 6-((3S,4S)-4-(3,4-dihydroisoquinolin-2(1H)-yl)-3-hydroxypiperidine-1-carbonyl)-2-ethyl-2H-benzo[b][1,4]oxazin-3(4H)-one, 6-((3R,4R)-4-(3,4-dihydroisoquinolin-2(1H)-yl)-3-hydroxypiperidine-1-carbonyl)-2-ethyl-2H-benzo[b][1,4]oxazin-3(4H)-one, 6-((3R,4R)-4-(3,4-dihydroisoquinolin-2(1H)-yl)-3-hydroxypiperidine-1-carbonyl)-2-ethyl-2H-benzo[b][1,4]oxazin-3(4H)-one, 1-(-4-((4-((3S,4S)-4-(3,4-dihydroisoquinolin-2(1H)-yl)-3-hydroxypiperidine-1-carbonyl)-3-fluoropyridin-2-yl)amino)-3,3-difluoropiperidin-1-yl)ethan-1-one, 1-(-4-((4-((3S,4S)-4-(3,4-dihydroisoquinolin-2(1H)-yl)-3-hydroxypiperidine-1-carbonyl)-3-fluoropyridin-2-yl)amino)-3,3-difluoropiperidin-1-yl)ethan-1-one, 1-(-4-((4-((3R,4R)-4-(3,4-dihydroisoquinolin-2(1H)-yl)-3-hydroxypiperidine-1-carbonyl)-3-fluoropyridin-2-yl)amino)-3,3-difluoropiperidin-1-yl)ethan-1-one, 1-(-4-((4-((3R,4R)-4-(3,4-dihydroisoquinolin-2(1H)-yl)-3-hydroxypiperidine-1-carbonyl)-3-fluoropyridin-2-yl)amino)-3,3-difluoropiperidin-1-yl)ethan-1-one, 1-(4-((4-((3S,4S)-4-(3,4-dihydroisoquinolin-2(1H)-yl)-3-hydroxypiperidine-1-carbonyl)-3-fluoropyridin-2-yl)amino)piperidin-1-yl)ethan-1-one, 1-(4-((4-((3R,4R)-4-(3,4-dihydroisoquinolin-2(1H)-yl)-3-hydroxypiperidine-1-carbonyl)-3-fluoropyridin-2-yl)amino)piperidin-1-yl)ethan-1-one, 1-(4-((4-(4-(3,4-dihydroisoquinolin-2(1H)-yl)-3-hydroxy-2-methylpiperidine-1-carbonyl)pyridin-2-yl)amino)piperidin-1-yl)ethan-1-one, 1-(4-((4-(4-(3,4-dihydroisoquinolin-2(1H)-yl)-3-hydroxy-2-methylpiperidine-1-carbonyl)pyridin-2-yl)amino)piperidin-1-yl)ethan-1-one, 1-(4-((4-(4-(3,4-dihydroisoquinolin-2(1H)-yl)-3-hydroxy-2,2-dimethylpiperidine-1-carbonyl)pyridin-2-yl)amino)piperidin-1-yl)ethan-1-one, 1-(4-((4-(4-(3,4-dihydroisoquinolin-2(1H)-yl)-3-hydroxy-2,2-dimethylpiperidine-1-carbonyl)pyridin-2-yl)amino)piperidin-1-yl)ethan-1-one, 1-(4-((4-(-4-(4,4-difluoro-3,4-dihydroisoquinolin-2(1H)-yl)-3-hydroxypiperidine-1-carbonyl)-5-fluoropyridin-2-yl)amino)piperidin-1-yl)ethan-1-one, 1-(4-((5-chloro-4-(-4-(4,4-difluoro-3,4-dihydroisoquinolin-2(1H)-yl)-3-hydroxypiperidine-1-carbonyl)pyridin-2-yl)amino)piperidin-1-yl)ethan-1-one, (-4-(4,4-difluoro-3,4-dihydroisoquinolin-2(1H)-yl)-3-hydroxypiperidin-1-yl)(6-(2,2,2-trifluoroethoxy)pyridin-3-yl)methanone, 1-(4-((5-fluoro-4-(-4-(4,4-difluoro-3,4-dihydroisoquinolin-2(1H)-yl)-3-hydroxypiperidine-1-carbonyl)pyridin-2-yl)amino)piperidin-1-yl)ethan-1-one, 1-(4-((5-chloro-4-(-4-(4,4-difluoro-3,4-dihydroisoquinolin-2(1H)-yl)-3-hydroxypiperidine-1-carbonyl)pyridin-2-yl)amino)piperidin-1-yl)ethan-1-one, (-4-(4,4-difluoro-3,4-dihydroisoquinolin-2(1H)-yl)-3-hydroxypiperidin-1-yl)(6-(2,2,2-trifluoroethoxy)pyridin-3-yl)methanone, 1-{4-[(4-{[(1R,4R)-5-(3,4-dihydroisoquinolin-2(1H)-yl)-6-hydroxy-2-azabicyclo[2.2.1]hept-2-yl]carbonyl}-5-fluoropyridin-2-yl)amino]piperidin-1-yl}ethenone, 4-((3S,4S)-4-(3,4-dihydroisoquinolin-2(1H)-yl)-3-hydroxypiperidine-1-carbonyl)-1-(2,2,2-trifluoroethyl)pyridin-2(1H)-one, 4-((3R,4R)-4-(3,4-dihydroisoquinolin-2(1H)-yl)-3-hydroxypiperidine-1-carbonyl)-1-(2,2,2-trifluoroethyl)pyridin-2(1H)-one, (4-(3-oxa-8-azabicyclo[3.2.1]octane-8-carbonyl)-2-ethoxyphenyl)((3S,4S)-4-(3,4-dihydroisoquinolin-2(1H)-yl)-3-hydroxypiperidin-1-yl)methanone, (4-(3-oxa-8-azabicyclo[3.2.1]octane-8-carbonyl)-2-ethoxyphenyl)((3R,4R)-4-(3,4-dihydroisoquinolin-2(1H)-yl)-3-hydroxypiperidin-1-yl)methanone, (4-(3-oxa-8-azabicyclo[3.2.1]octane-8-carbonyl)phenyl)((3S,4S)-4-(3,4-dihydroisoquinolin-2(1H)-yl)-3-hydroxypiperidin-1-yl)methanone, (4-(3-oxa-8-azabicyclo[3.2.1]octane-8-carbonyl)phenyl)((3R,4R)-4-(3,4-dihydroisoquinolin-2(1H)-yl)-3-hydroxypiperidin-1-yl)methanone, (4-(3-oxa-8-azabicyclo[3.2.1]octane-8-carbonyl)phenyl)((3S,4S)-4-(5-fluoro-3,4-dihydroisoquinolin-2(1H)-yl)-3-hydroxypiperidin-1-yl)methanone,
(4-(3-oxa-8-azabicyclo[3.2.1]octane-8-carbonyl)phenyl)((3R,4R)-4-(5-fluoro-3,4-dihydroisoquinolin-2(1H)-yl)-3-hydroxypiperidin-1-yl)methanone,
(4-(3-oxa-8-azabicyclo[3.2.1]octane-8-carbonyl)phenyl)((3S,4S)-4-(6-fluoro-3,4-dihydroisoquinolin-2(1H)-yl)-3-hydroxypiperidin-1-yl)methanone,
(4-(3-oxa-8-azabicyclo[3.2.1]octane-8-carbonyl)phenyl)((3R,4R)-4-(6-fluoro-3,4-dihydroisoquinolin-2(1H)-yl)-3-hydroxypiperidin-1-yl)methanone,
(4-(3-oxa-8-azabicyclo[3.2.1]octane-8-carbonyl)phenyl)((3S,4S)-4-(7-fluoro-3,4-dihydroisoquinolin-2(1H)-yl)-3-hydroxypiperidin-1-yl)methanone,
(4-(3-oxa-8-azabicyclo[3.2.1]octane-8-carbonyl)phenyl)((3R,4R)-4-(7-fluoro-3,4-dihydroisoquinolin-2(1H)-yl)-3-hydroxypiperidin-1-yl)methanone,
((3S,4S)-4-(3,4-dihydroisoquinolin-2(1H)-yl)-3-hydroxypiperidin-1-yl)(6-(2,2,2-trifluoroethoxy)pyridin-3-yl)methanone,
((3R,4R)-4-(3,4-dihydroisoquinolin-2(1H)-yl)-3-hydroxypiperidin-1-yl)(6-(2,2,2-trifluoroethoxy)pyridin-3-yl)methanone,
((3R,4R or 3S,4S)-3-hydroxy-4-(7-methyl-3,4-dihydroisoquinolin-2(1H)-yl)piperidin-1-yl)(6-(2,2,2-trifluoroethoxy)pyridin-3-yl)methanone,
((3S,4S or 3R,4R)-3-hydroxy-4-(7-methyl-3,4-dihydroisoquinolin-2(1H)-yl)piperidin-1-yl)(6-(2,2,2-trifluoroethoxy)pyridin-3-yl)methanone,
1-{4-[(5-chloro-4-{[(3S,4S)-4-(3,4-dihydroisoquinolin-2(1H)-yl)-3-hydroxypiperidin-1-yl]carbonyl}pyridin-2-yl)amino]piperidin-1-yl}ethenone,
((3S,4S)-4-(3,4-dihydroisoquinolin-2(1H)-yl)-3-hydroxypiperidin-1-yl)(5-(2,2,2-trifluoroethyl)-4,5,6,7-tetrahydropyrazolo[1,5-a]pyrazin-2-yl)methanone,
(6-bromo-8-ethoxyimidazo[1,2-a]pyrazin-2-yl)((3S,4S)-4-(3,4-dihydroisoquinolin-2(1H)-yl)-3-hydroxypiperidin-1-yl)methanone,
(2-(difluoromethyl)pyridin-4-yl)((3S,4S)-4-(3,4-dihydroisoquinolin-2(1H)-yl)-3-hydroxypiperidin-1-yl)methanone,
(2-(difluoromethoxy)pyridin-4-yl)((3S,4S)-4-(3,4-dihydroisoquinolin-2(1H)-yl)-3-hydroxypiperidin-1-yl)methanone,
[(3S,4S)-4-(3,4-dihydroisoquinolin-2(1H)-yl)-3-hydroxypiperidin-1-yl][6-(2,4-dimethyl-1,3-thiazol-5-yl)imidazo[1,2-a]pyrimidin-2-yl]methanone,
[(3S,4S)-4-(3,4-dihydroisoquinolin-2(1H)-yl)-3-hydroxypiperidin-1-yl][6-(1-methyl-1H-pyrazol-5-yl)imidazo[1,2-a]pyrimidin-2-yl]methanone,
[(3S,4S)-4-(3,4-dihydroisoquinolin-2(1H)-yl)-3-hydroxypiperidin-1-yl]{8-[(1R)-1-methoxyethyl]-6-(propan-2-yl)imidazo[1,2-a]pyridin-2-yl}methanone,
[(3S,4S)-4-(3,4-dihydroisoquinolin-2(1H)-yl)-3-hydroxypiperidin-1-yl]{8-[(1R)-1-methoxyethyl]-6-methylimidazo[1,2-a]pyridin-2-yl}methanone,
(4-(1-cyclopropyl-1H-1,2,4-triazol-5-yl)phenyl)((3S,4S)-4-(3,4-dihydroisoquinolin-2(1H)-yl)-3-hydroxypiperidin-1-yl)methanone,
(4-(1-cyclopropyl-1H-1,2,4-triazol-5-yl)phenyl)((3R,4R)-4-(3,4-dihydroisoquinolin-2(1H)-yl)-3-hydroxypiperidin-1-yl)methanone,
8-((3S,4S)-4-(3,4-dihydroisoquinolin-2(1H)-yl)-3-hydroxypiperidine-1-carbonyl)-4-isopropyl-1,2,3,4-tetrahydro-5H-benzo[e][1,4]diazepin-5-one,
(3-cyclopropyl-4-hydroxyquinolin-7-yl)((3S,4S)-4-(3,4-dihydroisoquinolin-2(1H)-yl)-3-hydroxypiperidin-1-yl)methanone,
8-((3S,4S)-4-(3,4-dihydroisoquinolin-2(1H)-yl)-3-hydroxypiperidine-1-carbonyl)-4-ethyl-1,2,3,4-tetrahydro-5H-benzo[e][1,4]diazepin-5-one,
8-((3S,4S)-4-(3,4-dihydroisoquinolin-2(1H)-yl)-3-hydroxypiperidine-1-carbonyl)-4-(tetrahydrofuran-3-yl)-1,2,3,4-tetrahydro-5H-benzo[e][1,4]diazepin-5-one,
(6-bromo-5-methylimidazo[1,2-a]pyrimidin-2-yl)((3S,4S)-4-(3,4-dihydroisoquinolin-2(1H)-yl)-3-hydroxypiperidin-1-yl)methanone,
(6-bromo-7-methylimidazo[1,2-a]pyrimidin-2-yl)((3S,4S)-4-(3,4-dihydroisoquinolin-2(1H)-yl)-3-hydroxypiperidin-1-yl)methanone,
(6-bromo-8-((R or S)-1-methoxyethyl)imidazo[1,2-a]pyridin-2-yl)((3S,4S)-4-(3,4-dihydroisoquinolin-2(1H)-yl)-3-hydroxypiperidin-1-yl)methanone,
(6-bromo-7-methoxyimidazo[1,2-a]pyrimidin-2-yl)((3S,4S)-4-(3,4-dihydroisoquinolin-2(1H)-yl)-3-hydroxypiperidin-1-yl)methanone,
(6-bromo-7-hydroxyimidazo[1,2-a]pyrimidin-2-yl)((3S,4S)-4-(3,4-dihydroisoquinolin-2(1H)-yl)-3-hydroxypiperidin-1-yl)methanone,
(6-bromoimidazo[1,2-a]pyrimidin-2-yl)[(3S,4S)-4-(3,4-dihydroisoquinolin-2(1H)-yl)-3-hydroxypiperidin-1-yl]methanone,
[(3S,4S)-4-(3,4-dihydroisoquinolin-2(1H)-yl)-3-hydroxypiperidin-1-yl](6-methylimidazo[1,2-a]pyrimidin-2-yl)methanone,
(6-bromo-7-methylimidazo[1,2-a]pyrimidin-3-yl)[(3S,4S)-4-(3,4-dihydroisoquinolin-2(1H)-yl)-3-hydroxypiperidin-1-yl]methanone,
(6-bromo-5-methylimidazo[1,2-a]pyrimidin-3-yl)[(3S,4S)-4-(3,4-dihydroisoquinolin-2(1H)-yl)-3-hydroxypiperidin-1-yl]methanone,
2-{2-[(3S,4S)-4-(3,4-dihydroisoquinolin-2(1H)-yl)-3-hydroxypiperidine-1-carbonyl]imidazo[1,2-a]pyrimidin-6-yl}propanenitrile,
(6-bromo-7-cyclopropylimidazo[1,2-a]pyrimidin-2-yl)[(3S,4S)-4-(3,4-dihydroisoquinolin-2(1H)-yl)-3-hydroxypiperidin-1-yl]methanone,
[6-bromo-7-(propan-2-yl)imidazo[1,2-a]pyrimidin-2-yl][(3S,4S)-4-(3,4-dihydroisoquinolin-2(1H)-yl)-3-hydroxypiperidin-1-yl]methanone,
2-cyclopropyl-6-((3S,4S)-4-(3,4-dihydroisoquinolin-2(1H)-yl)-3-hydroxypiperidine-1-carbonyl)-2H-benzo[b][1,4]oxazin-3(4H)-one,
2-cyclopropyl-6-((3S,4S)-4-(3,4-dihydroisoquinolin-2(1H)-yl)-3-hydroxypiperidine-1-carbonyl)-2H-benzo[b][1,4]oxazin-3(4H)-one,
((3S,4S)-4-(3,4-dihydroisoquinolin-2(1H)-yl)-3-hydroxypiperidin-1-yl)(-6-(trifluoromethyl)-5,6,7,8-tetrahydroimidazo[1,2-a]pyridin-2-yl)methanone,
((3S,4S)-4-(3,4-dihydroisoquinolin-2(1H)-yl)-3-hydroxypiperidin-1-yl)(-6-(trifluoromethyl)-5,6,7,8-tetrahydroimidazo[1,2-a]pyridin-2-yl)methanone,
6-((3S,4S)-4-(3,4-dihydroisoquinolin-2(1H)-yl)-3-hydroxypiperidine-1-carbonyl)-2-(-5,5-dimethyltetrahydrofuran-3-yl)-2H-benzo[b][1,4]oxazin-3(4H)-one,
6-((3S,4S)-4-(3,4-dihydroisoquinolin-2(1H)-yl)-3-hydroxypiperidine-1-carbonyl)-2-(-5,5-dimethyltetrahydrofuran-3-yl)-2H-benzo[b][1,4]oxazin-3(4H)-one,
1-(4-((4-((3S,4S)-4-(3,4-dihydroisoquinolin-2(1H)-yl)-3-hydroxypiperidine-1-carbonyl)-5-fluoropyridin-2-yl)amino)-3,3-difluoropiperidin-1-yl)ethan-1-one, 1-(4-((4-((3S,4S)-4-(3,4-dihydroisoquinolin-2(1H)-yl)-3-hydroxypiperidine-1-carbonyl)-5-fluoropyridin-2-yl)amino)-3,3-difluoropiperidin-1-yl)ethan-1-one,
1-(4-((4-((3S,4S)-4-(3,4-dihydroisoquinolin-2(1H)-yl)-3-hydroxypiperidine-1-carbonyl)-5-methoxypyridin-2-yl)amino)piperidin-1-yl)ethan-1-one,
2-(5-1{[(3S,4S)-4-(3,4-dihydroisoquinolin-2(1H)-yl)-3-hydroxypiperidin-1-yl]carbonyl}pyridin-2-yl)-2-methylpropanenitrile,
2-(5-{[(3R,4R)-4-(3,4-dihydroisoquinolin-2(1H)-yl)-3-hydroxypiperidin-1-yl]carbonyl}pyridin-2-yl)-2-methylpropanenitrile,
7-((3R,4R)-4-(3,4-dihydroisoquinolin-2(1H)-yl)-3-hydroxypiperidine-1-carbonyl)-4-methyl-1,4-dihydro-2H-benzo[d][1,3]oxazin-2-one,
7-((3S,4S)-4-(3,4-dihydroisoquinolin-2(1H)-yl)-3-hydroxypiperidine-1-carbonyl)-4-methyl-1,4-dihydro-2H-benzo[d][1,3]oxazin-2-one,
7-((3S,4S)-4-(3,4-dihydroisoquinolin-2(1H)-yl)-3-hydroxypiperidine-1-carbonyl)-4-methyl-1,4-dihydro-2H-benzo[d][1,3]oxazin-2-one,
7-((3R,4R)-4-(3,4-dihydroisoquinolin-2(1H)-yl)-3-hydroxypiperidine-1-carbonyl)-4-methyl-1,4-dihydro-2H-benzo[d][1,3]oxazin-2-one,
7-((3R,4R)-4-(3,4-dihydroisoquinolin-2(1H)-yl)-3-hydroxypiperidine-1-carbonyl)-4,4-dimethyl-3,4-dihydroquinolin-2(1H)-one,
7-((3S,4S)-4-(3,4-dihydroisoquinolin-2(1H)-yl)-3-hydroxypiperidine-1-carbonyl)-4,4-dimethyl-3,4-dihydroquinolin-2(1H)-one,
7-((3S,4S)-4-(3,4-dihydroisoquinolin-2(1H)-yl)-3-hydroxypiperidine-1-carbonyl)-4,4-dimethyl-1,4-dihydro-2H-benzo[d][1,3]oxazin-2-one,
7-((3R,4R)-4-(3,4-dihydroisoquinolin-2(1H)-yl)-3-hydroxypiperidine-1-carbonyl)-4,4-dimethyl-1,4-dihydro-2H-benzo[d][1,3]oxazin-2-one,
7-((3S,4S)-4-(3,4-dihydroisoquinolin-2(1H)-yl)-3-hydroxypiperidine-1-carbonyl)-6-fluoro-4-methyl-1,4-dihydro-2H-benzo[d][1,3]oxazin-2-one,
7-((3S,4S)-4-(3,4-dihydroisoquinolin-2(1H)-yl)-3-hydroxypiperidine-1-carbonyl)-6-fluoro-4-methyl-1,4-dihydro-2H-benzo[d][1,3]oxazin-2-one,
6-((3S,4S)-4-(3,4-dihydroisoquinolin-2(1H)-yl)-3-hydroxypiperidine-1-carbonyl)-2,2-dimethyl-2H-benzo[b][1,4]oxazin-3(4H)-one,
8-((3S,4S)-4-(3,4-dihydroisoquinolin-2(1H)-yl)-3-hydroxypiperidine-1-carbonyl)-4-(2,2,2-trifluoroethyl)-1,2,3,4-tetrahydro-5H-benzo[e][1,4]diazepin-5-one,
tert-butyl-3-((4-((3S,4S)-4-(3,4-dihydroisoquinolin-2(1H)-yl)-3-hydroxypiperidine-1-carbonyl)-5-fluoropyridin-2-yl)amino)-8-azabicyclo[3.2.1]octane-8-carboxylate,
((3S,4S)-4-(3,4-dihydroisoquinolin-2(1H)-yl)-3-hydroxypiperidin-1-yl)(5-fluoro-2-((1-(methylsulfonyl)piperidin-4-yl)amino)pyridin-4-yl)methanone,
ethyl 4-((4-((3S,4S)-4-(3,4-dihydroisoquinolin-2(1H)-yl)-3-hydroxypiperidine-1-carbonyl)-5-fluoropyridin-2-yl)amino)piperidine-1-carboxylate,
1-(4-((4-((3S,4S)-4-(3,4-dihydroisoquinolin-2(1H)-yl)-3-hydroxypiperidine-1-carbonyl)-5-ethoxypyridin-2-yl)amino)piperidin-1-yl)ethan-1-one,
(2-((1-(cyclopropanecarbonyl)piperidin-4-yl)amino)-5-fluoropyridin-4-yl)((3S,4S)-4-(3,4-dihydroisoquinolin-2(1H)-yl)-3-hydroxypiperidin-1-yl)methanone,
methyl 4-((4-((3S,4S)-4-(3,4-dihydroisoquinolin-2(1H)-yl)-3-hydroxypiperidine-1-carbonyl)-5-fluoropyridin-2-yl)amino)piperidine-1-carboxylate,
4-((4-((3S,4S)-4-(3,4-dihydroisoquinolin-2(1H)-yl)-3-hydroxypiperidine-1-carbonyl)-5-fluoropyridin-2-yl)amino)-N,N-dimethylpiperidine-1-carboxamide,
1-(4-((4-((3S,4S)-4-(3,4-dihydroisoquinolin-2(1H)-yl)-3-hydroxypiperidine-1-carbonyl)-5-fluoropyridin-2-yl)amino)piperidin-1-yl)propan-1-one,
4-((4-((3S,4S)-4-(3,4-dihydroisoquinolin-2(1H)-yl)-3-hydroxypiperidine-1-carbonyl)-5-fluoropyridin-2-yl)amino)-1-methylpiperidin-2-one,
1-(-3-((4-((3S,4S)-4-(3,4-dihydroisoquinolin-2(1H)-yl)-3-hydroxypiperidine-1-carbonyl)-5-fluoropyridin-2-yl)amino)pyrrolidin-1-yl)ethan-1-one,
1-(-3-((4-((3S,4S)-4-(3,4-dihydroisoquinolin-2(1H)-yl)-3-hydroxypiperidine-1-carbonyl)-5-fluoropyridin-2-yl)amino)pyrrolidin-1-yl)ethan-1-one,
7-[(4-{[(3S,4S)-4-(3,4-dihydroisoquinolin-2(1H)-yl)-3-hydroxypiperidin-1-yl]carbonyl}-5-fluoropyridin-2-yl)amino]hexahydroindolizin-3(2H)-one,
7-[(4-{[(3S,4S)-4-(3,4-dihydroisoquinolin-2(1H)-yl)-3-hydroxypiperidin-1-yl]carbonyl}-5-fluoropyridin-2-yl)amino]hexahydroindolizin-3(2H)-one,
7-[(4-{[(3S,4S)-4-(3,4-dihydroisoquinolin-2(1H)-yl)-3-hydroxypiperidin-1-yl]carbonyl}-5-fluoropyridin-2-yl)amino]hexahydroindolizin-3(2H)-one,
7-[(4-{[(3S,4S)-4-(3,4-dihydroisoquinolin-2(1H)-yl)-3-hydroxypiperidin-1-yl]carbonyl}-5-fluoropyridin-2-yl)amino]hexahydroindolizin-3(2H)-one,
1-(5-((4-((3S,4S)-4-(3,4-dihydroisoquinolin-2(1H)-yl)-3-hydroxypiperidine-1-carbonyl)-5-fluoropyridin-2-yl)amino)-2-azabicyclo[2.2.1]heptan-2-yl)ethan-1-one,
1-(5-((4-((3S,4S)-4-(3,4-dihydroisoquinolin-2(1H)-yl)-3-hydroxypiperidine-1-carbonyl)-5-fluoropyridin-2-yl)amino)-2-azabicyclo[2.2.1]heptan-2-yl)ethan-1-one,
(2-((8-azabicyclo[3.2.1]octan-3-yl)amino)-5-fluoropyridin-4-yl)((3S,4S)-4-(3,4-dihydroisoquinolin-2(1H)-yl)-3-hydroxypiperidin-1-yl)methanone,
1-(3-((4-((3S,4S)-4-(3,4-dihydroisoquinolin-2(1H)-yl)-3-hydroxypiperidine-1-carbonyl)-5-fluoropyridin-2-yl)amino)-8-azabicyclo[3.2.1]octan-8-yl)ethan-1-one,
1-((S)-3-(((4-((3S,4S)-4-(3,4-dihydroisoquinolin-2(1H)-yl)-3-hydroxypiperidine-1-carbonyl)-5-fluoropyridin-2-yl)amino)methyl)pyrrolidin-1-yl)ethan-1-one,
1-((1R,5S)-8-((4-((3S,4S)-4-(3,4-dihydroisoquinolin-2(1H)-yl)-3-hydroxypiperidine-1-carbonyl)-5-fluoropyridin-2-yl)amino)-3-azabicyclo[3.2.1]octan-3-yl)ethan-1-one,
1-(2-((3S,4S)-4-(3,4-dihydroisoquinolin-2(1H)-yl)-3-hydroxypiperidine-1-carbonyl)imidazo[1,2-a]pyridin-6-yl)cyclopropane-1-carbonitrile,
((3S,4S)-4-(3,4-dihydroisoquinolin-2(1H)-yl)-3-hydroxypiperidin-1-yl)(4-hydroxy-3-(2,2,2-trifluoroethyl)quinolin-7-yl)methanone,
1-(2-{[(3S,4S)-4-(3,4-dihydroisoquinolin-2(1H)-yl)-3-hydroxypiperidin-1-yl]carbonyl}imidazo[1,2-a]pyrimidin-6-yl)-2,2-dimethylcyclopropanecarbonitrile,
1-(2-{[(3S,4S)-4-(3,4-dihydroisoquinolin-2(1H)-yl)-3-hydroxypiperidin-1-yl]carbonyl}imidazo[1,2-a]pyrimidin-6-yl)-2,2-dimethylcyclopropanecarbonitrile,
((3S,4S)-4-(3,4-dihydroisoquinolin-2(1H)-yl)-3-hydroxypiperidin-1-yl)(6-(2-methylcyclopropyl)imidazo[1,2-a]pyrimidin-2-yl)methanone,
((3S,4S)-4-(3,4-dihydroisoquinolin-2(1H)-yl)-3-hydroxypiperidin-1-yl)(6-(2-methylcyclopropyl)imidazo[1,2-a]pyrimidin-2-yl)methanone,
((3S,4S)-4-(3,4-dihydroisoquinolin-2(1H)-yl)-3-hydroxypiperidin-1-yl)(6-(2-methylcyclopropyl)imidazo[1,2-a]pyrimidin-2-yl)methanone, (6-chloroimidazo[1,2-a]pyridin-2-yl)[(3S,4S)-4-(3,4-dihydroisoquinolin-2(1H)-yl)-3-hydroxypiperidin-1-yl]methanone, (6-bromo-3-chloropyrazolo[1,5-a]pyrimidin-2-yl)[(3S,4S)-4-(3,4-dihydroisoquinolin-2(1H)-yl)-3-hydroxypiperidin-1-yl]methanone, (8-bromo-6-methylimidazo[1,2-a]pyridin-2-yl)[(3S,4S)-4-(3,4-dihydroisoquinolin-2(1H)-yl)-3-hydroxypiperidin-1-yl]methanone, (6-bromo-8-methylimidazo[1,2-a]pyridin-2-yl)[(3S,4S)-4-(3,4-dihydroisoquinolin-2(1H)-yl)-3-hydroxypiperidin-1-yl]methanone, (8-chloro-6-methylimidazo[1,2-a]pyridin-2-yl)[(3S,4S)-4-(3,4-dihydroisoquinolin-2(1H)-yl)-3-hydroxypiperidin-1-yl]methanone,

[8-chloro-6-(trifluoromethyl)imidazo[1,2-a]pyridin-2-yl][(3S,4S)-4-(3,4-dihydroisoquinolin-2(1H)-yl)-3-hydroxypiperidin-1-yl]methanone, (8-bromo-6-chloroimidazo[1,2-a]pyridin-2-yl)[(3S,4S)-4-(3,4-dihydroisoquinolin-2(1H)-yl)-3-hydroxypiperidin-1-yl]methanone, (6-bromo-8-iodoimidazo[1,2-a]pyridin-2-yl)[(3S,4S)-4-(3,4-dihydroisoquinolin-2(1H)-yl)-3-hydroxypiperidin-1-yl]methanone, (6,8-dichloroimidazo[1,2-a]pyridin-2-yl)[(3S,4S)-4-(3,4-dihydroisoquinolin-2(1H)-yl)-3-hydroxypiperidin-1-yl]methanone, (6-bromo-8-fluoroimidazo[1,2-a]pyridin-2-yl)[(3S,4S)-4-(3,4-dihydroisoquinolin-2(1H)-yl)-3-hydroxypiperidin-1-yl]methanone, (6,8-dibromoimidazo[1,2-a]pyridin-2-yl)[(3S,4S)-4-(3,4-dihydroisoquinolin-2(1H)-yl)-3-hydroxypiperidin-1-yl]methanone, or (6-bromopyrazolo[1,5-a]pyrimidin-2-yl)[(3S,4S)-4-(3,4-dihydroisoquinolin-2(1H)-yl)-3-hydroxypiperidin-1-yl]methanone.

Reference to compounds of formula I encompasses formula Ii, Ia, Ib, Ic, Id, Ie, If, Ig, Ih, Ij, Ik, or In, and all subembodiments thereof, in the following.

In one embodiment, the present invention is a composition for treating cancer comprising an effective amount of at least one compound of formula I, I, Ii, Ia, Ib, Ic, Id, Ie, If, Ig, Ih, Ij, Ik, Im, or In, or a pharmaceutically acceptable salt thereof.

The invention also provides a pharmaceutical composition comprising an effective amount of at least one compound of Formula I, or a pharmaceutically acceptable salt thereof, and a pharmaceutically acceptable carrier.

In one embodiment, the present invention is a composition for treating cancer comprising an effective amount of at least one compound of formula I, I, Ii, Ia, Ib, Ic, Id, Ie, If, Ig, Ih, Ij, Ik, Im, or In, or a pharmaceutically acceptable salt thereof, and a pharmaceutically acceptable carrier.

The invention also provides a pharmaceutical composition comprising an effective amount of at least one compound of formula I, Ii, Ia, Ib, Ic, Id, Ie, If, Ig, Ih, Ij, Ik, Im, or In, or a pharmaceutically acceptable salt thereof, and an effective amount of at least one other pharmaceutically active ingredient (such as, for example, a chemotherapeutic agent), and a pharmaceutically acceptable carrier.

The invention also provides a pharmaceutical composition comprising an effective amount of at least one compound of formula I, Ii, Ia, Ib, Ic, Id, Ie, If, Ig, Ih, Ij, Ik, Im, or In, or a pharmaceutically acceptable salt thereof, and an effective amount of at least one other pharmaceutically active ingredient (such as, for example, a chemotherapeutic agent or an anti-cancer agent), and a pharmaceutically acceptable carrier.

In one embodiment, the present invention is a composition for treating hemoglobinopathies such as β-thalassemia or Sickle Cell Disease (SCD), comprising a compound of formula I, I, Ii, Ia, Ib, Ic, Id, Ie, If, Ig, Ih, Ij, Ik, Im, or In, or a pharmaceutically acceptable salt thereof.

In one embodiment, the present invention is a composition for treating hemoglobinopathies such as β-thalassemia or Sickle Cell Disease (SCD), comprising a compound of formula I, I, Ii, Ia, Ib, Ic, Id, Ie, If, Ig, Ih, Ij, Ik, Im, or In, or a pharmaceutically acceptable salt thereof, and a pharmaceutically acceptable carrier.

In one embodiment, the present invention is a method of inhibiting PRMT5 in a patient in need thereof comprising administering to said patient an effective amount of at least one compound of formula I, Ii, Ia, Ib, Ic, Id, Ie, If, Ig, Ih, Ij, Ik, Im or In, or a pharmaceutically acceptable salt thereof.

In another embodiment, the present invention is a method of treating cancer comprising administering to a patient in need thereof a an effective amount of at least one compound of formula I, I, Ii, Ia, Ib, Ic, Id, Ie, If, Ig, Ih, Ij, Ik, Im, or In, or a pharmaceutically acceptable salt thereof.

In another embodiment, the present invention is a method of treating cancer comprising administering to a patient in need thereof a an effective amount of at least one compound of formula I, I, Ii, Ia, Ib, Ic, Id, Ie, If, Ig, Ih, Ij, Ik, Im, or In, or a pharmaceutically acceptable salt thereof, and a pharmaceutically acceptable carrier.

In another embodiment, the present invention provides a method for treating cancer in a patient in need thereof comprising administering to said patient an effective amount of at least one compound of formula I, I, Ii, Ia, Ib, Ic, Id, Ie, If, Ig, Ih, Ij, Ik, Im, or In, or a pharmaceutically acceptable salt thereof, in combination with an effective amount of at least one chemotherapeutic agent.

The methods of the invention include the administration of a pharmaceutical composition comprising at least one compound of the invention and a pharmaceutically acceptable carrier.

In another embodiment, the present invention includes a method of treating hemoglobinopathies such as β-thalassemia or Sickle Cell Disease (SCD), comprising administering to a patient in need thereof a compound of formula I, I, Ii, Ia, Ib, Ic, Id, Ie, If, Ig, Ih, Ij, Ik, Im, or In, or a pharmaceutically acceptable salt thereof.

In another embodiment, the present invention is a method of treating cancer comprising administering to a patient in need thereof a compound of formula I, I, Ii, Ia, Ib, Ic, Id, Ie, If, Ig, Ih, Ij, Ik, Im, or In, or a pharmaceutically acceptable salt thereof.

In another embodiment, the present invention is a method of treating cancer comprising administering to a patient in need thereof a compound of formula I, I, Ii, Ia, Ib, Ic, Id, Ie, If, Ig, Ih, Ij, Ik, Im, or In, or a pharmaceutically acceptable salt thereof, and a pharmaceutically acceptable carrier.

In another embodiment, the present invention is a method of treating cancer comprising administering to a patient in need thereof, a composition comprising a compound of formula I, I, Ii, Ia, Ib, Ic, Id, Ie, If, Ig, Ih, Ij, Ik, Im, or In, or a pharmaceutically acceptable salt thereof, and a pharmaceutically acceptable carrier.

In another embodiment, the present invention is a method of treating hemoglobinopathies such as β-thalassemia or Sickle Cell Disease (SCD), comprising administering to a patient in need thereof a composition comprising a compound of formula I, I, Ii, Ia, Ib, Ic, Id, Ie, If, Ig, Ih, Ij, Ik, Im, or In, or a pharmaceutically acceptable salt thereof, and a pharmaceutically acceptable carrier.

In another embodiment, the present invention is the use of a compound of formula I, I, Ii, Ia, Ib, Ic, Id, Ie, If, Ig, Ih, Ij, Ik, Im, or In, or a pharmaceutically acceptable salt thereof, in the manufacture of a medicament for treating cancer.

In another embodiment of the present invention is the use of a compound of formula I, I, Ii, Ia, Ib, Ic, Id, Ie, If, Ig, Ih, Ij, Ik, Im, or In, or a pharmaceutically acceptable salt thereof, in the manufacture of a medicament for treating hemoglobinopathies such as β-thalassemia or Sickle Cell Disease (SCD).

In another embodiment, the present invention includes the use of compounds of formula I, Ii, Ia, Ib, Ic, Id, Ie, If, Ig, Ih, Ij, Ik, Im or In, or a pharmaceutically acceptable salt thereof, for the preparation of a medicament for the treatment of cancer, or hemoglobinopathies such as β-thalassemia or Sickle Cell Disease (SCD).

Another embodiment is the use of compounds of formula I, I, Ii, Ia, Ib, Ic, Id, Ie, If, Ig, Ih, Ij, Ik, Im, or In, or a pharmaceutically acceptable salt thereof, for the preparation of a medicament for the treatment of cancer. In a subembodiment, the cancer is i) cardiac cancer, ii) lung cancer, iii) gastrointestinal cancer, iv) genitourinary tract cancer, v) liver cancer, vi) bone cancer, vii) nervous system cancer, viii) gynecological cancer, ix) hematological cancer, x) skin cancer, or xi) adrenal cancer.

Another embodiment is the use of compounds of formula I, Ii, Ia, Ib, Ic, Id, Ie, If, Ig, Ih, Ij, Ik, Im or In, or a pharmaceutically acceptable salt thereof, for the preparation of a medicament for the treatment of hemoglobinopathies such as β-thalassemia or Sickle Cell Disease (SCD).

In another embodiment, the present invention includes compounds of formula I, Ii, Ia, Ib, Ic, Id, Ie, If, Ig, Ih, Ij, Ik, Im or In, for use in the treatment of cancer or hemoglobinopathies such as β-thalassemia or Sickle Cell Disease (SCD). In another embodiment, the present invention includes compounds of formula I, Ii, Ia, Ib, Ic, Id, Ie, If, Ig, Ih, Ij, Ik, Im or In, or a pharmaceutically acceptable salt thereof, for use in the treatment of cardiac cancer, lung cancer, gastrointestinal cancer, genitourinary tract cancer, liver cancer, bone cancer, nervous system cancer, gynecological cancer, hematological cancer, skin cancer, or adrenal cancer.

In one example of the invention the cancer treated is colo-rectal cancer (such as, for example, colon adenocarcinoma and colon adenoma). Thus, another example of the invention is directed to a method of treating colo-rectal cancer in a patient in need of such treatment, said method comprising administering an effective of a compound of formula I, Ii, Ia, Ib, Ic, Id, Ie, If, Ig, Ih, Ij, Ik, Im or In, or a pharmaceutically acceptable salt thereof, to said patient. Another example of the invention is directed to a method of treating colo-rectal cancer in a patient in need of such treatment, said method comprising administering to said patient an effective amount of a compound of formula I, Ii, Ia, Ib, Ic, Id, Ie, If, Ig, Ih, Ij, Ik, Im or In, or a pharmaceutically acceptable salt thereof, and an effective amount of at least one chemotherapeutic agent.

The invention also provides any of the above methods of treating cancer wherein the cancer is melanoma. Thus, another example of the invention is directed to a method of treating melanoma in a patient in need of such treatment, said method comprising administering an effective amount of a compound of formula I, Ii, Ia, Ib, Ic, Id, Ie, If, Ig, Ih, Ij, Ik, Im or In, or a pharmaceutically acceptable salt thereof, to said patient. Another example of the invention is directed to a method of treating melanoma in a patient in need of such treatment, said method comprising administering to said patient an effective amount of a compound of formula I, Ii, Ia, Ib, Ic, Id, Ie, If, Ig, Ih, Ij, Ik, Im or In, or a pharmaceutically acceptable salt thereof, and an effective amount of at least one chemotherapeutic agent.

The methods of treating cancers described herein can optionally include the administration of an effective amount of radiation (i.e., the methods of treating cancers described herein optionally include the administration of radiation therapy).

The methods of treating cancer described herein include methods of treating cancer that comprise administering a therapeutically effective amount of a compound of the instant invention, or a pharmaceutically acceptable salt thereof, in combination with radiation therapy and/or in combination with a second compound selected from: an estrogen receptor modulator, an androgen receptor modulator, a retinoid receptor modulator, a cytotoxicytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-6 agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed herein, or a pharmaceutically acceptable salt thereof.

In any of the methods of treating cancer described herein, unless stated otherwise, the methods can optionally include the administration of an effective amount of radiation therapy. For radiation therapy, γ-radiation is preferred.

In one embodiment, the compound disclosed herein is selected from the group consisting of the compounds exemplified herein, for example, in Examples 1-44, 47-53, 56-72, 75-102, 104-143, or a pharmaceutically acceptable salt thereof.

The term "composition" is intended to encompass a product comprising the specified ingredients in the specified amounts, as well as any product which results, directly or indirectly, from combination of the specified ingredients in the specified amounts. The term "anti-cancer agent" means a drug (medicament or pharmaceutically active ingredient), or antibody for treating cancer. The term "compound" with reference to the antineoplastic agents, includes the agents that are antibodies. The term "at least one" means one or more than one. The meaning of "at least one" with reference to the number of compounds of the invention is independent of the meaning with reference to the number of chemotherapeutic agents. The term "chemotherapeutic agent" means a drug (medicament or pharmaceutically active ingredient) for treating cancer (i.e., an antineoplastic agent). The term "compound" with reference to the antineoplastic agents, includes the agents that are antibodies. The term "effective amount" means a "therapeutically effective amount". The term "therapeutically effective amount" means that amount of active compound or pharmaceutical agent that elicits the biological or medicinal response in a tissue, system, animal or human that is being sought by a researcher, veterinarian, medical doctor or other clinician. Thus, for example, in the methods of treating cancer described herein "effective amount" (or "therapeutically effective amount") means, the amount of the compound (or drug), or radiation, that results in: (a) the reduction, alleviation or disappearance of one or more symptoms caused by the cancer, (b) the reduction of tumor size, (c) the elimination of the tumor, and/or (d) long-term disease stabilization (growth arrest) of the tumor. Also, for example, an effective amount, or a therapeutically effective amount of the PRMT5 inhibitor (i.e., a compound of the invention) is that amount which results in the reduction in PRMT5 activity. The term "treating cancer" or "treatment of cancer" refers to administration to a mammal afflicted with a cancerous condition and refers to an effect that alleviates the cancerous condition by killing the cancerous cells, and also refers to an effect that results in the inhibition of growth and/or metastasis of the cancer.

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR), e.g., the Physicians' Desk Reference, $64^{th}$ Edition, 2010 (published by PDR Network, LLC at Montvale, NJ 07645-1725), presently accessible through www.pdr.net; the disclosures of which are incorporated herein by reference thereto.

If the patient is responding, or is stable, after completion of the therapy cycle, the therapy cycle can be repeated according to the judgment of the skilled clinician. Upon completion of the therapy cycles, the patient can be continued on the compounds of the invention at the same dose that was administered in the treatment protocol. This maintenance dose can be continued until the patient progresses or can no longer tolerate the dose (in which case the dose can be reduced and the patient can be continued on the reduced dose).

Those skilled in the art will recognize that the actual dosages and protocols for administration employed in the methods of the invention may be varied according to the judgment of the skilled clinician. The actual dosage employed may be varied depending upon the requirements of the patient and the severity of the condition being treated. Determination of the proper dosage for a particular situation is within the skill of the art. A determination to vary the dosages and protocols for administration may be made after the skilled clinician takes into account such factors as the patient's age, condition and size, as well as the severity of the cancer being treated and the response of the patient to the treatment.

The amount and frequency of administration of the compound of formula (1) and the chemotherapeutic agents will be regulated according to the judgment of the attending clinician (physician) considering such factors as age, condition and size of the patient as well as severity of the cancer being treated.

The compounds of the invention are also useful in preparing a medicament that is useful in treating cancer.

The instant compounds are also useful in combination with therapeutic, chemotherapeutic and anti-cancer agents. Combinations of the presently disclosed compounds with therapeutic, chemotherapeutic and anti-cancer agents are within the scope of the invention. Examples of such agents can be found in *Cancer Principles and Practice of Oncology* by V T. Devita and S. Hellman (editors), $9^{th}$ edition (May 16, 2011), Lippincott Williams & Wilkins Publishers. A person of ordinary skill in the art would be able to discern which combinations of agents would be useful based on the particular characteristics of the drugs and the cancer involved. Such agents include the following: estrogen receptor modulators, programmed cell death protein 1 (PD-1) inhibitors, programmed death-ligand 1 (PD-L1) inhibitors, androgen receptor modulators, retinoid receptor modulators, cytotoxic/cytostatic agents, antiproliferative agents, prenyl-protein transferase inhibitors, HMG-CoA reductase inhibitors and other angiogenesis inhibitors, HIV protease inhibitors, reverse transcriptase inhibitors, inhibitors of cell proliferation and survival signaling, bisphosphonates, aromatase inhibitors, siRNA therapeutics, γ-secretase inhibitors, agents that interfere with receptor tyrosine kinases (RTKs) and agents that interfere with cell cycle checkpoints. The instant compounds are particularly useful when co-administered with radiation therapy.

The chemotherapeutic agent can be administered according to therapeutic protocols well known in the art. It will be apparent to those skilled in the art that the administration of the chemotherapeutic agent can be varied depending on the cancer being treated and the known effects of the chemotherapeutic agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of chemotherapeutic agent will depend upon the diagnosis of the attending physicians and their judgment of the condition of the patient and the appropriate treatment protocol.

The determination of the order of administration, and the number of repetitions of administration of the chemotherapeutic agent during a treatment protocol, is well within the knowledge of the skilled physician after evaluation of the cancer being treated and the condition of the patient.

Thus, in accordance with experience and knowledge, the practicing physician can modify each protocol for the administration of a chemotherapeutic agent according to the individual patient's needs, as the treatment proceeds. All such modifications are within the scope of the present invention.

The anti-cancer agent can be administered according to therapeutic protocols well known in the art. It will be apparent to those skilled in the art that the administration of the anti-cancer agent can be varied depending on the cancer being treated and the known effects of the anti-cancer agent on that disease. Also, in accordance with the knowledge of the skilled clinician, the therapeutic protocols (e.g., dosage amounts and times of administration) can be varied in view of the observed effects of the administered therapeutic agents on the patient, and in view of the observed responses of the cancer to the administered therapeutic agents.

The initial administration can be made according to established protocols known in the art, and then, based upon the observed effects, the dosage, modes of administration and times of administration can be modified by the skilled clinician.

The particular choice of anti-cancer agent will depend upon the diagnosis of the attending physicians and their judgment of the condition of the patient and the appropriate treatment protocol.

The determination of the order of administration, and the number of repetitions of administration of the anti-cancer agent during a treatment protocol, is well within the knowledge of the skilled physician after evaluation of the cancer being treated and the condition of the patient.

Thus, in accordance with experience and knowledge, the practicing physician can modify each protocol for the administration of an anti-cancer agent according to the individual patient's needs, as the treatment proceeds. All such modifications are within the scope of the present invention.

The attending clinician, in judging whether treatment is effective at the dosage administered, will consider the general well-being of the patient as well as more definite signs such as relief of cancer-related symptoms (e.g., pain), inhibition of tumor growth, actual shrinkage of the tumor, or inhibition of metastasis. Size of the tumor can be measured by standard methods such as radiological studies, e.g., CAT or MRI scan, and successive measurements can be used to judge whether or not growth of the tumor has been retarded or even reversed. Relief of disease-related symptoms such as pain, and improvement in overall condition can also be used to help judge effectiveness of treatment.

The compounds, compositions and methods provided herein are useful for the treatment of cancer. Cancers that may be treated by the compounds, compositions and methods disclosed herein include, but are not limited to: (1) Cardiac: sarcoma (angiosarcoma, fibrosarcoma, rhabdomyosarcoma, liposarcoma), myxoma, rhabdomyoma, fibroma, lipoma and teratoma; (2) Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma, non-small cell; (3) Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma), colon, colorectal, rectal; (4) Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); (5) Liver: hepatoma (hepatocellular carcinoma), cholangiocarcinoma, hepatoblastoma, angiosarcoma, hepatocellular adenoma, hemangioma; (6) Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; (7) Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); (8) Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; (9) Hematologic: blood (myeloid leukemia [acute and chronic], acute lymphoblastic leukemia, chronic lymphocytic leukemia, chronic myelomonocytic (CMML), myeloproliferative diseases, multiple myeloma, myelodysplastic syndrome), Hodgkin's disease, non-Hodgkin's lymphoma [malignant lymphoma]; (10) Skin: malignant melanoma, basal cell carcinoma, squamous cell carcinoma, Karposi's sarcoma, moles dysplastic nevi, lipoma, angioma, dermatofibroma, keloids, psoriasis; and (11) Adrenal glands: neuroblastoma. Examples of cancer that may be treated by the compounds, compositions and methods of the invention include thyroid cancer, anaplastic thyroid carcinoma, epidermal cancer, head and neck cancer (e.g., squamous cell cancer of the head and neck), sarcoma, tetracarcinoma, hepatoma and multiple myeloma. Thus, the term "cancerous cell" as provided herein, includes a cell afflicted by any one of the above-identified conditions.

In the treatment of breast cancer (e.g., postmenopausal and premenopausal breast cancer, e.g., hormone-dependent breast cancer) the compound of formula (1) may be used with an effective amount of at least one antihormonal agent selected from the group consisting of: (a) aromatase inhibitors, (b) antiestrogens, and (c) LHRH analogues; and optionally an effective amount of at least one chemotherapeutic agent. Examples of aromatase inhibitors include but are not limited to: Anastrozole (e.g., Arimidex), Letrozole (e.g., Femara), Exemestane (Aromasin), Fadrozole and Formestane (e.g., Lentaron). Examples of antiestrogens include but are not limited to: Tamoxifen (e.g., Nolvadex), Fulvestrant (e.g., Faslodex), Raloxifene (e.g., Evista), and Acolbifene. Examples of LHRH analogues include but are not limited to: Goserelin (e.g., Zoladex) and Leuprolide (e.g., Leuprolide Acetate, such as Lupron or Lupron Depot). Examples of chemotherapeutic agents include but are not limited to: Trastuzumab (e.g., Herceptin), Gefitinib (e.g., Iressa), Erlotinib (e.g., Erlotinib HCl, such as Tarceva), Bevacizumab (e.g., Avastin), Cetuximab (e.g., Erbitux), and Bortezomib (e.g., Velcade).

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

PD-1 inhibitors include pembrolizumab (lambrolizumab), nivolumab and MPDL3280A. PDL-inhibitors include atezolizumab, avelumab, and durvalumab.

The invention further relates to a method of treating cancer in a human patient comprising administration of a compound of the invention (i.e., a compound of Formula I) and a PD-1 antagonist to the patient. The compound of the invention and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, NJ, USA), nivolumab (OPDIVO™, Bristol-Myers Squibb Company, Princeton, NJ, USA), cemiplimab (LIBTAYO™, Regeneron Pharmaceuticals, Inc., Tarrytown, NY, USA), atezolizumab (TECENTRIQ™, Genentech, San Francisco, CA, USA), durvalumab (IMFINZI™, AstraZeneca Pharmaceuticals LP, Wilmington, DE), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular embodiments, the method comprises administering 350 mg of cemiplimab to the patient about every 3 weeks. In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refers to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis[diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032), Raf kinase inhibitors (such as Bay43-9006) and mTOR inhibitors (such as Wyeth's CCI-779).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include paclitaxel, vindesine sulfate, 3',4'-didehydro-4'-deoxy-8'-norvincaleukoblastine, docetaxol, rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, TDX258, the epothilones (see for example U.S. Pat. Nos. 6,284,781 and 6,288,237) and BMS188797. In an example the epothilones are not included in the microtubule inhibitors/microtubule-stabilising agents.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoguinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino)ethylamino]-7-methoxy-9-oxo-9H-thioxanthen-4-ylmethyl]formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an example inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors may be found in the following manuscript; Miller, T. A. et al. J Med. Chem. 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680 (tozasertib).

"Antiproliferative agents" include antisense RNA and DNA oligonucleotides such as G3139, ODN698, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydro-benzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"HMG-CoA reductase inhibitor" refer to inhibitors of 3-hydroxy-3-methylglutaryl-CoA reductase. Examples of HMG-CoA reductase inhibitors that may be used include but are not limited to lovastatin (MEVACOR®; see U.S. Pat. Nos. 4,231,938, 4,294,926 and 4,319,039), simvastatin (ZOCOR®; see U.S. Pat. Nos. 4,444,784, 4,820,850 and 4,916,239), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342,952), rosuvastatin (CRESTOR® U.S. Reissue Patent RE37,314) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", *Chemistry & Industry*, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of the invention.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase). For an example of the role of a prenyl-protein transferase inhibitor on angiogenesis see *European J. of Cancer*, Vol. 35, No. 9, pp. 1394-1401 (1999).

"Angiogenesis inhibitor" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (PNAS, Vol. 89, p. 7384 (1992); JNCI, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); Clin, Orthop. Vol. 313, p. 76 (1995); *J Mol. Endocrinol.*, Vol. 16, p. 107 (1996); *Jpn. J. Pharmacol.*, Vol. 75, p. 105 (1997); *Cancer Res.*, Vol. 57, p. 1625 (1997); *Cell*, Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., Nature, 362, 841-844 (1993); WO 00/44777; and WO 00/61186).

Other therapeutic agents that modulate or inhibit angiogenesis and may also be used in combination with the compounds of the instant invention include agents that modulate or inhibit the coagulation and fibrinolysis systems (see review in *Clin. Chem. La. Med.* 38:679-692 (2000)). Examples of such agents that modulate or inhibit the coagulation and fibrinolysis pathways include, but are not limited to, heparin (see *Thromb. Haemost.* 80:10-23 (1998)), low molecular weight heparins and carboxypeptidase U inhibitors (also known as inhibitors of active thrombin activatable fibrinolysis inhibitor [TAFIa]) (see *Thrombosis Res.* 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with cell cycle checkpoints" refers to compounds that inhibit protein kinases that transduce cell cycle checkpoint signals, thereby sensitizing the cancer cell to DNA damaging agents. Such agents include inhibitors of ATR, ATM, the CHK1 and CHK2 kinases and cdk and cdc kinase inhibitors and are specifically exemplified by 7-hydroxystaurosporin, flavopiridol, CYC202 (Cyclacel) and BMS-387032.

"Agents that interfere with receptor tyrosine kinases (RTKs)" refers to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, *Nature,* 411:355-365, 2001.

"Inhibitors of cell proliferation and survival signalling pathway" refers to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004/0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, U.S. Pat. Nos. 7,454,431, 7,589,068), inhibitors of Raf kinase (for example BAY-43-9006), inhibitors of MEK (for example CI-1040 and PD-098059), inhibitors of mTOR (for example Wyeth CCI-779), and inhibitors of PI3K (for example LY294002).

As described above, the combinations with NSAIDs are directed to the use of NSAIDs which are potent COX-2 inhibiting agents. For purposes of the specification an NSAID is potent if it possesses an $IC_{50}$ for the inhibition of COX-2 of 1 μM or less as measured by cell or microsomal assays.

The invention also encompasses combinations with NSAIDs which are selective COX-2 inhibitors. For purposes of the specification NSAIDs which are selective inhibitors of COX-2 are defined as those which possess a specificity for inhibiting COX-2 over COX-1 of at least 100 fold as measured by the ratio of $IC_{50}$ for COX-2 over $IC_{50}$ for COX-1 evaluated by cell or microsomal assays. Such compounds include, but are not limited to those disclosed in U.S. Pat. Nos. 5,474,995, 5,861,419, 6,001,843, 6,020,343, 5,409,944, 5,436,265, 5,536,752, 5,550,142, 5,604,260, 5,698,584, 5,710,140, WO 94/15932, U.S. Pat. Nos. 5,344,991, 5,134,142, 5,380,738, 5,393,790, 5,466,823, 5,633,272 and 5,932,598, all of which are hereby incorporated by reference.

Inhibitors of COX-2 that are particularly useful in the instant method of treatment are: 3-phenyl-4-(4-(methylsulfonyl)phenyl)-2-(5H)-furanone; and 5-chloro-3-(4-methylsulfonyl)-phenyl-2-(2-methyl-5-pyridinyl)pyridine; or a pharmaceutically acceptable salt thereof.

Compounds that have been described as specific inhibitors of COX-2 and are therefore useful in the present invention include, but are not limited to, the following: rofecoxib, etoricoxib, parecoxib, BEXTRA® and CELEBREX® or a pharmaceutically acceptable salt thereof.

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl)phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416), or a pharmaceutically acceptable salt thereof.

As used above, "integrin blockers" refers to compounds which selectively antagonize, inhibit or counteract binding of a physiological ligand to the αvβ3 integrin, to compounds which selectively antagonize, inhibit or counteract binding of a physiological ligand to the αvβ5 integrin, to compounds which antagonize, inhibit or counteract binding of a physiological ligand to both the αvβ3 integrin and the αvβ5 integrin, and to compounds which antagonize, inhibit or counteract the activity of the particular integrin(s) expressed on capillary endothelial cells. The term also refers to antagonists of the αvβ6, αvβ8, α1β1, α2β1, α5β1, α6β1 and α6β4 integrins. The term also refers to antagonists of any combination of αvβ3, αvβ5, αvβ6, αvβ8, a1β1, α2β1, α5β1, α6β1 and α6β4 integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl)indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974, or a pharmaceutically acceptable salt thereof.

Combinations with compounds other than anti-cancer compounds are also encompassed in the instant methods. For example, combinations of the instantly claimed compounds with PPAR-γ (i.e., PPAR-gamma) agonists and PPAR-δ (i.e., PPAR-delta) agonists are useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see *J Cardiovasc. Pharmacol.* 1998; 31:909-913; *J Biol. Chem.* 1999; 274:9116-9121; *Invest. Ophthalmol Vis. Sci.* 2000; 41:2309-2317). More recently, PPAR-γ agonists have been shown to inhibit the angiogenic response to VEGF in vitro; both troglitazone and rosiglitazone maleate inhibit the development of retinal neovascularization in mice (*Arch. Ophthamol.* 2001; 119:709-717). Examples of PPAR-γ agonists and PPAR-γ/α agonists include, but are not limited to, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, G1262570, PNU182716, DRF552926, 2-[(5,7-dipropyl-3-trifluoromethyl-1,2-benzisoxazol-6-yl)oxy]-2-methylpropionic acid (disclosed in U.S. Ser. No. 09/782,856), and 2(R)-7-(3-(2-chloro-4-(4-fluorophenoxy) phenoxy)propoxy)-2-ethylchromane-2-carboxylic acid (disclosed in U.S. Ser. No. 60/235,708 and 60/244,697), or a pharmaceutically acceptable salt thereof.

Another example of the instant invention is the use of the presently disclosed compounds in combination with gene therapy for the treatment of cancer. For an overview of genetic strategies to treating cancer see Hall et al., (*Am. J. Hum. Genet.* 61:785-789, 1997) and Kufe et al., (Cancer Medicine, 5th Ed, pp 876-889, BC Decker, Hamilton 2000). Gene therapy can be used to deliver any tumor suppressing gene. Examples of such genes include, but are not limited to, p53, which can be delivered via recombinant virus-mediated gene transfer (see U.S. Pat. No. 6,069,134, for example), a uPA/uPAR antagonist ("Adenovirus-Mediated Delivery of a uPA/uPAR Antagonist Suppresses Angiogenesis-Dependent Tumor Growth and Dissemination in Mice," Gene Therapy, August 1998; 5(8):1105-13), and interferon gamma (J Immunol. 2000; 164:217-222).

The compounds of the instant invention may also be administered in combination with an inhibitor of inherent multidrug resistance (MDR), in particular MDR associated with high levels of expression of transporter proteins. Such MDR inhibitors include inhibitors of p-glycoprotein (P-gp), such as LY335979, XR9576, OC144-093, R101922, VX853 and PSC833 (valspodar), or a pharmaceutically acceptable salt thereof.

A compound of the present invention may be employed in conjunction with anti-emetic agents to treat nausea or emesis, including acute, delayed, late-phase, and anticipatory emesis, which may result from the use of a compound of the present invention, alone or with radiation therapy. For the prevention or treatment of emesis, a compound of the present invention may be used in conjunction with other anti-emetic agents, especially neurokinin-1 receptor antagonists, 5HT3 receptor antagonists, such as ondansetron, granisetron, tropisetron, and zatisetron, GABAB receptor agonists, such as baclofen, a corticosteroid such as Decadron (dexamethasone), Kenalog, Aristocort, Nasalide, Preferid, Benecorten or others such as disclosed in U.S. Pat. Nos. 2,789,118, 2,990,401, 3,048,581, 3,126,375, 3,929,768, 3,996,359, 3,928,326 and 3,749,712, an antidopaminergic, such as the phenothiazines (for example prochlorperazine, fluphenazine, thioridazine and mesoridazine), metoclopramide or dronabinol. In another example, conjunctive therapy with an anti-emesis agent selected from a neurokinin-1 receptor antagonist, a 5HT3 receptor antagonist and a corticosteroid is disclosed for the treatment or prevention of emesis that may result upon administration of the instant compounds.

A compound of the instant invention, or a pharmaceutically acceptable salt thereof, may also be administered with an agent useful in the treatment of anemia. Such an anemia treatment agent is, for example, a continuous erythropoiesis receptor activator (such as epoetin alfa).

A compound of the instant invention, or a pharmaceutically acceptable salt thereof, may also be administered with an agent useful in the treatment of neutropenia. Such a neutropenia treatment agent is, for example, a hematopoietic growth factor which regulates the production and function of neutrophils such as a human granulocyte colony stimulating factor, (G-CSF). Examples of a G-CSF include filgrastim.

A compound of the instant invention, or a pharmaceutically acceptable salt thereof, may also be administered with an immunologic-enhancing drug, such as levamisole, isoprinosine and Zadaxin, or a pharmaceutically acceptable salt thereof.

A compound of the instant invention, or a pharmaceutically acceptable salt thereof, may also be useful for treating or preventing cancer in combination with P450 inhibitors including: xenobiotics, quinidine, tyramine, ketoconazole, testosterone, quinine, methyrapone, caffeine, phenelzine, doxorubicin, troleandomycin, cyclobenzaprine, erythromycin, cocaine, furafyline, cimetidine, dextromethorphan, ritonavir, indinavir, amprenavir, diltiazem, terfenadine, verapamil, cortisol, itraconazole, mibefradil, nefazodone and nelfinavir, or a pharmaceutically acceptable salt thereof.

A compound of the instant invention, or a pharmaceutically acceptable salt thereof, may also be useful for treating or preventing cancer in combination with Pgp and/or BCRP inhibitors including: cyclosporin A, PSC833, GF120918, cremophorEL, fumitremorgin C, Ko132, Ko134, Iressa, Imatnib mesylate, EKI-785, C11033, novobiocin, diethylstilbestrol, tamoxifen, resperpine, VX-710, tryprostatin A, flavonoids, ritonavir, saquinavir, nelfinavir, omeprazole, quinidine, verapamil, terfenadine, ketoconazole, nifidepine, FK506, amiodarone, XR9576, indinavir, amprenavir, cortisol, testosterone, LY335979, OC144-093, erythromycin, vincristine, digoxin and talinolol, or a pharmaceutically acceptable salt thereof.

A compound of the instant invention, or a pharmaceutically acceptable salt thereof, may also be useful for treating or preventing cancer, including bone cancer, in combination with bisphosphonates (understood to include bisphosphonates, diphosphonates, bisphosphonic acids and diphosphonic acids). Examples of bisphosphonates include but are not limited to: etidronate (Didronel), pamidronate (Aredia), alendronate (Fosamax), risedronate (Actonel), zoledronate (Zometa), ibandronate (Boniva), incadronate or cimadronate, clodronate, EB-1053, minodronate, neridronate, piridronate and tiludronate including any and all pharmaceutically acceptable salts, derivatives, hydrates and mixtures thereof.

A compound of the instant invention, or a pharmaceutically acceptable salt thereof, may also be useful for treating or preventing breast cancer in combination with aromatase inhibitors. Examples of aromatase inhibitors include but are not limited to: anastrozole, letrozole and exemestane, or a pharmaceutically acceptable salt thereof.

A compound of the instant invention, or a pharmaceutically acceptable salt thereof, may also be useful for treating or preventing cancer in combination with siRNA therapeutics.

The compounds of the instant invention may also be administered in combination with γ-secretase inhibitors and/or inhibitors of NOTCH signaling. Such inhibitors include compounds described in WO 01/90084, WO 02/30912, WO 01/70677, WO 03/013506, WO 02/36555, WO 03/093252, WO 03/093264, WO 03/093251, WO 03/093253, WO 2004/039800, WO 2004/039370, WO 2005/030731, WO 2005/014553, U.S. Ser. No. 10/957,251, WO 2004/089911, WO 02/081435, WO 02/081433, WO 03/018543, WO 2004/031137, WO 2004/031139, WO 2004/031138, WO 2004/101538, WO 2004/101539 and WO 02/47671 (including LY-450139), or a pharmaceutically acceptable salt thereof.

A compound of the instant invention, or a pharmaceutically acceptable salt thereof, may also be useful for treating or preventing cancer in combination with PARP inhibitors.

A compound of the instant invention, or a pharmaceutically acceptable salt thereof, may also be useful for treating cancer in combination with the following therapeutic agents: pembrolizumab (Keytruda®), abarelix (Plenaxis depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone injection®); Elliott's B Solution (Elliott's B Solution®); epirubicin (Ellence®); Epoetin alfa (epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); Ridaforolimus; sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); vorinostat (Zolinza®) and zoledronate (Zometa®), or a pharmaceutically acceptable salt thereof.

In an example, the angiogenesis inhibitor to be used as the second compound is selected from a tyrosine kinase inhibitor, an inhibitor of epidermal-derived growth factor, an inhibitor of fibroblast-derived growth factor, an inhibitor of platelet derived growth factor, an MMP (matrix metalloprotease) inhibitor, an integrin blocker, interferon-α, interleukin-12, pentosan polysulfate, a cyclooxygenase inhibitor, carboxyamidotriazole, combretastatin A-4, squalamine, 6-O-chloroacetyl-carbonyl)-fumagillol, thalidomide, angiostatin, troponin-1, or an antibody to VEGF. In an example, the estrogen receptor modulator is tamoxifen or raloxifene.

Thus, the scope of the instant invention encompasses the use of the instantly claimed compounds in combination with a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

Also included in the scope of the claims is a method of treating cancer that comprises administering a therapeutically effective amount of a compound of the instant invention, or a pharmaceutically acceptable salt thereof, in combination with radiation therapy and/or in combination with a second compound selected from: an estrogen receptor modulator, an androgen receptor modulator, a retinoid receptor modulator, a cytotoxiccytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, PPAR-γ agonists, PPAR-δ agonists, an inhibitor of inherent multidrug resistance, an anti-emetic agent, an agent useful in the treatment of anemia, an agent useful in the treatment of neutropenia, an immunologic-enhancing drug, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

And yet another example of the invention is a method of treating cancer that comprises administering a therapeutically effective amount of a compound of the instant invention, or a pharmaceutically acceptable salt thereof, in combination with paclitaxel or trastuzumab.

The invention further encompasses a method of treating or preventing cancer that comprises administering a therapeutically effective amount of a compound of the instant invention, or a pharmaceutically acceptable salt thereof, in combination with a COX-2 inhibitor, or a pharmaceutically acceptable salt thereof.

The therapeutic combination disclosed herein may be used in combination with one or more other active agents, including but not limited to, other anti-cancer agents that are used in the prevention, treatment, control, amelioration, or reduction of risk of a particular disease or condition (e.g., cell-proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, prior to, contemporaneously, or sequentially with a compound of the present disclosure.

The instant invention also includes a pharmaceutical composition useful for treating or preventing cancer that comprises a therapeutically effective amount of a compound of the instant invention, or a pharmaceutically acceptable salt thereof, and a second compound selected from: an estrogen receptor modulator, an androgen receptor modulator, a retinoid receptor modulator, a cytotoxic/cytostatic agent, an antiproliferative agent, a prenyl-protein transferase inhibitor, an HMG-CoA reductase inhibitor, an HIV protease inhibitor, a reverse transcriptase inhibitor, an angiogenesis inhibitor, a PPAR-γ agonist, a PPAR-δ agonist, an inhibitor of cell proliferation and survival signaling, a bisphosphonate, an aromatase inhibitor, an siRNA therapeutic, γ-secretase and/or NOTCH inhibitors, agents that interfere with receptor tyrosine kinases (RTKs), an agent that interferes with a cell cycle checkpoint, and any of the therapeutic agents listed above.

When any variable occurs more than one time in any constituent, its definition on each occurrence is independent at every other occurrence. Also, combinations of substituents and variables are permissible only if such combinations result in stable compounds. Lines drawn into the ring systems from substituents indicate that the indicated bond may be attached to any of the substitutable ring atoms. If the ring system is bicyclic, it is intended that the bond be attached to any of the suitable atoms on either ring of the bicyclic moiety.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. Also, "optionally substituted" means optional substitution with the specified groups, radicals or moieties.

The present invention includes compounds of structural formula I, I, Ii, Ia, Ib, Ic, Id, Ie, If, Ig, Ih, Ij, Ik, Im, or In, as well as the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of the invention which are generally prepared by reacting the free base with a suitable organic or inorganic acid. Representative salts of basic compounds of the present invention include, but are not limited to, the following: acetate, ascorbate, adipate, alginate, aspirate, benzenesulfonate, benzoate, bicarbonate, bisulfate, bitartrate, borate, bromide, 4-bromobenzenesulfonate, butyrate, camphorate, camphorsulfonate, camsylate, carbonate, chloride, clavulanate, citrate, cyclohexylamidosulfonate, cyclopentane propionate, diethylacetic, digluconate, dihydrochloride, dodecylsulfanate, edetate, edisylate, estolate, esylate, ethanesulfonate, formic, fumarate, gluceptate, glucoheptanoate, gluconate, glucuonate, glutamate, glycerophosphate, glycollylarsanilate, hemisulfate, heptanoate, hexanoate, hexylresorcinate, hydrabamine, hydrobromide, hydrochloride, 2-hydroxyethanesulfonate, hydroxynaphthoate, iodide, isonicotinic, isothionate, lactate, lactobionate, laurate, malate, maleate, mandelate, mesylate, methylbromide, methylnitrate, methylsulfate, methanesulfonate, mucate, 2-naphthalenesulfonate, napsylate, nicotinate, nitrate, N-methylglucamine ammonium salt, oleate, oxalate, pamoate (embonate), palmitate, pantothenate, pectinate, persulfate, phosphate/diphosphate, pimelic, phenylpropionic, polygalacturonate, propionate, salicylate, stearate, sulfate, subacetate, succinate, tannate, tartrate, teoclate, thiocyanate, tosylate, triethiodide, trifluoroacetate, trifluoromethylsulfonate, p-toluenesulfonate, undeconate, valerate and the like.

Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts.

With basic reagents such as hydroxides, carbonates, hydrogencarbonates, alkoxides and ammonia, organic bases or alternatively basic amino acids the compounds of the formula I, Ii, Ia, Ib, Ic, Id, Ie, If, Ig, Ih, Ij, Ik, Im or In form stable alkali metal, alkaline earth metal or optionally substituted ammonium salts. Salts derived from pharmaceutically acceptable organic non-toxic bases include salts of primary, secondary, and tertiary amines, cyclic amines, dicyclohexyl amines and basic ion-exchange resins, such as arginine, betaine, caffeine, choline, N,N-dibenzylethylenediamine, diethanolamine, diethylamine, 2-diethylaminoethanol, 2-dimethylaminoethanol, ethanolamine, ethylamine, ethylenediamine, N-ethylmorpholine, N-ethylpiperidine, glucamine, glucosamine, histidine, hydrabamine, isopropylamine, lysine, methylglucamine, morpholine, omithine, piperazine, piperidine, polyamine resins, procaine, purines, theobromine, triethanolamine, triethylamine, trimethylamine, tripropylamine, trometamol, tromethamine, and the like. Also, included are the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

The preparation of pharmacologically acceptable salts from compounds of the formula I, Ii, Ia, Ib, Ic, Id, Ie, If, Ig, Ih, Ij, Ik, Im or In capable of salt formation, including their stereoisomeric forms is carried out known methods, for example, by mixing a compound of the present invention with an equivalent amount and a solution containing a desired acid, base, or the like, and then collecting the desired salt by filtering the salt or distilling off the solvent. The compounds of the present invention and salts thereof may form solvates with a solvent such as water, ethanol, or glycerol. The compounds of the present invention may form an acid addition salt and a salt with a base at the same time according to the type of substituent of the side chain.

The present invention encompasses all stereoisomeric forms of the compounds of formula I, Ii, Ia, Ib, Ic, Id, Ie, If, Ig, Ih, Ij, Ik, Im, or In. Centers of asymmetry that are present in the compounds of formula I, Ii, Ia, Ib, Ic, Id, Ie, If, Ig, Ih, Ij, Ik, Im, or In can all independently of one another have (R) configuration or (S) configuration. When bonds to the chiral carbon are depicted as straight lines in the structural Formulas of the invention, it is understood that both the (R) and (S) configurations of the chiral carbon, and hence both enantiomers and mixtures thereof, are embraced within the Formulas. Similarly, when a compound name is recited without a chiral designation for a chiral carbon, it is understood that both the (R) and (S) configurations of the chiral carbon, and hence individual enantiomers and mixtures thereof, are embraced by the name. The production of specific stereoisomers or mixtures thereof may be identified in the Examples where such stereoisomers or mixtures were obtained, but this in no way limits the inclusion of all stereoisomers and mixtures thereof from being within the scope of the invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of formula I, I, Ii, Ia, Ib, Ic, Id, Ie, If, Ig, Ih, Ij, Ik, Im, or In, or it can be done on a final racemic product. Absolute stereochemistry may be determined by X-ray crystallography of crystalline products or crystalline intermediates which are derivatized, if necessary, with a reagent containing a stereogenic center of known configuration. Where compounds of the invention are capable of tautomerization, all individual tautomers as well as mixtures thereof are included in the scope of the invention. The present invention includes all such isomers, as well as salts, solvates (including hydrates) and solvated salts of such racemates, enantiomers, diastereomers and tautomers and mixtures thereof.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the specifically and generically described compounds. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds can be prepared without undue experimentation by conventional techniques well known to those skilled in the art or by processes analogous to those described in the general process schemes and examples herein using appropriate isotopically-enriched reagents and/or intermediates.

Furthermore, compounds of the present invention may exist in amorphous form and/or one or more crystalline forms, and as such all amorphous and crystalline forms and mixtures thereof of the compounds of formula I, Ii, Ia, Ib, Ic, Id, Ie, If, Ig, Ih, Ij, Ik, Im, or In are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of the invention, along with un-solvated and anhydrous forms.

The present invention includes compounds of structural formula I, I, Ii, Ia, Ib, Ic, Id, Ie, If, Ig, Ih, Ij, Ik, Im, or In, or any other generic structural formula or specific compound described or claimed herein, and is intended to encompass the specific compound or compounds falling within the scope of the formula or embodiment.

The present invention includes compounds of structural formula I, Ii, Ia, Ib, Ic, Id, Ie, If, Ig, Ih, Ij, Ik, Im, or In as well as salts thereof, particularly pharmaceutically acceptable salts, solvates of such compounds and solvated salt forms thereof, where such forms are possible unless specified otherwise.

Except where noted herein, “alkyl” refers to an aliphatic hydrocarbon group having one of its hydrogen atoms replaced with a bond. An alkyl group is intended to include both branched- and straight-chain saturated aliphatic hydrocarbon groups having the specified number of carbon atoms. Commonly used abbreviations for alkyl groups are used throughout the specification, e.g. methyl may be represented by conventional abbreviations including “Me” or $CH_3$ or a symbol that is an extended bond as the terminal group, e.g.

“”, ethyl may be represented by “Et” or $CH_2CH_3$, propyl may be represented by “Pr” or $CH_2CH_2CH_3$, butyl may be represented by “Bu” or $CH_2CH_2CH_2CH_3$, etc. “$C_{1-4}$ alkyl” (or “$C_1$-$C_4$ alkyl”) for example, means linear or branched chain alkyl groups, including all isomers, having the specified number of carbon atoms. For example, the structures

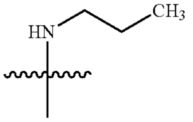

and

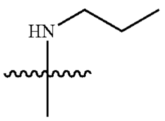

have equivalent meanings. $C_{1-4}$ alkyl includes n-, iso-, sec- and t-butyl, n- and isopropyl, ethyl and methyl. If no number is specified, 1-4 carbon atoms are intended for linear or branched alkyl groups.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Except where noted herein, structures containing substituent variables such as variable "R".

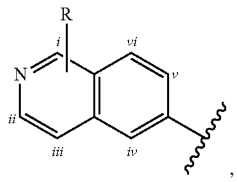

, which are depicted as not being attached to any one particular bicyclic ring carbon atom, represent structures in which the variable can be optionally attached to any bicyclic ring carbon atom. For example, variable R shown in the above structure can be attached to any one of 6 bicyclic ring carbon atoms i, ii, iii, iv, v or vi.

"Heterocycle" refers to a saturated, partially unsaturated or aromatic ring moiety having at least one ring heteroatom and at least one ring carbon atom. In one embodiment, the heteroatom is oxygen, sulfur, or nitrogen. A heterocycle containing more than one heteroatom may contain different heteroatoms. Heterocyclyl moieties include both monocyclic and multicyclic (e.g., bicyclic) ring moieties. Bicyclic ring moieties include fused, spirocycle and bridged bicyclic rings and may comprise one or more heteroatoms in either of the rings. The ring attached to the remainder of the molecule may or may not contain a heteroatom. Either ring of a bicyclic heterocycle may be saturated, partially unsaturated or aromatic. The heterocycle may be attached to the rest of the molecule via a ring carbon atom, a ring oxygen atom or a ring nitrogen atom. Non-limiting examples of heterocycles are described below.

"Aryl" refers to an aromatic monocyclic or multicyclic ring moiety comprising 6 to 14 ring carbon atoms. In one embodiment, an aryl group contains from about 6 to 10 ring carbon atoms. Monocyclic aryl rings include, but are not limited to, phenyl. Multicyclic rings include, but are not limited to, naphthyl and bicyclic rings wherein phenyl is fused to a $C_{5-7}$cycloalkyl or $C_{5-7}$cycloalkenyl ring. Aryl groups may be optionally substituted with one or more substituents as defined herein. Bonding can be through any of the carbon atoms of any ring.

"Cycloalkyl" refers to a non-aromatic mono- or multicyclic ring system comprising about 3 to 10 ring carbon atoms. In one embodiment, a cycloalkyl contains from about 5 to about 10 ring carbon atoms. In another embodiment, a cycloalkyl contains from about 3 to about 7 ring atoms. In another embodiment, a cycloalkyl contains from about 5 to about 6 ring atoms. The term "cycloalkyl" also encompasses a cycloalkyl group as defined above, which is fused to an aryl or heteroaryl ring. Non-limiting examples of monocyclic cycloalkyls include cyclopropyl, cyclobutyl, cyclopentyl, cyclohexyl, cycloheptyl and cyclooctyl. Non-limiting examples of monocyclic cycloalkyl include cyclopropyl, cyclobutyl, cyclopentyl, cyclohexyl, cycloheptyl, and cyclooctyl. A cycloalkyl group is unsubstituted or substituted with one or more ring system substituents which may be the same or different, and are as defined within. The term $C_{1-6}$cycloalkyl" refers to a cycloalkyl group having 1 to 6 ring carbon atoms.

"Optionally substituted" refers to "unsubstituted or substituted," and therefore, the generic structural formulas described herein encompass compounds containing the specified optional substituent(s) as well as compounds that do not contain the optional substituent(s). Each substituent is independently defined each time it occurs within the generic structural formula definitions. The term "substituted" means that one or more hydrogens on the designated atom is replaced with a selected from the indicated group, provided that the designated atom's normal valency under the existing circumstances is not exceeded, and that the substitution results in a stable compound. Combinations of substitute nets and/or variables are permissible only if such combinations result in stable compounds. By "stable compound" is meant a compound that is sufficiently robust to survive isolation to a useful degree of purity from a reaction mixture, and formulation into an efficacious therapeutic agent.

If the compounds of formula I, Ii, Ia, Ib, Ic, Id, Ie, If, Ig, Ih, Ij, Ik, Im, or In simultaneously contain acidic and basic groups in the molecule the invention also includes, in addition to the salt forms mentioned, inner salts or betaines (zwitterions). Salts can be obtained from the compounds of formula I, Ii, Ia, Ib, Ic, Id, Ie, If, Ig, Ih, Ij, Ik, Im, or In by customary methods which are known to the person skilled in the art, for example by combination with an organic or inorganic acid or base in a solvent or dispersant, or by anion exchange or cation exchange from other salts. The present invention also includes all salts of the compounds of formula I, Ii, Ia, Ib, Ic, Id, Ie, If, Ig, Ih, Ij, Ik, Im, or In which, owing to low physiological compatibility, are not directly suitable for use in pharmaceuticals but which can be used, for example, as intermediates for chemical reactions or for the preparation of physiologically acceptable salts.

The invention also includes derivatives of the compound of formula I, I, Ii, Ia, Ib, Ic, Id, Ie, If, Ig, Ih, Ij, Ik, Im, or In, acting as prodrugs and solvates. Any pharmaceutically acceptable pro-drug modification of a compound of the invention which results in conversion in vivo to a compound within the scope of the invention is also within the scope of the invention. Prodrugs, following administration to the patient, are converted in the body by normal metabolic or chemical processes, such as through hydrolysis in the blood, to the compound of formula I, Ii, Ia, Ib, Ic, Id, Ie, If, Ig, Ih, Ij, Ik, Im, or In. Such prodrugs include those that demonstrate enhanced bioavailability, tissue specificity, and/or cellular delivery, to improve drug absorption of the compound of formula I, Ii, Ia, Ib, Ic, Id, Ie, If, Ig, Ih, Ij, Ik, Im, or In. The effect of such prodrugs may result from modification of physicochemical properties such as lipophilicity, molecular weight, charge, and other physicochemical properties that determine the permeation properties of the drug.

For example, esters can optionally be made by esterification of an available carboxylic acid group or by formation of an ester on an available hydroxy group in a compound. Similarly, labile amides can be made. Pharmaceutically acceptable esters or amides of the compounds of the invention may be prepared to act as pro-drugs which can be hydrolyzed back to an acid (or —$COO^-$ depending on the pH of the fluid or tissue where conversion takes place) or hydroxy form particularly in vivo and as such are encompassed within the scope of the invention. Examples of pharmaceutically acceptable pro-drug modifications include, but are not limited to, $—C_{1-6}$alkyl esters and $—C_{1-6}$alkyl substituted with phenyl esters.

Except where noted, the term “halogen” or “halo” means fluorine, chlorine, bromine or iodine.

Where ring atoms are represented by variables such as “X”, e.g,

the variables are defined by indicating the atom located at the variable ring position without depicting the ring bonds associated with the atom. For example, when X in the above ring is nitrogen, the definition will show “N” and will not depict the bonds associated with it, e.g., will not show “═N—”. Likewise, when X is a carbon atom that is substituted with bromide, the definition will show “C—Br” and will not depict the bonds associated with it, e.g., will not show

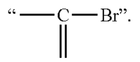

“Celite®” (Fluka) diatomite is diatomaceous earth, and can be referred to as “celite”.

The invention also relates to medicaments containing at least one compound of the formula I, Ii, Ia, Ib, Ic, Id, Ie, If, Ig, Ih, Ij, Ik, Im, or In and/or of a pharmaceutically acceptable salt of the compound of the formula I, Ii, Ia, Ib, Ic, Id, Ie, If, Ig, Ih, Ij, Ik, Im, or In and/or an optionally stereoisomeric form of the compound of the formula I, Ii, Ia, Ib, Ic, Id, Ie, If, Ig, Ih, Ij, Ik, Im, or In or a pharmaceutically acceptable salt of the stereoisomeric form of the compound of formula I, I, Ii, Ia, Ib, Ic, Id, Ie, If, Ig, Ih, Ij, Ik, Im, or In, together with a pharmaceutically acceptable vehicle, carrier, additive and/or other active substances and auxiliaries.

The medicaments according to the invention can be administered by oral, inhalative, rectal or transdermal administration or by subcutaneous, intraarticular, intraperitoneal or intravenous injection. Oral administration is preferred. Coating of stents with compounds of the formula I, Ii, Ia, Ib, Ic, Id, Ie, If, Ig, Ih, Ij, Ik, Im, or In and other surfaces which come into contact with blood in the body is possible.

The invention also relates to a process for the production of a medicament, which comprises bringing at least one compound of the formula I, Ii, Ia, Ib, Ic, Id, Ie, If, Ig, Ih, Ij, Ik, Im, or In into a suitable administration form using a pharmaceutically acceptable carrier and optionally further suitable active substances, additives or auxiliaries.

Suitable solid or galenical preparation forms are, for example, granules, powders, coated tablets, tablets, (micro) capsules, suppositories, syrups, juices, suspensions, emulsions, drops or injectable solutions and preparations having prolonged release of active substance, in whose preparation customary excipients such as vehicles, disintegrants, binders, coating agents, swelling agents, glidants or lubricants, flavorings, sweeteners and solubilizers are used. Frequently used auxiliaries which may be mentioned are magnesium carbonate, titanium dioxide, lactose, mannitol and other sugars, talc, lactose, gelatin, starch, cellulose and its derivatives, animal and plant oils such as cod liver oil, sunflower, peanut or sesame oil, polyethylene glycol and solvents such as, for example, sterile water and mono- or polyhydric alcohols such as glycerol.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the compounds, when used for the indicated effects, will range between about 0.01 mg per kg of body weight per day (mg/kg/day) to about 30 mg/kg/day, preferably 0.025-7.5 mg/kg/day, more preferably 0.1-2.5 mg/kg/day, and most preferably 0.1-0.5 mg/kg/day (unless specified otherwise, amounts of active ingredients are on free base basis). For example, an 80 kg patient would receive between about 0.8 mg/day and 2.4 g/day, preferably 2-600 mg/day, more preferably 8-200 mg/day, and most preferably 8-40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the compounds may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver about 0.01 mg per kg of body weight per day (mg/kg/day) to about 30 mg/kg/day, preferably 0.025-7.5 mg/kg/day, more preferably 0.1-2.5 mg/kg/day, and even more preferably 0.1-0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01-1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. The choice of appropriate buffer and pH of a formulation, depending on solubility of the drug to be administered, is readily made by a person having ordinary skill in the art.

The compounds of the invention may be prepared by employing reactions as shown in the following Reaction Schemes, in addition to other standard manipulations that are known in the literature or exemplified in the experimental procedures. The illustrative Reaction Schemes below, therefore, are not limited by the compounds listed or by any particular substituents employed for illustrative purposes. Substituent numbering as shown in the Reaction Schemes do not necessarily correlate to that used in the claims and often, for clarity, a single substituent is shown attached to the compound where multiple substituents are optionally allowed under the definitions of formula I, Ii, Ia, Ib, Ic, Id, Ie, If, Ig, Ih, Ij, Ik, Im, or In hereinabove.

Methods for Making the Compounds of Present Invention

General Methods

The compounds of the present invention can be readily produced from known compounds or commercially available compounds by, for example, known processes described in published documents, and produced by production processes described below. The present invention is not limited to the production processes described below. The invention also includes processes for the preparation of compounds of the invention.

It should be noted that, when a compound of structural formula I, Ii, Ia, Ib, Ic, Id, Ie, If, Ig, Ih, Ij, Ik, Im, or In has a reactive group such as hydroxy group, amino group, carboxyl group, or thiol group as its substituent, such group may be adequately protected with a protective group in each reaction step and the protective group may be removed at an subsequent stage. The process of such introduction and removal of the protective group may be adequately determined depending on the group to be protected and the type of the protective group, and such introduction and removal are conducted, for example, by the process described in the review section of Greene, T. W., et. al., "*Protective Groups in Organic Synthesis*", 2007, 4th Ed., Wiley, New York, or Kocienski, P., "*Protecting Groups*" 1994, Thieme.

It should be noted that, if a discrepancy between the chemical name and structure exists, the structure is understood to dominate.

The present invention is not limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the relevant art and are intended to fall within the scope of the appended claim.

All solvents used were commercially available and were used without further purification. Reactions were typically run using anhydrous solvents under an inert atmosphere of nitrogen.

Starting materials used were either available from commercial sources or prepared according to literature procedures and had experimental data in accordance with those reported.

Abbreviations used are those conventional in the art of the following.

ACN acetonitrile
AcOH acetic acid
$AgNO_3$ silver nitrate
Ar Aryl
Aq. Aqueous
9-BBN 9-Borabicyclo(3.3.1)nonane
$B_2pin_2$ bis(pinacolato)diboron
$BH_3$ borane
BSA bovine serum albumin
BuOH butanol
Boc tert-Butyloxycarbonyl protecting group
° C. degree Celsius
CBz-Cl benzyl chloroformate
$CDCl_3$ deuterated chloroform
$CD_3OD$ deuterated methanol
$CHCl_3$ chloroform
CO carbon monoxide
$CoCl_2$ cobalt(II) chloride
$Cs_2CO_3$ cesium carbonate
DBU 1,8-Diazabicyclo(5.4.0)undec-7-ene
DCM dichloromethane
DIAD di-tert-butylazodicarboxylate
DIC N,N-diisopropyldiimide
DIEA N,N-diisopropylethylamine
DMA N,N-dimethylacetamide
DMAP 4-(dimethylamino)pyridine
DME diemethoxyethane
DMF N,N-dimethylformamide
DMSO dimethylsulfoxide
DTT dithiothreitol
DPPF or dppf 1,1'-Bis(diphenylphosphino)ferrocene
EDC N-(3-dimethylaminopropyl)-N'-ethylcarbodiimide
EtI ethyl iodide
EtOAc ethyl acetate
EtOH ethanol
$Fe(acac)_3$ iron(III) acetylacetate
g gram
h hour(s)
$H_2SO_4$ sulfuric acid
HATU N-[(Dimethylamino)-1H-1,2,3-triazolo-[4,5-b]pyridin-1-ylmethylene]-N-methylmethanaminium hexafluorophosphate N-oxide
HCl hydrochloric acid
HPLC High Performance Liquid Chromatography
$K_2CO_3$ potassium carbonate
KOAc potassium acetate
$K_2S_2O_8$ potassium persulfate
LCMS liquid chromatography and mass spectrometry
LiBr lithium bromide
LiHMDS lithium bis(trimethylsilyl)amide
LiOH lithium hydroxide
m-CPBA meta-chloroperoxybenzoic acid
M molar
MeCN Acetonitrile
MeI methyl iodide
MeOH methanol
Mesyl-Cl methanesulfonyl chloride
MS mass spectrometry
MsCl methanesulfonyl chloride
MTBE methyl tert-butyl ether
mmol millimole
mg milligram
$MgSO_4$ magnesium sulfate
min minutes
mL milliliter(s)
$N_2$ nitrogen
$NaBH_4$ sodium borohydride
$NaBH(OAc)_3$ sodium triacetoxyborohydride
$Na_2CO_3$ sodium carbonate
NaH sodium hydride
NaI sodium iodide
NaOH Sodium Hydroxide
NaOtBu sodium tert-butoxide
NBS N-bromosuccinimide
nM nanomolar
NMP N-methyl-2-pyrrolidone
N normal
$NH_4HCO_3$ ammonium bicarbonate
$NH_3$ $H_2O$ ammonia in water
$NH_4OH$ ammonium hydroxide
$NiI_2$ nickel(II) iodide
NMR nuclear magnetic resonance N-XantPhos 4,6-Bis(diphenylphosphino)-10H-phenoxazine, 4,6-Bis(diphenylphosphino)phenoxazine OMs methanesulfonate Pd/C or Pd—C palladium on carbon $PdCl_2(dppf)$ [1,1-bis(diphenylphosphine)ferrocene]dichloropalladium(II)

$Pd_2(dba)_3$ Tris(dibenzylideneacetone)dipalladium(O)

$Pd(OAc)_2$ palladium(II) acetate $Pd(OH)_2$ palladium hydroxide on carbon $Pd(PPh_3)_4$ tetrakis(triphenylphosphine)palladium(O)

$POCl_3$ phosphorus(V) oxychloride psi pound per square inch

PyAOP (7-Azabenzotriazol-1-yloxy)trispyrrolidinophosphonium hexafluorophosphate rt room temperature RuPHOS 2-dicyclohexylphosphino-2',6'-diisopropoxybiphenyl RuPHOS G3 (2-dicyclohexylphosphino-2',6'-diisopropoxy-1,1'-biphenyl)[2-(2'-amino-1,1'-biphenyl)] palladium(II) methanesulfonate sat. saturated SM starting material SFC Supercritical fluid chromatography $SOCl_2$ thionyl chloride tBuOK potassium tert-butoxide (or t-BuOK)

T3P propylphosphonic anhydride

TBAB tetrabutylammonium bromide

TEA triethylamine

TFA trifluoroacetic acid

TFAA Trifluoroacetic anhydride (TFAA)

TfOH trifluromethane sulfonic acid

THF tetrahydrofuran

TLC thin layer chromatography

Prep. TLC preparative TLC $TMSCBrF_2$ (bromodifluoromethyl) trimethylsilane

TsCl p-toluenesulfonyl chloride

μL microliter vol volume $Zn(CN)_2$ zinc cyanide

General Synthetic Schemes

While the present invention has been described in conjunction with the specific examples set forth above, many alternatives, modifications and variations thereof will be apparent to those of ordinary skill in the art. In some cases, the order of carrying out the steps of the reaction schemes may be varied to facilitate the reaction or to avoid unwanted reaction products. All such alternatives, modifications and variations are intended to fall within the spirit and scope of the present invention. Starting materials and intermediates are purchased from commercial sources, made from known procedures, or are otherwise illustrated.

Several methods for preparing the compounds of this invention are described in the following Schemes and Examples. Unless otherwise indicated, all variables are as previously defined. In all general schemes Ar implies an optionally substituted aryl or heteroaryl moiety.

Scheme 1

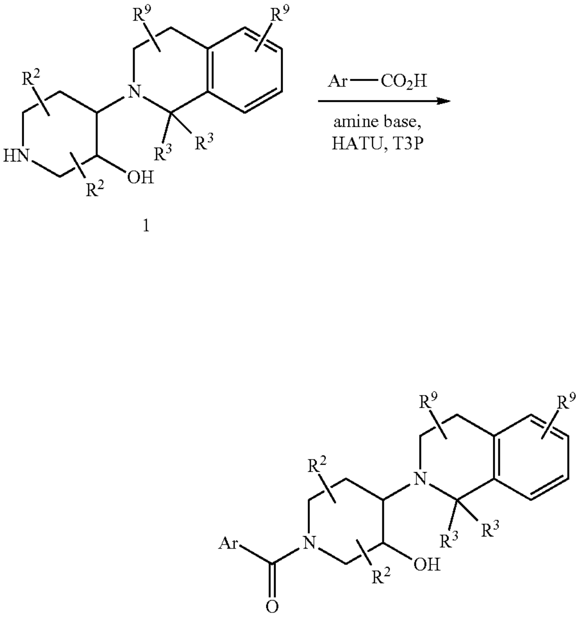

1

2

In Scheme 1, optionally substituted hydroxypiperidines 1 can be coupled to an optionally substituted aryl or heteroaryl carboxylic acid using standard amide coupling conditions to afford amide 2.

Scheme 2

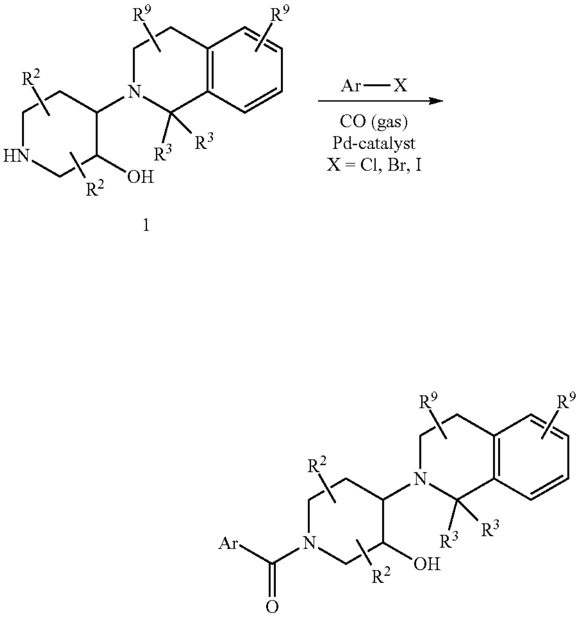

1

2

In Scheme 2, optionally substituted hydroxypiperidines 1 can be coupled to an optionally substituted aryl or heteroaryl halide utilizing palladium catalysis in the presence of carbon monoxide gas to afford amide 2.

Scheme 3

-continued

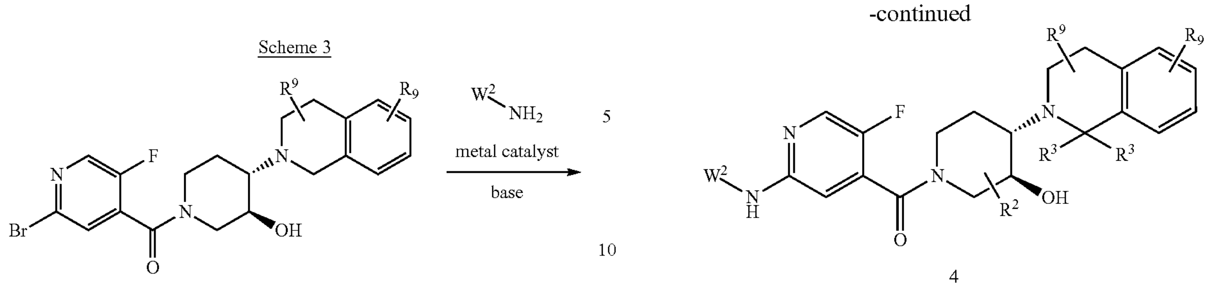

3 4

In Scheme 3, optionally substituted bromopyridines 3 can be cross-coupled with substituted amines in the presence of a metal catalyst to generate compounds of the form 4.

Scheme 4

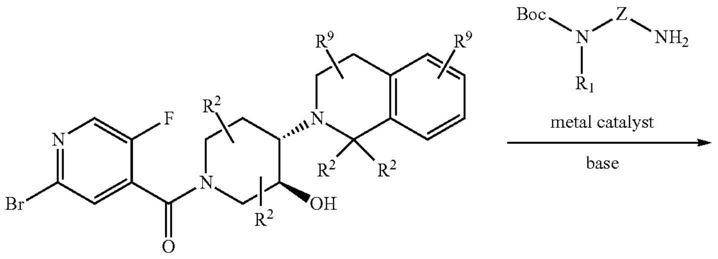

3

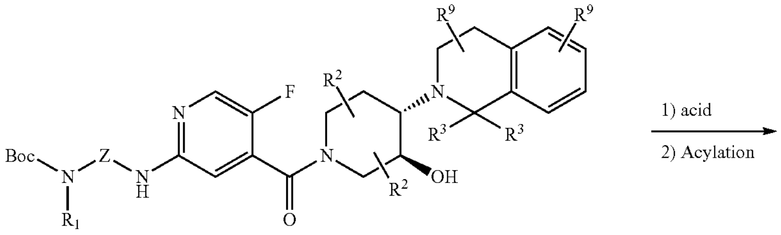

5

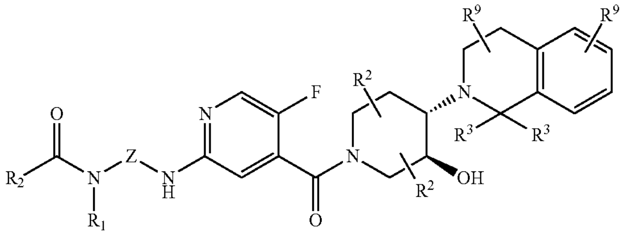

6

In Scheme 4, optionally substituted bromopyridines 3 can be cross-coupled with substituted protected amines in the presence of a metal catalyst to generate compounds of the form 5, which can be Boc-deprotected and then acylated to compounds of the form 6.

SYNTHESIS OF INTERMEDIATES

Intermediate 1: Trans-4-(34-dihydroisoquinolin-2 (1H)-yl)piperidin-3-ol

Intermediate 2: (3S,4S)-4-(3,4-dihydroisoquinolin-2 (1H)-yl)piperidin-3-ol

Intermediate 3: (3R,4R)-4-(3,4-dihydroisoquinolin-2 (1H)-yl)piperidin-3-ol

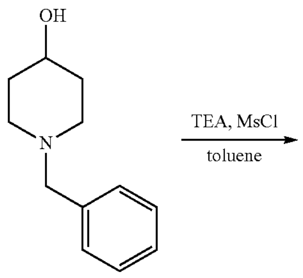

1

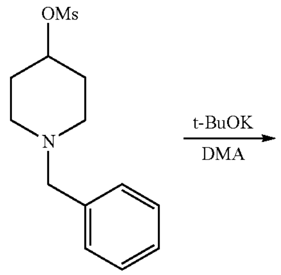

2

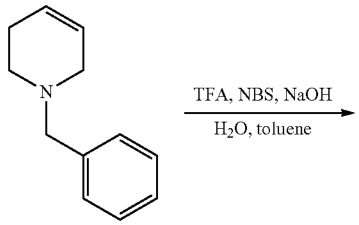

3

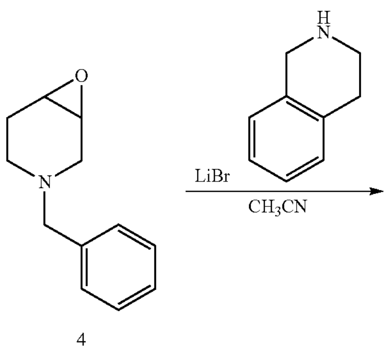

4

-continued

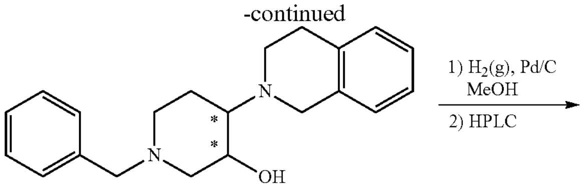

5-trans

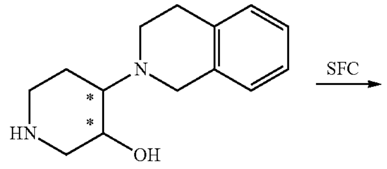

6-trans = Intermediate 1

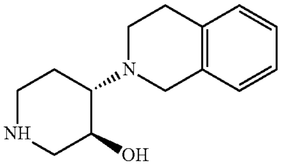

Intermediate 2

+

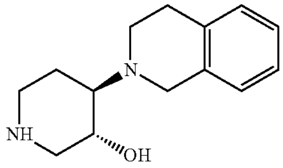

Intermediate 3

Step 1: To a solution of 1-benzylpiperidin-4-ol (200 g, 1.05 mol) in toluene (1.6 L) was added TEA (175 mL, 1.25 mol) dropwise at 25° C. MsCl (97.1 mL, 1.25 mol) was added to the mixture dropwise slowly at 0° C. The mixture was stirred at 25° C. for 2 h. Water (750 mL) was added to the mixture. The organic layer was washed with water (2×400 mL), dried over anhydrous sodium sulfate, filtered, and concentrated under reduced pressure to afford 1-benzylpiperidin-4-yl methanesulfonate, which was used without further purification.

Step 2: To a solution of 1-benzylpiperidin-4-yl methanesulfonate (280 g, 1.04 mol) in DMA (800 mL) was added t-BuOK (175 g, 1.56 mol) portionwise at 25° C. The mixture was stirred at 45° C. for 8 h. The reaction was quenched with water (1.0 L) and the mixture was extracted with EtOAc (600 mL×3). The organic layer was washed with brine (2×500 mL), dried over anhydrous sodium sulfate, filtered, and concentrated under reduced pressure to afford 1-benzyl-1,2,3,6-tetrahydropyridine as a solid. This material was used without further purification. $^1$H NMR (400 MHz, $CDCl_3$) δ 7.28-7.14 (m, 5H), 5.68-5.65 (m, 1H), 5.59-5.55 (m, 1H), 3.50 (s, 2H), 2.91-2.87 (m, 2H), 2.49-2.46 (m, 2H), 2.10-2.06 (m, 2H).

Step 3: To a solution of 1-benzyl-1,2,3,6-tetrahydropyridine (160 g, 924 mmol) in water (1.0 L) was added TFA (68.4 mL, 924 mmol) dropwise at 25° C. To the mixture was added NBS (197 g, 1.11 mol) portionwise slowly at 25° C. The mixture was stirred at 45° C. for 12 h. Toluene (1.2 L) at 25° C. was added to the mixture and then a solution of NaOH (240 g, 6.00 mol) in $H_2O$ (260 mL). The mixture was stirred at 45° C. for 1 h. The aqueous layer was extracted with EtOAc (1.2 L×2) and the combined organic layers were washed with brine (2×1.0 L), dried over anhydrous sodium sulfate, filtered, and concentrated under reduced pressure. The residue was purified by column chromatography on silica (0-15% ethyl acetate/pet. ether gradient) to give 3-benzyl-7-oxa-3-azabicyclo[4.1.0]heptane as an oil, which was used without further purification.

Step 4: To a solution of 3-benzyl-7-oxa-3-azabicyclo[4.1.0]heptane (80 g, 423 mmol) in ACN (600 mL) was added LiBr (66.1 g, 761 mmol) portionwise at 25° C. The mixture was stirred at 30° C. for 0.5 h. To the mixture was added 1,2,3,4-tetrahydroisoquinoline (53.1 mL, 423 mmol) portionwise slowly at 25° C. The mixture was stirred at 30° C. for 10 h. To the mixture was added water (250 mL) and EtOAc (250 mL). The combined organic layers were washed with brine (2×250 L), dried over anhydrous sodium sulfate, filtered, and concentrated under reduced pressure. The residue was purified by column chromatography on silica (60% ethyl acetate/pet. ether gradient) to give trans-1-benzyl-4-(3,4-dihydroisoquinolin-2(1H)-yl)piperidin-3-ol as an oil. $^1$H NMR (400 MHz, $CDCl_3$) δ 7.28-7.21 (m, 5H), 7.10-7.07 (m, 3H), 7.07-6.97 (m, 1H), 3.91-3.87 (m, 1H), 3.72-3.64 (m, 2H), 3.54-3.52 (m, 2H), 3.20-3.15 (m, 1H), 3.03-2.99 (m, 1H), 2.98-2.96 (m, 1H), 2.87-2.84 (m, 2H), 2.61-2.58 (m, 1H), 2.37-2.30 (m, 1H), 1.97-1.96 (m, 1H), 1.89-1.83 (m, 1H), 1.73-1.69 (m, 1H), 1.61-1.55 (m, 1H).

Step 5: A solution of trans-1-benzyl-4-(3,4-dihydroisoquinolin-2(1H)-yl)piperidin-3-ol (90 g, 279 mmol) in MeOH (800 mL) was added to a bottle containing Pd—C (10% wt; 40 g) under a $N_2$ atmosphere. The mixture was degassed and backfilled with H2 (three times). The resultant mixture was stirred under H2 (50 psi) at 50° C. for 6 h. The catalyst was filtered, and the filtrate was concentrated under reduced pressure. The residue was purified by preparative HPLC (water/ACN with 0.05% ammonium hydroxide modifier) to give trans-4-(3,4-dihydroisoquinolin-2(1H)-yl)piperidin-3-ol (Intermediate 1) as an oil, which could be used in subsequent reactions. MS: 233 (M+1).

Trans-4-(3,4-dihydroisoquinolin-2(1H)-yl)piperidin-3-ol (Intermediate 1) was purified by chiral SFC (Chiralpak AD-H column, isopropanol/$CO_2$) to afford two products as solids:

Intermediate 2 (peak 1): (3S,4S)-4-(3,4-dihydroisoquinolin-2(1H)-yl)piperidin-3-ol. $^1$H NMR (400 MHz, DMSO-$d_6$) δ 7.10-7.01 (m, 4H), 4.16 (br s, 1H), 3.85-3.71 (m, 2H), 3.48-3.46 (m, 1H), 3.02-2.91 (m, 1H), 2.89-2.88 (m, 2H), 2.79-2.73 (m, 3H), 2.39-2.35 (m, 2H), 2.22-2.19 (m, 1H), 2.0 (br s, 1H), 1.70-1.65 (m, 1H), 1.37-1.30 (m, 1H)

Intermediate 3 (peak 2): (3R,4R)-4-(3,4-dihydroisoquinolin-2(1H)-yl)piperidin-3-ol. $^1$H NMR (400 MHz, DMSO-$d_6$) δ 7.15-7.01 (m, 4H), 4.18 (br s, 1H), 3.86-3.72 (m, 2H), 3.49-3.47 (m, 1H), 3.01-2.90 (m, 1H), 2.90-2.89 (m, 2H), 2.80-2.72 (m, 3H), 2.39-2.35 (m, 2H), 2.21-2.20 (m, 1H), 2.0 (br s, 1H), 1.70-1.65 (m, 1H), 1.38-1.31 (m, 1H)

Intermediate 4: (Trans) 4-(5-fluoro-3,4-dihydroisoquinolin-2(1H)-yl)piperidin-3-ol

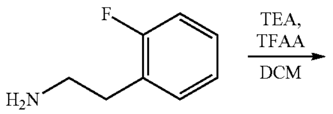

1

-continued

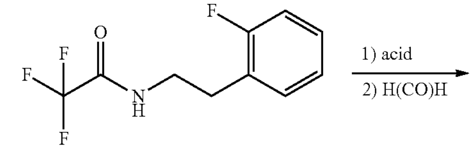

2

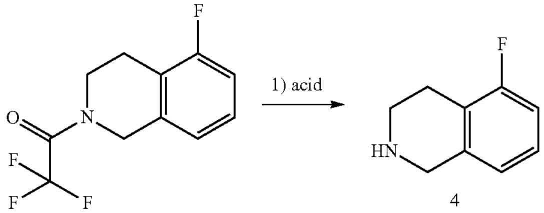

3

4

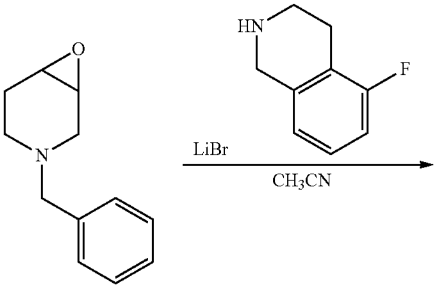

5

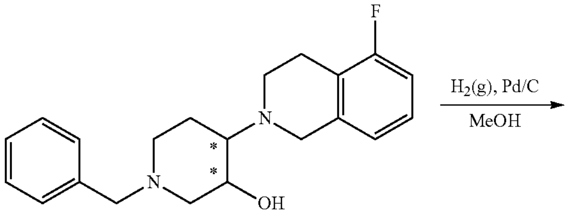

6-trans

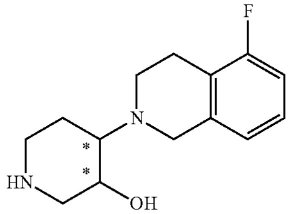

Intermediate 4

Intermediate 4: (Trans) 4-(5-fluoro-3,4-dihydroisoquinolin-2(1H)-yl)piperidin-3-ol Step 1: To a stirred solution of 2-(2-fluorophenyl)ethan-1-amine (5 g, 36 mmol) and TEA (15 mL, 108 mmol) in DCM (60 mL) at 0° C. was added 2,2,2-trifluoroacetic anhydride (7.6 mL, 54 mmol) dropwise. The mixture was allowed to warm to 20° C. and stirred for 2 h. The mixture was filtered, and the filtrate was concentrated under reduced pressure. The residue was purified by column chromatography on silica (0-20% EtOAc/pet. ether) to give 2,2,2-trifluoro-N-(2-fluorophenethyl)acetamide as an oil. $^1$H NMR (400 MHz, $CDCl_3$) δ 7.26-7.01 (m, 4H), 6.46 (br s, 1H), 3.60 (q, J=6.7 Hz, 2H), 2.92 (t, J=6.9 Hz, 2H).

Step 2: To a stirred solution of 2,2,2-trifluoro-N-(2-fluorophenethyl)acetamide (7.5 g, 32 mmol) and formaldehyde (2.87 g, 96 mmol) in AcOH (60 mL) was added concentrated $H_2SO_4$ (20 mL) at 0° C. The mixture was stirred at 30° C. for 15 h. The mixture was slowly added into ice water (200 mL) and the solution was basified with $K_2CO_3$ to pH ~8. The aqueous layer was extracted with EtOAc (200 mL×3) and the combined organic layers were washed with brine (200 mL), dried over anhydrous sodium sulfate, filtered, and concentrated under reduced pressure. The residue was purified by column chromatography on silica (0-10% ethyl acetate/pet. ether gradient) to give 2,2,2-trifluoro-1-(5-fluoro-3,4-dihydroisoquinolin-2(1H)-yl)ethanone as an oil. MS: 248 (M+1).

Step 3: To a stirred solution of 2,2,2-trifluoro-1-(5-fluoro-3,4-dihydroisoquinolin-2(1H)-yl)ethan-1-one (1.5 g, 6.1 mmol) in 1,4-dioxane (10 mL) was added HCl (10 mL, 60 mmol) at room temperature. The mixture was stirred at 90° C. for 2 h. The mixture was concentrated under reduced pressure to give 5-fluoro-1,2,3,4-tetrahydroisoquinoline as a solid HCl salt. The crude product was used directly for the next step without purification. MS: 152 (M+1).

Step 4: To a solution of 3-benzyl-7-oxa-3-azabicyclo[4.1.0]heptane (300 mg, 1.59 mmol) in acetonitrile (5 mL) was added lithium bromide (248 mg, 2.85 mmol) and DIEA (0.554 mL, 3.17 mmol). The mixture was stirred at 30° C. for 30 min. Then 5-fluoro-1,2,3,4-tetrahydroisoquinoline hydrochloride (297 mg, 1.59 mmol) was added, and the reaction mixture was stirred at 30° C. for 12 h. The mixture was concentrated under reduced pressure. The residue was purified by preparative TLC (silica gel, 1/1 ethyl acetate/pet. ether) to give (trans)-1-benzyl-4-(5-fluoro-3,4-dihydroisoquinolin-2(1H)-yl)piperidin-3-ol as a solid. MS: 341 (M+1).

Step 5: To a solution of (trans)-1-benzyl-4-(5-fluoro-3,4-dihydroisoquinolin-2(II)-yl)piperidin-3-ol (300 mg, 0.881 mmol) in MeOH (3 mL) was added Pd—C (10%, 94 mg, 0.881 mmol) under a $N_2$ atmosphere. The mixture was degassed and backfilled with H2 (three times). The resulting mixture was stirred under 15 psi of H2 at 30° C. for 12 h. The catalyst was filtered, and filtrate was concentrated under reduced pressure to give crude (trans)-4-(5-fluoro-3,4-dihydroisoquinolin-2(II)-yl)piperidin-3-ol as an oil, which was directly used in the next step without further purification. MS: 251 (M+1).

TABLE 1

The following intermediates were prepared using a similar procedure as Intermediate 4.

| Int. # | Structure | Compound Name | Exact Mass [M + 1] |
|---|---|---|---|
| 5 | 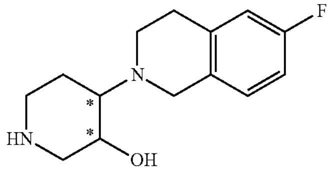 [SMILES: OC1CNCCC1N1CCc2cc(F)ccc2C1] | (Trans)-4-(6-fluoro-3,4-dihydroisoquinolin-2(1H)-yl)piperidin-3-ol | 251 |
| 6 | 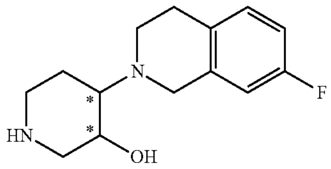 [SMILES: OC1CNCCC1N1CCc2ccc(F)cc2C1] | (Trans)-4-(7-fluoro-3,4-dihydroisoquinolin-2(1H)-yl)piperidin-3-ol | 251 |

Intermediate 7: (Trans)-4-(6-methyl-3,4-dihydroisoquinolin-2(1H)-yl)piperidin-3-ol

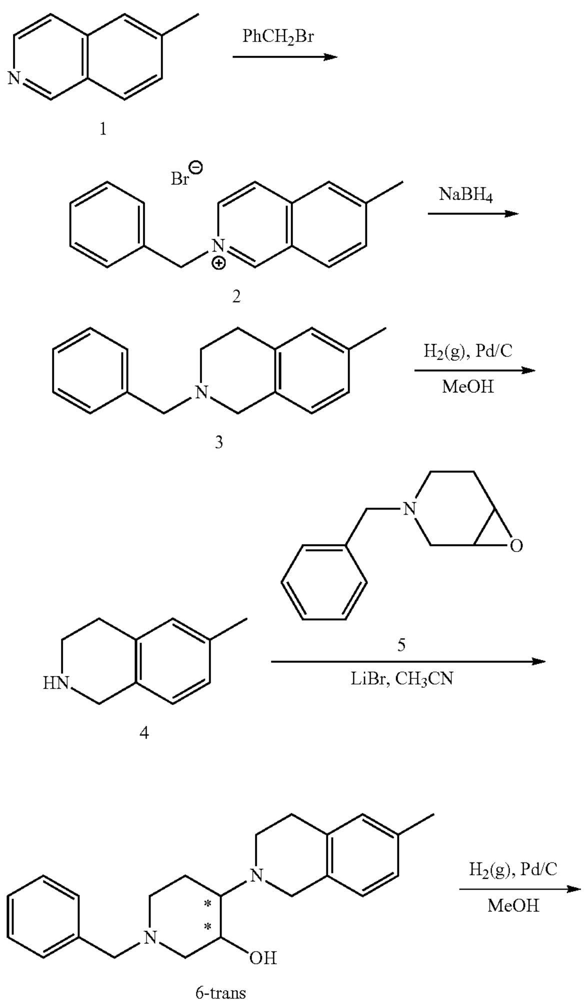

-continued

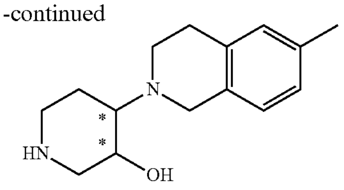

Intermediate 7

Step 1: A mixture of 6-methylisoquinoline (1 g, 7 mmol) and (bromomethyl)benzene (1.79 g, 10.5 mmol) was stirred at 75° C. for 3 h. The mixture was diluted with a mixture of ethyl acetate/pet. ether (2:1) and the solid was filtered to give to 2-benzyl-6-methylisoquinolin-2-ium bromide, which was used in the next step without purification. MS: 234 (M-Br). $^1$H NMR (400 MHz, $CD_3OD$-$d_4$) δ 9.97 (s, 1H), 8.61 (dd, J=6.8, 1.3 Hz, 1H), 8.37 (m, 2H), 8.09 (s, 1H), 7.94 (dd, J=8.6, 1.3 Hz, 1H), 7.58-7.53 (m, 2H), 7.49-7.43 (m, 3H), 5.93 (s, 2H), 2.71 (s, 3H).

Step 2: To a solution of 2-benzyl-6-methylisoquinolin-2-ium bromide (2.5 g, 7.9 mmol) in MeOH (30 mL) was added sodium tetrahydroborate (0.45 g, 11 mmol) portion-wise. The reaction was stirred at 35° C. for 15 h. The reaction was quenched with water (20 mL), and the mixture was concentrated under reduced pressure. The aqueous layer was extracted with EtOAc (50 mL×3) and the combined organic layers were dried over anhydrous sodium sulfate, filtered, and concentrated under reduced pressure. The residue was purified by column chromatography on silica (0-40% ethyl acetate/pet. ether) to give 2-benzyl-6-methyl-1,2,3,4-tetrahydroisoquinoline as a solid. MS: 238 (M+1). $^1$H NMR (400 MHz, $CDCl_3$) δ 7.43-7.38 (m, 2H), 7.36-7.32 (m, 2H), 7.30-7.25 (m, 1H), 6.92 (br d, J=5.70 Hz, 2H), 6.90-6.87 (m, 1H), 3.68 (s, 2H), 3.60 (s, 2H), 2.90-2.83 (m, 2H), 2.76-2.71 (m, 2H), 2.29 (s, 3H)

Step 3: To a solution of 2-benzyl-6-methyl-1,2,3,4-tetrahydroisoquinoline (1.12 g, 4.72 mmol) in methanol (15 mL) was added Pd—C (10%, 0.050 g, 0.472 mmol) under a $N_2$ atmosphere. The mixture was degassed and backfilled with H2 (three times). The resulting mixture was stirred under H2 (15 psi) at 30° C. for 16 h. The mixture was filtered, and the filtrate was concentrated under reduced pressure to give 6-methyl-1,2,3,4-tetrahydroisoquinoline as a solid. MS: 148 (M+1). $^1$H NMR (400 MHz, $CD_3OD$-$d_4$) δ 6.96-6.86 (m, 3H), 3.90 (s, 2H), 3.07-3.04 (m, 2H), 2.80-2.77 (m, 2H), 2.27 (s, 3H)

Step 4: To a solution of 3-benzyl-7-oxa-3-azabicyclo[4.1.0]heptane (411 mg, 2.17 mmol) in acetonitrile (20 mL) was added lithium bromide (340 mg, 3.91 mmol). The mixture was stirred at 15° C. for 30 min. Then, 6-methyl-1,2,3,4-tetrahydroisoquinoline (320 mg, 2.17 mmol) was added, and the reaction mixture was stirred at 30° C. for 15 h. The reaction mixture was concentrated under reduced pressure. To the residue was added water (20 mL) and the mixture was extracted with EtOAc (30 mL×3). The combined organic layers were concentrated under reduced pressure. The residue was purified by preparative HPLC (water/MeCN with 0.05% ammonium hydroxide modifier) to give the (trans)-1-benzyl-4-(6-methyl-3,4-dihydroisoquinolin-2(1H)-yl)piperidin-3-ol as a solid. MS: 337 (M+1). $^1$H NMR (400 MHz, $CDCl_3$) δ 7.35-7.28 (m, 4H), 7.28-7.26 (m, 1H), 6.97-6.89 (m, 3H), 3.89 (d, J=14.9 Hz, 1H), 3.72-3.70 (m, 1H), 3.62 (d, J=14.5 Hz, 1H), 3.57 (d, J=3.1 Hz, 2H), 3.53 (s, 1H), 3.25 (br dd, J=10.3, 2.9 Hz, 1H), 3.07-2.94 (m, 2H), 2.86-2.83 (m, 2H), 2.65-2.56 (m, 1H), 2.44-2.36 (m, 1H), 2.29 (s, 3H), 2.08-1.99 (m, 1H), 1.95-1.90 (m, 1H), 1.81-1.74 (m, 1H), 1.68-1.60 (m, 1H)

Step 5: To a solution of (trans)-1-benzyl-4-(6-methyl-3,4-dihydroisoquinolin-2(1H)-yl)piperidin-3-ol (400 mg, 1.2 mmol) in methanol (15 mL) was added Pd—C (10%, 1275 mg, 0.119 mmol) under a $N_2$ atmosphere. The mixture was degassed and backfilled with H2 (three times). The resulting mixture was stirred under 15 psi of H2 at 30° C. for 16 h. The mixture was filtered, and the filtrate was concentrated under reduced pressure to give (trans)-4-(6-methyl-3,4-dihydroisoquinolin-2(II)-yl)piperidin-3-ol as a solid. MS: 247 (M+1). $^1$H NMR (400 MHz, $CD_3OD$) δ 6.91-6.90 (m, 3H), 3.91-3.76 (m, 2H), 3.69-3.67 (m, 1H), 3.20-3.14 (m, 1H), 3.07-2.96 (m, 2H), 2.87-2.77 (m, 3H), 2.60-2.48 (m, 2H), 2.38-2.35 (m, 1H), 2.25 (s, 3H), 1.88-1.85 (m, 1H), 1.54-1.49 (m, 1H).

TABLE 2

The following intermediate was prepared using a similar procedure as described for Intermediate 7. The intermediate was synthesized from commercially available 7-methyl-1,2,3,4-tetrahydroisoquinoline and was isolated as a mixture of trans isomers.

| Int. # | Structure | Compound Name | Exact Mass (M + 1) |
|---|---|---|---|
| 8 | 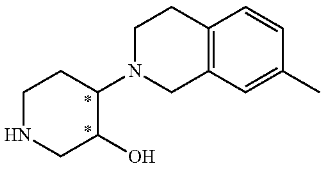 [SMILES: Cc1ccc2c(c1)CN(C1CCNCC1O)CC2] | (Trans)-4-(7-methyl-3,4-dihydroisoquinolin-2(1H)-yl)piperidin-3-ol | 247 |

Intermediate 9: (Trans)-4-(3,4-dihydroisoquinolin-2(1H)-yl-1,1-$d_2$)piperidin-3-ol

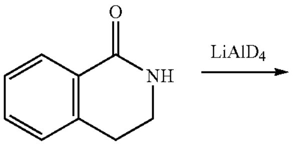

1

-continued

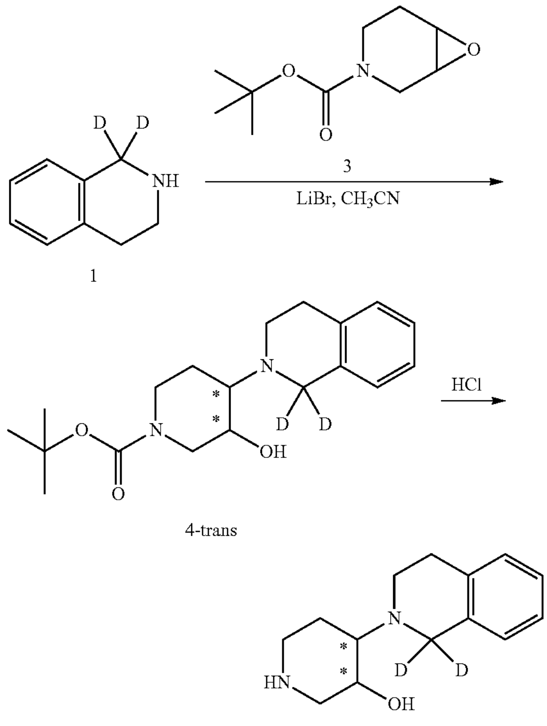

1
4-trans
Intermediate 9

Step 1: A stirred solution of 3,4-dihydroisoquinolin-1(2H)-one (300 mg, 2.04 mmol) in $LiAlD_4$ (171 mg, 4.08 mmol) was added THF (10 mL) at 0° C. The resulting mixture was stirred at 80° C. for 0.5 h under $N_2$. The mixture was quenched by water (5 drops), and the mixture was dried over anhydrous $Na_2SO_4$, filtered, and the filtrate was concentrated under reduced pressure to give 1,2,3,4-tetrahydroisoquinoline-1,1-d as an oil, which was used in the next step without further purification. MS: 136 (M+1).

Step 2: To a solution of tert-butyl 7-oxa-3-azabicyclo[4.1.0]heptane-3-carboxylate (407 mg, 2.04 mmol) in acetonitrile (6 mL) was added lithium bromide (319 mg, 3.67 mmol) at 15° C. and stirred at 15° C. for 30 min. Then 1,2,3,4-tetrahydroisoquinoline-1,1-$d_2$ (276 mg, 2.04 mmol) was added and the reaction mixture was stirred at 30° C. for 15 h. The solvent was removed under reduced pressure, and the residue was purified by reverse phase HPLC (ACN/water with 0.05% ammonia hydroxide modifier) to give trans tert-butyl 4-(3,4-dihydroisoquinolin-2(II)-yl-1,1-$d_2$)-3-hydroxypiperidine-1-carboxylate (trans) as a solid. MS: 335 (M+1).

$^1H$ NMR (400 MHz, $CDCl_3$) δ 7.21-7.07 (m, 3H), 7.07-6.97 (m, 1H), 4.51-4.24 (m, 2H), 3.76-3.49 (m, 2H), 3.06-2.98 (m, 1H), 2.91-2.89 (m, 2H), 2.68-2.47 (m, 4H), 1.82 (br d, J=12.1 Hz, 1H), 1.47 (s, 9H).

Step 3: A solution of trans tert-butyl 4-(3,4-dihydroisoquinolin-2(1H)-yl-1,1-$d_2$)-3-hydroxypiperidine-1-carboxylate (140 mg, 0.419 mmol) in HCl (4 M in EtOAc, 15 mL) was stirred at 15° C. for 2 h. The mixture was concentrated under reduced pressure to give trans-4-(3,4-dihydroisoquinolin-2(II)-yl-1,1-$d_2$)piperidin-3-ol as a solid, which was used in the next step without further purification. MS: 235 (M+1).

Intermediate 10: trans-4-(4,4-difluoro-3,4-dihydroisoquinolin-2(1H)-yl)piperidin-3-ol

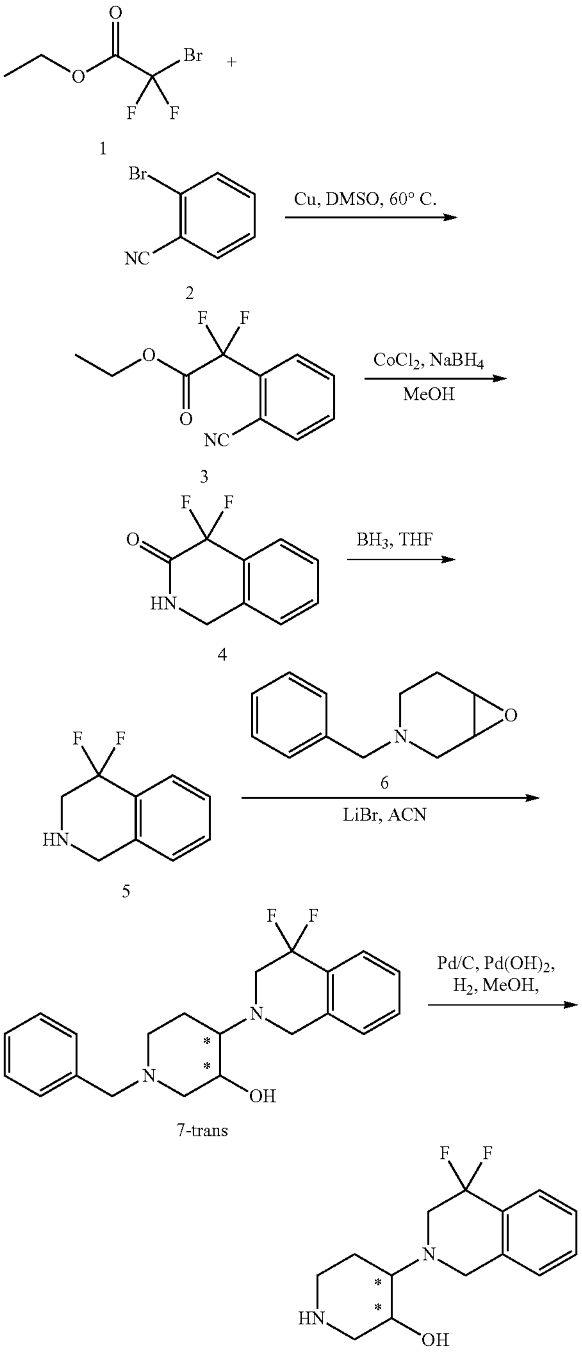

1
2
3
4
5
7-trans
Intermediate 10

Step 1: To a suspension of copper (24.4 g, 385 mmol) and 2-bromobenzonitrile (25 g, 137 mmol) in DMSO (100 mL) was added ethyl bromodifluoroacetate (27.9 g, 137 mmol). The reaction was stirred at 60° C. for 18 h. The mixture was cooled to room temperature and poured into a cold solution of sat. $NH_4Cl$ in water (800 mL). The solution was extracted with EtOAc (3×400 mL). The combined organic layers were washed with a solution of 1.0 N aqueous HCl (2×200 mL), dried over anhydrous sodium sulfate, filtered, and concentrated under reduced pressure. The residue was purified by column chromatography on silica (8% ethyl acetate/pet. ether) to afford ethyl 2-(2-cyanophenyl)-2,2-difluoroacetate as an oil. $^1$H NMR (400 MHz, Chloroform-d) δ 7.84-7.76 (m, 2H), 7.72 (t, J=7.8 Hz, 1H), 7.67-7.61 (m, 1H), 4.40-4.37 (m, 2H), 1.37-1.34 (m, 3H).

Step 2: To a mixture of ethyl 2-(2-cyanophenyl)-2,2-difluoroacetate (6 g, 27 mmol) in MeOH (50 mL) at 0° C. was added cobalt(II) chloride (20.7 g, 160 mmol) and then $NaBH_4$ (6.05 g, 160 mmol). The mixture was stirred at 0° C. for 2 h. The reaction was quenched with sat. aqueous $NH_4Cl$ (100 mL), and the aqueous layer was extracted with EtOAc (3×150 mL). The combined organic layers were dried over anhydrous sodium sulfate, filtered, and concentrated under reduced pressure. The residue was purified by column chromatography on silica (51% ethyl acetate/pet. ether) to afford 4,4-difluoro-1,2-dihydroisoquinolin-3(4H)-one as a solid. MS: 184 (M+1).

Step 3: To a solution of 4,4-difluoro-1,2-dihydroisoquinolin-3(4H)-one (2 g, 11 mmol) in THF (30 mL) was added borane (19.5 mL, 1 M in THF, 19.5 mmol) under an atmosphere of $N_2$. The mixture was stirred at 80° C. for 2 h. The reaction was cooled to room temperature and then quenched with MeOH (60 mL). The mixture was stirred at 80° C. for 2 h. Upon cooling to room temperature, the mixture was concentrated under reduced pressure to afford 4,4-difluoro-1,2,3,4-tetrahydroisoquinoline as a solid, which was used directly in the next step without further purification. MS: 170 (M+1). $^1$H NMR (400 MHz, Chloroform-d) δ 7.70 (d, J=7.9 Hz, 1H), 7.42-7.31 (m, 2H), 7.11 (br d, J=7.5 Hz, 1H), 4.04 (br s, 2H), 3.39 (m, 2H).

Step 4: To a solution of 3-benzyl-7-oxa-3-azabicyclo[4.1.0]heptane (1.35 g, 7.13 mmol) in acetonitrile (20 mL) was added lithium bromide (1.12 g, 12.8 mmol). The mixture was stirred at room temperature for 20 min. Then 4,4-difluoro-1,2,3,4-tetrahydroisoquinoline (1.20 g, 7.13 mmol) was added and the reaction mixture was stirred at 30° C. for 16 h. The mixture was concentrated under reduced pressure, and then diluted with water (30 mL). The solution was extracted with EtOAc (3×50 mL). The combined organic layers were dried over anhydrous sodium sulfate, filtered, and concentrated under reduced pressure. The residue was purified by column chromatography on silica (90% ethyl acetate/pet. ether) to afford trans-1-benzyl-4-(4,4-difluoro-3,4-dihydroisoquinolin-2(1H)-yl)piperidin-3-ol as a solid. MS: 359 (M+1). The compound is a mixture of trans isomers.

Step 5: To trans-1-benzyl-4-(4,4-difluoro-3,4-dihydroisoquinolin-2(1H)-yl)piperidin-3-ol (1.1 g, 3.1 mmol), Pd/C (0.163 g, 10 mol % 1.53 mmol), and $Pd(OH)_2$ (0.215 g, 20 mol % 1.53 mmol) was added MeOH (20 mL). The mixture was evacuated and backfilled with hydrogen gas 3×, and the reaction was stirred under an atmosphere of hydrogen (15 psi) at 30° C. for 2 h. The reaction mixture was filtered, and the filtrate was concentrated under reduced pressure. The residue was purified by reverse phase HPLC (ACN/water with 0.05% ammonia hydroxide modifier) to afford trans-4-(4,4-difluoro-3,4-dihydroisoquinolin-2(1H)-yl)piperidin-3-ol as a solid. MS: 269 (M+1). $^1$H NMR (400 MHz, Methanol-$d_4$) δ 7.61 (d, J=7.7 Hz, 1H), 7.43-7.37 (m, 1H), 7.36-7.31 (m, 1H), 7.21 (d, J=7.5 Hz, 1H), 3.97 (br s, 2H), 3.69-3.67 (m, 1H), 3.39-3.32 (m, 1H), 3.29-3.21 (m, 1H), 3.20-3.14 (m, 1H), 3.05-3.00 (m, 1H), 2.65-2.51 (m, 2H), 2.43-2.37 (m, 1H), 1.91-1.84 (m, 1H), 1.56-1.48 (m, 1H). The compound is a mixture of trans isomers.

Intermediate 11: 4-(3,4-dihydroisoquinolin-2(1H)-yl)-2-methylpiperidin-3-ol

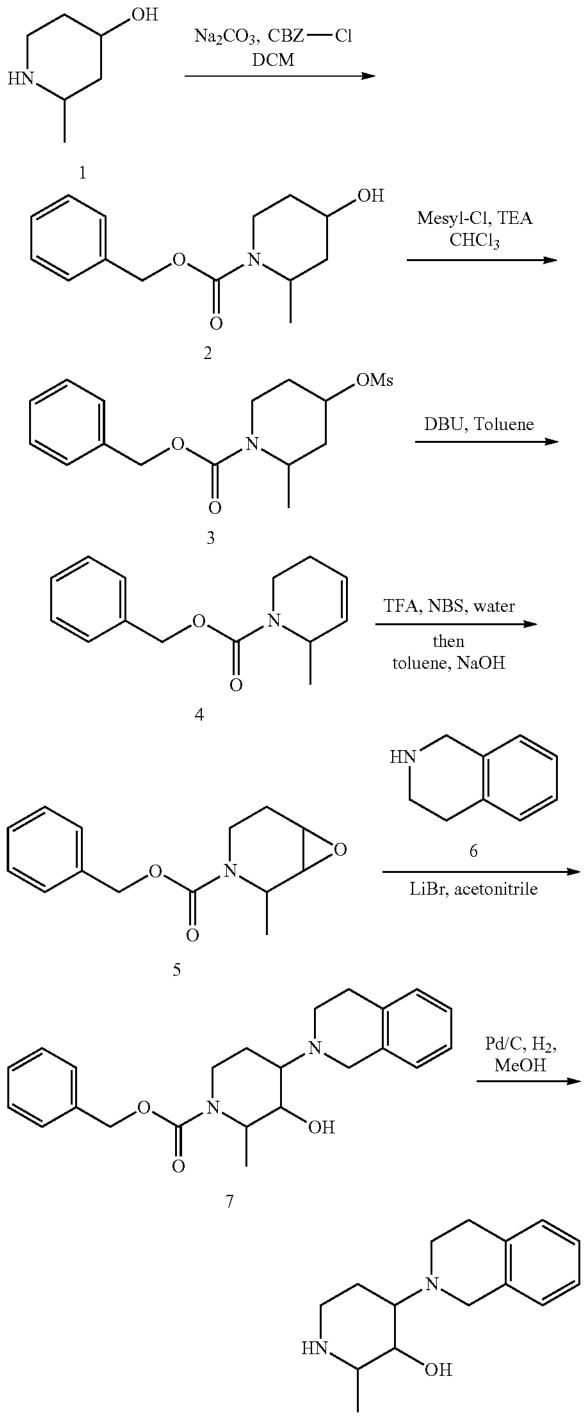

1
2
3
4
5
7

Intermediate 11

Step 1: To a solution of 2-methylpiperidin-4-ol (1 g, 8.7 mmol) in DCM (22 mL) was added sodium carbonate (13 ml, 26 mmol, 2.0 M in water) and benzyl chloroformate (1.24 mL, 8.68 mmol) dropwise. The mixture was stirred at room temperature for 18 h. The mixture was diluted with water and extracted with DCM (2×). The combined organic layers were washed with brine, dried over anhydrous sodium sulfate, filtered, and concentrated under reduced pressure. The residue was purified by column chromatography on silica (0-50% 3:1 EtOAc:EtOH in hexanes) to afford benzyl 4-hydroxy-2-methylpiperidine-1-carboxylate as an oil. MS: 250 (M+1).

Step 2: Methanesulfonyl chloride (0.74 mL, 9.5 mmol) was added dropwise to a stirred solution of benzyl 4-hydroxy-2-methylpiperidine-1-carboxylate (1.97 g, 7.90 mmol) and TEA (1.65 ml, 11.8 mmol) in chloroform (20 mL) at 0° C. under a nitrogen atmosphere. The mixture was allowed to slowly warm to room temperature and was stirred for 16 h at room temperature. Water was added, and the layers were separated. The organic layer was washed with water and then dried over sodium sulfate, filtered, and concentrated under reduced pressure to afford benzyl 2-methyl-4-((methylsulfonyl)oxy)piperidine-1-carboxylate as an oil. 1H NMR (600 MHz, $CDCl_3$) δ 7.38-7.26 (m, 5H), 5.15-5.04 (m, 3H), 4.67-4.43 (m, 1H), 4.20-3.97 (m, 1H), 3.28-3.20 (m, 1H), 3.03-2.97 (m, 4H), 2.03-1.96 (m, 1H), 1.85-1.73 (m, 1H), 1.70-1.62 (m, 1H), 1.32-1.16 (m, 3H).

Step 3: DBU (4.77 mL, 31.6 mmol) was added to a stirred solution of benzyl 2-methyl-4-((methylsulfonyl)oxy)piperidine-1-carboxylate (2.59 g, 7.91 mmol) in toluene (16 mL). The mixture was stirred at 75° C. for 6 h. The mixture was concentrated, poured into ice water, neutralized with HCl (1.0 M in water) to ~pH 4-5, and extracted with EtOAc (3×20 mL). The combined organic layers were washed with brine, dried over anhydrous sodium sulfate, filtered, and concentrated under reduced pressure. The residue was purified by column chromatography on silica (5-20% EtOAc in hexanes) to afford benzyl 2-methyl-5,6-dihydropyridine-1(2H)-carboxylate as an oil. MS: 232 (M+1).

Step 4: To a solution of benzyl 2-methyl-5,6-dihydropyridine-1(2H)-carboxylate (953 mg, 4.12 mmol) in water (4.6 mL) was added TFA (0.318 mL, 4.12 mmol) dropwise. NBS (880 mg, 4.95 mmol) was added to the mixture portion wise, and the mixture was stirred at 45° C. for 18 h. The reaction mixture was cooled to room temperature, and toluene (5.7 mL) was added. NaOH (16.5 mL, 33.0 mmol, 2.0 M in water) was added dropwise. The reaction was stirred at 40° C. for 6 h. The organic layer was separated, and the aqueous layer was extracted with EtOAc (2×10 mL). The combined organic layers were washed with brine (10 mL), dried over anhydrous sodium sulfate, filtered, and concentrated under reduced pressure. The residue was purified by column chromatography on silica (5-60% EtOAc in Hexanes) to afford benzyl 2-methyl-7-oxa-3-azabicyclo[4.1.0]heptane-3-carboxylate as an oil. MS: 248 (M+1).

Step 5: To a solution of benzyl 2-methyl-7-oxa-3-azabicyclo[4.1.0]heptane-3-carboxylate (309 mg, 1.25 mmol) in acetonitrile (5 mL) was added lithium bromide (217 mg, 2.50 mmol). The mixture was stirred for 30 min at room temperature, then 1,2,3,4-tetrahydroisoquinoline (196 μL, 1.56 mmol) was added. The reaction mixture was stirred at 75° C. for 16 h. The reaction was cooled to room temperature, water was added (10 mL), and the solution was extracted with EtOAc (2×20 mL). The combined organic layers were washed with brine, dried over anhydrous sodium sulfate, filtered, and concentrated under reduced pressure. The residue was purified by column chromatography on silica (0-35% 3:1 EtOAc:EtOH in hexanes) to afford benzyl 4-(3,4-dihydroisoquinolin-2(1H)-yl)-3-hydroxy-2-methylpiperidine-1-carboxylate as an oil. MS: 381 (M+1).

Step 6: To benzyl 4-(3,4-dihydroisoquinolin-2(1H)-yl)-3-hydroxy-2-methylpiperidine-1-carboxylate (411 mg, 1.08 mmol) under a nitrogen atmosphere was added Pd—C (115 mg, 0.108 mmol, 10 mol %). MeOH (7.2 mL) was added to the mixture under a nitrogen atmosphere. The mixture was evacuated and backfilled with $H_2$ 3×, and the mixture was stirred under a balloon of H2 for 16 h at room temperature. The mixture was quenched by flowing nitrogen gas through the mixture. The mixture was diluted with EtOAc and filtered over Celite®. The filtrate was concentrated under reduced pressure to afford 4-(3,4-dihydroisoquinolin-2(1H)-yl)-2-methylpiperidin-3-ol as an oil. MS: 247 (M+1).

TABLE 3

The following intermediate was prepared using a similar procedure as Intermediate 11.

| Int. # | Structure | Compound Name | Exact Mass [M + 1] |
|---|---|---|---|
| 12 | 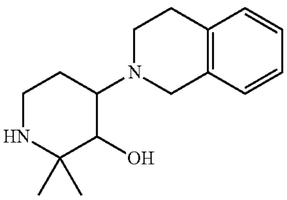 [SMILES: CC1(C)NCCC(N2CCc3ccccc3C2)C1O] | 4-(3,4-dihydroisoquinolin-2(H)-yl)-2,2-dimethylpiperidin-3-ol | 261 |

Intermediate 13: (1R,4R)-5-(3,4-dihydroisoquinolin-2(1H)-yl)-2-azabicyclo[2.2.1]heptan-6-ol

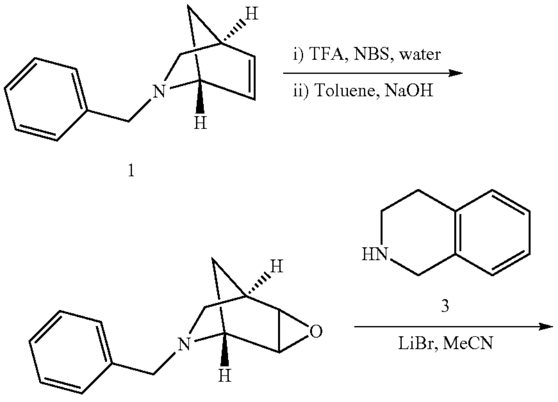

1
2
3

-continued

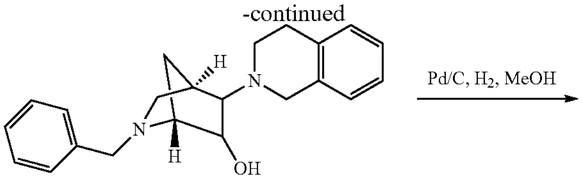

4

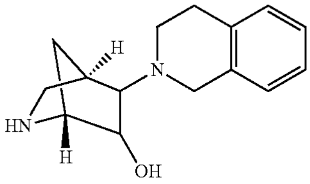

Intermediate 13

Step 1: To a solution of 2-benzyl-2-azabicyclo[2.2.1]hept-5-ene (109 mg, 0.588 mmol) in water (0.662 mL) was added TFA (0.045 mL, 0.59 mmol) dropwise. NBS (126 mg, 0.706 mmol) was added to the mixture portionwise, and the mixture was stirred at 45° C. for 18 h. The reaction mixture was cooled to room temperature, and toluene (0.81 mL) was added. NaOH (1.88 mL, 2.5 M in water, 4.71 mmol) was added dropwise, and the reaction was stirred at 40° C. for 6 h. The organic layer was separated, and the aqueous layer was extracted with EtOAc (2×10 mL). The combined organic layers were washed with brine (10 mL), dried over anhydrous sodium sulfate, filtered, and concentrated under reduced pressure. The residue was purified by column chromatography on silica (5-60% EtOAc/Hexanes) to afford (1R,5R)-6-benzyl-3-oxa-6-azatricyclo[3.2.1.$0^{2,4}$]octane as an oil. $^1$H NMR (600 MHz, Chloroform-d) δ 7.32-7.24 (m, 4H), 7.23-7.18 (m, 1H), 4.16 (s, 1H), 4.12-4.03 (m, 1H), 3.75-3.66 (m, 2H), 3.20 (s, 1H), 2.57 (s, 2H), 2.25 (d, J=11.5 Hz, 1H), 2.18-2.09 (m, 1H), 2.05-1.97 (m, 1H).

Step 2: To a solution of (1R,5R)-6-benzyl-3-oxa-6-azatricyclo[3.2.1.$0^{2,4}$]octane (83 mg, 0.41 mmol) in acetonitrile (1.65 mL) was added lithium bromide (72 mg, 0.83 mmol). The mixture was stirred for 30 min, and then 1,2,3,4-tetrahydroisoquinoline (0.064 mL, 0.51 mmol) was added and the reaction mixture was stirred at 60° C. for 18 h. The reaction was cooled to room temperature, and diluted with water (10 mL). The mixture was extracted with EtOAc (2×20 mL), and the combined organic layers were washed with brine, dried over anhydrous sodium sulfate, filtered, and concentrated under reduced pressure. The residue was purified by column chromatography on silica (5-100% EtOAc/Hexanes) to afford (1R,4R)-2-benzyl-5-(3,4-dihydroisoquinolin-2(1H)-yl)-2-azabicyclo[2.2.1]heptan-6-ol as an oil. MS: 335 (M+1).

Step 3: To (1R,4R)-2-benzyl-5-(3,4-dihydroisoquinolin-2(1H)-yl)-2-azabicyclo[2.2.1]heptan-6-ol (71 mg, 0.21 mmol) under a nitrogen atmosphere was added Pd/C (23 mg, 10 mol %, 0.021 mmol). MeOH (2.1 mL) was added to the mixture under a nitrogen atmosphere, and the mixture was evacuated and backfilled with hydrogen gas 3×. The reaction was stirred under a balloon of hydrogen for 18 h at room temperature. The mixture was quenched by flowing nitrogen through the mixture. The mixture was diluted with EtOAc and filtered over Celite®. The filtrate was concentrated under reduced pressure to afford (1R,4R)-5-(3,4-dihydroisoquinolin-2(1H)-yl)-2-azabicyclo[2.2.1]heptan-6-ol as an oil. MS: 245 (M+1).

Intermediate 14: 4-(3-oxa-8-azabicyclo[3.2.1]octane-8-carbonyl)benzoic acid

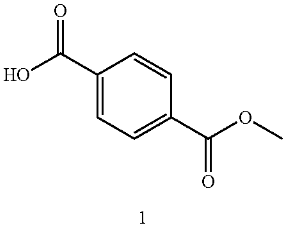

1

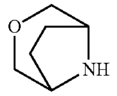

2

HATU, DIEA

DCM

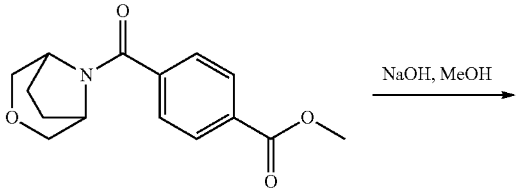

3

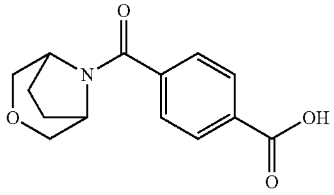

Intermediate 14

Step 1: To a solution of 4-(methoxycarbonyl)benzoic acid (10 g, 55.5 mmol) and HATU (25.3 g, 66.6 mmol) in DCM (150 ml) was added DIEA (29.1 ml, 167 mmol). The mixture was stirred at 25° C. for 5 min. To the mixture was added 3-oxa-8-azabicyclo[3.2.1]octane hydrochloride (8.72 g, 58.3 mmol) at 25° C. The mixture was stirred at 25° C. for 10 min and concentrated under reduced pressure. The residue was purified by column chromatography on silica (50% ethyl acetate/pet. ether) to give methyl 4-(3-oxa-8-azabicyclo[3.2.1]octane-8-carbonyl)benzoate as a solid. MS: 276 (M+1). 1H NMR (400 MHz, $CDCl_3$) δ 8.06 (d, J=8.41 Hz, 2H), 7.52 (d, J=8.41 Hz, 2H), 4.71 (br s, 1H), 3.91 (s, 3H), 3.86-3.83 (m, 2H), 3.76-3.51 (m, 3H), 2.09-2.02 (m, 2H), 2.00-1.81 (m, 2H)

Step 2: To a solution of methyl 4-(3-oxa-8-azabicyclo[3.2.1]octane-8-carbonyl)benzoate (10 g, 36.3 mmol) in MeOH (60 mL) was added sodium hydroxide (2.1 g, 54.5 mmol) in water (30 mL). The mixture was stirred at 30° C. for 1.5 h. The resultant mixture was quenched with water (30 mL) and extracted with ethyl acetate (30 mL×3). The combined organic layers were concentrated under reduced pressure to give 4-(3-oxa-8-azabicyclo[3.2.1]octane-8-carbonyl)benzoic acid as a solid, which was used in next step directly. MS: 262 (M+1). $^1$H NMR (400 MHz, MeOH-$d_4$) δ 8.10 (d, J=8.2 Hz, 2H), 7.59 (d, J=8.2 Hz, 2H), 4.64 (br s, 1H), 3.92 (br s, 1H), 3.85-3.76 (m, 1H), 3.72-3.68 (m, 2H), 3.61-3.51 (m, 1H), 2.04-1.93 (m, 4H).

Intermediate 15: 4-(3-oxa-8-azabicyclo[3.2.1]octane-8-carbonyl)-2-ethoxybenzoic acid

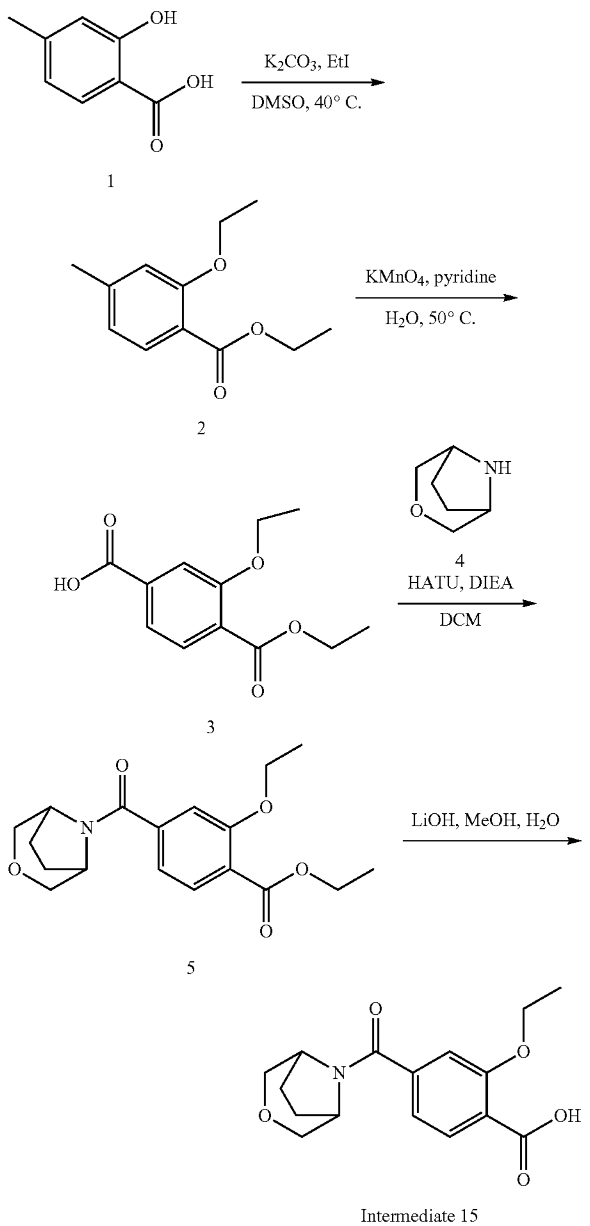

1
2
4
3
5
Intermediate 15

Step 1: To a mixture of 2-hydroxy-4-methylbenzoic acid (50 g, 329 mmol) and $K_2CO_3$ (136 g, 986 mmol) in DMSO (700 mL) at 40° C. was added ethyl iodide (77 g, 493 mmol) dropwise over a period of 30 min. The reaction was stirred for 2 h and additional ethyl iodide (77 g, 493 mmol) was added over 30 min at 40° C. The resulting mixture was stirred for 8 h at 40° C. The mixture was poured into water (7 L) and the aqueous layer was extracted with EtOAc (3 L×3). The combined organic layers were washed with brine (1 L), dried over anhydrous $Na_2SO_4$, filtered, and concentrated under reduced pressure to give ethyl 2-ethoxy-4-methylbenzoate as an oil, which was used next step directly without further purification. MS: 209 (M+1). $^1$H NMR (400 MHz, $CDCl_3$) δ 7.68 (d, J=7.43 Hz, 1H), 6.82-6.65 (m, 2H), 4.31 (q, J=7.04 Hz, 2H), 4.13-4.00 (m, 2H), 2.34 (s, 3H), 1.43 (t, J=7.04 Hz, 3H), 1.35 (t, J=7.04 Hz, 3H).

Step 2: To a solution of ethyl 2-ethoxy-4-methylbenzoate (46 g, 221 mmol) in pyridine (115 mL) and water (345 mL) was added $KMnO_4$ (34.9 g, 221 mmol). The resulting mixture was heated at 50° C. for 48 h, then cooled to room temperature and allowed to stir at room temperature for 24 h. The mixture was filtered, and the filter cake was washed with hot water. The combined aqueous filtrates were washed with EtOAc (1 L×3) and acidified with 2M aqueous HCl solution to pH 3. The mixture was extracted with EtOAc (2 L×3). The combined organic layers were washed with brine, dried over anhydrous $Na_2SO_4$, and concentrated under reduced pressure to give 3-ethoxy-4-(ethoxycarbonyl)benzoic acid as a solid, which was used in next step without purification. MS: 239 (M+1). $^1$H NMR (400 MHz, $CDCl_3$) δ 7.80 (d, J=7.94 Hz, 1H), 7.74-7.64 (m, 2H), 4.39 (q, J=7.20 Hz, 2H), 4.25-4.14 (m, 2H), 1.48 (t, J=6.95 Hz, 3H), 1.40 (t, J=7.06 Hz, 3H).

Step 3: To a mixture of 3-oxa-8-azabicyclo[3.2.1]octane hydrochloride (10 g, 66.8 mmol), 3-ethoxy-4-(ethoxycarbonyl)benzoic acid (15.9 g, 66.8 mmol) and HATU (30.5 g, 80 mmol) in DCM (120 mL) was added DIEA (35 mL, 201 mmol). The mixture was stirred for 20 min and then concentrated under reduced pressure. The residue was purified by column chromatography on silica (50% ethyl acetate/pet. ether) to give ethyl 4-(3-oxa-8-azabicyclo[3.2.1]octane-8-carbonyl)-2-ethoxybenzoate as an oil. MS: 356 (M+Na). $^1$H NMR (400 MHz, $CDCl_3$) δ 7.75 (d, J=7.6 Hz, 1H), 7.06 (s, 1H), 6.99 (d, J=8.0 Hz, 1H), 4.68 (s, 1H), 4.32 (q, J=7.2 Hz, 2H), 4.11 (q, J=7.2 Hz, 2H), 4.00-3.82 (m, 2H), 3.69-3.62 (m, 2H), 3.56 (m, 1H), 2.02-1.89 (m, 4H), 1.44 (t, J=6.8 Hz, 3H), 1.35 (t, J=6.8 Hz, 3H).

Step 4: To a solution of ethyl 4-(3-oxa-8-azabicyclo[3.2.1]octane-8-carbonyl)-2-ethoxybenzoate (24 g, 72.0 mmol) in THF (150 mL), MeOH (50 mL) and water (15 mL) was added LiOH·$H_2O$ (15.1 g, 360 mmol). The resultant mixture was stirred at room temperature for 12 h. The mixture was concentrated under reduced pressure. Water (500 mL) was added to the residue, and the mixture was acidified with 4 M HCl in water to pH 2. The mixture was extracted with $CH_2Cl_2$ (200 mL×3). The combined organic layers were washed with brine (200 mL), dried over $Na_2SO_4$, filtered, and the filtrate was concentrated under reduced pressure to give 4-(3-oxa-8-azabicyclo[3.2.1]octane-8-carbonyl)-2-ethoxybenzoic acid as a solid, which was used without further purification. MS: 306 (M+1). $^1$H NMR (400 MHz, $CDCl_3$) δ 10.86 (s, 1H), 8.19 (d, J=8.4 Hz, 1H), 7.21 (s, 1H), 7.14 (d, J=7.6 Hz, 1H), 4.71 (s, 1H), 4.35 (q, J=7.2 Hz, 2H), 3.91-3.84 (m, 2H), 3.72-3.60 (m, 3H), 2.06-1.94 (m, 4H), 1.56 (t, J=7.2 Hz, 3H).

Intermediate 16: 2-((1-acetyl-3,3-difluoropiperidin-4-yl)amino)isonicotinic acid

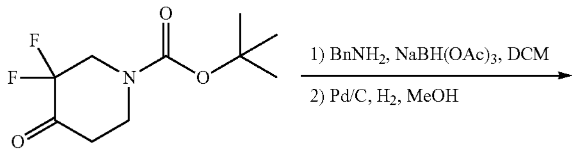

1

-continued

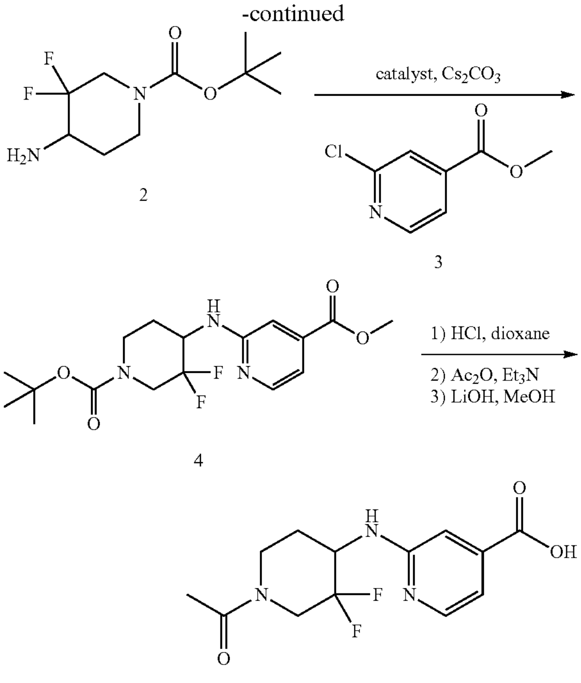

2

3

4

Intermediate 16

Step 1: To a solution of tert-butyl 3,3-difluoro-4-oxopiperidine-1-carboxylate (10 g, 42.5 mmol) in DCM (60 mL) was added phenylmethanamine (6.38 g, 59.5 mmol) and NaBH$(OAc)_3$ (27.0 g, 128 mmol) at 20° C. The reaction mixture was stirred at 20° C. for 10 h. The mixture was concentrated under reduced pressure. To the residue was added water (40 mL), and the mixture was extracted with EtOAc (3×40 mL). The combined organic layers were dried over anhydrous sodium sulfate, filtered, and the filtrate was concentrated under reduced pressure. The residue was purified by column chromatography on silica (0-50% EtOAc/petroleum ether) to give tert-butyl 4-(benzylamino)-3,3-difluoropiperidine-1-carboxylate as an oil. MS: 327 (M+1). $^1$H NMR (400 MHz, CD3Cl) δ 7.41-7.19 (m, 5H), 4.14-3.99 (m, 1H), 3.93 (s, 2H), 3.80 (s, 1H), 3.40-3.23 (m, 1H), 3.14-3.12 (m, 1H), 2.99-2.89 (m, 1H), 1.90 (s, 1H), 1.64-1.62 (m, 2H), 1.47 (s, 9H).

Step 2: To a solution of tert-butyl 4-(benzylamino)-3,3-difluoropiperidine-1-carboxylate (6.5 g, 19.9 mmol) in MeOH (20 mL) was added palladium (0.65 g, 0.61 mmol) under a $N_2$ atmosphere. The mixture was degassed and backfilled with H2 (three times). The resulting mixture was stirred under H2 (50 psi) at 25° C. for 10 h. The mixture was filtered, and the filtrate was concentrated under reduced pressure to give tert-butyl 4-amino-3,3-difluoropiperidine-1-carboxylate as an oil, which was used directly in next step. $^1$H NMR (400 MHz, $CD_3OD$) δ 4.23-4.12 (m, 1H), 3.98-3.95 (m, 1H), 3.13-3.06 (m, 3H), 1.92-1.85 (m, 1H), 1.55-1.52 (m, 1H), 1.51-1.46 (m, 9H).

Step 3: A mixture of tert-butyl 4-amino-3,3-difluoropiperidine-1-carboxylate (1.5 g, 6.35 mmol), methyl 2-chloroisonicotinate (1.31 g, 7.62 mmol), RuPhos G3 ((2-Dicyclohexylphosphino-2',6'-diisopropoxy-1,1'-biphenyl)[2-(2'-amino-1,1'-biphenyl)]palladium(II) methanesulfonate) (0.53 g, 0.635 mmol) and $Cs_2CO_3$ (4.14 g, 12.7 mmol) in 1,4-dioxane (15 mL) was stirred at 100° C. for 5 h. The mixture was concentrated under reduced pressure. The residue was purified by column chromatography on silica (22% ethyl acetate/pet. ether) to give methyl 2-((1-(tert-butoxycarbonyl)-3,3-difluoropiperidin-4-yl)amino)isonicotinate as a solid. MS: 372 (M+1).

Step 4: The mixture of methyl 2-((1-(tert-butoxycarbonyl)-3,3-difluoropiperidin-4-yl)amino)isonicotinate (2.3 g, 6.19 mmol) in HCl (4 M in 1,4-dioxane, 50 mL) was stirred at 20° C. for 0.5 h. The mixture was concentrated under reduced pressure to give crude methyl 2-((3,3-difluoropiperidin-4-yl)amino)isonicotinate hydrochloride as an oil, which was used directly in next step. MS: 272 (M+1).

Step 5: To a mixture of methyl 2-((3,3-difluoropiperidin-4-yl)amino)isonicotinate hydrochloride (1.9 g, 6.17 mmol) and $Et_3N$ (2.58 mL, 18.5 mmol) in DCM (20 mL) was added dropwise acetic anhydride (0.756 g, 7.41 mmol) at 20° C. The mixture was stirred at 20° C. for 1 h. The mixture was concentrated under reduced pressure. The residue was purified by column chromatography on silica (90% ethyl acetate/pet. ether) to give methyl 2-((1-acetyl-3,3-difluoropiperidin-4-yl)amino)isonicotinate as a solid. MS: 314 (M+1).

Step 6: A mixture of methyl 2-((1-acetyl-3,3-difluoropiperidin-4-yl)amino)isonicotinate (1.5 g, 4.79 mmol) and lithium hydroxide hydrate (0.502 g, 12.0 mmol) in MeOH (20 mL) and water (10 mL) was stirred at 20° C. for 2 h. The mixture was concentrated under reduced pressure to give 2-((1-acetyl-3,3-difluoropiperidin-4-yl)amino)isonicotinic acid lithium salt as a solid, which was used directly in the next step. MS: 300 (M+1).

Intermediate 17: 2-((1-acetylpiperidin-4-yl)amino)-5-chloroisonicotinic acid

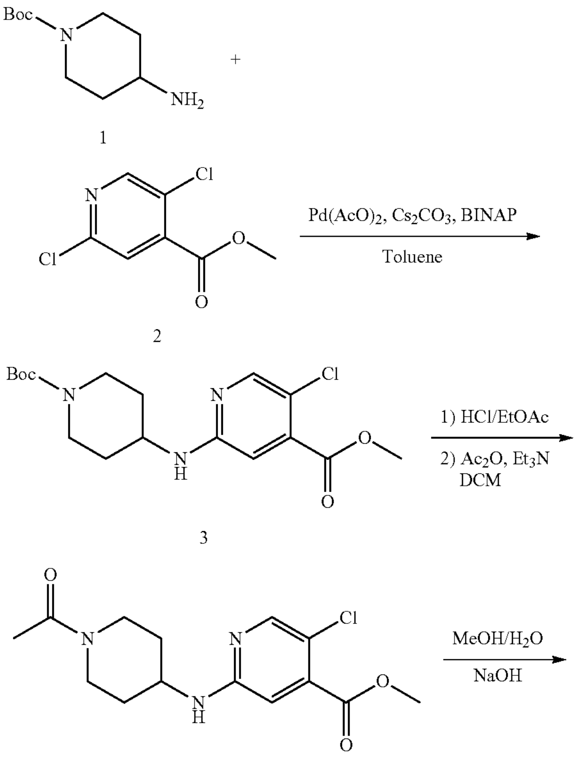

1

2

3

4

-continued

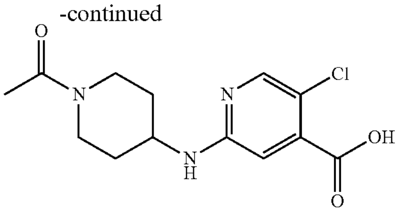

Intermediate 17

Step 1: To a solution of tert-butyl 4-aminopiperidine-1-carboxylate (4.6 g, 2.30 mmol) in toluene (20 mL) were added palladium(II) acetate (0.516 g, 2.30 mmol), $Cs_2CO_3$ (9.73 g, 29.9 mmol), 2,2'-bis(diphenylphosphino)-1,1'-bi-naphthalene (1.43 g, 2.30 mmol) and methyl 2,5-dichloroisonicotinate (4.50 g, 21.8 mmol) at 10° C. under $N_2$ (degassed and backfilled with $N_2$ three times). The reaction mixture was stirred at 90° C. for 10 h. The mixture was cooled to room temperature and quenched with brine (50 mL). The mixture was extracted with EtOAc (30 mL×3), and the combined organic layers were dried over anhydrous $Na_2SO_4$, filtered, and the filtrate was concentrated under reduced pressure. The residue was purified by column chromatography on silica (0-50% EtOAc/petroleum ether) to give methyl 2-((1-(tert-butoxycarbonyl)piperidin-4-yl)amino)-5-chloroisonicotinate as a solid. MS: 370 (M+1). $^1H$ NMR (400 MHz, $CDCl_3$) δ 8.11 (s, 1H), 6.71 (s, 1H), 4.64 (br d, J=7.9 Hz, 1H), 4.12-3.95 (m, 2H), 3.92 (s, 3H), 3.85-3.69 (m, 1H), 2.93 (br t, J=11.8 Hz, 2H), 2.07-1.94 (m, 2H), 1.46 (s, 9H), 1.40-1.26 (m, 2H).

Step 2: A mixture of methyl 2-((1-(tert-butoxycarbonyl)piperidin-4-yl)amino)-5-chloroisonicotinate (3.6 g, 9.7 mmol) in HCl (1M in dioxane, 30 mL) was stirred at 10° C. for 1 h. The mixture was concentrated under reduced pressure to give the crude product methyl 5-chloro-2-(piperidin-4-ylamino)isonicotinate hydrochloride, which was used directly in next step. $^1H$ NMR (400 MHz, DMSO-$d_6$) δ 9.19 (br s, 2H), 8.09 (s, 1H), 7.11 (s, 1H), 4.10-3.94 (m, 1H), 3.86 (s, 3H), 3.28 (br d, J=12.7 Hz, 2H), 3.05-2.84 (m, 2H), 2.04 (br dd, J=3.4, 13.7 Hz, 2H), 1.85-1.61 (m, 2H).

Step 3: To a solution of methyl 5-chloro-2-(piperidin-4-ylamino)isonicotinate hydrochloride (2.9 g, 9.47 mmol) and TEA (3.96 mL, 28.4 mmol) in $CH_2Cl_2$ (16 mL) was added acetic anhydride (0.967 g, 9.47 mmol) at 0° C. The resulting mixture was stirred at 0° C. for 1.5 h. To the mixture was added saturated $NaHCO_3$ (50 mL), and the resultant mixture was extracted with DCM (30 mL×3). The combined organic layers were dried over anhydrous sodium sulfate, filtered, and the filtrate was concentrated under reduced pressure. The residue was purified by column chromatography on silica (0-50% EtOAc/petroleum ether) to give methyl 2-((1-acetylpiperidin-4-yl)amino)-5-chloroisonicotinate as a solid. MS: 312 (M+1). $^1H$ NMR (400 MHz, $CD_3OD$) δ 8.02 (s, 1H), 6.81 (s, 1H), 4.46-4.33 (m, 1H), 4.05-3.85 (m, 5H), 3.29-3.22 (m, 1H), 2.98-2.81 (m, 1H), 2.18-1.92 (m, 5H), 1.55-1.28 (m, 2H).

Step 4: To a solution of methyl 2-((1-acetylpiperidin-4-yl)amino)-5-chloroisonicotinate (2.35 g, 7.54 mmol) in MeOH (30 mL) and water (2 mL) was added lithium hydroxide hydrate (0.443 g, 10.6 mmol). The mixture was stirred at 15° C. for 15 h. The mixture was acidified with concentrated HCl to pH ~2 and concentrated under reduced pressure to afford 2-((1-acetylpiperidin-4-yl)amino)-5-chloroisonicotinic acid as a solid which was used in the next step directly without further purification. MS: 298 (M+1). $^1H$ NMR (400 MHz, $CD_3OD$) δ 7.87 (s, 1H), 6.54 (s, 1H), 4.39 (br dd, J=1.5, 13.3 Hz, 1H), 3.99-3.81 (m, 2H), 3.28-3.21 (m, 1H), 2.97-2.82 (m, 1H), 2.14-1.92 (m, 5H), 1.50-1.27 (m, 2H).

TABLE 4

The following intermediate was prepared using a similar procedure as Intermediate 17.

| Int. # | Structure | Compound Name | Exact Mass [M + 1] |
|---|---|---|---|
| 18 | 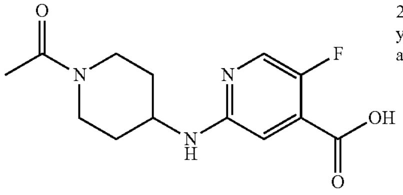 | 2-((l-acetylpiperidin-4-yl)amino)-5-fluoroisonicotinic acid | 282 |

Intermediate 19: 4-butoxy-3-(2,2,2-trifluoroethyl) quinoline-7-carboxylic acid

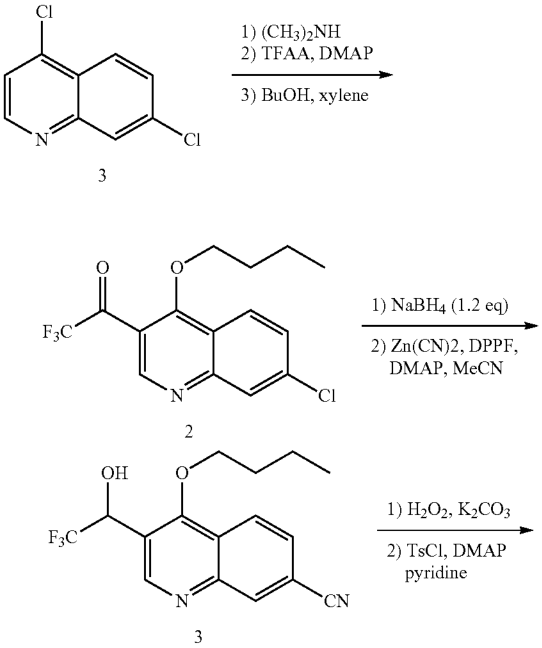

-continued

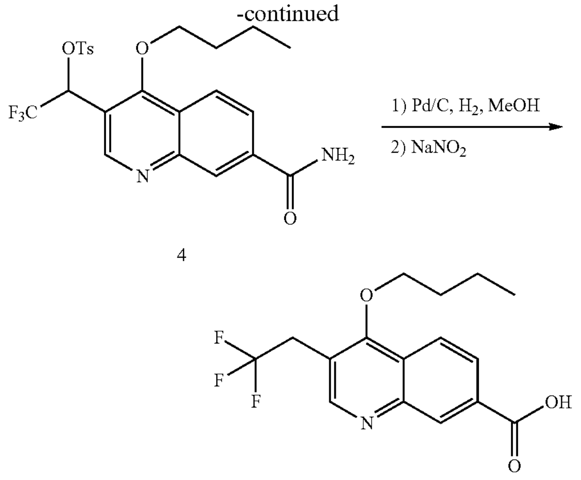

4

Intermediate 19

Step 1: A mixture of 4,7-dichloroquinoline (5 g, 25.2 mmol) and dimethylamine (24.1 g, 177 mmol) (33% Wt, in water) in acetonitrile (100 mL) was stirred at 50° C. for 48 h. To the mixture was added sat. $Na_2CO_3$ (200 mL). The mixture was concentrated under reduced pressure. The aqueous layer was extracted with EtOAc (100 mL×3). The combined organic layers were washed with brine (200 mL), dried over anhydrous sodium sulfate, filtered, and the filtrate was concentrated under reduced pressure. The residue was purified by column chromatography on silica (0-50% ethyl acetate/pet. ether) to give 7-chloro-N,N-dimethylquinolin-4-amine as an oil. MS: 207 (M+1). $^1$H NMR (400 MHz, $CDCl_3$) δ 8.62 (d, J=5.3 Hz, 1H), 8.03-7.92 (m, 2H), 7.37 (dd, J=2.2, 9.0 Hz, 1H), 6.71 (d, J=5.3 Hz, 1H), 3.01 (s, 6H).

Step 2: To a solution of DMAP (8.51 g, 69.7 mmol) in xylene (80 mL) was added TFAA (9.84 mL, 69.7 mmol) at 15° C. The mixture was stirred at 15° C. for 30 min. To the mixture was added 7-chloro-N, N-dimethylquinolin-4-amine (4.8 g, 23.2 mmol) in xylene (40 mL) at 15° C. The resultant mixture was stirred at 130° C. for 12 h. The mixture was cooled to room temperature and concentrated under reduced pressure. The residue was diluted with dichloromethane (100 mL), and the organic layer was washed with a saturated aqueous solution of sodium carbonate (200 mL) and dried over anhydrous sodium sulfate, filtered, and the filtrate was concentrated under reduced pressure. The residue was purified by column chromatography on silica (0-10% ethyl acetate/pet. ether) to give 1-(7-chloro-4-(dimethylamino)quinolin-3-yl)-2,2,2-trifluoroethanone as a solid. MS: 303 (M+1). $^1$H NMR (400 MHz, $CDCl_3$) δ 8.95 (d, J=1.3 Hz, 1H), 8.12 (d, J=9.2 Hz, 1H), 8.04 (d, J=2.2 Hz, 1H), 7.47 (dd, J=2.2, 9.2 Hz, 1H), 3.13 (s, 6H).

Step 3: A mixture of 1-(7-chloro-4-(dimethylamino)quinolin-3-yl)-2,2,2-trifluoroethanone (3 g, 9.91 mmol) and butan-1-ol (7.35 g, 99 mmol) in xylene (60 mL) was stirred at 130° C. for 96 h. The mixture was concentrated under reduced pressure to give the crude product 1-(4-butoxy-7-chloroquinolin-3-yl)-2,2,2-trifluoroethan-1-one as an oil which was used directly in next the step. MS: 332 (M+1).

Step 4: To a solution of 1-(4-butoxy-7-chloroquinolin-3-yl)-2,2,2-trifluoroethan-1-one (3 g, 8.58 mmol) in MeOH (100 mL) was added $NaBH_4$ (0.649 g, 17.2 mmol) at 25° C. The mixture was stirred at 25° C. for 0.5 h. The mixture was quenched with water (100 mL) and concentrated under reduced pressure. The mixture was extracted with EtOAc (50 mL×3). The combined organic layers were washed with brine (100 mL), dried over anhydrous sodium sulfate, filtered, and the filtrate was concentrated under reduced pressure. The residue was purified by column chromatography on silica (0-10% ethyl acetate/petroleum ether) to give 1-(4-butoxy-7-chloroquinolin-3-yl)-2,2,2-trifluoroethanol as a solid. MS: 334 (M+1). $^1$H NMR (400 MHz, $CDCl_3$) δ 8.93 (s, 1H), 8.03 (d, J=2.2 Hz, 1H), 7.95 (d, J=8.8 Hz, 1H), 7.51 (dd, J=2.0, 9.0 Hz, 1H), 5.60 (q, J=7.0 Hz, 1H), 4.75 (br s, 1H), 4.21-4.03 (m, 2H), 1.98-1.85 (m, 2H), 1.56 (qd, J=7.5, 14.9 Hz, 2H), 1.01 (t, J=7.2 Hz, 3H).

Step 5: A mixture of 1-(4-butoxy-7-chloroquinolin-3-yl)-2,2,2-trifluoroethanol (280 mg, 0.84 mmol), nickel(II) chloride hexahydrate (19.9 mg, 0.084 mmol), $Zn(CN)_2$ (158 mg, 1.34 mmol), zinc (219 mg, 3.36 mmol), dppf (55.8 mg, 0.101 mmol) and DMAP (205 mg, 1.68 mmol) in MeCN (10 mL) was degassed and backfilled with $N_2$ (three times). The mixture was stirred under $N_2$ atmosphere at 80° C. for 3 h. The reaction mixture was filtered, and the filtrate was concentrated under reduced pressure. The residue was purified by column chromatography on silica (0-25% ethyl acetate/pet. ether) to give 4-butoxy-3-(2,2,2-trifluoro-1-hydroxyethyl)quinoline-7-carbonitrile as a solid. MS: 325 (M+1). $^1$H NMR (400 MHz, $CDCl_3$) δ 9.13 (s, 1H), 8.47 (d, J=1.3 Hz, 1H), 8.15 (d, J=8.3 Hz, 1H), 7.73 (dd, J=1.5, 8.6 Hz, 1H), 5.65 (br s, 1H), 4.22-4.10 (m, 2H), 4.01 (br s, 1H), 2.01-1.87 (m, 2H), 1.59 (qd, J=7.5, 14.9 Hz, 2H), 1.03 (t, J=7.2 Hz, 3H).

Step 6: To a solution of 4-butoxy-3-(2,2,2-trifluoro-1-hydroxyethyl)quinoline-7-carbonitrile (170 mg, 0.524 mmol) and $K_2CO_3$ (145 mg, 1.05 mmol) in DMSO (5 mL) was added $H_2O_2$ (0.229 mL, 2.62 mmol) (35% Wt) at 25° C. The mixture was stirred at 25° C. for 15 min. The mixture was quenched with water (50 mL). To the aqueous layer was added sat. $Na_2SO_3$ (200 mL) slowly. The mixture was extracted with EtOAc (30 mL×3). The combined organic layers were washed with brine (50 mL), dried over anhydrous sodium sulfate, filtered, and the filtrate was concentrated under reduced pressure to give 4-butoxy-3-(2,2,2-trifluoro-1-hydroxyethyl)quinoline-7-carboxamide as a solid, which was used directly in the next step. MS: 343 (M+1). $^1$H NMR (400 MHz, DMSO-$d_6$) δ 9.01 (s, 1H), 8.59 (d, J=0.9 Hz, 1H), 8.32 (s, 1H), 8.19-8.14 (m, 1H), 8.11-8.06 (m, 1H), 7.64 (s, 1H), 7.24 (d, J=5.7 Hz, 1H), 5.64-5.48 (m, 1H), 4.16 (t, J=6.4 Hz, 2H), 1.93-1.78 (m, 2H), 1.53 (sxt, J=7.5 Hz, 2H), 0.97 (t, J=7.5 Hz, 3H).

Step 7: To a solution of 4-butoxy-3-(2,2,2-trifluoro-1-hydroxyethyl)quinoline-7-carboxamide (200 mg, 0.584 mmol) in DCM (5 mL) and DMF (3 mL) was added pyridine (0.047 mL, 0.584 mmol), DMAP (71.4 mg, 0.584 mmol) and TsCl (123 mg, 0.643 mmol) at 25° C. The mixture was stirred at 25° C. for 1 h. The mixture was concentrated under reduced pressure. The mixture was quenched with water (30 mL). The mixture was extracted with EtOAc (20 mL×3). The combined organic layers were washed with brine (30 mL), dried over anhydrous sodium sulfate, filtered, and the filtrate was concentrated under reduced pressure. The residue was purified by Preparative TLC (2:1 ethyl acetate/petroleum ether) to give 1-(4-butoxy-7-carbamoylquinolin-3-yl)-2,2,2-trifluoroethyl 4-methylbenzenesulfonate as a solid. MS: 497 (M+1).

Step 8: To a solution of 1-(4-butoxy-7-carbamoylquinolin-3-yl)-2,2,2-trifluoroethyl 4-methylbenzenesulfonate (220 mg, 0.443 mmol) in MeOH (20 mL) was added Pd—C (10% Wt) (200 mg, 0.188 mmol) under a $N_2$ atmosphere. The mixture was degassed and backfilled with H2 (three times). The resulting mixture was stirred under H2 (15 psi) at 25°

C. for 1 h. The mixture was filtered, and the filtrate was concentrated under reduced pressure to give 4-butoxy-3-(2,2,2-trifluoroethyl)quinoline-7-carboxamide as a solid, which was used in next step directly. MS: 327 (M+1). $^1$H NMR (400 MHz, $CDCl_3$) δ 8.89 (s, 1H), 8.46 (s, 1H), 8.17-8.12 (m, 1H), 8.10-8.05 (m, 1H), 6.32 (s, 1H), 5.75 (s, 1H), 4.15 (t, J=6.8 Hz, 2H), 3.67 (q, J=10.5 Hz, 2H), 2.00-1.91 (m, 2H), 1.67-1.62 (m, 2H), 1.05 (t, J=7.2 Hz, 3H).

Step 9: To a solution of 4-butoxy-3-(2,2,2-trifluoroethyl) quinoline-7-carboxamide (120 mg, 0.368 mmol) in $H_2SO_4$ (70% Wt) (10 mL) was added sodium nitrite (76 mg, 1.10 mmol) at 25° C. The mixture was stirred at 40° C. for 30 min. The mixture was quenched with water (40 mL). The mixture was extracted with DCM (10 mL×15). The combined organic layers were dried over anhydrous sodium sulfate, filtered, and the filtrate was concentrated under reduced pressure to give 4-butoxy-3-(2,2,2-trifluoroethyl) quinoline-7-carboxylic acid as a solid, which was used directly in the next step. MS: 328 (M+1). $^1$H NMR (400 MHz, DMSO-$d_6$) δ 9.01 (s, 1H), 8.61 (s, 1H), 8.25 (d, J=8.3 Hz, 1H), 8.13 (dd, J=1.3, 8.8 Hz, 1H), 4.22 (t, J=6.6 Hz, 2H), 3.93 (q, J 11.3 Hz, 2H), 1.92-1.80 (m, 2H), 1.59-1.47 (m, 3H), 0.97 (t, J=7.5 Hz, 3H).

Intermediate 20: 3-cyclopropyl-4-hydroxyquinoline-7-carboxylic acid

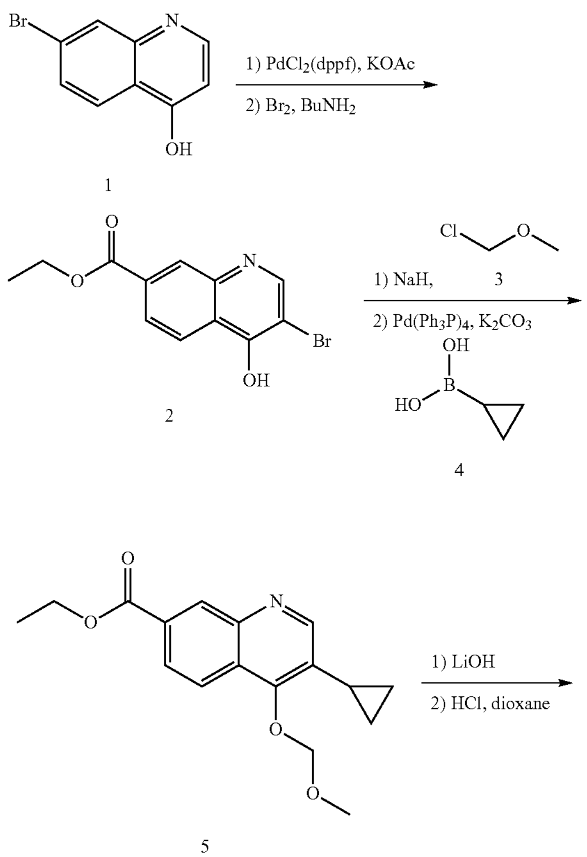

-continued

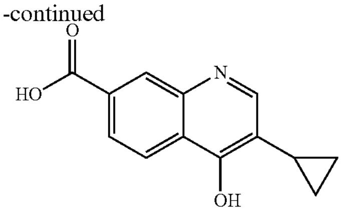

Intermediate 20

Step 1: To a solution of 7-bromoquinolin-4-ol (1 g, 4.46 mmol), KOAc (1.31 g, 13.4 mmol) in EtOH (80 mL) was added $PdCl_2$(dppf) (0.327 g, 0.446 mmol) under $N_2$ atmosphere. The mixture was degassed and backfilled with CO (three times). The resulting mixture was stirred under CO (50 psi) at 80° C. for 3 h. The mixture was concentrated under reduced pressure, and the residue was purified by column chromatography on silica (0-10% MeOH/DCM) to give ethyl 4-hydroxyquinoline-7-carboxylate as a solid. MS: 218 (M+1). $^1$H NMR (400 MHz, $CD_3OD$) δ 8.32 (d, J=8.38 Hz, 1H), 8.29-8.24 (m, 1H), 8.05 (br d, J=7.1 Hz, 1H), 7.99-7.93 (m, 1H), 6.37 (d, J=7.3 Hz, 1H), 4.43 (q, J=7.1 Hz, 2H), 1.43 (t, J=7.1 Hz, 3H).

Step 2: A mixture of butan-1-amine (2.69 g, 36.8 mmol), $Br_2$ (0.285 mL, 5.52 mmol) and ethyl 4-hydroxyquinoline-7-carboxylate (800 mg, 3.68 mmol) in DMF (20 mL) was stirred at 15° C. for 10 min. To the mixture was added $Na_2SO_3$ (0.1 M, 150 mL), and the resultant mixture was extracted with DCM (100 mL×2). The combined organic layers were concentrated under reduced pressure to give ethyl 3-bromo-4-hydroxyquinoline-7-carboxylate as a solid. MS: 296, 298 (M+1). $^1$H NMR (400 MHz, DMSO-$d_6$) δ 8.60 (s, 1H), 8.24-8.21 (m, 2H), 7.85 (dd, J 1.5, 8.38 Hz, 1H), 4.35 (q, J=7.1 Hz, 2H), 1.33 (t, J=7.1 Hz, 3H).

Step 3: To a solution of ethyl 3-bromo-4-hydroxyquinoline-7-carboxylate (0.4 g, 1.35 mmol) in DMF (8 mL) was added NaH (81 mg, 2.03 mmol) at 0° C. The mixture was stirred at 0° C. for 15 min. To the mixture was added chloro (methoxy)methane (0.585 mL, 7.70 mmol) at 0° C. The resultant mixture was stirred at 15° C. for 12 h. The mixture was quenched with sat. $NH_4Cl$ (100 mL), and the aqueous layer was extracted with EtOAc (50 mL×4). The combined organic layers were dried over anhydrous sodium sulfate, filtered, and the filtrate was concentrated under reduced pressure. The residue was purified by column chromatography on silica (0-3% ethyl acetate/DCM) to give ethyl 3-bromo-4-(methoxymethoxy)quinoline-7-carboxylate as a solid. MS: 340, 342 (M+1). $^1$H NMR (400 MHz, $CD_3OD$) δ 8.73 (s, 1H), 8.51 (d, J=0.9 Hz, 1H), 8.43 (d, J=8.3 Hz, 1H), 8.06 (dd, J=1.3, 8.3 Hz, 1H), 5.68 (s, 2H), 4.45 (q, J=7.3 Hz, 2H), 3.40 (s, 3H), 1.43 (t, J=7.2 Hz, 3H)

Step 4: A solution of ethyl 3-bromo-4-(methoxymethoxy) quinoline-7-carboxylate (600 mg, 1.76 mmol), cyclopropylboronic acid (1.52 g, 17.6 mmol) and $K_2CO_3$ (731 mg, 5.29 mmol) in DME (10 mL) was purged with nitrogen followed by the addition of $Pd(Ph_3P)_4$ (408 mg, 0.353 mmol) under $N_2$. The resulting mixture was heated to 100° C. for 12 h. The mixture was concentrated under reduced pressure. The residue was purified by column chromatography on silica (0-2% DCM/MeOH) to give ethyl 3-cyclopropyl-4-(methoxymethoxy)quinoline-7-carboxylate as a solid. MS: 302 (M+1). $^1$H NMR (400 MHz, CD3Cl) δ 8.51 (d, J=8.3 Hz, 1H), 8.31 (d, J=0.9 Hz, 1H), 7.97 (dd, J=1.5, 8.6 Hz, 1H), 7.36 (s, 1H), 5.43 (s, 2H), 4.46-4.39 (m, 2H), 3.39-3.34

(m, 3H), 2.08-2.00 (m, 1H), 1.43 (t, J=7.2 Hz, 3H), 0.97-0.90 (m, 2H), 0.62-0.53 (m, 2H).

Step 5: A solution of ethyl 3-cyclopropyl-4-(methoxymethoxy)quinoline-7-carboxylate (600 mg, 1.99 mmol) in EtOH (5 mL) and water (1 mL) was added lithium hydroxide hydrate (167 mg, 3.98 mmol), the mixture was stirred at 15° C. for 30 min. To the mixture was added HCl/MeOH (4 M) to acidify the mixture to pH 3. The solid was filtered to give 3-cyclopropyl-4-(methoxymethoxy)quinoline-7-carboxylic acid as a solid, which was used to next step without further purification. MS: 274 (M+1). $^1$H NMR (400 MHz, $CD_3OD$-$d_4$) δ 8.49 (s, 1H), 8.42 (d, J 8.8 Hz, 1H), 8.01 (d, J=9.7 Hz, 1H), 7.94 (s, 1H), 5.64 (s, 2H), 3.35 (s, 3H), 1.99 (s, 1H), 0.96-0.90 (m, 2H), 0.68-0.62 (m, 2H).

Step 6: A mixture of 3-cyclopropyl-4-(methoxymethoxy)quinoline-7-carboxylic acid (100 mg, 0.366 mmol) in HCl/dioxane (4 M) (20 mL) and water (1 mL) was stirred at 80° C. for 12 h. The mixture was concentrated under reduced pressure to give 3-cyclopropyl-4-hydroxyquinoline-7-carboxylic acid as a solid, which was used to next step without further purification. MS: 230 (M+1).

Intermediate 21: 2-ethyl-3-oxo-3,4-dihydro-2H-benzo[b][1,4]oxazine-6-carboxylic acid

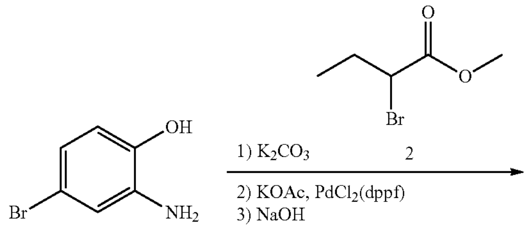

1

-continued

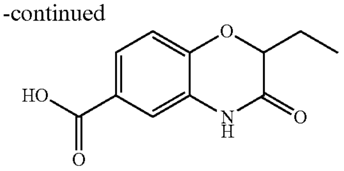

Intermediate 21

Step 1: To a stirred suspension of 2-amino-4-bromophenol (5 g, 26.6 mmol) and $K_2C_{O3}$ (3.85 g, 27.8 mmol) in acetone (80 mL) was added methyl 2-bromobutanoate (4.2 g, 23.2 mmol). The mixture was heated to 70° C. for 16 h. Then the reaction was stirred at 80° C. for another 16 h. The mixture was concentrated under reduced pressure, and the residue was dissolved in EtOAc (150 mL) and washed with water (100 mL×2). The organic layer was dried ($MgSO_4$), filtered, and concentrated under reduced pressure. The residue was purified by column chromatography on silica (1% MeOH/DCM) to give 6-bromo-2-ethyl-2H-benzo[b][1,4]oxazin-3(4H)-one as a solid. MS: 256, 258 (M+1). $^1$H NMR (400 MHz, $CDCl_3$) δ 9.48 (br s, 1H), 7.08 (dd, J=2.4, 8.6 Hz, 1H), 6.99 (d, J=2.2 Hz, 1H), 6.85 (d, J=8.3 Hz, 1H), 4.51 (dd, J=4.4, 8.3 Hz, 1H), 2.03-1.84 (m, 2H), 1.09 (t, J=7.5 Hz, 3H).

Step 2: To a solution of 6-bromo-2-ethyl-2H-benzo[b][1,4]oxazin-3(4H)-one (500 mg, 1.95 mmol) in EtOH (40 mL) was added $PdCl_2$(dppf) (286 mg, 0.390 mmol) and potassium acetate (575 mg, 5.86 mmol) under argon. The mixture was degassed and backfilled with argon (three times). The resulting mixture was stirred under CO (50 psi) at 80° C. for 16 h. The mixture was filtered, and the filtrate was concentrated under reduced pressure. The residue was purified by column chromatography on silica (20% ethyl acetate/pet. ether) to give ethyl 2-ethyl-3-oxo-3,4-dihydro-2H-benzo[b][1,4]oxazine-6-carboxylate as a solid. MS: 250 (M+1).

Step 3: To a solution of ethyl 2-ethyl-3-oxo-3,4-dihydro-2H-benzo[b][1,4]oxazine-6-carboxylate (120 mg, 0.481 mmol) in EtOH (4 mL) and water (2 mL) was added sodium hydroxide (57.8 mg, 1.44 mmol). The mixture was stirred at 20° C. for 18 h. The mixture was acidified by HCl in MeOH (4 M) to pH ~3. The mixture was concentrated under reduced pressure to give 2-ethyl-3-oxo-3,4-dihydro-2H-benzo[b][1,4]oxazine-6-carboxylic acid as a solid, which was used in the next step without further purification. MS: 222 (M+1).

TABLE 5

The following intermediate was prepared using a similar procedure as Intermediate 21.

| Int. # | Structure | Compound Name | Exact Mass [M + 1] |
|---|---|---|---|
| 22 | 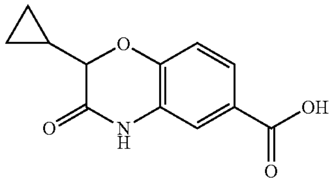 [SMILES: O=C(O)c1ccc2c(c1)NC(=O)C(C1CC1)O2] | 2-cyclopropyl-3-oxo-3,4-dihydro-2H-benzo[b][1,4]oxazine-6-carboxylic acid | 234 |

Intermediate 23: 5',5'-Dimethyl-3-oxo-3,4,4',5'-tetrahydro-2'H-spiro[benzo[b][1,4]oxazine-2,3'-furan]-6-carboxylic acid

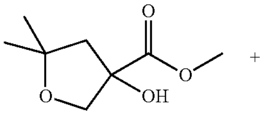

1

-continued

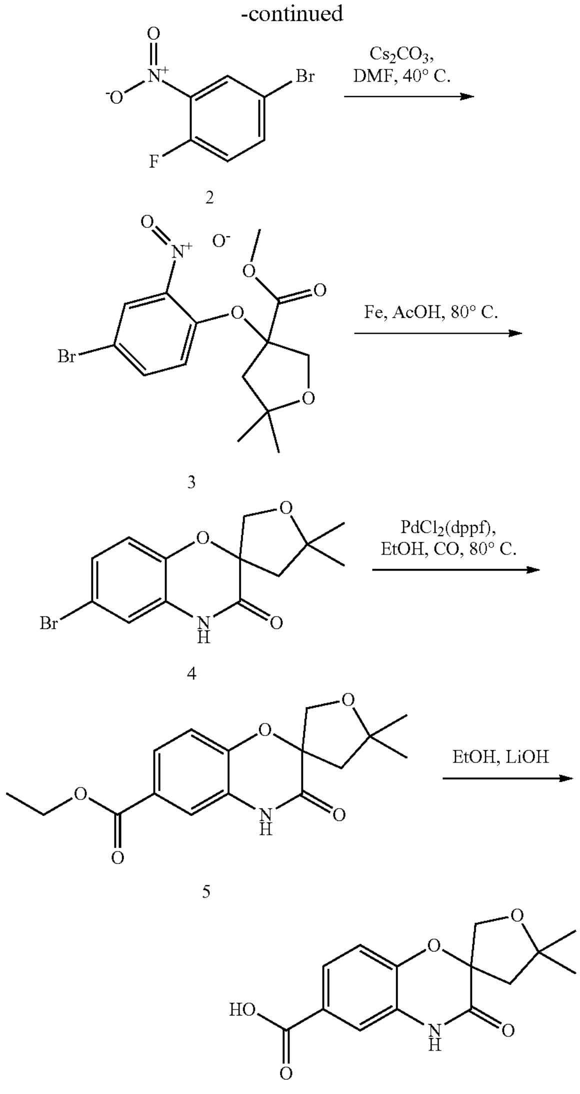

2

3

4

5

Intermediate 23

Step 1: To a solution of methyl 3-hydroxy-5,5-dimethyltetrahydrofuran-3-carboxylate (200 mg, 1.15 mmol) in DMF (5 mL) was added $Cs_2CO_3$ (1.12 g, 3.44 mmol) and 4-bromo-1-fluoro-2-nitrobenzene (303 mg, 1.38 mmol) at 40° C. under $N_2$. The mixture was stirred at 40° C. for 1 h. The mixture was diluted with water (10 mL) and extracted with DCM (10 mL×3). The combined organic layers were washed with brine (10 mL), dried over anhydrous $Na_2SO_4$, filtered, and concentrated under reduced pressure. The residue was purified by column chromatography on silica (0-50% ethyl acetate/pet. ether) to give methyl 3-(4-bromo-2-nitrophenoxy)-5,5-dimethyltetrahydrofuran-3-carboxylate as an oil.

Step 2: A solution of methyl 3-(4-bromo-2-nitrophenoxy)-5,5-dimethyltetrahydrofuran-3-carboxylate (102 mg, 0.273 mmol) and iron (76 mg, 1.4 mmol) in AcOH (1.5 mL) was stirred at 80° C. for 1 h. The reaction was concentrated under reduced pressure, diluted with sat. aq. $NaHCO_3$ (5 mL), filtered, and extracted with EtOAc (10 mL×2). The combined organic layers were concentrated to give crude 6-bromo-5',5'-dimethyl-4',5'-dihydro-2'H-spiro[benzo[b][1,4]oxazine-2,3'-furan]-3(4H)-one as a solid. MS: 312 and 314 (M+1).

Step 3: To a solution of 6-bromo-5',5'-dimethyl-4',5'-dihydro-2'H-spiro[benzo[b][1,4]oxazine-2,3'-furan]-3(4H)-one (100 mg, 0.320 mmol) in EtOH (5 mL) was added Pd(dppf)$Cl_2$ (23.4 mg, 0.032 mmol) and potassium acetate (94 mg, 0.96 mmol). The mixture was stirred at 80° C. under CO (50 psi) for 12 h. The mixture was concentrated under reduced pressure. The residue was purified by preparative TLC (2:1 pet. ether/EtOAc) to give ethyl 5',5'-dimethyl-3-oxo-3,4,4',5'-tetrahydro-2'H-spiro[benzo[b][1,4]oxazine-2,3'-furan]-6-carboxylate as a solid. MS: 306 (M+1).

Step 4: To a mixture of ethyl 5',5'-dimethyl-3-oxo-3,4,4',5'-tetrahydro-2'H-spiro[benzo[b][1,4]oxazine-2,3'-furan]-6-carboxylate (50 mg, 0.16 mmol) in EtOH (3 mL) and water (1 mL) was added lithium hydroxide hydrate (13.7 mg, 0.328 mmol) at 13° C., then the solution was stirred at 40° C. for 2.5 h. The mixture was concentrated under reduced pressure, and $H_2O$ (20 mL) was added. The pH of the mixture was adjusted to pH=2 with HCl (1M). The mixture was extracted with EtOAc (30 mL×3). The combined organic layers were washed with brine (20 mL), dried over $Na_2SO_4$, and concentrated under reduced pressure to give 5',5'-dimethyl-3-oxo-3,4,4',5'-tetrahydro-2'H-spiro[benzo[b][1,4]oxazine-2,3'-furan]-6-carboxylic acid as a solid, which was used in the next step without further purification. MS: 278 (M+1).

Intermediate 24: 6-Bromo-2,2-dimethyl-2H-benzo[b][1,4]oxazin-3(4H)-one

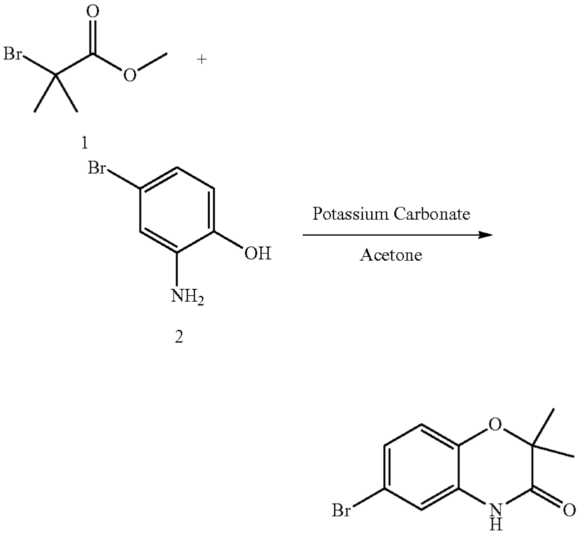

1

2

Intermediate 24

Step 1: To a solution of methyl 2-bromo-2-methylpropanoate (0.438 g, 2.42 mmol) and 2-amino-4-bromophenol (0.35 g, 1.9 mmol) in acetone (18.6 ml) was added potassium carbonate (0.257 g, 1.86 mmol). The reaction was allowed to stir for 18 h at room temperature. The reaction was filtered, and the solvent removed under reduced pressure. The material was purified by column chromatography on silica (0-100% EtOAc/Hex) to afford 6-bromo-2,2-dimethyl-2H-benzo[b][1,4]oxazin-3(4H)-one. MS: 256 and 258 (M+1).

Intermediate 25: 6-(Trifluoromethyl)-5,6,7,8-tetrahydroimidazo[1,2-a]pyridine-2-carboxylic acid

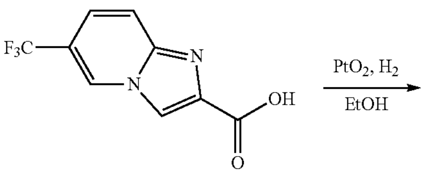

1

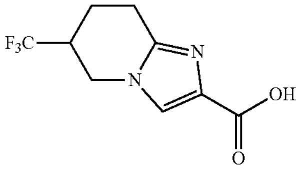

Intermediate 25

To a mixture of 6-(trifluoromethyl)imidazo[1,2-a]pyridine-2-carboxylic acid (580 mg, 2.52 mmol) in EtOH (5 mL) was added platinum(IV) oxide (114 mg, 0.504 mmol). The mixture was placed on a Parr shaker under a hydrogen atmosphere (50 psi) for 18 h. The mixture was filtered, and the filtrate was concentrated under reduced pressure to give 6-(trifluoromethyl)-5,6,7,8-tetrahydroimidazo[1,2-a]pyridine-2-carboxylic acid as a solid, which was used without further purification. MS: 235 (M+1).

Intermediate 26: ethyl 6-bromo-7-methylimidazo[1,2-a]pyrimidine-2-carboxylate

Intermediate 27: ethyl 6-bromo-7-methylimidazo[1,2-a]pyrimidine-2-carboxylate

Intermediate 28: ethyl 6-bromo-5-methylimidazo[1,2-a]pyrimidine-3-carboxylate

Intermediate 29: ethyl 6-bromo-7-methylimidazo[1,2-a]pyrimidine-3-carboxylate

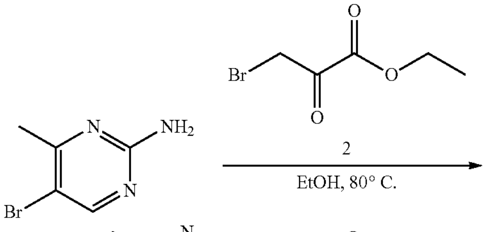

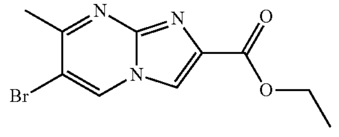

+

Intermediate 26

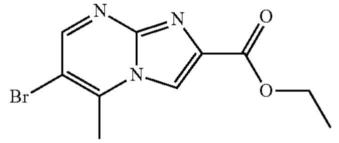

+

Intermediate 27

-continued

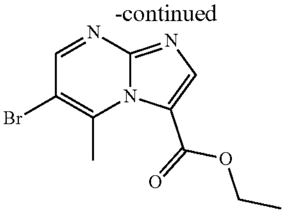

+

Intermediate 28

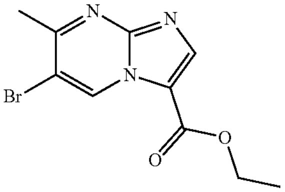

Intermediate 29

To a mixture of 5-bromo-4-methylpyrimidin-2-amine (5.0 g, 27 mmol) in EtOH (50 mL) was added ethyl 3-bromo-2-oxopropanoate (10.4 g, 39.9 mmol) at room temperature. The mixture was stirred at 80° C. for 12 h. The reaction was cooled to room temperature and then concentrated under reduced pressure. The residue was purified by column chromatography on silica (20% ethyl acetate/pet. ether) to afford two peaks. The major peak contained a mixture of ethyl 6-bromo-7-methylimidazo[1,2-a]pyrimidine-2-carboxylate and ethyl 6-bromo-5-methylimidazo[1,2-a]pyrimidine-2-carboxylate while the minor peak contained a mixture of ethyl 6-bromo-7-methylimidazo[1,2-a]pyrimidine-3-carboxylate and ethyl 6-bromo-5-methylimidazo[1,2-a]pyrimidine-3-carboxylate.

The mixture of ethyl 6-bromo-7-methylimidazo[1,2-a]pyrimidine-2-carboxylate and ethyl 6-bromo-5-methylimidazo[1,2-a]pyrimidine-2-carboxylate was purified by reverse phase HPLC (ACN/water with 0.1% TFA modifier) to afford the following:

ethyl 6-bromo-7-methylimidazo[1,2-a]pyrimidine-2-carboxylate (peak 1) as a solid: MS: 284 and 286 (M+1). $^1H$ NMR (400 MHz, $CDCl_3$) δ 8.72 (s, 1H), 8.09 (s, 1H), 4.41 (q, J=7.2 Hz, 2H), 2.79 (s, 3H), 1.39 (t, J=7.0 Hz, 3H).

ethyl 6-bromo-5-methylimidazo[1,2-a]pyrimidine-2-carboxylate (peak 2) as a solid: MS: 284 and 286 (M+1). $^1H$ NMR (400 MHz, $CDCl_3$) δ 8.71 (s, 1H), 8.13 (s, 1H), 4.44 (q, J=7.2 Hz, 2H), 2.85 (s, 3H), 1.41 (t, J=7.2 Hz, 3H).

The mixture of ethyl 6-bromo-7-methylimidazo[1,2-a]pyrimidine-3-carboxylate and ethyl 6-bromo-5-methylimidazo[1,2-a]pyrimidine-3-carboxylate was purified by reverse phase HPLC (ACN/water with 0.1% TFA modifier) to afford the following:

ethyl 6-bromo-5-methylimidazo[1,2-a]pyrimidine-3-carboxylate (peak 1) as a solid: MS: 284 and 286 (M+1).

ethyl 6-bromo-7-methylimidazo[1,2-a]pyrimidine-3-carboxylate (peak 2) as a solid: MS: 284 and 286 (M+1). $^1H$ NMR (400 MHz, Methanol-$d_4$) δ 9.66 (br s, 1H), 8.34 (br s, 1H), 4.44 (br d, J=6.58 Hz, 2H), 2.75 (s, 3H), 1.41 (br s, 3H).

Intermediate 30: 6-bromo-7-methylimidazo[1,2-a]pyrimidine-2-carboxylic acid

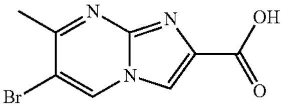

A solution of ethyl 6-bromo-7-methylimidazo[1,2-a]pyrimidine-2-carboxylate (1.0 g, 3.5 mmol) in HCl (12 M in water, 8 mL) was stirred at 75° C. for 2 h. The reaction was cooled to room temperature and concentrated under reduced pressure to afford 6-bromo-7-methylimidazo[1,2-a]pyrimidine-2-carboxylic acid as a solid, which was used in the next step without purification. MS: 256 and 258 (M+1).

TABLE 6

The following intermediates were prepared using a similar procedure as Intermediate 30.

| Int. # | Structure | Compound Name | Exact Mass [M + 1] |
|---|---|---|---|
| 31 | 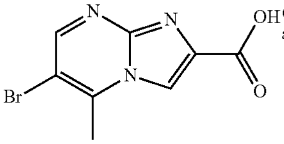 | 6-bromo-5-methylimidazo[1,2-a]pyrimidine-2-carboxylic acid | 256 and 258 |
| 32 | 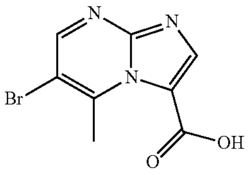 | 6-bromo-5-methylimidazo[1,2-a]pyrimidine-3-carboxylic acid | 256 and 258 |
| 33 | 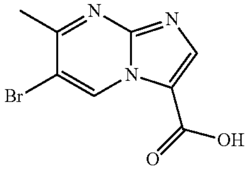 | 6-bromo-7-methylimidazo [1,2-a]pyrimidine-3-carboxylic acid | 256 and 258 |

Intermediate 34: 6-Bromo-7-methoxyimidazo[1,2-a]pyrimidine-2-carboxylic acid

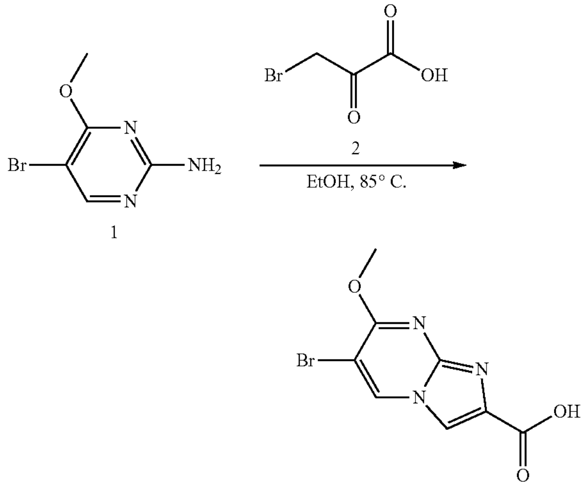

Intermediate 34

Step 1: To a mixture of 5-bromo-4-methoxypyrimidin-2-amine (300 mg, 1.47 mmol) in EtOH (6 mL) was added 3-bromo-2-oxopropanoic acid (368 mg, 2.21 mmol) at 15° C. The mixture was stirred at 85° C. for 12 h. The mixture was concentrated under reduced pressure to give 6-bromo-7-methoxyimidazo[1,2-a]pyrimidine-2-carboxylic acid as an oil, which was used directly in the next step without further purification. MS: 272 and 274 (M+1).

TABLE 7

The following intermediate was prepared using a similar procedure as Intermediate 34.

| Int. # | Structure | Compound Name | Exact Mass [M + 1] |
|---|---|---|---|
| 35 | 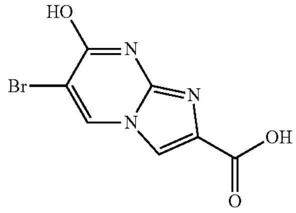 [SMILES: O=C(O)c1cn2cc(Br)c(O)nc2n1] | 6-bromo-7-hydroxyimidazo[1,2-α]pyrimidine-2-carboxylic acid | 258 and 260 |

Intermediate 36: 6-methylimidazo[1,2-a]pyrimidine-2-carboxylic acid

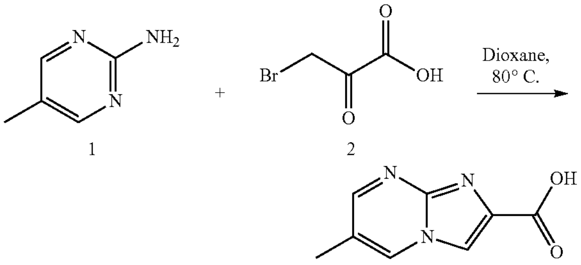

Intermediate 36

Step 1: To a mixture of 5-methylpyrimidin-2-amine (0.50 g, 4.6 mmol) in 1,4-dioxane (10 mL) was added 3-bromo-2-oxopropanoic acid (0.92 g, 5.5 mmol). The reaction was stirred at 85° C. for 16 h. The mixture was concentrated under reduced pressure to afford 6-methylimidazo[1,2-a]pyrimidine-2-carboxylic acid as a solid, which was used in the next step without purification. MS: 178 (M+1).

Intermediate 37: 6-bromo-8-(1-methoxyethyl)imidazo[1,2-a]pyridine-2-carboxylic acid

Intermediate 38: 6-bromo-8-(1-methoxyethyl)imidazo[1,2-a]pyridine-2-carboxylic acid

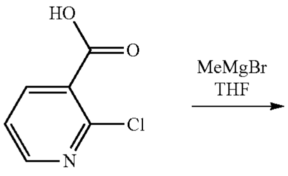

1

-continued

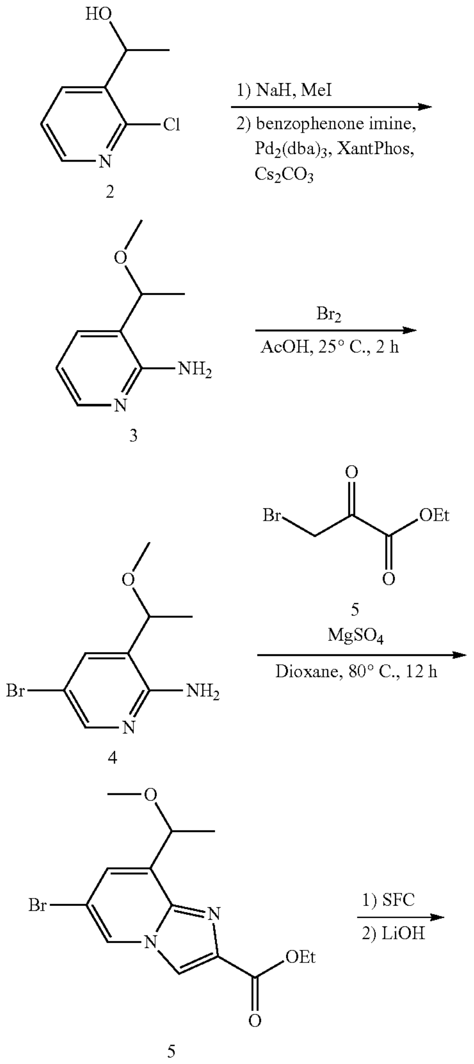

-continued

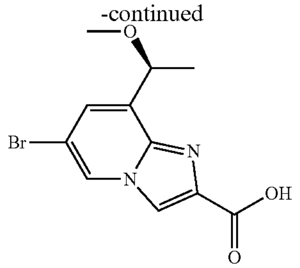

Intermediate 37

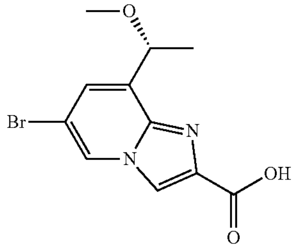

Intermediate 38

Step 1: To a solution of 2-chloronicotinaldehyde (4.0 g, 28 mmol) in THF (100 mL) was added methylmagnesium bromide (14.1 mL, 42.4 mmol, 3M in diethyl ether) drop-wise at −78° C. The mixture was stirred at −78° C. for 0.5 h. To the reaction was added sat. $NH_4Cl$ (50 mL) and water (80 mL). The aqueous layer was extracted with ethyl acetate (70 mL×3). The combined organic layers were washed with brine (100 mL), dried over anhydrous $Na_2SO_4$, filtered, and concentrated under reduced pressure to give 1-(2-chloro-pyridin-3-yl)ethanol as an oil, which was used in the next step directly. MS: 158 (M+1). $^1$H NMR (400 MHz, $CDCl_3$) δ 8.28-8.23 (m, 1H), 7.96 (dd, J=1.3, 7.9 Hz, 1H), 7.30-7.24 (m, 1H), 5.26-5.18 (m, 1H), 2.60 (d, J=3.5 Hz, 1H), 1.49 (d, J=6.6 Hz, 3H)

Step 2: To a mixture of 1-(2-chloropyridin-3-yl)ethanol (4.4 g, 28 mmol) and MeI (2.22 mL, 35.4 mmol) in DMF (60 mL) was added NaH (1.34 g, 33.5 mmol) at 0° C. The mixture was stirred at 0° C. for 0.5 h. To the reaction was added water (500 mL). The aqueous layer was extracted with ethyl acetate (200 mL×3). The combined organic layers were washed with brine (300 mL), dried over anhydrous $Na_2SO_4$, filtered, and concentrated under reduced pressure. The residue was purified by column chromatography on silica (5% ethyl acetate/pet. ether) to give 2-chloro-3-(1-methoxyethyl)pyridine as an oil. MS: 172 (M+1). $^1$H NMR (400 MHz, $CDCl_3$) δ 8.34 (dd, J=2.0, 4.9 Hz, 1H), 7.85 (dd, J=2.0, 7.8 Hz, 1H), 7.31 (dd, J=4.9, 7.8 Hz, 1H), 4.71 (q, J=6.4 Hz, 1H), 3.30 (s, 3H), 1.45 (d, J=6.4 Hz, 3H).

Step 3: To a solution of 2-chloro-3-(1-methoxyethyl)pyridine (4.3 g, 25 mmol), diphenylmethanimine (5.45 g, 30.1 mmol), and Xantphos (1.45 g, 2.51 mmol) in 1,4-dioxane (60 mL) was added $Cs_2CO_3$ (19.6 g, 60.1 mmol) and $Pd_2(dba)_3$ (1.15 g, 1.25 mmol) at 25° C. The resultant mixture was degassed and backfilled with $N_2$ (three times) and stirred at 90° C. for 12 h. The reaction was cooled to room temperature and concentrated under reduced pressure.

The residue was diluted with water (60 mL) and the mixture was extracted with ethyl acetate (40 mL×3). The organic layers were dried over $Na_2SO_4$, filtered, and the filtrate was concentrated under reduced pressure. The residue was dissolved in MeOH (30 mL), and the mixture was adjusted to pH 5 with HCl solution (aq. 1 M) and stirred for 20 min. The mixture was basified with ammonium hydroxide (1 M) to pH 8, and the mixture was concentrated under reduced pressure. The residue was purified by column chromatography on silica (50% ethyl acetate/pet. ether) to give 3-(1-methoxyethyl)pyridin-2-amine as a solid. MS: 153 (M+1). $^1$H NMR (400 MHz, $CDCl_3$) δ 8.02 (dd, J=1.7, 5.1 Hz, 1H), 7.26 (dd, J=1.8, 7.3 Hz, 1H), 6.63 (dd, J=5.0, 7.3 Hz, 1H), 5.10 (br s, 2H), 4.34 (q, J=6.9 Hz, 1H), 3.31-3.26 (m, 3H), 1.53 (d, J=6.9 Hz, 3H).

Step 4: To a mixture of 3-(1-methoxyethyl)pyridin-2-amine (500 mg, 3.29 mmol) in AcOH (5 mL) was added $Br_2$ (0.25 mL, 4.93 mmol) at 25° C. The mixture was stirred at 25° C. for 2 h. The mixture was concentrated under reduced pressure. The residue was dissolved in water (5 mL), and the mixture was adjusted to pH 8 with sat. $NaHCO_3$. The aqueous layer was extracted with ethyl acetate (10 mL×5), and the combined organic layers were washed with brine (20 mL), dried over anhydrous $Na_2SO_4$, filtered, and concentrated under reduced pressure. The residue was purified by column chromatography on silica (25% ethyl acetate/pet. ether) to give 5-bromo-3-(1-methoxyethyl)pyridin-2-amine as a solid. MS: 231 and 233 (M+1). $^1$H NMR (400 MHz, $CDCl_3$) δ 8.05 (d, J=2.5 Hz, 1H), 7.37 (d, J=2.5 Hz, 1H), 5.14 (br s, 2H), 4.33-4.23 (m, 1H), 3.29 (s, 3H), 1.51 (d, J=6.9 Hz, 3H).

Step 5: To a mixture of 5-bromo-3-(1-methoxyethyl)pyridin-2-amine (270 mg, 1.17 mmol) in 1,4-dioxane (15 mL) was added $MgSO_4$ (422 mg, 3.51 mmol) and ethyl 3-bromo-2-oxopropanoate (349 mg, 1.75 mmol) at 25° C. The mixture was stirred at 80° C. for 12 h. After cooling to 25° C., TEA (0.20 mL, 1.40 mmol) was added. The mixture was stirred at 25° C. for 1 h and the precipitate was filtered. The filtrate was concentrated under reduced pressure. The residue was purified by column chromatography on silica (22% ethyl acetate/pet. ether) to give ethyl 6-bromo-8-(1-methoxyethyl)imidazo[1,2-a]pyridine-2-carboxylate as a solid. MS: 327 and 329 (M+1). $^1$H NMR (400 MHz, $CDCl_3$) δ 8.20 (d, J=1.8 Hz, 1H), 8.13 (s, 1H), 7.42-7.37 (m, 1H), 5.20 (q, J=6.6 Hz, 1H), 4.50-4.42 (m, 2H), 3.38 (s, 3H), 1.54 (d, J=6.6 Hz, 3H), 1.42 (t, J 7.0 Hz, 3H).

Step 6: A racemate of ethyl 6-bromo-8-(1-methoxyethyl)imidazo[1,2-a]pyridine-2-carboxylate (210 mg, 0.64 mmol) was separated by SFC (AD Column, $NH_3 \cdot H_2O/EtOH/CO_2$) to afford ethyl (S or R)-6-bromo-8-(1-hydroxyethyl)imidazo[1,2-a]pyridine-2-carboxylate as a solid (Peak 1) and ethyl (S or R)-6-bromo-8-(1-methoxyethyl)imidazo[1,2-a]pyridine-2-carboxylate as a solid (Peak 2).

Step 7: To a solution of ethyl (R or S)-6-bromo-8-(1-methoxyethyl)imidazo[1,2-a]pyridine-2-carboxylate (70 mg, 0.21 mmol) in EtOH (2 mL) and water (0.5 mL) was added $LiOH \cdot H_2O$ (178 mg, 0.43 mmol) at 25° C. The mixture was stirred at 25° C. for 2 h. The mixture was concentrated under reduced pressure to give (R or S)-6-bromo-8-(1-methoxyethyl)imidazo[1,2-a]pyridine-2-carboxylic acid as a solid, which was used in the next step without further purification. MS: 299 and 301 (M+1). The same procedure was carried out with the corresponding epimer.

Intermediate 39: 8-[(1R)-1-methoxyethyl]-6-methylimidazo[1,2-a]pyridine-2-carboxylic acid

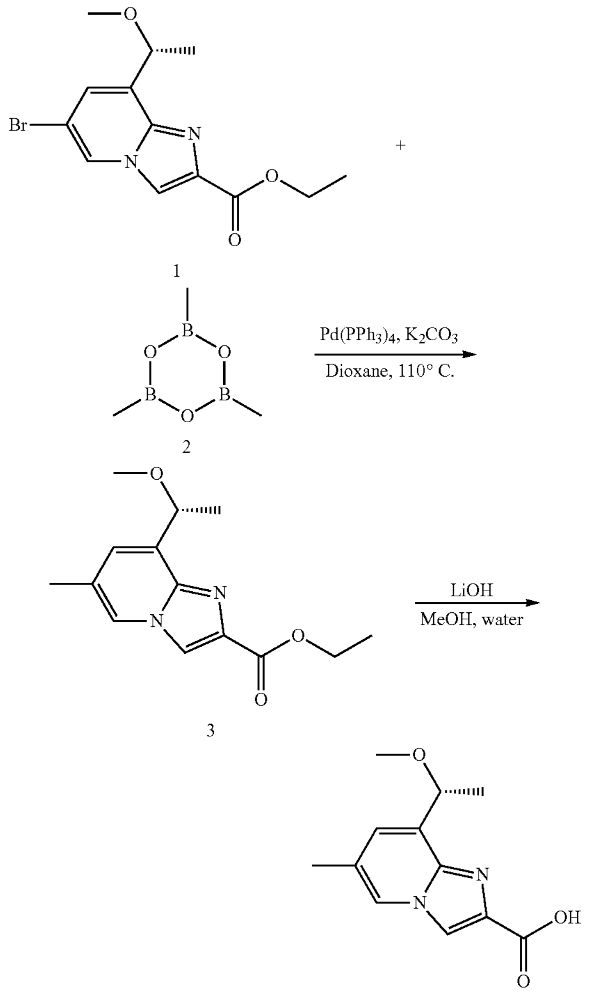

Intermediate 39

Step 1: A mixture of tetrakis(triphenylphosphine)palladium (0) (0.353 g, 0.306 mmol), $K_2C_{03}$ (1.27 g, 9.17 mmol), ethyl 6-bromo-8-[(1R)-1-methoxyethyl]imidazo[1,2-a]pyridine-2-carboxylate (1.0 g, 3.1 mmol) and trimethylboroxine (1.92 g, 15.3 mmol) in dioxane (10 mL) was stirred at 110° C. for 4 h. The reaction was cooled to room temperature and concentrated under reduced pressure. The residue was purified by column chromatography on silica (50% ethyl acetate/pet. ether) to afford ethyl 8-[(1R)-1-methoxyethyl]-6-methylimidazo[1,2-a]pyridine-2-carboxylate as an oil. MS: 263 (M+1). $^1$H NMR (400 MHz, $CDCl_3$) δ 8.09 (s, 1H), 7.81 (s, 1H), 7.17 (s, 1H), 5.21 (q, J=6.14 Hz, 1H), 4.49-4.40 (m, 2H), 3.37 (s, 3H), 2.34 (d, J=0.88 Hz, 3H), 1.54 (d, J=6.58 Hz, 3H), 1.41 (t, J=7.02 Hz, 3H).

Step 2: To a solution of ethyl 8-[(1R)-1-methoxyethyl]-6-methylimidazo[1,2-a]pyridine-2-carboxylate (340 mg, 1.29 mmol) in MeOH (3 mL) and water (0.6 mL) was added LiOH (62 mg, 2.6 mmol). The mixture was stirred at room temperature for 3 h. The reaction was concentrated under reduced pressure, and the residue was purified by reverse phase HPLC (ACN/water with 0.1% TFA modifier) to afford 8-[(1R)-1-methoxyethyl]-6-methylimidazo[1,2-a]pyridine-2-carboxylic acid as a solid. MS: 235 (M+1). $^1$H NMR (400 MHz, $CD_3OD$) δ 8.60 (s, 1H), 8.49 (s, 1H), 7.80 (s, 1H), 4.98-4.93 (m, 1H), 3.35 (s, 3H), 2.47 (s, 3H), 1.53 (d, J=6.14 Hz, 3H).

Intermediate 40: 8-[(1R)-1-methoxyethyl]-6-(propan-2-yl)imidazo[1,2-a]pyridine-2-carboxylic acid

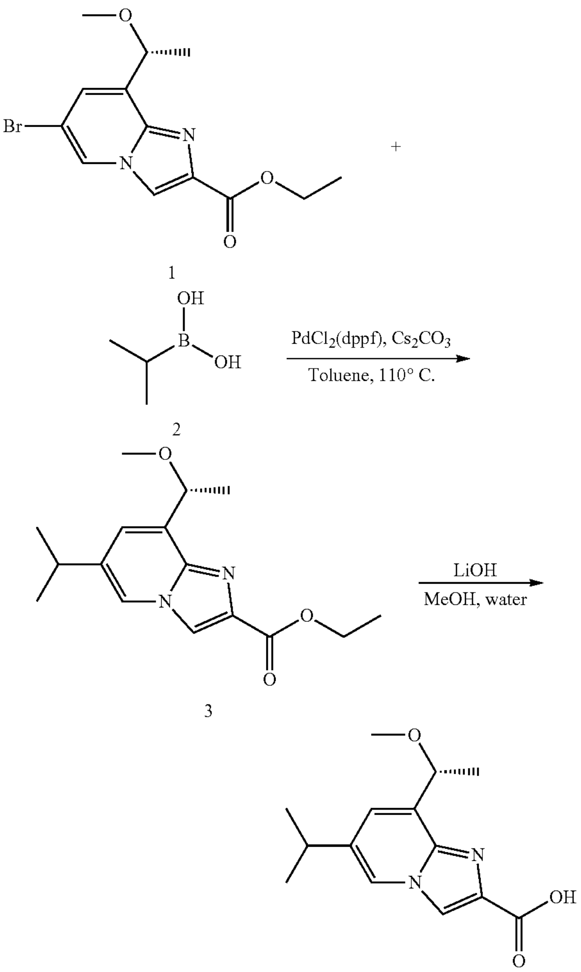

Intermediate 40

Step 1: A mixture of $PdCl_2$(dppf) (0.224 g, 0.306 mmol), $Cs_2CO_3$ (2.99 g, 9.17 mmol), ethyl 6-bromo-8-[(1R)-1-methoxyethyl]imidazo[1,2-a]pyridine-2-carboxylate (1.0 g, 3.1 mmol) and isopropylboronic acid (404 mg, 4.59 mmol) in toluene (8 mL) was stirred at 110° C. for 10 h. The reaction was cooled to room temperature and concentrated under reduced pressure. The residue was purified by column chromatography on silica (50% ethyl acetate/pet. ether) to afford ethyl 8-[(1R)-1-methoxyethyl]-6-(propan-2-yl)imidazo[1,2-a]pyridine-2-carboxylate as an oil. MS: 291 (M+1). $^1$H NMR (500 MHz, $CDCl_3$) δ 8.16 (s, 1H), 7.87 (s, 1H), 7.26 (s, 1H), 4.56-4.46 (m, 3H), 3.43 (s, 3H), 2.65 (s, 1H), 1.47 (t, J=7.10 Hz, 3H), 1.34-1.26 (m, 3H), 1.07 (br d, J=7.17 Hz, 6H).

Step 2: To a mixture of ethyl 8-[(1R)-1-methoxyethyl]-6-(propan-2-yl)imidazo[1,2-a]pyridine-2-carboxylate (290 mg, 0.999 mmol) in MeOH (3 ml) and water (0.6 mL) was added LiOH (47.8 mg, 1.99 mmol). The mixture was stirred at room temperature for 3 h. The reaction was concentrated under reduced pressure, and the residue was purified by reverse phase HPLC (ACN/water with 0.1% TFA modifier) to afford 8-[(1R)-1-methoxyethyl]-6-(propan-2-yl)imidazo[1,2-a]pyridine-2-carboxylic acid as a solid. MS: 263 (M+1). $^1$H NMR (500 MHz, $CD_3OD$) δ 8.61-8.56 (m, 1H), 8.49 (br s, 1H), 7.78 (br s, 1H), 5.00 (q, J=6.41 Hz, 1H), 3.39-3.37 (m, 3H), 2.77 (t, J=7.55 Hz, 2H), 1.77 (sxt, J=7.45 Hz, 2H), 1.58-1.53 (m, 3H), 1.04 (t, J=7.32 Hz, 3H).

Intermediate 41: 6-(2,2-difluorocyclopropyl)imidazo[1,2-a]pyrimidine-2-carboxylic acid Intermediate 42: 6-(2,2-difluorocyclopropyl)imidazo[1,2-a]pyrimidine-2-carboxylic acid

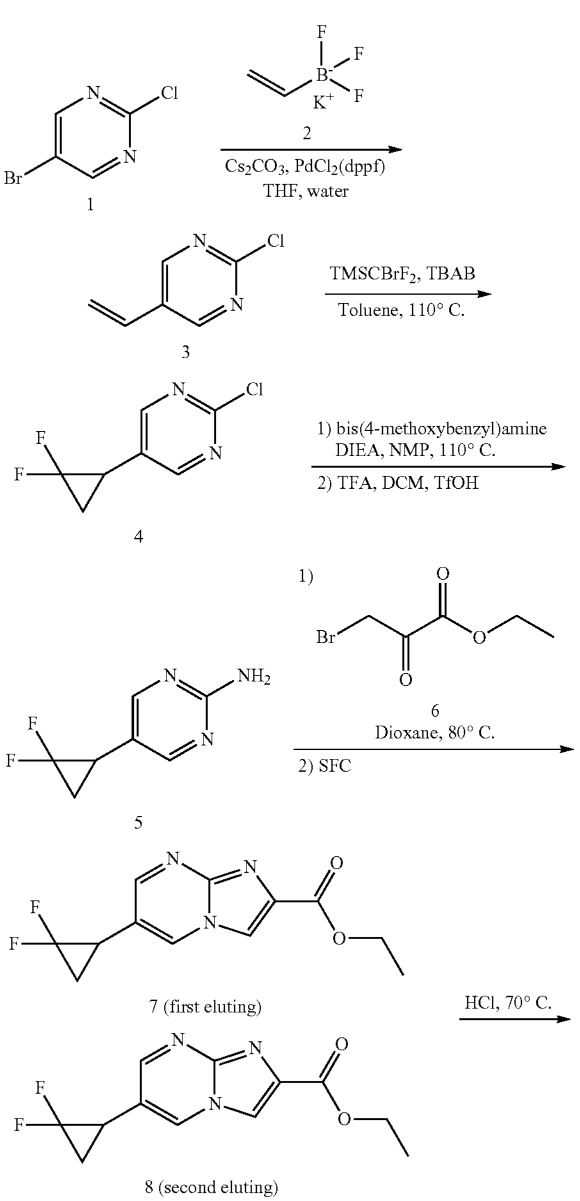

-continued

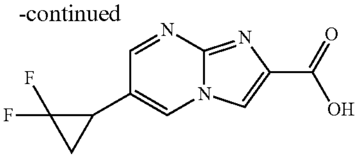

Intermediate 41

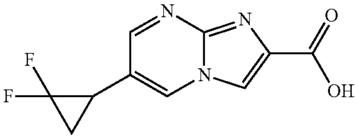

Intermediate 42

Step 1: To a solution of 5-bromo-2-chloropyrimidine (200 mg, 1.03 mmol) in THF (5 mL) and water (1 mL) was added potassium trifluoro(vinyl)borate (230 mg, 1.55 mmol), $Cs_2CO_3$ (1010 mg, 3.10 mmol), and $PdCl_2$(dppf) (151 mg, 0.207 mmol). The reaction mixture was stirred at 85° C. for 2 h under an atmosphere of nitrogen. The reaction was cooled to room temperature and treated with water. The mixture was extracted with EtOAc (3×30 mL), and the combined organic layers were dried over anhydrous sodium sulfate, filtered, and concentrated under reduced pressure. The residue was purified by column chromatography on silica (3% ethyl acetate/pet. ether) to afford 2-chloro-5-vinylpyrimidine as a solid. MS: 141 (M+1).

Step 2: A mixture of tetrabutylammonium bromide (0.193 g, 0.598 mmol), 2-chloro-5-vinylpyrimidine (1.4 g, 10 mmol) and (bromodifluoromethyl)trimethylsilane (6.07 g, 29.9 mmol) in toluene (5 mL) was stirred at 110° C. for 2 h. After cooling to room temperature, the mixture was concentrated under reduced pressure, and the residue was purified by column chromatography on silica (10/1 to 5/1 v/v pet. ether/ethyl acetate) to afford 2-chloro-5-(2,2-difluorocyclopropyl) pyrimidine as a solid. MS: 191 (M+1). $^1$H NMR (400 MHz, $CDCl_3$) δ 8.51 (s, 2H), 2.79-2.60 (m, 1H), 2.08-1.98 (m, 1H), 1.76-1.62 (m, 1H).

Step 3: A mixture of DIEA (9.6 mL, 55 mmol), bis(4-methoxybenzyl)amine (9.5 g, 37 mmol) and 2-chloro-5-(2,2-difluorocyclopropyl)pyrimidine (3.5 g, 18 mmol) in NMP (70 mL) was heated at 110° C. for 12 h. The reaction was cooled to room temperature and diluted with water. The mixture was extracted with EtOAc (3×50 mL). The combined organic layers were dried over anhydrous sodium sulfate, filtered, and concentrated under reduced pressure. The residue was purified by column chromatography on silica (5% ethyl acetate/pet. ether) to afford 5-(2,2-difluorocyclopropyl)-N,N-bis(4-methoxybenzyl)pyrimidin-2-amine as an oil. MS: 412 (M+1).

Step 4: A mixture of 5-(2,2-difluorocyclopropyl)-N,N-bis(4-methoxybenzyl)pyrimidin-2-amine (6.0 g, 15 mmol) in DCM (10 mL), TFA (10 mL), and TfOH (0.1 mL) was stirred at room temperature for 12 h. The mixture was concentrated under reduced pressure, and the residue was dissolved in water (50 mL) and basified with $NH_3H_2O$ to pH ~10. The aqueous layer was extracted with DCM (3×50 mL), and the combined organic layers were washed with brine (50 mL), dried over anhydrous sodium sulfate, filtered, and concentrated under reduced pressure. The residue was purified by column chromatography on silica (100/1 to 1/3, v/v pet. ether/ethyl acetate) to afford 5-(2,2-difluorocyclopropyl)pyrimidin-2-amine as a solid. MS: 172 (M+1).

Step 5: A mixture of 5-(2,2-difluorocyclopropyl)pyrimidin-2-amine (1.5 g, 8.8 mmol) and ethyl 3-bromo-2-oxopropanoate (2.96 g, 11.4 mmol) in dioxane (20 mL) was stirred at 80° C. for 2 h. The mixture was cooled to room temperature and concentrated under reduced pressure. The residue was purified by reverse phase HPLC (ACN/water with 0.10% TFA modifier) to afford ethyl 6-(2,2-difluorocyclopropyl)imidazo[1,2-a]pyrimidine-2-carboxylate. The racemic mixture was purified by chiral SFC (OD column, 20-30% EtOH/$CO_2$) to afford ethyl 6-(2,2-difluorocyclopropyl)imidazo[1,2-a] pyrimidine-2-carboxylate (isomer 1, first eluting) as a solid. MS: 268 (M+1) and ethyl 6-(2,2-difluorocyclopropyl)imidazo[1,2-a] pyrimidine-2-carboxylate (isomer 2, second eluting) as a solid. MS: 268 (M+1).

Step 6: A solution of ethyl 6-(2,2-difluorocyclopropyl)imidazo[1,2-a]pyrimidine-2-carboxylate (isomer 1, first eluting) (180 mg, 0.674 mmol) in HCl (35% in water, 5 mL) was stirred at 70° C. for 12 h. The mixture was cooled to room temperature, concentrated under reduced pressure to afford 6-(2,2-difluorocyclopropyl)imidazo [1,2-a] pyrimidine-2-carboxylic acid as a solid, which was used in the next step without further purification. MS: 240 (M+1). Note that both isomers could be hydrolyzed via the conditions described above.

Intermediate 43: 6-cyclopropylimidazo[1,2-a]pyrimidine-2-carboxylic acid

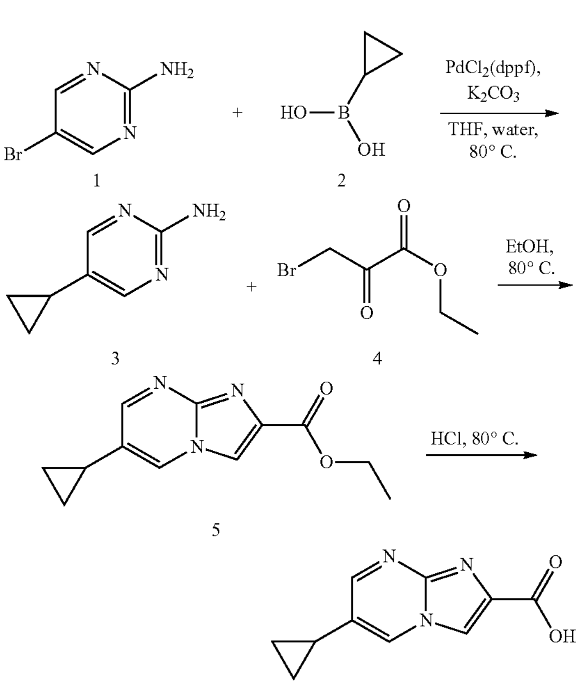

Intermediate 43

Step 1: To a mixture of 5-bromopyrimidin-2-amine (2.0 g, 12 mmol) in THF (15 mL) and water (3 mL) was added $K_2C_{03}$ (4.77 g, 34.5 mmol), cyclopropylboronic acid (4.94 g, 57.5 mmol), and $PdCl_2$(dppf) (0.841 g, 1.15 mmol). The mixture was degassed and backfilled with $N_2$ (3×), and the reaction was stirred at 80° C. for 12 h. The mixture was cooled to room temperature and concentrated under reduced pressure. The residue was purified by column chromatography on silica (0-45% ethyl acetate/pet. ether) to afford 5-cyclopropylpyrimidin-2-amine as a solid. MS: 136 (M+1).

Step 2: To a mixture of 5-cyclopropylpyrimidin-2-amine (3.5 g, 26 mmol) in EtOH (50 mL) was added ethyl 3-bromo-2-oxopropanoate (6.1 g, 31 mmol). The mixture was stirred at 80° C. for 16 h. The reaction was cooled to room temperature, and TEA (7.2 mL, 52 mmol) was added. The mixture was stirred at room temperature for 0.5 h. The mixture was concentrated under reduced pressure, and the residue was purified by column chromatography on silica (60% ethyl acetate/pet. ether) to afford ethyl 6-cyclopropylimidazo[1,2-a]pyrimidine-2-carboxylate as a solid. MS: 232 (M+1). $^1H$ NMR (500 MHz, $CDCl_3$) δ 8.50 (d, J=2.4 Hz, 1H), 8.16 (d, J=2.0 Hz, 1H), 8.04 (s, 1H), 4.44 (q, J=7.2 Hz, 2H), 2.03-1.87 (m, 1H), 1.42 (t, J=7.2 Hz, 3H), 1.12-1.04 (m, 2H), 0.80-0.72 (m, 2H).

Step 3: A mixture of ethyl 6-cyclopropylimidazo[1,2-a] pyrimidine-2-carboxylate (100 mg, 0.432 mmol) in HCl (4 M in dioxane, 2 mL) was stirred at 80° C. for 3 h. The reaction was cooled to room temperature, and concentrated under reduced pressure to afford 6-cyclopropylimidazo[1,2-a]pyrimidine-2-carboxylic acid as a solid, which was used in next step without purification. MS: 204 (M+1).

Intermediate 44: 6-(2,4-dimethyl-1,3-thiazol-5-yl) imidazo[1,2-a]pyrimidine-2-carboxylic acid

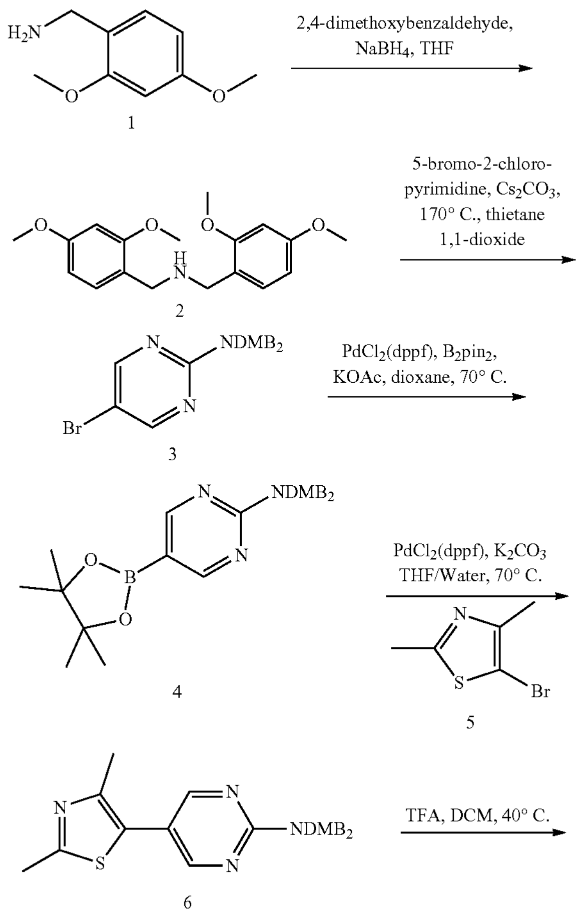

-continued

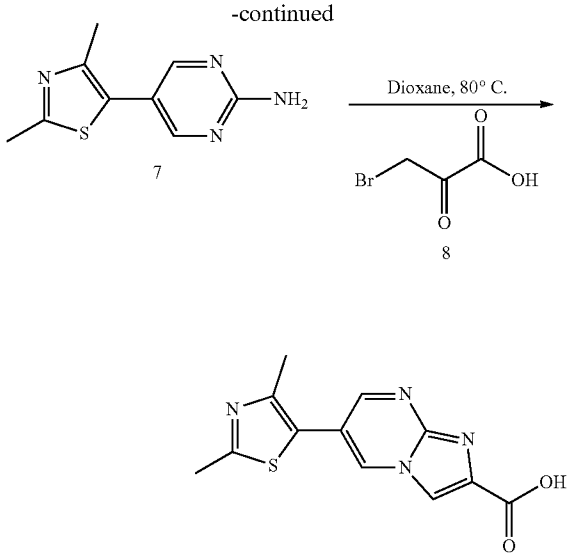

7

8

Intermediate 44

Step 1: A mixture of (2,4-dimethoxyphenyl)methanamine (75.0 g, 451 mmol) and 2,4-dimethoxybenzaldehyde (50.0 g, 301 mmol) in THF (600 mL) was stirred at room temperature for 2 h. To the mixture was added $NaBH_4$ (11.4 g, 301 mmol) and the reaction was stirred at room temperature for 2 h. The mixture was treated with sat. aq. sodium bicarbonate (1500 mL), and then extracted with EtOAc (3×300 mL). The combined organic layers were washed with brine (1000 mL), dried over anhydrous sodium sulfate, filtered, and concentrated under reduced pressure. The residue was purified by column chromatography on silica (10% ethyl acetate/petroleum ether) to give bis(2,4-dimethoxybenzyl)amine as an oil. MS: 318 (M+1). $^1$H NMR (500 MHz, $CDCl_3$) δ 7.28 (s, 1H), 7.26 (s, 1H), 6.54 (s, 3H), 6.53 (d, J=2.4 Hz, 1H), 3.90 (d, J=3.7 Hz, 12H), 3.81 (s, 4H), 1.96 (br d, J=2.8 Hz, 1H)

Step 2: A mixture of 5-bromo-2-chloropyrimidine (3.0 g, 16 mmol), bis(2,4-dimeth-oxybenzyl)amine (5.22 g, 16.4 mmol) and $Cs_2CO_3$ (15.2 g, 46.5 mmol) in thietane 1,1-dioxide (40 mL) was stirred at 170° C. for 1 h. The reaction was cooled to room temperature and treated with water (600 mL). The mixture was extracted with EtOAc (3×100 mL), and the combined organic layers were washed with brine (600 mL), dried over anhydrous sodium sulfate, filtered, and concentrated under reduced pressure. The residue was purified by column chromatography on silica (20% ethyl acetate/petroleum) to afford 5-bromo-N,N-bis(2,4-dimethoxybenzyl)pyrimidin-2-amine as an oil. MS: 474 and 476 (M+1). $^1$H NMR (500 MHz, $CDCl_3$) δ 8.55 (s, 2H), 7.27 (d, J=8.4

Hz, 2H), 6.70 (d, J=2.3 Hz, 2H), 6.66 (dd, J=2.3, 8.2 Hz, 2H), 5.03 (s, 4H), 4.04 (s, 6H), 4.00 (s, 6H).

Step 3: A mixture of potassium acetate (1.86 g, 18.9 mmol), $PdCl_2$(dppf) (0.46 g, 0.63 mmol), 5-bromo-N,N-bis(2,4-dimethoxybenzyl)pyrimidin-2-amine (3.0 g, 6.3 mmol), and bis(pinacolato)diboron (4.82 g, 18.9 mmol) in dioxane (30 mL) was degassed and backfilled with $N_2$ (3×). The mixture was stirred at 70° C. for 12 h. After cooling to room temperature, the mixture was filtered, and the filtrate was concentrated under reduced pressure. The residue was purified by column chromatography on silica (5% ethyl acetate/pet. ether) to afford N,N-bis(2,4-dimethoxybenzyl)-5-(4,4,5,5-tetramethyl-1,3,2-dioxaborolan-2-yl)pyrimidin-2-amine as an oil. MS: 522 (M+1).

Step 4: A mixture of potassium carbonate (1.35 g, 9.78 mmol), $PdCl_2$(dppf) (0.24 g, 0.33 mmol), N,N-bis(2,4-dimethoxybenzyl)-5-(4,4,5,5-tetramethyl-1,3,2-dioxaborolan-2-yl)pyrimidin-2-amine (1.7 g, 3.3 mmol) and 5-bromo-2,4-dimethylthiazole (0.69 g, 3.6 mmol) in THF (10 mL) and water (2 mL) was degassed and backfilled with $N_2$ (3×). The mixture was stirred at 70° C. for 2 h. The reaction was cooled to room temperature, and extracted with EtOAc (3×20 mL). The combined organic layers were washed with brine (20 mL), dried over anhydrous sodium sulfate, filtered, and concentrated under reduced pressure. The residue was purified by column chromatography on silica (11% ethyl acetate/pet. ether) to afford N,N-bis(2,4-dimethoxybenzyl)-5-(2,4-dimethylthiazol-5-yl)pyrimidin-2-amine as a solid. MS: 507 (M+1). $^1$H NMR (400 MHz, $CDCl_3$) δ 8.36 (s, 2H), 7.05 (d, J=8.3 Hz, 2H), 6.52-6.32 (m, 4H), 4.84 (s, 4H), 3.77 (d, J=12.7 Hz, 12H), 2.67 (s, 3H), 2.41 (s, 3H).

Step 5: A mixture of N,N-bis(2,4-dimethoxybenzyl)-5-(2,4-dimethylthiazol-5-yl)pyrimidin-2-amine (1.1 g, 2.2 mmol) in DCM (10 mL) and TFA (10 mL) was stirred at 40° C. for 3 h. The reaction was cooled to room temperature and treated with water. The mixture was extracted with EtOAc (3×20 mL). The combined organic layers were washed with brine (20 mL), dried over anhydrous sodium sulfate, filtered, and concentrated under reduced pressure. The residue was purified by column chromatography on silica (100% ethyl acetate/pet. ether) to afford 5-(2,4-dimethylthiazol-5-yl)pyrimidin-2-amine as a solid. MS: 207 (M+1). $^1$H NMR (500 MHz, $CDCl_3$) δ 8.33 (s, 2H), 2.69 (s, 3H), 2.40 (s, 3H).

Step 6: A mixture of 3-bromo-2-oxopropanoic acid (146 mg, 0.873 mmol) and 5-(2,4-dimethylthiazol-5-yl)pyrimidin-2-amine (150 mg, 0.727 mmol) in dioxane (10 mL) was stirred at 80° C. for 2 h. The mixture was cooled to room temperature and concentrated under reduced pressure. The residue was purified by reverse phase HPLC (ACN/water with 0.1% TFA modifier) to afford 6-(2,4-dimethylthiazol-5-yl)imidazo[1,2-a]pyrimidine-2-carboxylic acid as a solid. MS: 275 (M+1).

TABLE 8

The following intermediate was prepared using a similar procedure as Intermediate 44.

| Int. # | Structure | Compound Name | Exact Mass (M+1) |
|---|---|---|---|
| 45 | 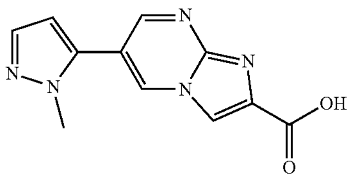 [SMILES: Cn1nccc1-c1cnc2nc(C(=O)O)cn2c1] | 6-(1-methyl-1H-pyrazol-5-yl)imidazo[1,2-a]pyrimidine-2-carboxylic acid | 244 |

Intermediate 46: 6-(1-cyano-2,2-dimethylcyclopropyl)imidazo[1,2-a]pyrimidine-2-carboxylic acid

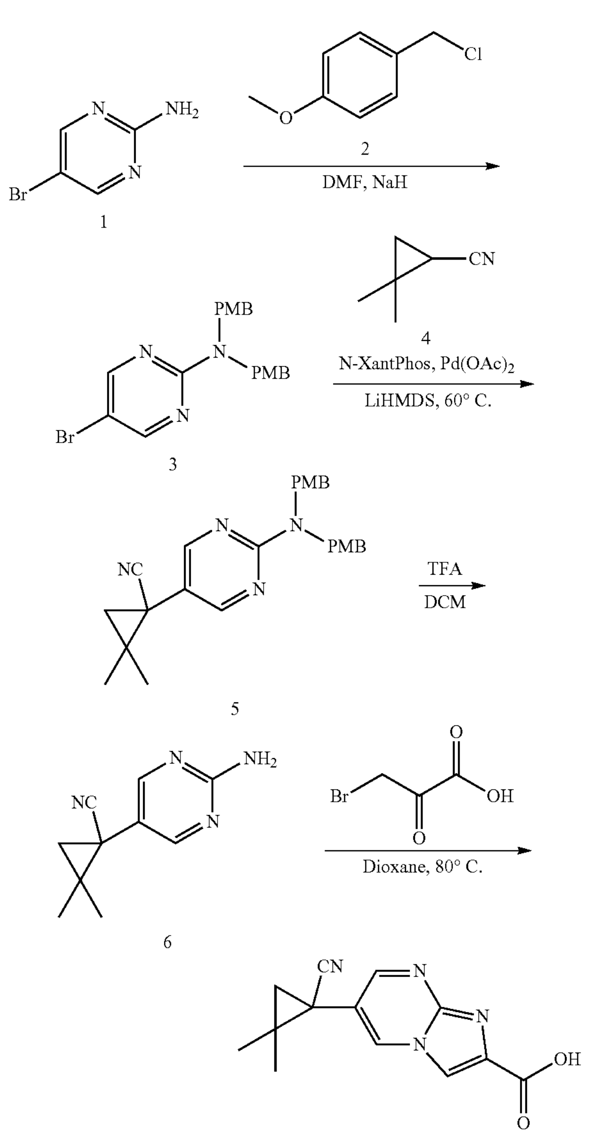

Intermediate 46

Step 1: To a mixture of 5-bromopyrimidin-2-amine (10 g, 57.5 mmol) in DMF (20 mL) was added NaH (5.75 g, 144 mmol). The mixture was stirred for 0.5 h at room temperature, and then 1-(chloromethyl)-4-methoxybenzene (19.8 g, 126 mmol) was added. The mixture was stirred at room temperature for 0.5 h. The reaction was quenched with water (100 mL), extracted with EtOAc (100 mL), and the organic layer was dried over anhydrous sodium sulfate, filtered, and concentrated under reduced pressure. The residue was purified by column chromatography on silica (7% ethyl acetate/pet. ether) to afford 5-bromo-N,N-bis(4-methoxybenzyl)pyrimidin-2-amine as an oil. MS: 414 and 416 (M+1).

Step 2: A mixture of N-XantPhos (1.6 g, 2.9 mmol), 2,2-dimethylcyclopropanecarbonitrile (2.8 g, 29 mmol), 5-bromo-N,N-bis(4-methoxybenzyl)pyrimidin-2-amine (8 g, 19 mmol), and $Pd(OAc)_2$ (0.65 g, 2.9 mmol) was evacuated and refilled with $N_2$ (3×). To the stirring mixture of solids was added THF (30 mL) and methoxycyclopentane (30 mL). The mixture was allowed to stir for 5 min before LiHMDS (48 mL, 1 M in THF, 48 mmol) was added dropwise at room temperature. The reaction mixture was heated at 60° C. for 2 h. The mixture was cooled to room temperature and then concentrated under reduced pressure. The residue was purified by column chromatography on silica (15% ethyl acetate/pet. ether) to afford 1-(2-(bis(4-methoxybenzyl)amino)pyrimidin-5-yl)-2,2-dimethylcyclopropanecarbonitrile as an oil. MS: 429 (M+1)

Step 3: A mixture of 1-(2-(bis(4-methoxybenzyl)amino)pyrimidin-5-yl)-2,2-dimethylcyclopropanecarbonitrile (1.4 g, 3.3 mmol) in DCM (15 mL) and TFA (15 mL) was stirred at 40° C. for 10 h. The mixture was cooled to room temperature and poured into $H_2O$ (60 mL). The mixture was basified by the addition of sat. aq. sodium bicarbonate to ~pH 9, then extracted with DCM (3×40 mL). The combined organic layers were dried over sodium sulfate, filtered, and concentrated under reduced pressure. The residue was purified by column chromatography on silica (45% ethyl acetate/pet. ether) to afford 1-(2-aminopyrimidin-5-yl)-2,2-dimethylcyclopropanecarbonitrile as a solid. MS: 189 (M+1). $^1H$ NMR (400 MHz, $CDCl_3$) δ 8.24 (s, 2H), 5.32 (br s, 2H), 1.53 (s, 3H), 1.47 (d, J=5.70 Hz, 1H), 1.37 (d, J=5.26 Hz, 1H), 0.92 (s, 3H).

Step 4: To a solution of 1-(2-aminopyrimidin-5-yl)-2,2-dimethylcyclopropanecarbonitrile (450 mg, 2.39 mmol) in 1,4-dioxane (10 mL) was added 3-bromo-2-oxopropanoic acid (599 mg, 3.59 mmol). The reaction was stirred at 80° C. for 2 h. The mixture was cooled to room temperature and concentrated under reduced pressure to afford 6-(1-cyano-2,2-dimethylcyclopropyl)imidazo[1,2-a]pyrimidine-2-carboxylic acid as a solid, which was used directly in next step without further purification. MS: 257 (M+1).

Intermediate 47: 6-(1-cyanoethyl)imidazo[1,2-a]pyrimidine-2-carboxylic acid

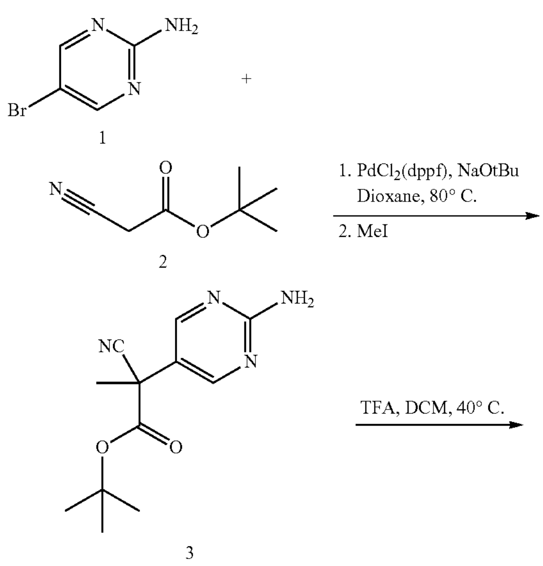

-continued

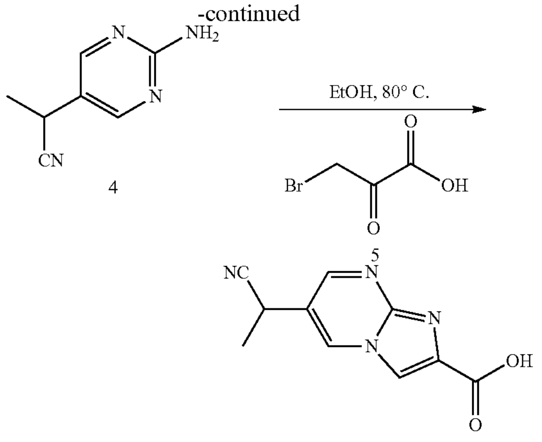

4

5

Intermediate 47

Step 1: A mixture of sodium tert-butoxide (8.8 g, 92 mmol), $PdCl_2$(dppf)-$CH_2Cl_2$ adduct (1.88 g, 2.30 mmol), 5-bromopyrimidin-2-amine (8 g, 46 mmol), and tert-butyl 2-cyanoacetate (7.14 g, 50.6 mmol) in 1,4-dioxane (100 mL) was evacuated and backfilled with $N_2$ (3×). The reaction was heated at 80° C. for 12 h. The mixture was cooled to room temperature, and then MeI (9.79 mL, 157 mmol) was added. The reaction was stirred at room temperature for 1 h. The mixture was concentrated under reduced pressure. The residue was diluted with brine (200 mL) and stirred at room temperature for 20 min. The mixture was filtered, and the filtrate was concentrated under reduced pressure. The residue was diluted with pet. ether/EtOAc (10/3, 130 mL) and stirred at room temperature for 20 min. The mixture was filtered, the filtrate was concentrated under reduced pressure to afford tert-butyl 2-(2-aminopyrimidin-5-yl)-2-cyanopropanoate as a solid, which was used directly in next step without purification. MS: 249 (M+1).

Step 2: A mixture of tert-butyl 2-(2-aminopyrimidin-5-yl)-2-cyanopropanoate (1.2 g, 4.8 mmol) in DCM (10 mL) and TFA (10 mL) was stirred at 40° C. for 12 h. The mixture was cooled to room temperature and concentrated under reduced pressure. The residue was purified by reverse phase HPLC (ACN/water with 0.1% TFA modifier) to afford 2-(2-aminopyrimidin-5-yl)propanenitrile (200 mg) as a solid. MS: 149 (M+1). $^1$H NMR (500 MHz, $CD_3OD$) δ 8.52-8.44 (m, 2H), 4.16 (q, J=7.27 Hz, 1H), 1.64 (d, J=7.17 Hz, 3H).

Step 3: A mixture of 2-(2-aminopyrimidin-5-yl)propanenitrile (100 mg, 0.675 mmol) and 3-bromo-2-oxopropanoic acid (146 mg, 0.877 mmol) in EtOH (3 mL) was stirred at 80° C. for 3 h. The mixture was cooled to room temperature and concentrated under reduced pressure to afford 6-(1-cyanoethyl)imidazo[1,2-a]pyrimidine-2-carboxylic acid as an oil, which was used directly in next step. MS: 217 (M+1).

Intermediate 48: 6-(2-methylcyclopropyl)imidazo[1,2-a]pyrimidine-2-carboxylic acid

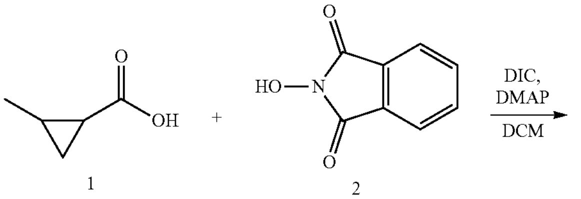

1

2

-continued

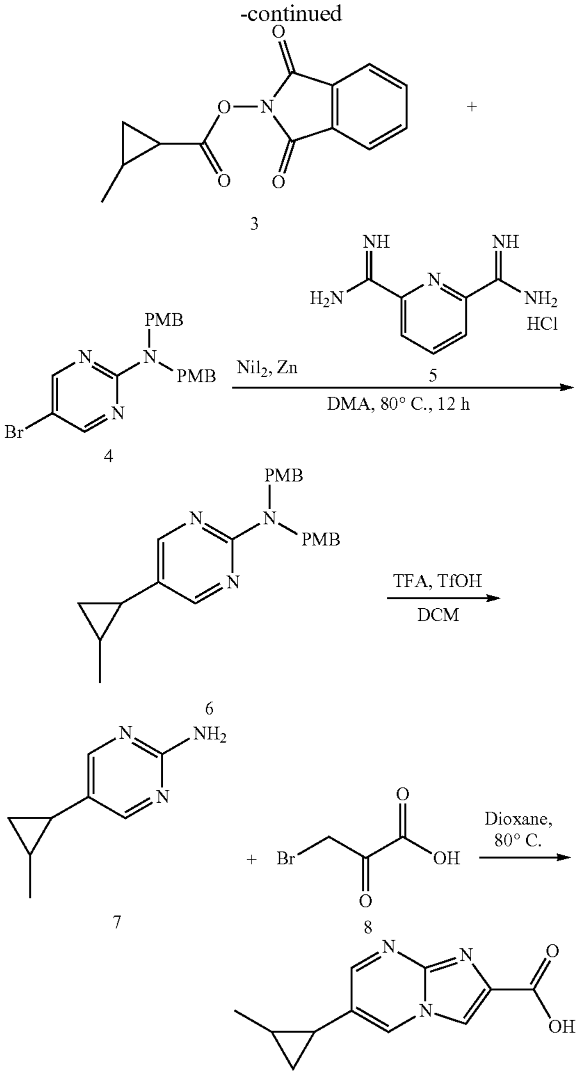

3

4

5

6

7

8

Intermediate 48

Step 1: To a mixture of 2-methylcyclopropanecarboxylic acid (8 g, 80 mmol), 2-hydroxyisoindoline-1,3-dione (13 g, 80 mmol), and DMAP (0.976 g, 7.99 mmol) in anhydrous DCM (200 mL) was added DIC (12.3 mL, 80 mmol) dropwise. The mixture was stirred at room temperature under an $N_2$ atmosphere for 12 h. The reaction was filtered through a pad of Celite® and the pad was washed with DCM (3×60 mL). The filtrate was concentrated under reduced pressure. The residue was purified by column chromatography on silica (25% EtOAc/pet. ether) to afford 1,3-dioxoisoindolin-2-yl-2-methylcyclopropanecarboxylate as an oil. $^1$H NMR (500 MHz, $CDCl_3$) δ 7.90-7.84 (m, 2H), 7.81-7.73 (m, 2H), 1.69-1.57 (m, 2H), 1.41 (td, J=4.52, 8.81 Hz, 1H), 1.27-1.19 (m, 3H), 1.11-0.94 (m, 1H).

Step 2: A suspension of pyridine-2,6-bis(carboximidamide) hydrochloride (0.98 g, 4.9 mmol), nickel(II) iodide (0.76 g, 2.4 mmol), and zinc (3.2 g, 49 mmol) in anhydrous DMA (30 mL) was stirred at room temperature for 10 min. A solution of 1,3-dioxoisoindolin-2-yl-2-methylcyclopropanecarboxylate (3 g, 12.2 mmol) and 5-bromo-N,N-bis(4-methoxybenzyl)pyrimidin-2-amine (5.58 g, 13.5 mmol) in DMA (30 mL) was added, and the resulting mixture was stirred at 80° C. under an atmosphere of $N_2$ for 16 h. The mixture was cooled to room temperature and concentrated under reduced pressure. The residue was purified by column chromatography on silica (40% ethyl acetate/pet. ether) to afford N,N-bis(4-methoxybenzyl)-5-(2-methylcyclopropyl) pyrimidin-2-amine as an oil. MS: 390 (M+1).

Step 3: To a solution of N,N-bis(4-methoxybenzyl)-5-(2-methylcyclopropyl)pyrimidin-2-amine (660 mg, 1.69 mmol) in DCM (8 mL) and TFA (8 mL) was added TfOH (2.54 mg, 0.017 mmol). The mixture was stirred at room temperature for 12 h. The reaction was diluted with water (20 mL) and basified with $NH_3 \cdot H_2O$ to ~pH 10. The aqueous layer was extracted with DCM (3×20 mL) and the combined organic layers were washed with brine (20 mL), dried over anhydrous sodium sulfate, filtered, and concentrated under reduced pressure. The residue was purified by column chromatography on silica (20% ethyl acetate/pet. ether) to afford 5-(2-methylcyclopropyl)pyrimidin-2-amine as an oil. MS: 150 (M+1).

Step 4: A mixture of $MgSO_4$ (242 mg, 2.01 mmol), 3-bromo-2-oxopropanoic acid (168 mg, 1.00 mmol) and 5-(2-methylcyclopropyl)pyrimidin-2-amine (100 mg, 0.670 mmol) in dioxane (5 mL) was stirred at 80° C. for 3 h. The reaction was cooled to room temperature and purified by reverse phase HPLC (ACN/water with 0.1% TFA modifier) to afford 6-(2-methylcyclopropyl)imidazo[1,2-a]pyrimidine-2-carboxylic acid as a solid. MS: 218 (M+1).

Intermediate 49: 6-bromo-7-isopropylimidazo[1,2-a] pyrimidine-2-carboxylic acid

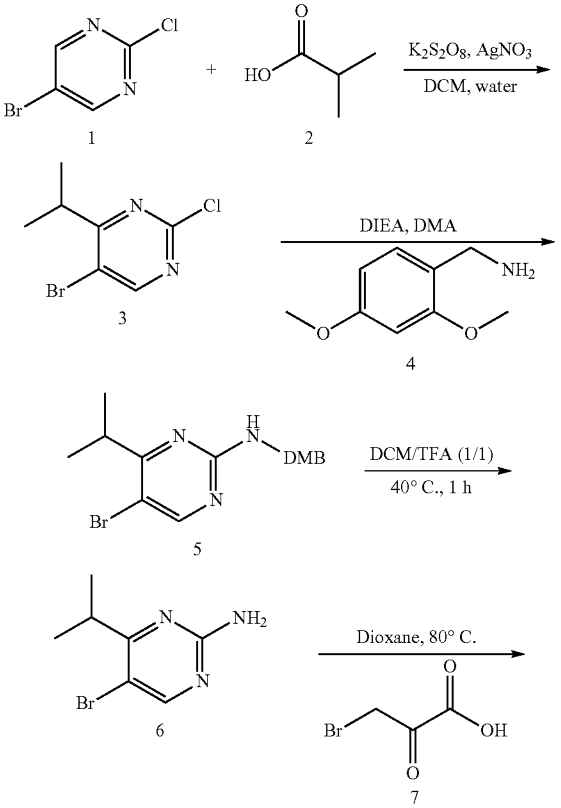

-continued

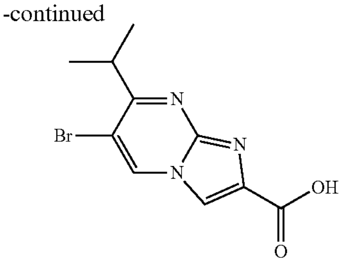

Intermediate 49

Step 1: A mixture of 5-bromo-2-chloropyrimidine (8 g, 41 mmol), isobutyric acid (3.3 g, 37 mmol), silver nitrate (0.646 mL, 16.5 mmol), and potassium persulfate (10 g, 37 mmol) in DCM (200 mL) and water (200 mL) was stirred at room temperature for 12 h. The mixture was concentrated under reduced pressure, and the residue was diluted with EtOAc (200 mL). The mixture was washed with water (200 mL), and the organic layer was dried over anhydrous sodium sulfate, filtered, and concentrated under reduced pressure to afford 5-bromo-2-chloro-4-isopropylpyrimidine as a solid, which was used in the next step without purification. MS: 235 and 237 (M+1).

Step 2: A mixture of DIEA (20 mL, 115 mmol), 5-bromo-2-chloro-4-isopropylpyrimidine (9.0 g, 38 mmol) and (2,4-dimethoxyphenyl)methanamine (8.31 g, 49.7 mmol) dissolved in DMA (180 mL) was heated to 140° C. for 1 h. The reaction was cooled to room temperature, diluted with EtOAc (500 mL), and washed with water (500 mL) and brine (200 mL). The organic layer was dried over anhydrous sodium sulfate, filtered, and concentrated under reduced pressure. The residue was purified by column chromatography on silica (10% ethyl acetate/pet. ether) to afford 5-bromo-N-(2,4-dimethoxybenzyl)-4-isopropylpyrimidin-2-amine as a solid. MS: 366 and 368 (M+1).

Step 3: A solution of 5-bromo-N-(2,4-dimethoxybenzyl)-4-isopropylpyrimidin-2-amine (450 mg, 1.23 mmol) in TFA (5 mL) and DCM (5 mL) was stirred at 40° C. for 1 h. The reaction was cooled to room temperature and concentrated under reduced pressure. The residue was dissolved in DCM (20 mL) and diluted with $NH_3 \cdot H_2O$ (35%, 2 mL). The mixture was concentrated under reduced pressure, and the residue was purified by column chromatography on silica (22% ethyl acetate/pet. ether) to afford 5-bromo-4-isopropylpyrimidin-2-amine as a solid. MS: 216 and 218 (M+1). $^1H$ NMR (400 MHz, $CDCl_3$) δ 8.22 (s, 1H), 5.00 (br s, 2H), 3.31 (td, J=6.80, 13.59 Hz, 1H), 1.20 (d, J=6.58 Hz, 6H).

Step 4: A mixture of 5-bromo-4-isopropylpyrimidin-2-amine (100 mg, 0.463 mmol) and 3-bromo-2-oxopropanoic acid (100 mg, 0.602 mmol) in 1,4-dioxane (3 mL) was stirred at 80° C. for 3 h. The mixture was cooled to room temperature and concentrated under reduced pressure. The residue was purified by reverse phase HPLC (ACN/water with 0.1% TFA modifier) to afford 6-bromo-7-isopropylimidazo[1,2-a]pyrimidine-2-carboxylic acid as a solid. MS: 284 and 286 (M+1).

Intermediate 50: 6-bromo-7-ethylimidazo[1,2-a] pyrimidine-2-carboxylic acid

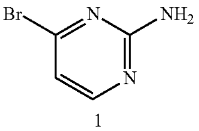

1

+

-continued

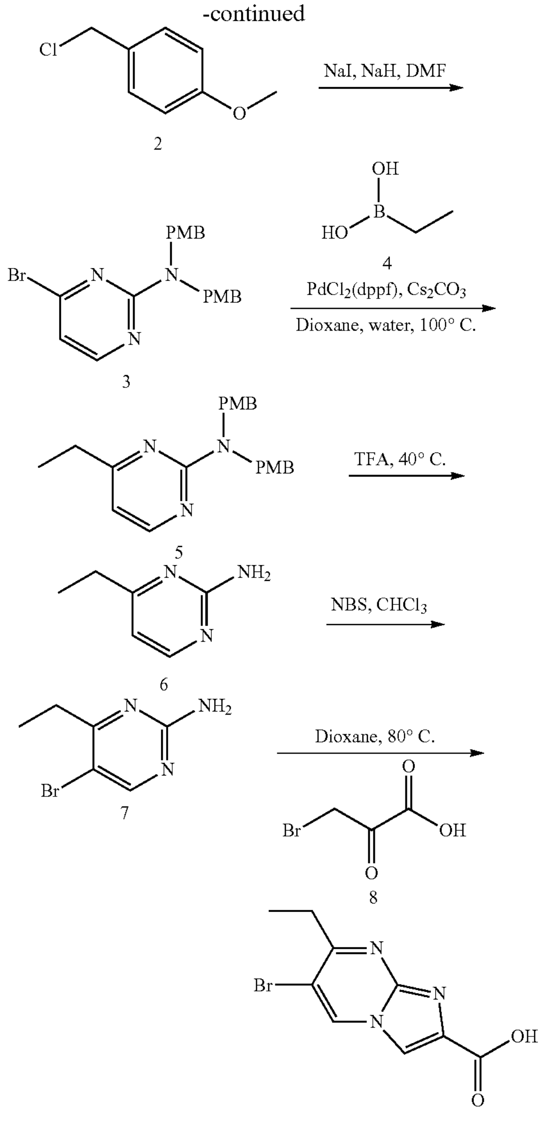

Intermediate 50

Step 1: To a mixture of 4-bromopyrimidin-2-amine (1 g, 5.8 mmol) and sodium iodide (0.086 g, 0.58 mmol) in DMF (20 mL) was added NaH (0.575 g, 14.4 mmol) at 0° C. The mixture was stirred at 0° C. for 0.5 h, and then 1-(chloromethyl)-4-methoxybenzene (1.98 g, 12.6 mmol) was added. The reaction was stirred at room temperature for 30 min. The mixture was quenched with saturated aqueous ammonium chloride solution (100 mL) and extracted with EtOAc (100 mL). The organic layer was dried over anhydrous sodium sulfate, filtered, and concentrated under reduced pressure. The residue was purified by column chromatography on silica (10% ethyl acetate/pet. ether) to afford 4-bromo-N,N-bis(4-methoxybenzyl)pyrimidin-2-amine as an oil. MS: 414 and 416 (M+1).

Step 2: A mixture of 4-bromo-N,N-bis(4-methoxybenzyl) pyrimidin-2-amine (2 g, 4.8 mmol), ethylboronic acid (1.07 g, 14.5 mmol), $PdCl_2$(dppf) (0.71 g, 0.96 mmol), and $Cs_2CO_3$ (3.15 g, 9.65 mmol) in 1,4-dioxane (10 mL) and water (10 mL) was stirred at 100° C. under an atmosphere of $N_2$ for 10 h. The mixture was cooled to room temperature and concentrated under reduced pressure. The residue was purified by column chromatography on silica (10% ethyl acetate/pet. ether) to afford 4-ethyl-N,N-bis(4-methoxybenzyl)pyrimidin-2-amine as an oil. MS: 364 (M+1). $^1$H NMR (500 MHz, $CDCl_3$) δ 8.29 (d, J=5.04 Hz, 1H), 7.30-7.24 (m, 4H), 6.94-6.89 (m, 4H), 6.48 (d, J=5.04 Hz, 1H), 4.86 (s, 4H), 3.90-3.84 (m, 6H), 2.77-2.63 (m, 2H), 1.33 (t, J=7.63 Hz, 3H).

Step 3: A mixture of 4-ethyl-N,N-bis(4-methoxybenzyl) pyrimidin-2-amine (900 mg, 2.48 mmol) in TFA (5 mL) was stirred at 40° C. for 12 h. The mixture was cooled to room temperature and quenched with $NH_3·H_2O$ to ~pH 7. The mixture was concentrated under reduced pressure, and the residue was purified by column chromatography on silica (30-60% ethyl acetate/pet. ether) to afford 4-ethylpyrimidin-2-amine as a solid. MS: 124 (M+1). $^1$H NMR (400 MHz, $CDCl_3$) δ 8.17 (d, J=4.82 Hz, 1H), 6.50 (d, J=5.26 Hz, 1H), 5.04 (br s, 2H), 2.59 (q, J=7.75 Hz, 2H), 1.24 (t, J=7.67 Hz, 3H).

Step 4: To a solution of 4-ethylpyrimidin-2-amine (200 mg, 1.62 mmol) in chloroform (4 mL) was added NBS (318 mg, 1.79 mmol). The mixture was stirred at room temperature for 1 h. The mixture was concentrated under reduced pressure, and the residue was purified by column chromatography on silica (10-80% ethyl acetate/pet. ether) to afford 5-bromo-4-ethylpyrimidin-2-amine as a solid. MS: 202 and 204 (M+1). $^1$H NMR (400 MHz, $CDCl_3$) δ 8.22 (s, 1H), 5.00 (br s, 2H), 2.74 (q, J=7.45 Hz, 2H), 1.23 (t, J=7.67 Hz, 3H).

Step 5: To a solution of 5-bromo-4-ethylpyrimidin-2-amine (100 mg, 0.495 mmol) in 1,4-dioxane (3 mL) was added 3-bromo-2-oxopropanoic acid (99 mg, 0.59 mmol). The reaction was stirred at 80° C. for 15 min. The mixture was cooled to room temperature and concentrated under reduced pressure. The residue was purified by reverse phase HPLC (ACN/water with 0.10% TFA modifier) to afford 6-bromo-7-ethylimidazo[1,2-a]pyrimidine-2-carboxylic acid as a solid. LCSM: 270 and 272 (M+1).

Intermediate 51: 6-bromo-7-cyclopropylimidazo[1,2-a]pyrimidine-2-carboxylic acid

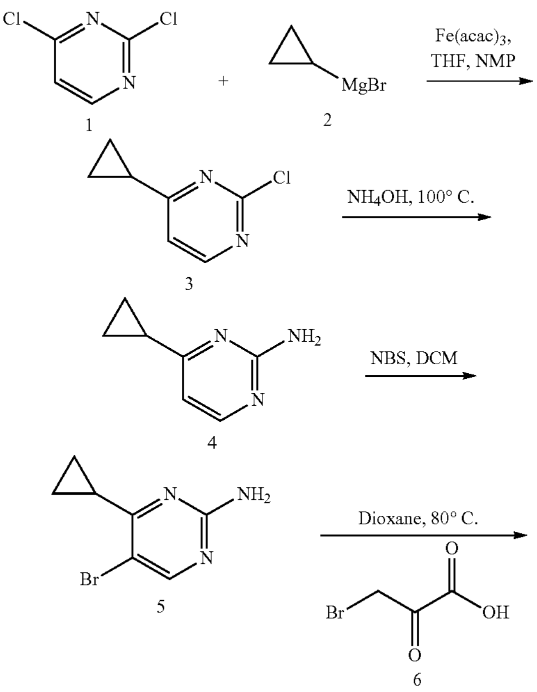

-continued

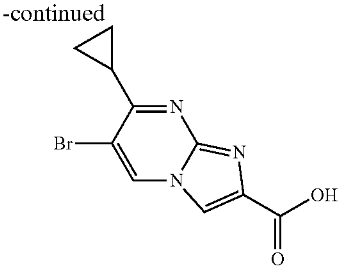

Intermediate 51

Step 1: To a solution of 2,4-dichloropyrimidine (10 g, 67 mmol) and iron(III) acetylacetonate (4.74 g, 13.4 mmol) in THF (60 mL) and NMP (10 mL) at 0° C. was added cyclopropylmagnesium bromide (268 mL, 134 mmol, 0.5 M solution in THF) dropwise via syringe. The resulting mixture was allowed to warm to room temperature and stirred for 1 h. The reaction was quenched with water (500 mL) and extracted with EtOAc (3×200 mL). The combined organic layers were washed with brine (2×150 mL), dried over anhydrous sodium sulfate, filtered, and concentrated under reduced pressure. The residue was purified by column chromatography on silica (5% ethyl acetate/pet. ether gradient) to afford 2-chloro-4-cyclopropylpyrimidine as an oil. MS: 155 (M+1). $^1H$ NMR (400 MHz, $CDCl_3$) δ 8.33 (d, J=4.82 Hz, 1H), 7.06 (d, J=4.82 Hz, 1H), 2.00-1.92 (m, 1H), 1.21-1.16 (m, 2H), 1.15-1.09 (m, 2H).

Step 2: A mixture of 2-chloro-4-cyclopropylpyrimidine (3 g, 19 mmol) and ammonium hydroxide (30 mL, 216 mmol) in a sealed tube was stirred at 100° C. for 5 h. The reaction was cooled to room temperature and concentrated under reduced pressure. The residue was purified by column chromatography on silica (40% ethyl acetate/pet. ether) to afford 4-cyclopropylpyrimidin-2-amine as a solid. MS: 136 (M+1). $^1H$ NMR (400 MHz, $CDCl_3$) δ 8.05 (d, J=5.26 Hz, 1H), 6.44 (d, J=4.82 Hz, 1H), 4.99 (br s, 2H), 1.84-1.77 (m, 1H), 1.04-1.00 (m, 2H), 0.98 (td, J=2.85, 7.89 Hz, 2H).

Step 3: To a solution of 4-cyclopropylpyrimidin-2-amine (1.5 g, 11 mmol) in DCM (15 mL) was added NBS (2.17 g, 12.2 mmol). The reaction was stirred at 25° C. for 1 h. The mixture was concentrated under reduced pressure, and the residue was purified by column chromatography on silica (12% ethyl acetate/pet. ether) to afford 5-bromo-4-cyclopropylpyrimidin-2-amine as a solid. MS: 214 and 216 (M+1). $^1H$ NMR (400 MHz, $CDCl_3$) δ 8.16 (s, 1H), 4.91 (br s, 2H), 2.38-2.29 (m, 1H), 1.13-1.08 (m, 2H), 1.03 (td, J=3.07, 7.89 Hz, 2H).

Step 4: To a solution of 5-bromo-4-cyclopropylpyrimidin-2-amine (1 g, 4.7 mmol) in 1,4-dioxane (15 mL) was added 3-bromo-2-oxopropanoic acid (0.936 g, 5.61 mmol). The reaction was stirred at 80° C. for 15 min. The mixture was cooled to room temperature and concentrated under reduced pressure. The residue was purified by reverse phase HPLC (ACN/water with 0.1% TFA modifier) to afford 6-bromo-7-cyclopropylimidazo[1,2-a]pyrimidine-2-carboxylic acid as a solid. MS: 282 and 284 (M+1). $^1H$ NMR (500 MHz, $CD_3OD$) δ 9.18 (s, 1H), 8.23 (s, 1H), 2.70 (br t, J=6.10 Hz, 1H), 1.30-1.27 (m, 4H).

Intermediate 52: 4-ethyl-5-oxo-2,3,4,5-tetrahydro-1H-1,4-benzodiazepine-8-carboxylic acid

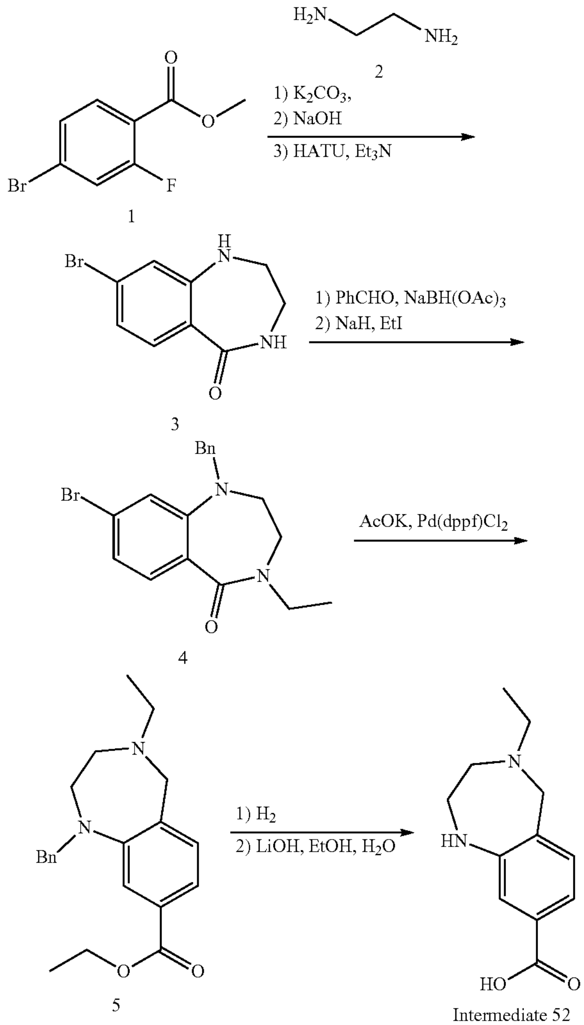

Intermediate 52

Step 1: A solution of ethane-1,2-diamine (2.51 g, 41.7 mmol), methyl 4-bromo-2-fluorobenzoate (5.4 g, 23.2 mmol) and $K_2CO_3$ (3.20 g, 23.2 mmol) in DMF (20 mL) was stirred at 80° C. for 1 h. The mixture was diluted with water (150 mL) and then extracted with EtOAc (150 mL×2). The combined organic layers were washed with brine (100 mL), dried over anhydrous $Na_2SO_4$, filtered, and concentrated under reduced pressure. The residue was purified by column chromatography on silica (0-10% MeOH/EtOAc) to give methyl 2-((2-aminoethyl)amino)-4-bromobenzoate as a solid. MS: 273 and 275 (M+1).

Step 2: To a solution of methyl 2-((2-aminoethyl)amino)-4-bromobenzoate (3.1 g, 11.4 mmol) in MeOH (200 mL) was added NaOH (9.85 g, 246 mmol) at 18° C. The mixture was stirred at 70° C. for 4 h. The mixture was neutralized with conc. HCl to pH 7. The mixture was concentrated to give the crude product 2-((2-aminoethyl)amino)-4-bromobenzoic acid as a solid, which was used directly in the next step. MS: 259 and 261 (M+1).

Step 3: To a solution of 2-((2-aminoethyl)amino)-4-bromobenzoic acid (3 g, 11.6 mmol) and TEA (6.46 mL, 46.3 mmol) in DMF (100 mL) was added HATU (4.84 g, 12.7 mmol) at 18° C. The mixture was stirred at 18° C. for 0.5 h. To the mixture was added water (300 mL) and the mixture was extracted with EtOAc (300 mL×2). The combined organic layers were washed with brine (200 mL), dried over anhydrous $Na_2SO_4$, filtered, and concentrated under reduced pressure to give the crude product. The residue was purified by column chromatography on silica (20-100% EtOAc/pet. ether) to afford 8-bromo-1,2,3,4-tetrahydro-5H-benzo[e][1,4]diazepin-5-one as a solid. MS: 241 and 243 (M+1).

Step 4: To a stirred solution of 8-bromo-1,2,3,4-tetrahydro-5H-benzo[e][1,4]diazepin-5-one (200 mg, 0.830 mmol) in DCE (5 mL) was added AcOH (2 drops), benzaldehyde (0.336 mL, 3.32 mmol) and sodium triacetoxyborohydride (527 mg, 2.49 mmol). The mixture was stirred at 20° C. for 14 h and then stirred at 40° C. for 2 h. To the mixture was added saturated aqueous $NaHCO_3$ (30 mL), and the mixture was extracted with DCM (30 mL×2). The combined organic layers were dried over $Na_2SO_4$, filtered, and concentrated under reduced pressure. The residue was purified by preparative TLC (EtOAc) to afford 1-benzyl-8-bromo-1,2,3,4-tetrahydro-5H-benzo[e][1,4]diazepin-5-one as a solid. MS: 331 and 333 (M+1).

Step 5: To a solution of 1-benzyl-8-bromo-1,2,3,4-tetrahydro-5H-benzo[e][1,4]diazepin-5-one (150 mg, 0.453 mmol) in DMF (1.5 mL) was added iodoethane (0.183 mL, 2.26 mmol) and NaH (23.6 mg, 0.589 mmol, 60 wt %) at −10° C. The mixture was stirred at −10° C. for 20 min. To the mixture was added iodoethane (0.183 mL, 2.26 mmol) and the mixture was stirred at 25° C. for 30 min. To the mixture was added sat. $NH_4Cl$ (20 mL), and the mixture was extracted with EtOAc (15 mL×2). The combined organic layers were washed with brine (20 mL), dried over $Na_2SO_4$ and filtered. The filtrate was concentrated under reduced pressure. The residue was purified by preparative TLC (1:1 petroleum/EtOAc) to afford 1-benzyl-8-bromo-4-ethyl-1,2,3,4-tetrahydro-5H-benzo[e][1,4]diazepin-5-one as a solid. MS: 359 and 361 (M+1).

Step 6: To a solution of 1-benzyl-8-bromo-4-ethyl-1,2,3,4-tetrahydro-5H-benzo[e][1,4]diazepin-5-one (104 mg, 0.289 mmol) in EtOH (5 mL) were added $PdCl_2$(dppf) (21.2 mg, 0.029 mmol) and potassium acetate (85 mg, 0.868 mmol). The mixture was stirred at 80° C. under CO (50 psi) for 16 h. The mixture was concentrated under reduced pressure, and the residue was purified by preparative TLC (2:1 pet. ether: EtOAc) to give ethyl 1-benzyl-4-ethyl-5-oxo-2,3,4,5-tetrahydro-1H-benzo[e][1,4]diazepine-8-carboxylate as an oil. MS: 353 (M+1).

Step 7: To a solution of ethyl 1-benzyl-4-ethyl-5-oxo-2,3,4,5-tetrahydro-1H-benzo[e][1,4]diazepine-8-carboxylate (100 mg, 0.284 mmol) in EtOH (3 mL) was added Pd—C (302 mg, 0.284 mmol) (10 wt %) under a $N_2$ atmosphere. The mixture was degassed and backfilled with H2 (three times). The resulting mixture was stirred under (15 psi) of H2 at 25° C. for 16 h. The mixture was filtered, and the filtrate was concentrated under reduced pressure to give ethyl 4-ethyl-5-oxo-2,3,4,5-tetrahydro-1H-benzo[e][1,4]diazepine-8-carboxylate as a solid, which was used in the next step directly. MS: 263 (M+1).

Step 8: A solution of ethyl 4-ethyl-5-oxo-2,3,4,5-tetrahydro-1H-benzo[e][1,4]diazepine-8-carboxylate (65 mg, 0.248 mmol) and $LiOH \cdot H_2O$ (41.6 mg, 0.991 mmol) in EtOH (3 mL) and water (1 mL) was stirred at 25° C. for 0.5 h. The solvent was removed under reduced pressure to give 4-ethyl-5-oxo-2,3,4,5-tetrahydro-1H-1,4-benzodiazepine-8-carboxylic acid as a solid lithium salt, which was used in the next step directly. MS: 235 (M+1).

TABLE 9

The following intermediate was prepared using a similar procedure as Intermediate 52

| Int. # | Structure | Compound Name | Exact Mass [M + 1] |
|---|---|---|---|
| 53 | 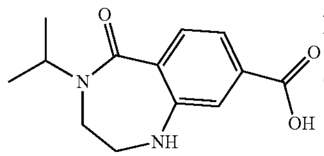 | 4-isopropyl-5-oxo-2,3,4,5-tetrahydro-1H-benzo[e][1,4]diazepine-8-carboxylic acid | 255 |

Intermediate 54: 5-oxo-4-(tetrahydrofuran-3-yl)-2,3,4,5-tetrahydro-1H-1,4-benzodiazepine-8-carboxylic acid

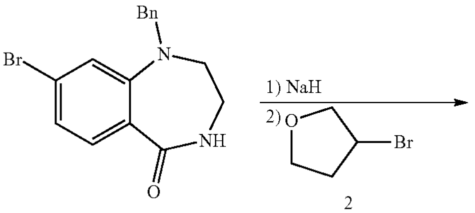

1 2

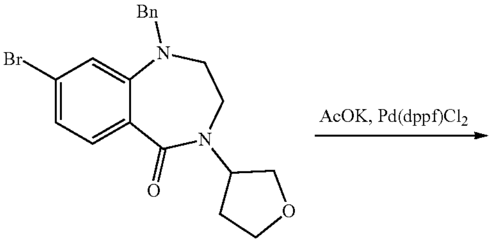

3

-continued

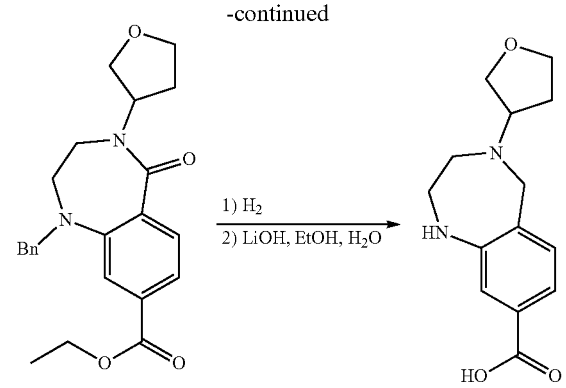

4

Intermediate 54

Step 1: To a solution of 1-benzyl-8-bromo-1,2,3,4-tetrahydro-5H-benzo[e][1,4]diazepin-5-one (330 mg, 0.996 mmol) in DMF (2 mL) was added 3-bromotetrahydrofuran (602 mg, 3.99 mmol) and NaH (59.8 mg, 1.50 mmol) at −10° C. The mixture was stirred at −10° C. for 20 min. The mixture was allowed to warm to 20° C. and stirring continued at 20° C. for 16 h. The mixture was concentrated under reduced pressure. The residue was purified by column chromatography on silica (20-50% EtOAc/pet. ether gradient) to afford 1-benzyl-8-bromo-4-(tetrahydrofuran-3-yl)-1,2,3,4-tetrahydro-5H-benzo[e][1,4]diazepin-5-one as an oil. MS: 401 and 403 (M+1).

Step 2: To a solution of 1-benzyl-8-bromo-4-(tetrahydrofuran-3-yl)-1,2,3,4-tetrahydro-5H-benzo[e][1,4]diazepin-5-one (55 mg, 0.137 mmol) in EtOH (5 mL) was added $Pd(dppf)Cl_2$ (10.03 mg, 0.014 mmol) and potassium acetate (40.4 mg, 0.411 mmol). The mixture was stirred at 80° C. under CO (50 psi) for 16 h. The mixture was concentrated under reduced pressure. The residue was purified by preparative TLC (1:1 pet. ether/EtOAc) to give ethyl 1-benzyl-5-oxo-4-(tetrahydrofuran-3-yl)-2,3,4,5-tetrahydro-1H-benzo[e][1,4]diazepine-8-carboxylate as an oil. MS: 395 (M+1).

Step 3: To a solution of ethyl 1-benzyl-5-oxo-4-(tetrahydrofuran-3-yl)-2,3,4,5-tetrahydro-1H-benzo[e][1,4]diazepine-8-carboxylate (40 mg, 0.101 mmol) in EtOH (3 mL) was added a drop of $NH_3 \cdot H_2O$ and Pd—C (10%, 108 mg, 0.101 mmol) under a $N_2$ atmosphere. The mixture was degassed and backfilled with H2 (three times) and stirred at 20° C. under H2 (15 psi) for 16 h. The mixture was filtered, and the filtrate was concentrated under reduce pressure to afford ethyl 5-oxo-4-(tetrahydrofuran-3-yl)-2,3,4,5-tetrahydro-1H-benzo[e][1,4]diazepine-8-carboxylate as an oil, which was used in the next step without further purification. MS: 305 (M+1).

Step 4: To a solution of ethyl 5-oxo-4-(tetrahydrofuran-3-yl)-2,3,4,5-tetrahydro-1H-benzo[e][1,4]diazepine-8-carboxylate (35 mg, 0.115 mmol) in EtOH (3 mL) and water (1 mL) was added lithium hydroxide hydrate (5.51 mg, 0.230 mmol). The mixture was stirred at 20° C. for 1.5 h. The mixture was concentrated under reduced pressure to afford 5-oxo-4-(tetrahydrofuran-3-yl)-2,3,4,5-tetrahydro-1H-1,4-benzodiazepine-8-carboxylic acid as a solid lithium salt, which was used in the next step without further purification. MS: 277 (M+1).

Intermediate 55: 8-bromo-4-(2,2,2-trifluoroethyl)-1,2,3,4-tetrahydro-5H-benzo[e][1,4]diazepin-5-one

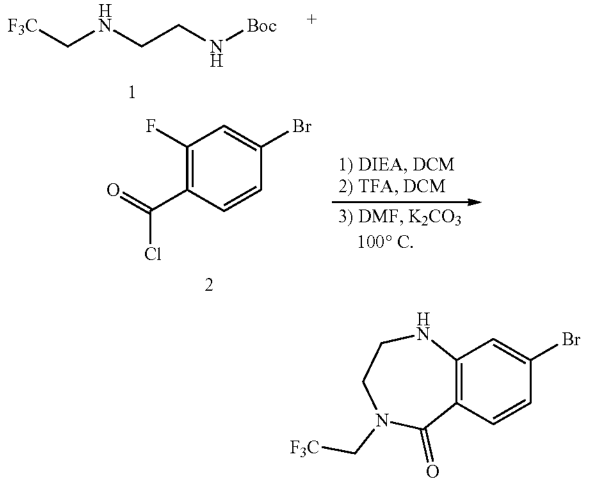

1

2

Intermediate 55

Step 1-3: To a mixture of 4-bromo-2-fluorobenzoyl chloride (530 mg, 2.23 mmol) in DCM (4 mL) was added a solution of tert-butyl (2-((2,2,2-trifluoroethyl)amino)ethyl)carbamate (530 mg, 2.19 mmol) and DIEA (0.420 mL, 2.41 mmol) in DCM (4 mL). The mixture was stirred for 10 min at room temperature. To the reaction was added tert-butyl (2-((2,2,2-trifluoroethyl)amino)ethyl)carbamate (530 mg, 2.19 mmol) and the mixture was stirred overnight at room temperature. The mixture was concentrated under reduced pressure. The residue was dissolved in 1:1 TFA/DCM (5 mL) and allowed to stir for 30 min at room temperature. The mixture was concentrated under reduced pressure. To this crude material was added DMF (4.0 mL) and potassium carbonate (907 mg, 6.56 mmol), and the resultant mixture was heated to 100° C. for 2 h. The reaction was diluted with water (20 mL) and stirred for 1 h at room temperature. A precipitate formed which was filtered, and dried under reduced pressure to provide 8-bromo-4-(2,2,2-trifluoroethyl)-3,4-dihydro-1H-benzo[e][1,4]diazepin-5(2H)-one which was used without further purification. MS: 323 and 325 (M+1).

Intermediate 56: 6-bromoimidazo[1,2-a]pyrimidine-2-carboxylic acid

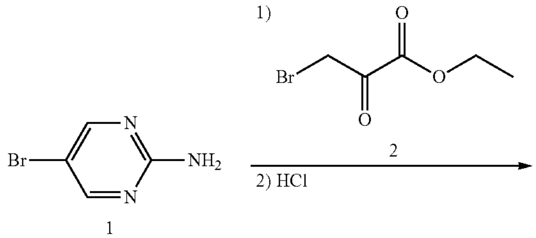

1

-continued

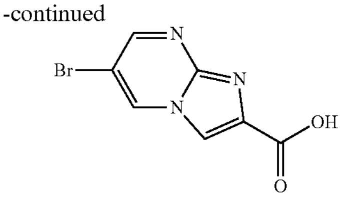

Intermediate 56

Step 1: To a solution of 5-bromopyrimidin-2-amine (3.0 g, 17 mmol) in EtOH (20 mL) was added ethyl 3-bromo-2-oxopropanoate (5.04 g, 25.9 mmol). The reaction was stirred at 80° C. for 3 h. After cooling to room temperature, TEA (2.40 mL, 17.2 mmol) was added. The mixture was stirred at 25° C. for 0.5 h. The mixture was concentrated, and the residue was purified by column chromatography on silica (0-50% ethyl acetate/petroleum ether) to give ethyl 6-bromoimidazo[1,2-a]pyrimidine-2-carboxylate. MS: 270 and 272 (M+1). $^1$H NMR (500 MHz, $CDCl_3$) δ 8.70-8.62 (m, 2H), 8.12 (s, 1H), 4.46 (q, J=5.40 Hz, 2H), 1.43 (t, J=3.60 Hz, 3H) and ethyl 6-bromoimidazo[1,2-a]pyrimidine-3-carboxylate as a solid. MS: 270 and 272 (M+1). $^1$H NMR (500 MHz, $CDCl_3$) δ 9.72 (s, 1H), 8.01 (s, 1H), 8.40 (s, 1H), 4.44 (q, J=5.10 Hz, 2H), 1.44 (t, J=4.40 Hz, 3H).

Step 2: A solution of ethyl 6-bromoimidazo[1,2-a]pyrimidine-2-carboxylate (300 mg, 1.11 mmol) in HCl (4M in water; 8 mL) was stirred at 75° C. for 16 h. The mixture was concentrated to give 6-bromoimidazo[1,2-a]pyrimidine-2-carboxylic acid. MS: 242 and 244 (M+1).

Intermediate 57: 5-(2,2,2-Trifluoroethyl)-4,5,6,7-tetrahydropyrazolo[1,5-a]pyrazine-2-carboxylic acid

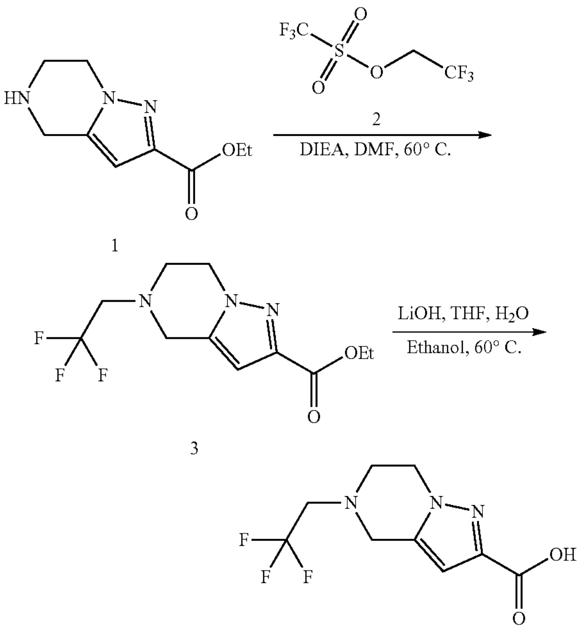

Intermediate 57

Step 1: To a mixture of ethyl 4,5,6,7-tetrahydropyrazolo[1,5-a]pyrazine-2-carboxylate (250 mg, 1.28 mmol) in DMF (5 mL) was added DIEA (447 μL, 2.56 mmol) and 2,2,2-trifluoroethyl trifluoromethanesulfonate (277 μL, 1.92 mmol), and the resultant mixture was allowed to stir overnight at 60° C. The mixture was cooled to room temperature, poured into water (30 mL) and allowed to stir for 10 min. A precipitate formed which was filtered off, washed with water (2×10 mL) and concentrated under reduced pressure to provide crude ethyl 5-(2,2,2-trifluoroethyl)-4,5,6,7-tetrahydropyrazolo[1,5-a]pyrazine-2-carboxylate, which was used without further purification. MS: 278 (M+1).

Step 2: To a mixture of ethyl 5-(2,2,2-trifluoroethyl)-4,5,6,7-tetrahydropyrazolo[1,5-a]pyrazine-2-carboxylate (177 mg, 0.638 mmol) in THF (2.1 mL), water (0.85 mL) and ethanol (0.21 mL) was added lithium hydroxide (76 mg, 3.2 mmol). The mixture was heated to 50° C. for 2 h. The reaction was carefully quenched by slow addition of aq. HCl (3.2 mL, 3.2 mmol, 1 M). The mixture was extracted with EtOAc (2×25 mL). The combined organic layers were washed with brine, dried over anhydrous sodium sulfate, filtered, and concentrated under reduced pressure to provide 5-(2,2,2-trifluoroethyl)-4,5,6,7-tetrahydropyrazolo[1,5-a]pyrazine-2-carboxylic acid. MS: 250 (M+1).

Intermediate 58: 6-Bromo-8-ethoxyimidazo[1,2-a]pyrazine-2-carboxylic acid

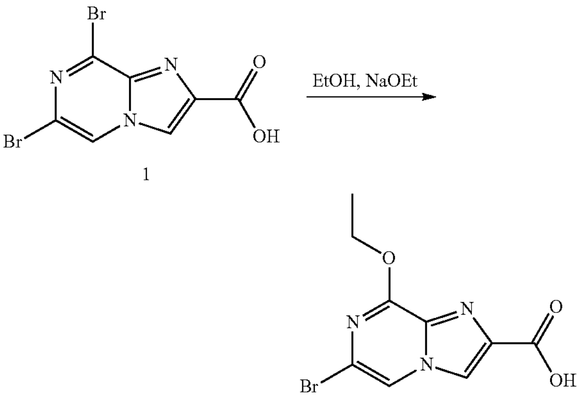

Intermediate 58

To a mixture of 6,8-dibromoimidazo[1,2-a]pyrazine-2-carboxylic acid (110 mg, 0.343 mmol) in THF (1.7 mL) was added sodium ethoxide (223 μL, 0.686 mmol, 3M in EtOH) and the mixture was stirred at 25° C. for 1 h. To the mixture was added $H_2O$ (10 mL) and the resultant precipitate was filtered, and dried under reduced pressure to afford 6-bromo-8-ethoxyimidazo[1,2-a]pyrazine-2-carboxylic acid. MS: 286 and 288 (M+1).

Intermediate 59: 7-aminohexahydroindolizin-3(2H)-one

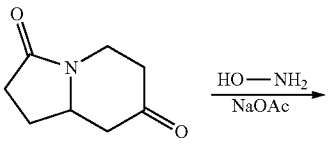

1

-continued

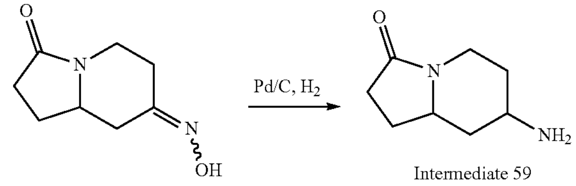

2

Intermediate 59

Step 1: A mixture of hexahydroindolizine-3,7-dione (500 mg, 3.26 mmol), hydroxylamine hydrochloride (247 mg, 3.55 mmol), and sodium acetate (291 mg, 3.55 mmol) in water (14 ml) and EtOH (70 ml) was stirred at rt for 18 h. The reaction mixture was concentrated under reduced pressure to give 7-(hydroxyimino)hexahydroindolizin-3(2H)-one. MS: 169 (M+1).

Step 2: A mixture of 7-(hydroxyimino)hexahydroindolizin-3(2H)-one (0.548 g, 3.26 mmol) and 10% Pd—C (0.347 g, 0.326 mmol) in MeOH (70.9 ml) was stirred under a hydrogen atmosphere (balloon) overnight. The mixture was filtered through Celite® and the filtrate was concentrated under reduced pressure to give racemic 7-aminohexahydroindolizin-3(2H)-one. $^1$H NMR ($CD_3OD$, 500 MHz): δ 4.10-4.00 (m, 1H), 3.74-5.58 (m, 1H), 3.02-2.85 (m, 1H), 2.77-2.71 (m, 1H), 2.50-2.34 (m, 2H), 2.32-2.21 (m, 1H), 2.15-2.06 (m, 1H), 2.03-1.87 (m, 1H), 1.69-1.62 (m, 1H), 1.29-0.99 (m, 2H).

Intermediate 60: 2-((1-acetylpiperidin-4-yl)amino)-5-methoxyisonicotinic acid

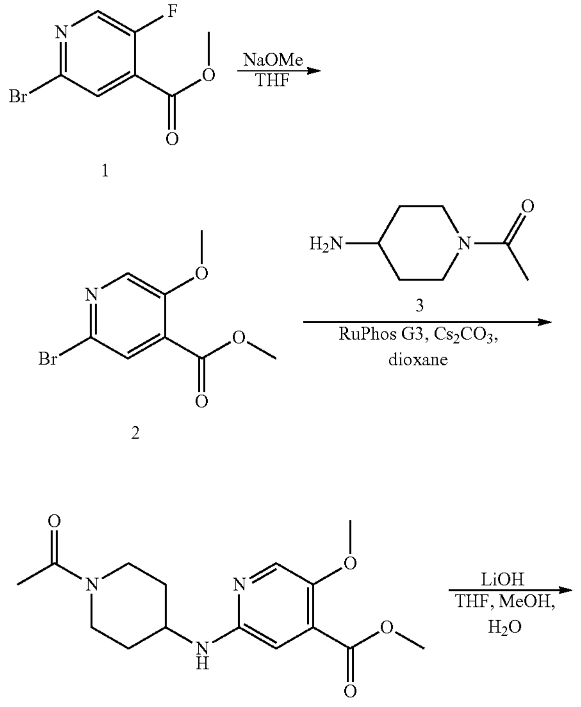

-continued

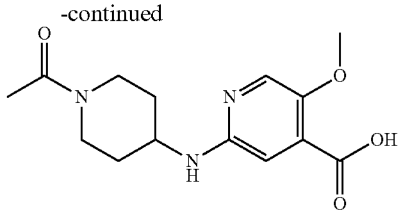

Intermediate 60

Step 1: To a solution of methyl 2-bromo-5-fluoroisonicotinate (1.54 g, 6.56 mmol) in THF (40 mL) was added sodium methoxide (30% wt in methanol, 1.09 mL, 5.90 mmol) dropwise. The mixture was stirred at 25° C. for 1.5 h. To the mixture were added water (50 mL) and EtOAc (100 mL). The organic layers were washed with brine, dried ($Na_2SO_4$), filtered, and concentrated under reduced pressure. The residue was purified by column chromatography on silica (0-30% ethyl acetate/hexane) to give methyl 2-bromo-5-methoxyisonicotinate. MS: 246 and 248 (M+1).

Step 2: Methyl 2-bromo-5-methoxyisonicotinate (250 mg, 1.02 mmol), 1-(4-aminopiperidin-1-yl)ethanone (173 mg, 1.22 mmol), cesium carbonate (662 mg, 2.03 mmol), and RuPhos G3 (85 mg, 0.10 mmol) were added to a 20 mL microwave tube. The mixture was evacuated under nitrogen and charged with dioxane (6 mL). The reaction mixture was allowed to stir at 100° C. for 18 h. The reaction was cooled to room temperature and then diluted with ethyl acetate (25 mL), washed with water (10 mL×2), dried over anhydrous magnesium sulfate, filtered, and concentrated under reduced pressure. The residue was purified by column chromatography on silica (methanol/DCM) to afford methyl 2-((1-acetylpiperidin-4-yl)amino)-5-methoxyisonicotinate. MS: 308 (M+1).

Step 3: To a mixture of methyl 2-((1-acetylpiperidin-4-yl) amino)-5-methoxyisonicotinate (82 mg, 0.27 mmol) in THF (111 μL), MeOH (1.1 mL), and water (111 μL) was added lithium hydroxide (31.9 mg, 1.33 mmol). The reaction mixture was allowed to stir at 20° C. for 2 h. The mixture was concentrated under reduced pressure. The residue was diluted with water and the pH of the mixture was adjusted to pH ~6 using aq. 1M HCl. The solution was lyophilized to afford 2-((1-acetylpiperidin-4-yl)amino)-5-methoxyisonicotinic acid. MS: 294 (M+1)

Intermediate 61: (2-bromo-5-fluoropyridin-4-yl)((3S,4S)-4-(3,4-dihydroisoquinolin-2(1H)-yl)-3-hydroxypiperidin-1-yl)methanone

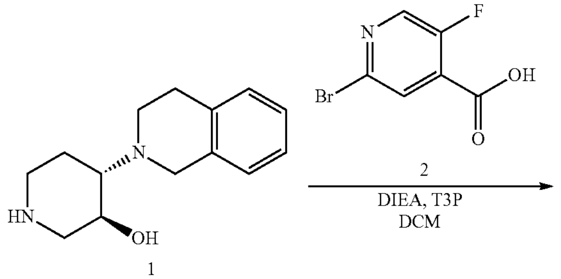

-continued

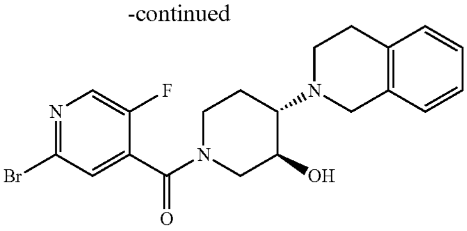

Intermediate 61

To a solution of 2-bromo-5-fluoroisonicotinic acid (538 mg, 2.44 mmol) and (3S,4S)-4-(3,4-dihydroisoquinolin-2(1H)-yl)piperidin-3-ol (568 mg, 2.44 mmol) in DCM (11 mL) and DMF (5 mL) at 0° C. was added DIEA (1.7 mL, 9.8 mmol) and T3P (1.7 mL, 2.9 mmol, 50% in DMF). The mixture was stirred at room temperature for 1 h. The reaction was quenched with saturated aqueous $NaHCO_3$ (25 mL), and extracted with EtOAc (50 mL×2). The combined organic layers were washed with brine, dried over anhydrous sodium sulfate, filtered, and concentrated under reduced pressure. The residue was purified by column chromatography on silica (0-60% 3:1 EtOAc:EtOH in hexanes) to give (2-bromo-5-fluoropyridin-4-yl)((3S,4S)-4-(3,4-dihydroisoquinolin-2(1H)-yl)-3-hydroxypiperidin-1-yl)methanone. MS: 434 and 436 (M+1).

Intermediate 62: (2-bromo-5-ethoxypyridin-4-yl)((3S,4S)-4-(3,4-dihydroisoquinolin-2(1H)-yl)-3-hydroxypiperidin-1-yl)methanone

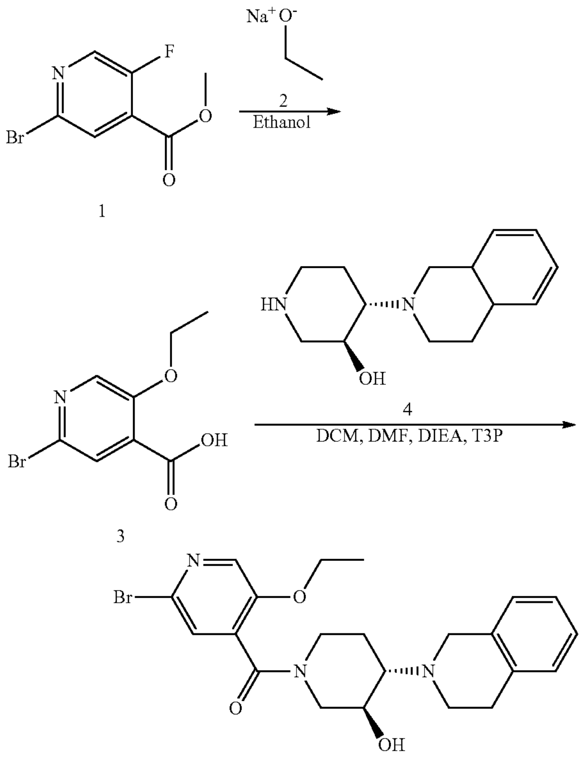

Intermediate 62

Step 1: To a solution of methyl 2-bromo-5-fluoroisonicotinate (227 mg, 0.97 mmol) in ethanol (2 mL) was added sodium ethoxide (21 wt % in ethanol, 1.81 mL, 4.85 mmol). The mixture was stirred at room temperature for 15 min, and the reaction mixture was diluted with water (5 mL). The resulting mixture was washed with ethyl acetate (10 mL). The aqueous layer was acidified to pH-6 by addition of aq. 1N HCl. The resultant precipitate was filtered, washed with water (20 mL), and dried to afford 2-bromo-5-ethoxyisonicotinic acid. MS: 246 and 248 (M+1).

Step 2: (2-bromo-5-ethoxypyridin-4-yl)((3S,4S)-4-(3,4-dihydroisoquinolin-2(1H)-yl)-3-hydroxypiperidin-1-yl)methanone was made using standard T3P coupling of 2-bromo-5-ethoxyisonicotinic acid with (3S,4S)-4-(3,4-dihydroisoquinolin-2(1H)-yl)piperidin-3-ol. MS: 460 and 462 (M+1).

Intermediate 63: 7-bromo-6-fluoro-4-methyl-1,4-dihydro-2H-benzo[d][1,3]oxazin-2-one

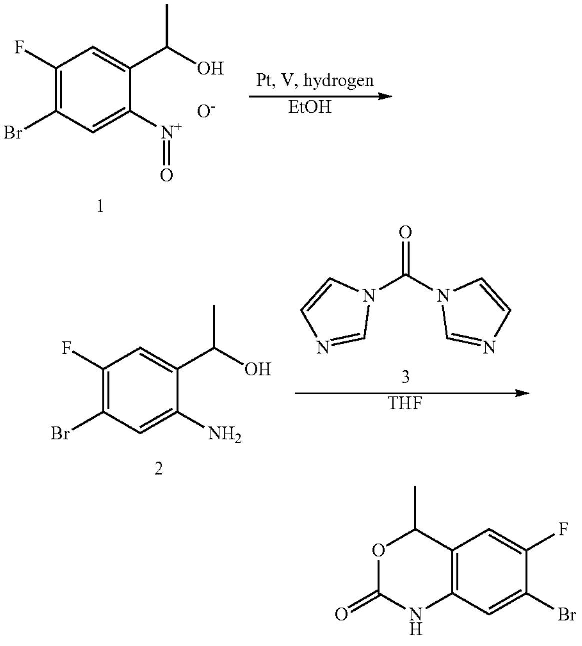

Intermediate 63

Step 1: To a solution of 1-(4-bromo-5-fluoro-2-nitrophenyl)ethanol (1.0 g, 3.8 mmol) in ethanol (18.9 ml) under an atmosphere of nitrogen was added platinum and vanadium on activated carbon (0.932 g, 3.79 mmol). Hydrogen gas was bubbled through, and the reaction was allowed to stir at room temperature for 2 h. The catalyst was filtered off using a Celite® pad, and the solvent was removed under reduced pressure to afford 1-(2-amino-4-bromo-5-fluorophenyl)ethanol. MS: 234 and 236 (M+1).

Step 2: To a solution of 1-(2-amino-4-bromo-5-fluorophenyl)ethanol (0.88 g, 3.8 mmol) in THF (18.8 ml) was added 1,1'-carbonyldiimidazole (0.732 g, 4.51 mmol) at room temperature. The reaction was allowed to stir for 18 h at 60° C. The mixture was concentrated under reduced pressure, and the residue was dissolved in EtOAc and washed with 1M HCl and brine, then dried over sodium sulfate. After removal of the solvent the residue was crystallized from DCM and hexane to afford 7-bromo-6-fluoro-4-methyl-1,4-dihydro-2H-benzo[d][1,3]oxazin-2-one. MS: 260 and 262 (M+1).

Intermediate 64: (R or S)-7-bromo-4-methyl-1A-dihydro-2H-benzo[d][1,3]oxazin-2-one (isomer 1, first eluting Intermediate 65: (S or R)-7-bromo-4-methyl-1,4-dihydro-2H-benzo[d][1,3]oxazin-2-one (isomer 2, second eluting

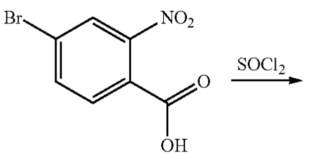

1

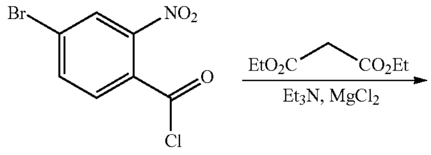

2

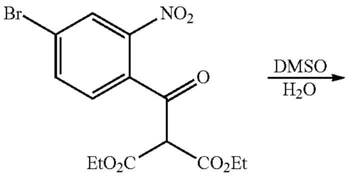

3

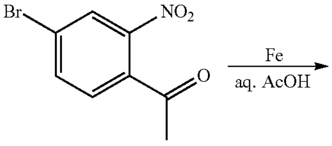

4

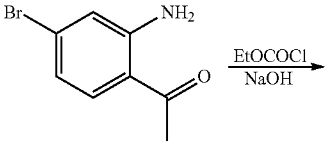

5

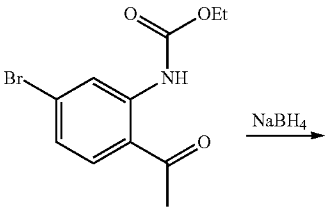

6

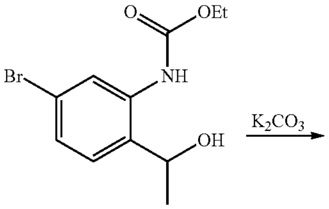

7

-continued

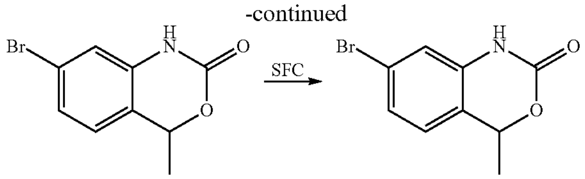

8

Intermediate 64
(first eluting)

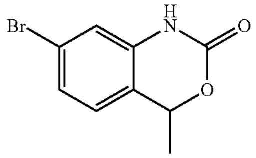

Intermediate 65
(second eluting)

Step 1: A solution of 4-bromo-2-nitrobenzoic acid (140 g, 0.56 mol) in thionyl chloride (1.4 L) was heated to 80° C. for 14 h. The reaction mixture was brought to room temperature and concentrated under reduced pressure to afford 4-bromo-2-nitrobenzoyl chloride as a liquid, which was used without further purification.

Step 2: A solution of diethyl malonate (102 g, 0.63 mol) in toluene (1.4 L) was charged with triethylamine (185 mL, 1.32 mol) and magnesium chloride (16.0 g, 0.2656 mol). A solution of 4-bromo-2-nitrobenzoyl chloride (140 g, 0.531 mol) in toluene (500 mL) was added dropwise to the reaction mixture over 30 min at room temperature, and the reaction mixture was stirred for 12 h. The reaction mixture was quenched with water (1.0 L) and extracted with EtOAc (3×1.5 L). The combined organic layers were washed with brine (1.0 L), dried over anhydrous sodium sulfate, and concentrated under reduced pressure to afford diethyl 2-(4-bromo-2-nitrobenzoyl)malonate, which was used in the next step without further purification.

Step 3: A solution of diethyl 2-(4-bromo-2-nitrobenzoyl) malonate (280 g, 0.72 mol) in a mixture of DMSO (1.5 L) and water (50 mL) was heated to 140° C. for 14 h. The reaction mixture was then cooled to room temperature, diluted with water (3.0 L), and extracted with EtOAc (3×2.0 L). The combined organic layers were washed with water (3×2.0 L) and brine (1.0 L), dried over anhydrous sodium sulfate, and concentrated under reduced pressure to afford 1-(4-bromo-2-nitrophenyl)ethan-1-one, which was used without further purification. $^1H$ NMR (400 MHz, $CDCl_3$) δ 8.23 (d, J=2.0 Hz, 1H), 7.85 (dd, J=8.0 Hz, 1.6 Hz, 1H), 7.34 (d, J=6.4 Hz, 1H), 2.54 (s, 3H).

Step 4: A solution of 1-(4-bromo-2-nitrophenyl)ethan-1-one (130 g, 0.53 mol) in a mixture of acetic acid (780 mL) and water (2.6 L) was charged with iron powder (148 g, 2.66 mol), and the reaction mixture was heated to 120° C. for 12 h. The reaction mixture was cooled to room temperature and filtered through a pad of diatomaceous earth. The filtrate was extracted with EtOAc (3×1.5 L). The combined organic layers were washed with water (2.0 L) and brine (2.0 L), dried over anhydrous sodium sulfate, and concentrated under reduced pressure to afford 1-(2-amino-4-bromophenyl)ethan-1-one, which was used without further purification.

Step 5: A solution of 1-(2-amino-4-bromophenyl)ethan-1-one (90.0 g, 0.51 mol) and ethyl chloroformate (74 mL, 0.77 mol) in THF (500 mL) was charged with 20% aqueous NaOH (450 mL) dropwise over 40 min at −10° C. The reaction mixture was stirred at room temperature for 4 days.

The reaction mixture was then charged with water (1.5 L) and extracted with EtOAc (3×1.5 L). The combined organic layers were washed with brine (1.0 L), dried over anhydrous sodium sulfate, and concentrated under reduced pressure. The residue was purified by silica-gel chromatography to afford ethyl (2-acetyl-5-bromophenyl)carbamate. $^1$H NMR (400 MHz, $CDCl_3$) δ 8.76 (d, J=2.0 Hz, 1H), 7.72 (d, J=8.4 Hz, 1H), 7.19 (dd, J=8.4 Hz, 2.0 Hz, 1H), 4.26-4.21 (m, 2H), 2.63 (s, 3H) 1.35 (t, J=7.0 Hz, 3H).

Step 6: A solution of ethyl (2-acetyl-5-bromophenyl)carbamate (109 g, 0.38 mol) in THF (1.0 L) was charged with sodium borohydride (13.7 g, 0.38 mol) portion-wise over 30 min at −10° C. The reaction mixture was stirred at room temperature for 16 h. The reaction mixture was then quenched with saturated aqueous $NaHCO_3$ (250 mL) and extracted with EtOAc (3×1.0 L). The combined organic layers were washed with water (1.0 L) and brine (1.0 L), dried over anhydrous sodium sulfate, and concentrated under reduced pressure to afford ethyl (5-bromo-2-(1-hydroxyethyl)phenyl)carbamate, which was used without further purification.

Step 7: A solution of ethyl (5-bromo-2-(1-hydroxyethyl) phenyl)carbamate (90.0 g, 0.31 mol) in MeOH (900 mL) was charged with a solution of $K_2CO_3$ (86.0 g, 0.624) in water (200 mL) at 0° C. The reaction mixture was stirred at room temperature for 16 h. The reaction mixture was concentrated under reduced pressure, and the residue was diluted with EtOAc (2.0 L). The organic phase was washed with water (1.0 L) and brine (1.0 L), dried over anhydrous sodium sulfate, and concentrated under reduced pressure to afford 7-bromo-4-methyl-1,4-dihydro-2H-benzo[d][1,3]oxazin-2-one. $^1$H NMR (300 MHz, DMSO-$d_6$) δ 10.30 (s, 1H), 7.23-7.04 (m, 3H), 5.52-5.46 (m, 1H), 1.55 (d, J=6.6 Hz, 3H). MS: 242 and 244 (M+1).

Step 8: Preparative resolution of 7-bromo-4-methyl-1,4-dihydro-2H-benzo[d][1,3]oxazin-2-one was performed using supercritical fluid chromatography AS-H column 60% carbon dioxide and 40% methanol with 0.25% dimethylethyl amine as the mobile phase, 70 m/min total flow rate to afford: (R or S)-7-bromo-4-methyl-1,4-dihydro-2H-benzo[d][1,3]oxazin-2-one (isomer 1, first eluting). MS: 242 and 244 (M+1) and (S or R)-7-bromo-4-methyl-1,4-dihydro-2H-benzo[d][1,3]oxazin-2-one (isomer 2, second eluting). MS: 242 and 244 (M+1).

Intermediate 66: 2-Oxo-1-(2,2,2-trifluoroethyl)-1,2-dihydropyridine-4-carboxylic acid

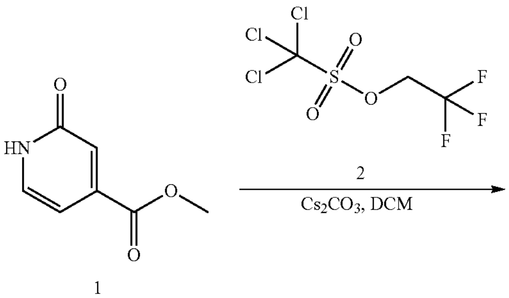

1

-continued

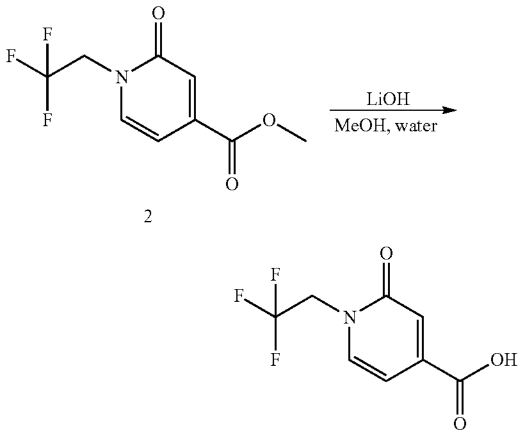

2

Intermediate 66

Step 1: To a solution of methyl 2-hydroxyisonicotinate (150 mg, 0.980 mmol) in DCM (3 mL) was added $Cs_2CO_3$ (638 mg, 1.96 mmol). The reaction mixture was stirred for 10 min at 60° C. To the mixture was added 2,2,2-trifluoroethyl trichloromethanesulfonate (303 mg, 1.08 mmol) and the reaction mixture was stirred at 30° C. for 16 h. The reaction was concentrated under reduced pressure. To the residue was added water (30 mL) and the mixture was extracted with EtOAc (15 mL×2). The combined organic layers were washed with brine (15 mL), dried ($Na_2SO_4$), filtered, and concentrated under reduced pressure. The residue was purified by preparative TLC (EtOAc) to give methyl 2-oxo-1-(2,2,2-trifluoroethyl)-1,2-dihydropyridine-4-carboxylate. MS: 236 (M+1). $^1$H NMR (400 MHz, $CDCl_3$) δ 7.26 (d, J=7.3 Hz, 1H), 7.23-7.15 (m, 1H), 6.65 (dd, J=7.3, 1.8 Hz, 1H), 4.56 (q, J=8.6 Hz, 2H), 3.86 (s, 3H).

Step 2: To a solution of methyl 2-oxo-1-(2,2,2-trifluoroethyl)-1,2-dihydropyridine-4-carboxylate (280 mg, 1.19 mmol) in MeOH (3 mL) and water (1 mL) was added LiOH (57.0 mg, 2.38 mmol) at 15° C. The mixture was stirred at 15° C. for 1 h. The mixture was concentrated under reduced pressure. To the residue was added water (30 mL), and the pH of the mixture was adjusted to pH (2-4) with HCl (1 M). The mixture was extracted with EtOAc (30 mL×2). The organic layers were combined, dried over $Na_2SO_4$, filtered, and concentrated under reduced pressure to afford 2-oxo-1-(2,2,2-trifluoroethyl)-1,2-dihydropyridine-4-carboxylic acid. MS: 222 (M+1). $^1$H NMR (400 MHz, $CD_3OD$) δ 7.71 (d, J=7.3 Hz, 1H), 7.14 (d, J=1.1 Hz, 1H), 6.81 (dd, J=7.2, 1.9 Hz, 1H), 4.84 (q, J=8.8 Hz, 2H).

Intermediate 67: 2-((1-Acetylpiperidin-4-yl)amino)-3-fluoroisonicotinic acid

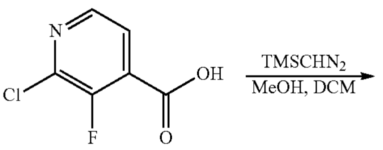

1

-continued

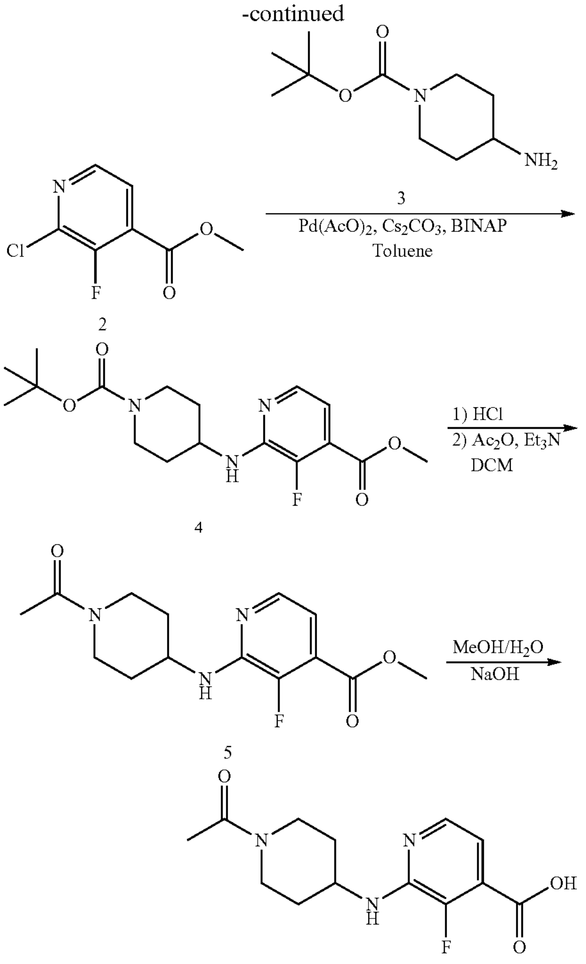

Intermediate 67

Step 1: A suspension of 2-chloro-3-fluoroisonicotinic acid (5.0 g, 29 mmol) in MeOH (18 mL) and DCM (50 mL) at 0° C. was treated with (diazomethyl)trimethylsilane (22.8 mL, 45.6 mmol) via drop-wise addition. The reaction was stirred at 15° C. for 5 h. The reaction was quenched with AcOH (2 mL) and concentrated under reduced pressure. The residue was purified by column chromatography on silica (0-50% EtOAc/petroleum ether) to give methyl 2-chloro-3-fluoroisonicotinate. MS: 190 (M+1). $^1$H NMR (400 MHz, $CDCl_3$) δ 8.32 (d, J=4.89 Hz, 1H), 7.72 (t, J=4.89 Hz, 1H), 4.00 (s, 3H).

Step 2: To a solution of tert-butyl 4-aminopiperidine-1-carboxylate (1.27 g, 6.33 mmol) in toluene (40 mL) was added palladium(II) acetate (0.118 g, 0.528 mmol), $Cs_2CO_3$ (5.16 g, 15.8 mmol), 2,2'-bis(diphenylphosphino)-1,1'-binaphthalene (0.328 g, 0.528 mmol) and methyl 2-chloro-3-fluoroisonicotinate (1.0 g, 5.3 mmol) at 15° C. under $N_2$ (degassed and backfilled with $N_2$ three times). The reaction mixture was stirred at 100° C. for 10 h. The reaction was concentrated under reduced pressure. To the mixture was added water (100 mL), and the mixture was extracted with EtOAc (50 mL×3). The combined organic layers were dried over anhydrous $Na_2SO_4$, filtered, and the filtrate was concentrated under reduced pressure. The residue was purified by column chromatography on silica (13% ethyl acetate/petroleum ether) to give methyl 2-((1-(tert-butoxycarbonyl)piperidin-4-yl)amino)-3-fluoroisonicotinate. MS: 354 (M+1).

Step 3: A mixture of methyl 2-((1-(tert-butoxycarbonyl)piperidin-4-yl)amino)-3-fluoroisonicotinate (1.6 g, 4.5 mmol) in HCl (4M in MeOH, 30 mL) was stirred at 15° C. for 1 h. The mixture was concentrated under reduced pressure to give methyl 3-fluoro-2-(piperidin-4-ylamino)isonicotinate which was used directly in next step. MS: 254 (M+1).

Step 4: To a solution of methyl 3-fluoro-2-(piperidin-4-ylamino)isonicotinate (1.2 g, 4.7 mmol) and TEA (1.98 mL, 14.2 mmol) in DCM (20 mL) was added acetic anhydride (0.493 mL, 5.21 mmol) at 0° C. The resulting mixture was stirred at 0° C. for 0.5 h. The mixture was concentrated under reduced pressure. The residue was purified by column chromatography on silica (40-50% ethyl acetate/petroleum ether) to give methyl 2-((1-acetylpiperidin-4-yl)amino)-3-fluoroisonicotinate. MS: 296 (M+1). $^1$H NMR (400 MHz, $CDCl_3$) δ 7.92 (d, J=5.26 Hz, 1H), 6.91 (t, J=4.82 Hz, 1H), 4.57 (br d, J=11.84 Hz, 1H), 4.26-4.09 (m, 1H), 3.93 (s, 3H), 3.84-3.81 (m, 1H), 3.31-3.18 (m, 1H), 2.90-2.75 (m, 1H), 2.22-2.14 (m, 1H), 2.12 (s, 3H), 2.11-2.05 (m, 1H), 1.50-1.33 (m, 2H).

Step 5: To a mixture of methyl 2-((1-acetylpiperidin-4-yl)amino)-3-fluoroisonicotinate (0.90 g, 3.1 mmol) in MeOH (20 mL) and water (5 mL) was added lithium hydroxide hydrate (0.256 g, 6.10 mmol) at 20° C. The mixture was stirred at 20° C. for 1 h. The mixture was concentrated under reduced pressure to give 2-((1-acetylpiperidin-4-yl)amino)-3-fluoroisonicotinic acid. MS: 282 (M+1).

Intermediate 68: tert-butyl 5-((4-((3S,4S)-4-(3,4-dihydroisoquinolin-2(1H)-yl)-3-hydroxypiperidine-1-carbonyl)-5-fluoropyridin-2-yl)amino)-2-azabicyclo[2.2.1]heptane-2-carboxylate

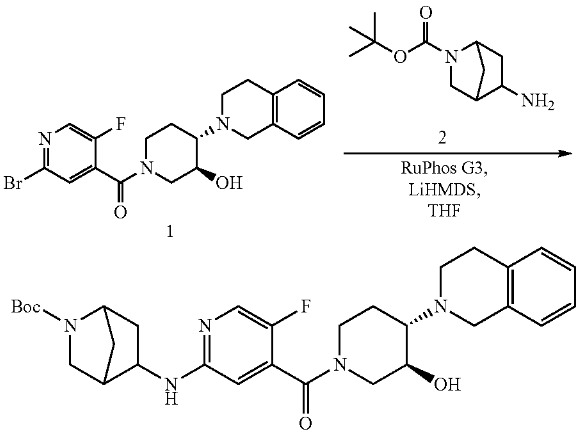

Intermediate 68

To an oven dried 20 mL microwave vial was added (2-bromo-5-fluoropyridin-4-yl)((3S,4S)-4-(3,4-dihydroisoquinolin-2(1H)-yl)-3-hydroxypiperidin-1-yl)methanone (250 mg, 0.58 mmol), tert-butyl 5-amino-2-azabicyclo[2.2.1]heptane-2-carboxylate (183 mg, 0.863 mmol), and RuPHOS G3 (72.2 mg, 0.086 mmol) under a nitrogen atmosphere. The mixture was charged with THF (5.8 mL) via syringe and lithium bis(trimethylsilyl)amide (1M in THF, 1.73 mL, 1.73 mmol) was also added via syringe. The reaction mixture was evacuated under nitrogen and allowed to stir at 60° C. for 16 h. The reaction was quenched by adding water (10 mL) and extracted with EtOAc (20 mL×2).

The combined organic layers were dried over anhydrous sodium sulfate, filtered, and concentrated under reduced pressure. The residue was purified by column chromatography on silica (0-6% methanol/DCM) to afford tert-butyl (1S,4S)-5-((4-((3S,4S)-4-(3,4-dihydroisoquinolin-2(1H)-yl)-3-hydroxypiperidine-1-carbonyl)-5-fluoropyridin-2-yl)amino)-2-azabicyclo[2.2.1]heptane-2-carboxylate. MS: 566 (M+1).

EXAMPLES

The following experimental procedures detail the preparation of specific examples of the instant disclosure. The examples are for illustrative purposes only and are not intended to limit the scope of the instant disclosure in any way.

Note: Many of the compounds claimed exist as a mixture of rotamers in solution at room temperature, which complicates their analyses by 1H-NMR spectroscopy. In these cases, the peak shifts are listed as ranges of multiplets that encompass the signals from both rotamers, rather than describing individual rotamer peaks.

Example 1: (6-Bromoimidazo[1,2-a]pyridin-2-yl)((3S,4S)-4-(3,4-dihydroisoquinolin-2(1H)-yl)-3-hydroxypiperidin-1-yl)methanone

Example 2: (6-Bromoimidazo[1,2-a]pyridin-2-yl)((3R,4R)-4-(3,4-dihydroisoquinolin-2(1H)-yl)-3-hydroxypiperidin-1-yl)methanone

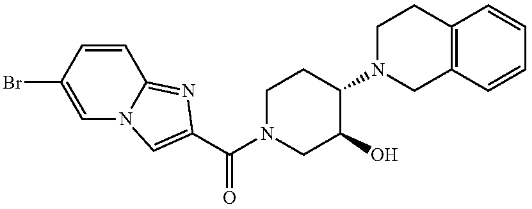

-continued

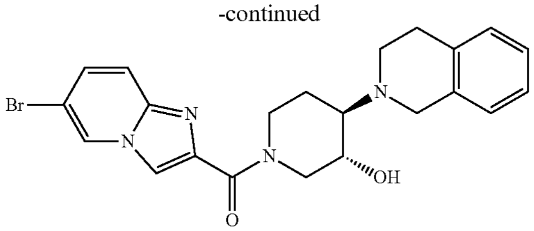

Step 1: To a solution of 6-bromoimidazo[1,2-a]pyridine-2-carboxylic acid (57.1 mg, 0.237 mmol), trans-4-(3,4-dihydroisoquinolin-2(1H)-yl)piperidin-3-ol (50 mg, 0.215 mmol) and DIEA (0.113 mL, 0.646 mmol) in DMF (1 mL) was added 2,4,6-tripropyl-1,3,5,2,4,6-trioxatriphosphinane 2,4,6-trioxide (274 mg, 0.430 mmol) (50% wt in DMF) at 17° C. The mixture was stirred at 17° C. for 1 h then concentrated under reduced pressure. The residue was purified by reverse phase HPLC (ACN/water with 0.1% $NH_4HCO_3$ modifier) to give (6-bromoimidazo[1,2-a]pyridin-2-yl)((trans)-4-(3,4-dihydroisoquinolin-2(1H)-yl)-3-hydroxypiperidin-1-yl)methanone as a solid. MS: 455 and 457 (M+1).

$^1$H NMR (400 MHz, $CD_3OD$) δ 8.76 (s, 1H), 8.18 (s, 1H), 7.59-7.41 (m, 2H), 7.13-6.99 (m, 4H), 4.81-4.54 (m, 2H), 4.06-3.74 (m, 3H), 3.14-2.64 (m, 7H), 2.11-1.85 (m, 1H), 1.69 (br d, J=14.03 Hz, 1H).

Step 2: The racemic mixture was purified by chiral SFC (OD column, ethanol/$CO_2$) to afford (6-bromoimidazo[1,2-a]pyridin-2-yl)((3R,4R)-4-(3,4-dihydroisoquinolin-2(1H)-yl)-3-hydroxypiperidin-1-yl)methanone (Example 2, first eluting peak): MS: 455 and 457 (M+1). $^1$H NMR (400 MHz, DMSO-$d_6$) δ 8.92 (s, 1H), 8.26 (s, 1H), 7.67-7.57 (m, 1H), 7.43 (br d, J=9.39 Hz, 1H), 7.11-6.98 (m, 4H), 5.09 (br s, 1H), 4.86-4.63 (m, 1H), 4.62-4.35 (m, 1H), 3.91-3.69 (m, 2H), 3.61 (br s, 1H), 2.89 (br d, J=6.65 Hz, 1H), 2.83-2.74 (m, 3H), 2.65 (br s, 1H), 2.05-1.72 (m, 1H), 1.59-1.39 (m, 1H), 1.22 (s, 2H) and (6-bromoimidazo[1,2-a]pyridin-2-yl)((3S,4S)-4-(3,4-dihydroisoquinolin-2(1H)-yl)-3-hydroxypiperidin-1-yl)methanone (Example 1, second eluting peak): MS: 455 and 457 (M+1). $^1$H NMR (400 MHz, DMSO-$d_6$) δ 8.93 (br s, 1H), 8.28 (s, 1H), 7.61 (br d, J=9.78 Hz, 1H), 7.44 (br d, J=9.00 Hz, 1H), 7.12-6.99 (m, 4H), 5.57-4.98 (m, 1H), 4.94-4.31 (m, 1H), 4.13-3.52 (m, 3H), 3.18-2.62 (m, 6H), 2.09-1.69 (m, 1H), 1.67-1.41 (m, 1H), 1.32-1.13 (m, 2H).

TABLE 10

The following examples were prepared as above examples 1 and 2.

| Ex | Structure | Compound Name | Exact Mass (M + 1) |
|---|---|---|---|
| 3 | 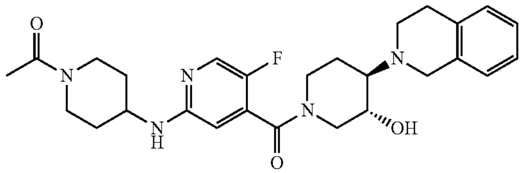 [SMILES: CC(=O)N1CCC(Nc2cc(C(=O)N3CC[C@@H](N4CCc5ccccc5C4)[C@H](O)C3)c(F)cn2)CC1] | 1-(4-((4-((3R,4R)-4-(3,4-dihydroisoquinolin-2(1H)-yl)-3-hydroxypiperidine-l-carbonyl)-5-fluoropyridin-2-yl)amino)piperidin-l-yl)ethan-l-one | 496 |

TABLE 10-continued

The following examples were prepared as above examples 1 and 2.

| Ex | Structure | Compound Name | Exact Mass (M + 1) |
|---|---|---|---|
| 4 | 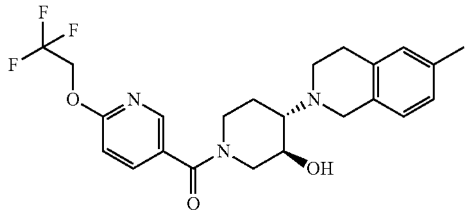 [SMILES: Cc1ccc2c(c1)CCN([C@H]1CCN(C(=O)c3ccc(OCC(F)(F)F)nc3)C[C@@H]1O)C2] | ((3S,4S)-3-hydroxy-4-(6-methyl-3,4-dihydroisoquinolin-2(1H)-yl)piperidin-1-yl)(6-(2,2,2-trifluoroethoxy)pyridin-3-yl)methanone | 450 |
| 5 | 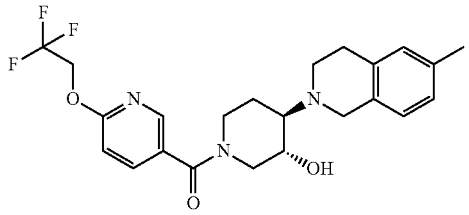 [SMILES: Cc1ccc2c(c1)CCN([C@@H]1CCN(C(=O)c3ccc(OCC(F)(F)F)nc3)C[C@H]1O)C2] | ((3R,4R)-3-hydroxy-4-(6-methyl-3,4-dihydroisoquinolin-2(1H)-yl)piperidin-1-yl)(6-(2,2,2-trifluoroethoxy)pyridin-3-yl)methanone | 450 |
| 6 | 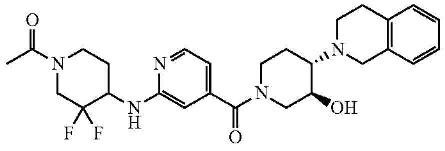 First eluting peak | 1-(-4-((4-((3S,4S)-4-(3,4-dihydroisoquinolin-2(1H)-yl)-3-hydroxypiperidine-1-carbonyl)pyridin-2-yl)amino)-3,3-difluoropiperidin-1-yl)ethan-1-one | 514 |
| 7 | 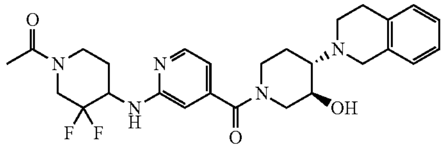 Second eluting peak | 1-(-4-((4-((3S,4S)-4-(3,4-dihydroisoquinolin-2(1H)-yl)-3-hydroxypiperidine-1-carbonyl)pyridin-2-yl)amino)-3,3-difluoropiperidin-1-yl)ethan-1-one | 514 |
| 8 | 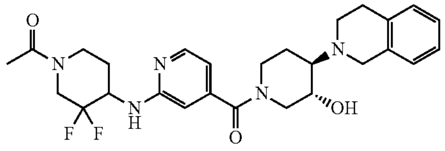 First eluting peak | 1-(-4-((4-((3R,4R)-4-(3,4-dihydroisoquinolin-2(1H)-yl)-3-hydroxypiperidine-1-carbonyl)pyridin-2-yl)amino)-3,3-difluoropiperidin-1-yl)ethan-1-one | 514 |
| 9 | 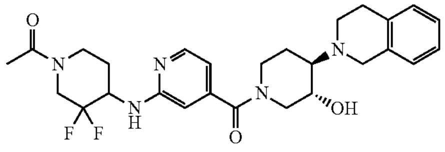 Second eluting peak | 1-(-4-((4-((3R,4R)-4-(3,4-dihydroisoquinolin-2(1H)-yl)-3-hydroxypiperidine-1-carbonyl)pyridin-2-yl)amino)-3,3-difluoropiperidin-1-yl)ethan-1-one | 514 |
| 10 | 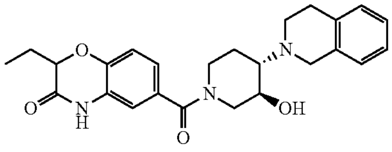 First eluting peak | 6-((3S,4S)-4-(3,4-dihydroisoquinolin-2(1H)-yl)-3-hydroxypiperidine-l-carbonyl)-2-ethyl-2H-benzo[b][1,4]oxazin-3(4H)-one | 436 |

TABLE 10-continued

The following examples were prepared as above examples 1 and 2.

| Ex | Structure | Compound Name | Exact Mass (M + 1) |
|---|---|---|---|
| 11 | 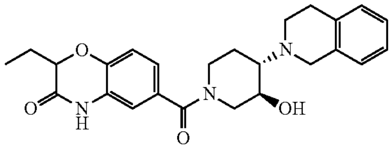 Second eluting peak | 6-((3S,4S)-4-(3,4-dihydroisoquinolin-2(1H)-yl)-3-hydroxypiperidine-1-carbonyl)-2-ethyl-2H-benzo[b][1,4]oxazin-3(4H)-one | 436 |
| 12 | 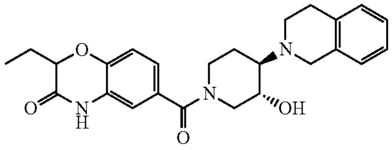 First eluting peak | 6-((3R,4R)-4-(3,4-dihydroisoquinolin-2(1H)-yl)-3-hydroxypiperidine-1-carbonyl)-2-ethyl-2H-benzo[b][1,4]oxazin-3(4H)-one | 436 |
| 13 | 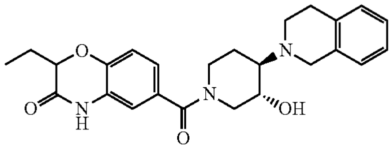 Second eluting peak | 6-((3R,4R)-4-(3,4-dihydroisoquinolin-2(1H)-yl)-3-hydroxypiperidine-1-carbonyl)-2-ethyl-2H-benzo[b][1,4]oxazin-3(4H)-one | 436 |
| 14 | 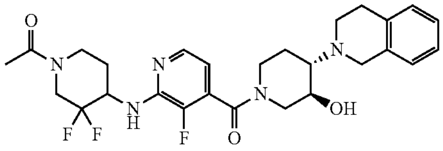 First eluting peak | 1-(-4-((4-((3S,4S)-4-(3,4-dihydroisoquinolin-2(1H)-yl)-3-hydroxypiperidine-1-carbonyl)-3-fluoropyridin-2-yl)amino)-3,3-difluoropiperidin-1-yl)ethan-1-one | 532 |
| 15 | 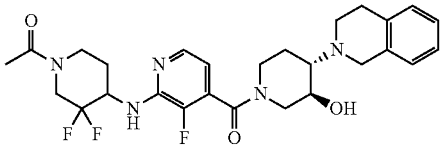 Second eluting peak | 1-(-4-((4-((3S,4S)-4-(3,4-dihydroisoquinolin-2(1H)-yl)-3-hydroxypiperidine-1-carbonyl)-3-fluoropyridin-2-yl)amino)-3,3-difluoropiperidin-1-yl)ethan-1-one | 532 |
| 16 | 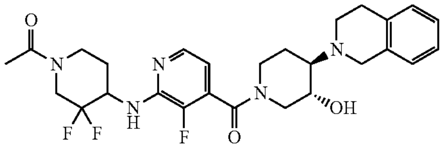 First eluting peak | 1-(-4-((4-((3R,4R)-4-(3,4-dihydroisoquinolin-2(1H)-yl)-3-hydroxypiperidine-1-carbonyl)-3-fluoropyridin-2-yl)amino)-3,3-difluoropiperidin-1-yl)ethan-1-one | 532 |
| 17 | 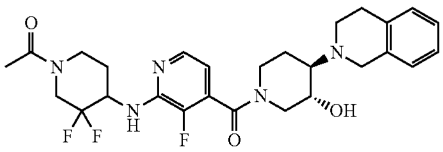 Second eluting peak | 1-(-4-((4-((3R,4R)-4-(3,4-dihydroisoquinolin-2(1H)-yl)-3-hydroxypiperidine-1-carbonyl)-3-fluoropyridin-2-yl)amino)-3,3-difluoropiperidin-1-yl)ethan-1-one | 532 |

TABLE 10-continued

The following examples were prepared as above examples 1 and 2.

| Ex | Structure | Compound Name | Exact Mass (M + 1) |
|---|---|---|---|
| 18 | 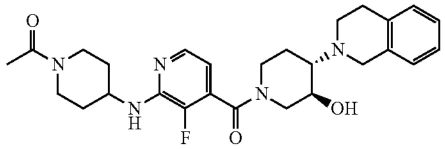 [SMILES: CC(=O)N1CCC(Nc2nccc(C(=O)N3CC[C@H](N4CCc5ccccc5C4)[C@@H](O)C3)c2F)CC1] | 1-(4-((4-((3S,4S)-4-(3,4-dihydroisoquinolin-2(1H)-yl)-3-hydroxypiperidine-l-carbonyl)-3-fluoropyridin-2-yl)amino)piperidin-1-yl)ethan-1-one | 496 |
| 19 | 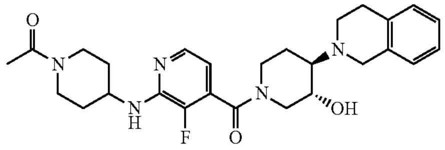 [SMILES: CC(=O)N1CCC(Nc2nccc(C(=O)N3CC[C@@H](N4CCc5ccccc5C4)[C@H](O)C3)c2F)CC1] | 1-(4-((4-((3R,4R)-4-(3,4-dihydroisoquinolin-2(1H)-yl)-3-hydroxypiperidine-1-carbonyl)-3-fluoropyridin-2-yl)amino)piperidin-1-yl)ethan-1-one | 496 |
| 20 | 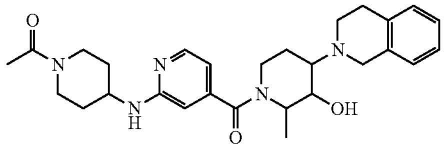 First eluting peak | l-(4-((4-(4-(3,4-dihydroisoquinolin-2(1H)-yl)-3-hydroxy-2-methylpiperidine-1-carbonyl)pyridin-2-yl)amino)piperidin-1-yl)ethan-1-one | 492 |
| 21 | 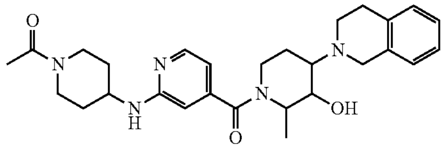 Second eluting peak | 1-(4-((4-(4-(3,4-dihydroisoquinolin-2(1H)-yl)-3-hydroxy-2-methylpiperidine-1-carbonyl)pyridin-2-yl)amino)piperidin-1-yl)ethan-1-one | 492 |
| 22 | 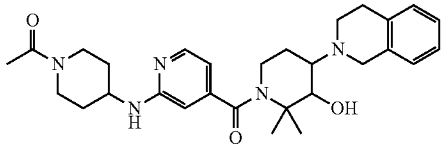 First eluting peak | l-(4-((4-(4-(3,4-dihydroisoquinolin-2(1H)-yl)-3-hydroxy-2,2-dimethylpiperidine-1-carbonyl)pyridin-2-yl)amino)piperidin-1-yl)ethan-1-one | 506 |
| 23 | 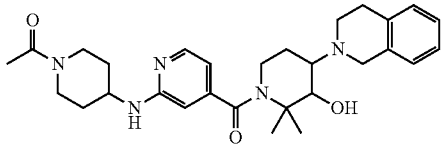 Second eluting peak | l-(4-((4-(4-(3,4-dihydroisoquinolin-2(1H)-yl)-3-hydroxy-2,2-dimethylpiperidine-1-carbonyl)pyridin-2-yl)amino)piperidin-1-yl)ethan-1-one | 506 |
| 24 | 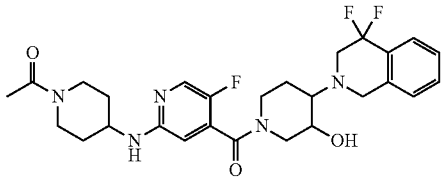 First eluting peak | 1-(4-((4-(-4-(4,4-difluoro-3,4-dihydroisoquinolin-2(1H)-yl)-3-hydroxypiperidine-1-carbonyl)-5-fluoropyridin-2-yl)amino)piperidin-1-yl)ethan-1-one | 532 |

TABLE 10-continued

| The following examples were prepared as above examples 1 and 2. | | | |
|---|---|---|---|
| Ex | Structure | Compound Name | Exact Mass (M + 1) |
| 25 | 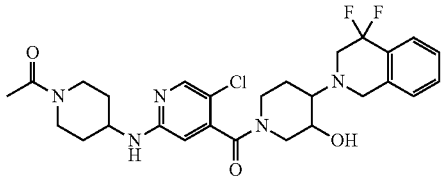 First eluting peak | l-(4-((5-chloro-4-(-4-(4,4-difluoro-3,4-dihydroisoquinolin-2(1H)-yl)-3-hydroxypiperidine-1-carbonyl)pyridin-2-yl)amino)piperidin-1-yl)ethan-1-one | 548 |
| 26 | 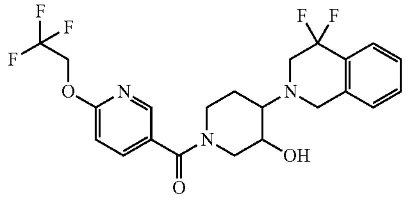 First eluting peak | (-4-(4,4-difluoro-3,4-dihydroisoquinolin-2(1H)-yl)-3-hydroxypiperidin-1-yl)(6-(2,2,2-trifluoroethoxy)pyridin-3-yl)methanone | 472 |
| 27 | 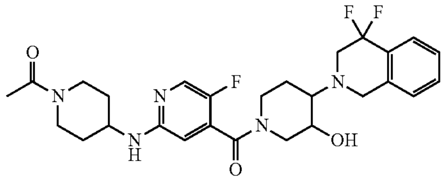 Second eluting peak | 1-(4-((5-fluoro-4-(-4-(4,4-difluoro-3,4-dihydroisoquinolin-2(1H)-yl)-3-hydroxypiperidine-1-carbonyl)pyridin-2-yl)amino)piperidin-1-yl)ethan-1-one | 532 |
| 28 | 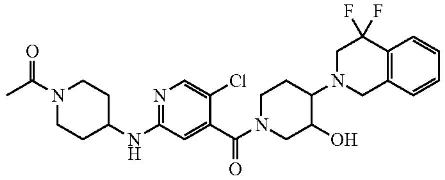 Second eluting peak | l-(4-((5-chloro-4-(-4-(4,4-difluoro-3,4-dihydroisoquinolin-2(lH)-yl)-3-hydroxypiperidine-1 -carbonyl)pyridin-2-yl)amino)piperidin-1-yl)ethan-1-one | 548 |
| 29 | 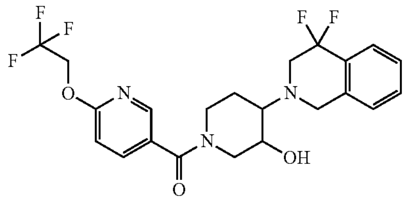 Second eluting peak | (-4-(4,4-difluoro-3,4-dihydroisoquinolin-2(1H)-yl)-3-hydroxypiperidin-1-yl)(6-(2,2,2-trifluoroethoxy)pyridin-3-yl)methanone | 472 |
| 30 | 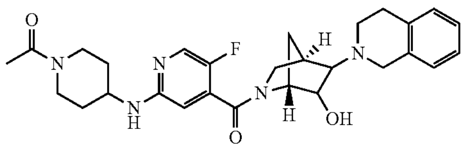 First eluting peak | l-{4-[(4-{[(lR,4R)-5-(3,4-dihydroisoquinolin-2(1H)-yl)-6-hydroxy-2-azabicyclo[2.2.1]hept-2-yl]carbonyl}-5-fluoropyridin-2-yl)amino]piperidin-l-yl}ethanone | 508 |

Example 31: 4-((3S,4S)-4-(3,4-dihydroisoquinolin-2(1H)-yl)-3-hydroxypiperidine-1-carbonyl)-1-(2,22-trifluoroethyl)pyridin-2(1H)-one Example 32: 4-((3R,4R)-4-(3,4-dihydroisoquinolin-2(1H)-yl)-3-hydroxypiperidine-1-carbonyl)-1-(2,2,2-trifluoroethyl)pyridin-2(1H)-one

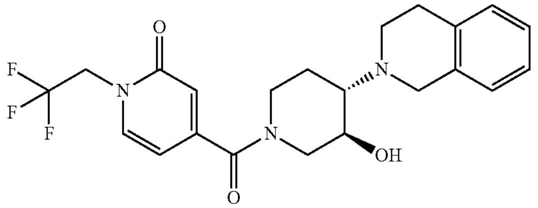

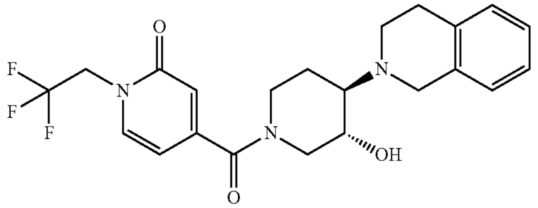

Step 1: To a solution of 2-oxo-1-(2,2,2-trifluoroethyl)-1,2-dihydropyridine-4-carboxylic acid (50 mg, 0.226 mmol) in DCM (2 mL) was added HATU (215 mg, 0.565 mmol) and DIEA (0.118 mL, 0.678 mmol) at 15° C., and then (trans)-4-(3,4-dihydroisoquinolin-2(1H)-yl)piperidin-3-ol (63.0 mg, 0.271 mmol) was added at 15° C. The mixture was stirred at 15° C. for 1 h. The solution was concentrated under reduced pressure, and the residue was purified by reverse phase HPLC (ACN/water with 0.100 $NH_4HCO_3$ modifier) to afford 4-((trans)-4-(3,4-dihydroisoquinolin-2(1H)-yl)-3-hydroxypiperidine-1-carbonyl)-1-(2,2,2-trifluoroethyl)pyridin-2(1H)-one as a solid. MS: 436 (M+1).

Step 2: The racemic mixture was purified by chiral SFC (AD column, ethanol/$CO_2$) to afford 4-((3R,4R)-4-(3,4-dihydroisoquinolin-2(1H)-yl)-3-hydroxypiperidine-1-carbonyl)-1-(2,2,2-trifluoroethyl)pyridin-2(1H)-one (Example 32): MS: 436 (M+1). $^1H$ NMR (400 MHz, CD3D-$d_4$) 67.76 (t, J=6.3 Hz, 1H), 7.16-7.02 (m, 4H), 6.63 (d, J=10.6 Hz, 1H), 6.50-6.40 (m, 1H), 4.88-4.81 (m, 2H), 4.72-4.43 (m, 1H), 4.02-3.87 (m, 2H), 3.86-3.71 (m, 2H), 3.28-2.95 (m, 3H), 2.95-2.86 (m, 3H), 2.81-2.73 (m, 1H), 2.10-1.89 (m, 1H), 1.78-1.57 (m, 1H) and 4-((3S,4S)-4-(3,4-dihydroisoquinolin-2(1H)-yl)-3-hydroxypiperidine-1-carbonyl)-1-(2,2,2-trifluoroethyl)pyridin-2(1H)-one (Example 31): MS: 436 (M+1). $^1H$ NMR (400 MHz, CD3D-$d_4$) δ 7.76 (t, J=6.3 Hz, 1H), 7.17-7.00 (m, 4H), 6.63 (d, J=10.6 Hz, 1H), 6.49-6.39 (m, 1H), 4.88-4.80 (m, 2H), 4.72-4.43 (m, 1H), 4.01-3.86 (m, 2H), 3.86-3.70 (m, 2H), 3.27-2.93 (m, 3H), 2.93-2.82 (m, 3H), 2.81-2.73 (m, 1H), 2.10-1.89 (m, 1H), 1.78-1.57 (m, 1H).

TABLE 11

The following examples were prepared as above examples 31 and 32.

| Ex | Structure | Compound Name | Exact Mass (M + 1) |
|---|---|---|---|
| 33 | 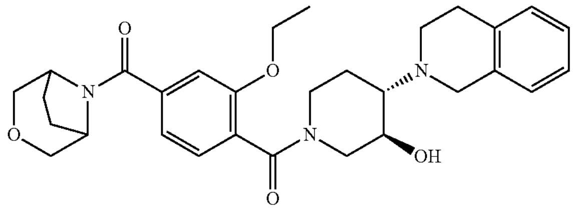 [SMILES: CCOc1cc(C(=O)N2C3CCC2COC3)ccc1C(=O)N1CC[C@H](N2CCc3ccccc3C2)[C@@H](O)C1] | (4-(3-oxa-8-azabicyclo[3.2.1]octane-8-carbonyl)-2-ethoxyphenyl)(3S,4S)-4-(3,4-dihydroisoquinolin-2(1H)-yl)-3-hydroxypiperidin-1-yl)methanone | 520 |
| 34 | 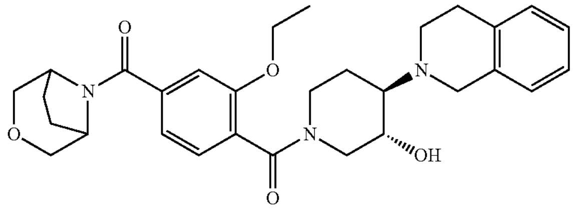 [SMILES: CCOc1cc(C(=O)N2C3CCC2COC3)ccc1C(=O)N1CC[C@@H](N2CCc3ccccc3C2)[C@H](O)C1] | (4-(3-oxa-8-azabicyclo[3.2.1]octane-8-carbonyl)-2-ethoxyphenyl)((3R,4R)-4-(3,4-dihydroisoquinolin-2(1H)-yl)-3-hydroxypiperidin-1-yl)methanone | 520 |
| 35 | 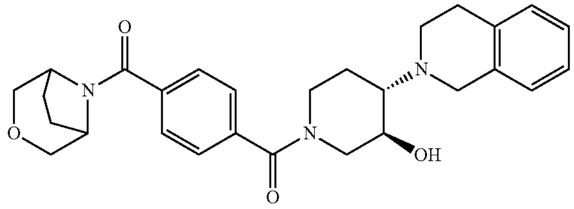 [SMILES: O=C(c1ccc(C(=O)N2C3CCC2COC3)cc1)N1CC[C@H](N2CCc3ccccc3C2)[C@@H](O)C1] | (4-(3-oxa-8-azabicyclo[3.2.1]octane-8-carbonyl)phenyl)(3S,4S)-4-(3,4-dihydroisoquinolin-2(1H)-yl)-3-hydroxypiperidin-1-yl)methanone | 476 |

TABLE 11-continued

| The following examples were prepared as above examples 31 and 32. | | | |
|---|---|---|---|
| Ex | Structure | Compound Name | Exact Mass (M + 1) |
| 36 | 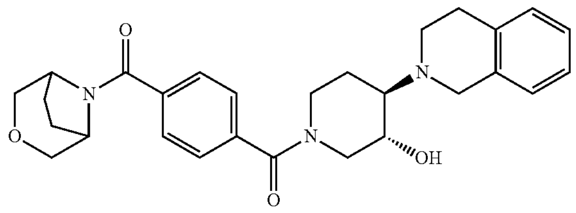 [SMILES: O=C(c1ccc(C(=O)N2C3CCC2COC3)cc1)N1CC[C@@H](N2CCc3ccccc3C2)[C@H](O)C1] | (4-(3-oxa-8-azabicyclo[3.2.1]octane-8-carbonyl)phenyl)((3R,4R)-4-(3,4-dihydroisoquinolin-2(1H)-yl)-3-hydroxypiperidin-1-yl)methanone | 476 |
| 37 | 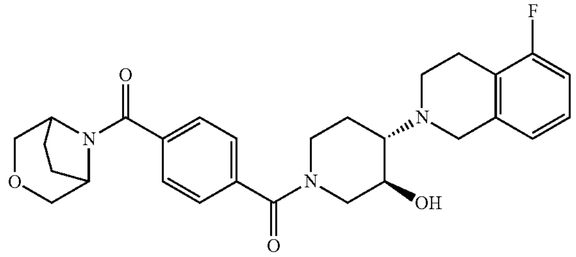 [SMILES: O=C(c1ccc(C(=O)N2C3CCC2COC3)cc1)N1CC[C@H](N2CCc3c(F)cccc3C2)[C@@H](O)C1] | (4-(3-oxa-8-azabicyclo[3.2.1]octane-8-carbonyl)phenyl)((3S,4S)-4-(5-fluoro-3,4-dihydroisoquinolin-2(1H)-yl)-3-hydroxypiperidin-1-yl)methanone | 494 |
| 38 | 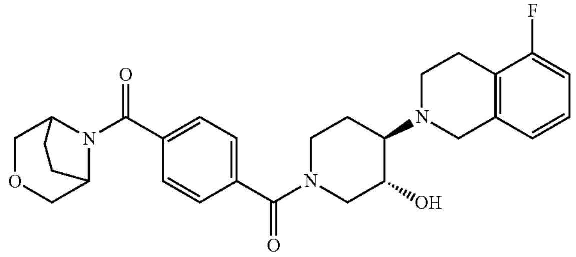 [SMILES: O=C(c1ccc(C(=O)N2C3CCC2COC3)cc1)N1CC[C@@H](N2CCc3c(F)cccc3C2)[C@H](O)C1] | (4-(3-oxa-8-azabicyclo[3.2.1]octane-8-carbonyl)phenyl)((3R,4R)-4-(5-fluoro-3,4-dihydroisoquinolin-2(1H)-yl)-3-hydroxypiperidin-1-yl)methanone | 494 |
| 39 | 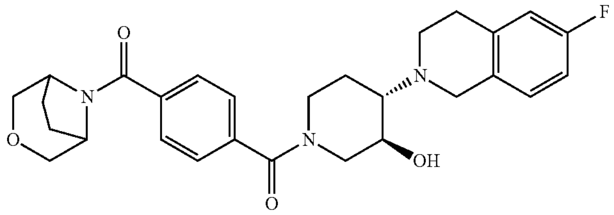 [SMILES: O=C(c1ccc(C(=O)N2C3CCC2COC3)cc1)N1CC[C@H](N2CCc3cc(F)ccc3C2)[C@@H](O)C1] | (4-(3-oxa-8-azabicyclo[3.2.1]octane-8-carbonyl)phenyl)((3S,4S)-4-(6-fluoro-3,4-dihydroisoquinolin-2(1H)-yl)-3-hydroxypiperidin-1-yl)methanone | 494 |
| 40 | 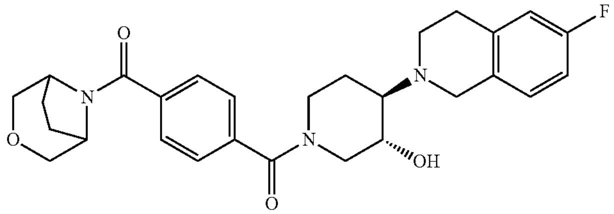 [SMILES: O=C(c1ccc(C(=O)N2C3CCC2COC3)cc1)N1CC[C@@H](N2CCc3cc(F)ccc3C2)[C@H](O)C1] | (4-(3-oxa-8-azabicyclo[3.2.1]octane-8-carbonyl)phenyl)((3R,4R)-4-(6-fluoro-3,4-dihydroisoquinolin-2(1H)-yl)-3-hydroxypiperidin-1-yl)methanone | 494 |
| 41 | 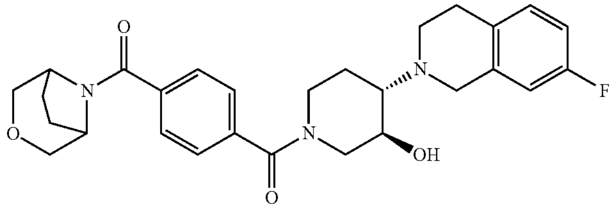 [SMILES: O=C(c1ccc(C(=O)N2C3CCC2COC3)cc1)N1CC[C@H](N2CCc3ccc(F)cc3C2)[C@@H](O)C1] | (4-(3-oxa-8-azabicyclo[3.2.1]octane-8-carbonyl)phenyl)((3S,4S)-4-(7-fluoro-3,4-dihydroisoquinolin-2(1H)-yl)-3-hydroxypiperidin-1-yl)methanone | 494 |

TABLE 11-continued

The following examples were prepared as above examples 31 and 32.

| Ex | Structure | Compound Name | Exact Mass (M + 1) |
|---|---|---|---|
| 42 | 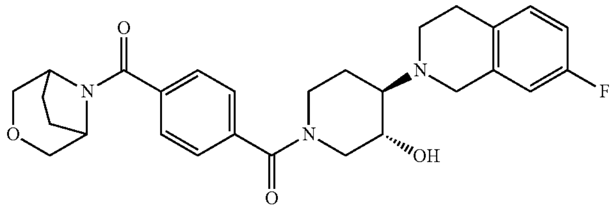 [SMILES: O=C(c1ccc(C(=O)N2C3CCC2COC3)cc1)N1CC[C@@H](N2CCc3ccc(F)cc3C2)[C@H](O)C1] | (4-(3-oxa-8-azabicyclo[3.2.1]octane-8-carbonyl)phenyl)(3R,4R)-4-(7-fluoro-3,4-dihydroisoquinolin-2(1H)-yl)-3-hydroxypiperidin-1-yl)methanone | 494 |
| 43 | 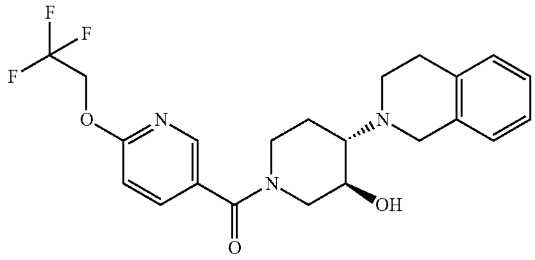 [SMILES: O=C(c1ccc(OCC(F)(F)F)nc1)N1CC[C@H](N2CCc3ccccc3C2)[C@@H](O)C1] | ((3S,4S)-4-(3,4-dihydroisoquinolin-2(1H)-yl)-3-hydroxypiperidin-1-yl)(6-(2,2,2-trifluoroethoxy)pyridin-3-yl)methanone | 436 |
| 44 | 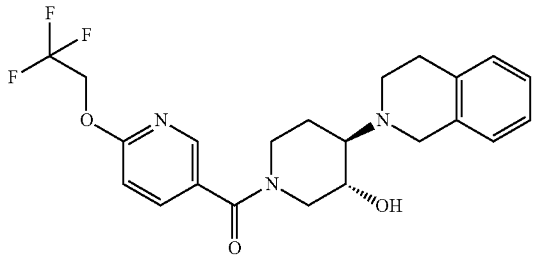 [SMILES: O=C(c1ccc(OCC(F)(F)F)nc1)N1CC[C@@H](N2CCc3ccccc3C2)[C@H](O)C1] | ((3R,4R)-4-(3,4-dihydroisoquinolin-2(1H)-yl)-3-hydroxypiperidin-1-yl)(6-(2,2,2-trifluoroethoxy)pyridin-3-yl)methanone | 436 |
| 47 | 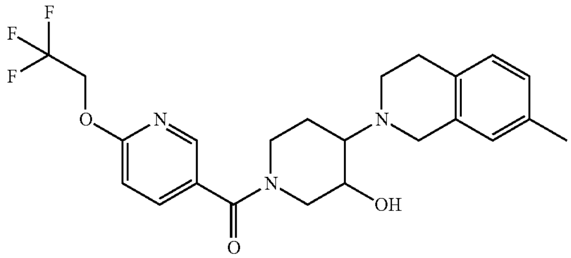 [SMILES: Cc1ccc2c(c1)CN(C1CCN(C(=O)c3ccc(OCC(F)(F)F)nc3)CC1O)CC2] First eluting peak | ((3R,4R or 3S,4S)-3-hydroxy-4-(7-methyl-3,4-dihydroisoquinolin-2(1H)-yl)piperidin-1-yl)(6-(2,2,2-trifluoroethoxy)pyridin-3-yl)methanone | 450 |
| 48 | 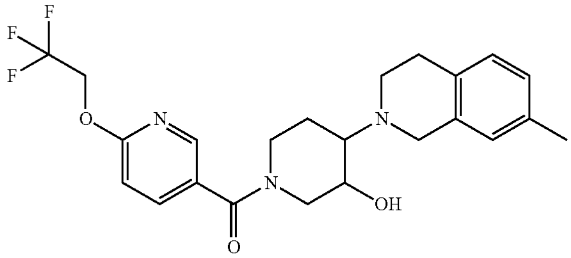 [SMILES: Cc1ccc2c(c1)CN(C1CCN(C(=O)c3ccc(OCC(F)(F)F)nc3)CC1O)CC2] Second eluting peak | ((3S,4S or 3R,4R)-3-hydroxy-4-(7-methyl-3,4-dihydroisoquinolin-2(1H)-yl)piperidin-1-yl)(6-(2,2,2-trifluoroethoxy)pyridin-3-yl)methanone | 450 |

Example 49: 1-{4-[(5-chloro-4-{[(3S,4S)-4-(3,4-dihydroisoquinolin-2(1H)-yl)-3-hydroxypiperidin-1-yl]carbonyl}pyridin-2-yl)amino]piperidin-1-yl}ethanone

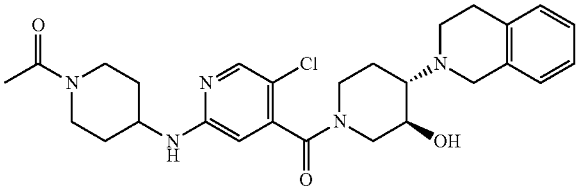 [SMILES: CC(=O)N1CCC(Nc2cc(C(=O)N3CC[C@H](N4CCc5ccccc5C4)[C@@H](O)C3)c(Cl)cn2)CC1]

To a solution of (3S,4S)-4-(3,4-dihydroisoquinolin-2(1H)-yl)piperidin-3-ol (38.6 mg, 0.166 mmol) in DCM (2 mL) and DMF (1 mL) was added 2-((1-acetylpiperidin-4-yl) amino)-5-chloroisonicotinic acid (49.5 mg, 0.166 mmol), DIEA (0.116 mL, 0.665 mmol), and T3P (0.116 mL, 0.200 mmol). The mixture was stirred at room temperature for 1 h, then concentrated under reduced pressure. The residue was purified by mass triggered reverse phase HPLC (acetonitrile/water gradient with 0.1% TFA modifier) to afford 1-{4-[(5-chloro-4-{[(3S,4S)-4-(3,4-dihydroisoquinolin-2(1H)-yl)-3-hydroxypiperidin-1-yl]carbonyl}pyridin-2-yl)amino] piperidin-1-yl}ethanone TFA salt as a solid. MS: 512 (M+1). 1H NMR (600 MHz, $CD_3OD-d_4$) δ 8.07-8.01 (m, 1H), 7.32-7.23 (m, 4H), 7.22-7.17 (m, 1H), 6.68-6.51 (m, 1H), 4.82-4.59 (m, 1H), 4.43-4.37 (m, 1H), 4.08-3.85 (m, 4H), 3.73-3.53 (m, 4H), 3.24-3.02 (m, 3H), 2.96-2.74 (m, 2H), 2.12-2.02 (m, 6H), 2.02-1.95 (m, 1H), 1.91-1.78 (m, 1H), 1.67-1.56 (m, 1H), 1.52-1.42 (m, 1H), 1.41-1.30 (m, 1H), 1.05-0.98 (m, 1H).

TABLE 12

The following examples were prepared as above example 49.

| Ex | Structure | Compound Name | Exact Mass (M + 1) |
|---|---|---|---|
| 50 | 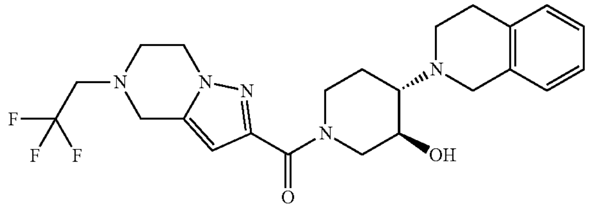 [SMILES: O=C(c1cc2n(n1)CCN(CC(F)(F)F)C2)N1CC[C@H](N2CCc3ccccc3C2)[C@@H](O)C1] | ((3S,4S)-4-(3,4-dihydroisoquinolin-2(1H)-yl)-3-hydroxypiperidin-1-yl)(5-(2,2,2-trifluoroethyl)-4,5,6,7-tetrahydropyrazolo[1,5-a]pyrazin-2-yl)methanone TFA salt | 464 |
| 51 | 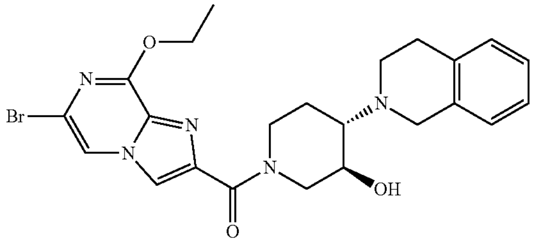 [SMILES: CCOc1nc(Br)cn2cc(C(=O)N3CC[C@H](N4CCc5ccccc5C4)[C@@H](O)C3)nc12] | (6-bromo-8-ethoxyimidazo[1,2-a]pyrazin-2-yl)((3S,4S)-4-(3,4-dihydroisoquinolin-2(1H)-yl)-3-hydroxypiperidin-1-yl)methanone TFA salt | 500 and 502 |
| 52 | 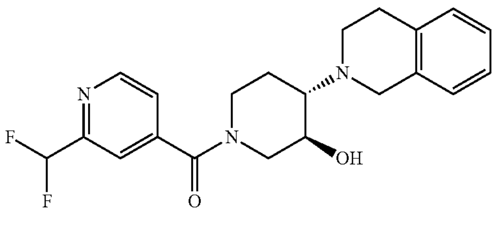 [SMILES: O=C(c1ccnc(C(F)F)c1)N1CC[C@H](N2CCc3ccccc3C2)[C@@H](O)C1] | (2-(difluoromethyl)pyridin-4-yl)((3S,4S)-4-(3,4-dihydroisoquinolin-2(1H)-yl)-3-hydroxypiperidin-1-yl)methanone | 388 |
| 53 | 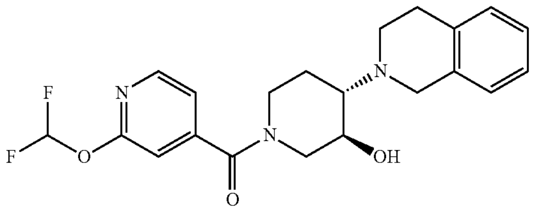 [SMILES: O=C(c1ccnc(OC(F)F)c1)N1CC[C@H](N2CCc3ccccc3C2)[C@@H](O)C1] | (2-(difluoromethoxy)pyridin-4-yl)((3S,4S)-4-(3,4-dihydroisoquinolin-2(1H)-yl)-3-hydroxypiperidin-1-yl)methanone | 404 |

TABLE 12-continued

The following examples were prepared as above example 49.

| Ex | Structure | Compound Name | Exact Mass (M + 1) |
|---|---|---|---|
| 56 | 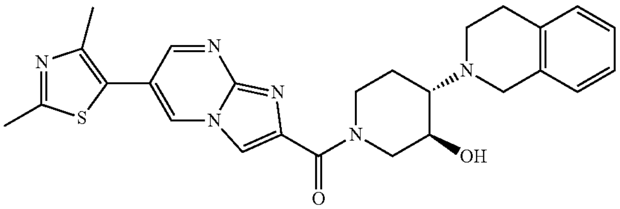 [SMILES: Cc1nc(C)c(-c2cnc3nc(C(=O)N4CC[C@H](N5CCc6ccccc6C5)[C@@H](O)C4)cn3c2)s1] | [(3S,4S)-4-(3,4-dihydroisoquinolin-2(1H)-yl)-3-hydroxypiperidin-1-yl][6-(2,4-dimethyl-1,3-thiazol-5-yl)imidazo[1,2-a]pyrimidin-2-yl]methanone | 489 |
| 57 | 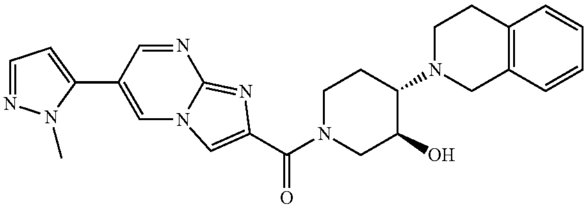 [SMILES: Cn1nccc1-c1cnc2nc(C(=O)N3CC[C@H](N4CCc5ccccc5C4)[C@@H](O)C3)cn2c1] | [(3S,4S)-4-(3,4-dihydroisoquinolin-2(1H)-yl)-3-hydroxypiperidin-1-yl][6-(1-methyl-1H-pyrazol-5-yl)imidazo[1,2-a]pyrimidin-2-yl]methanone | 458 |
| 58 | 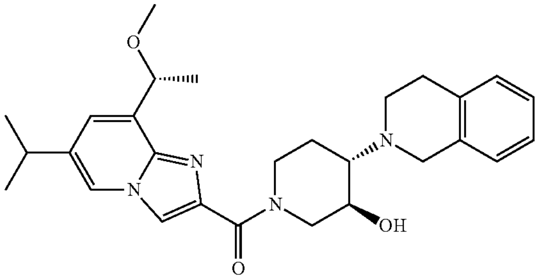 [SMILES: CO[C@H](C)c1cc(C(C)C)cn2cc(C(=O)N3CC[C@H](N4CCc5ccccc5C4)[C@@H](O)C3)nc12] | [(3S,4S)-4-(3,4-dihydroisoquinolin-2(1H)-yl)-3-hydroxypiperidin-1-yl]{8-[(1R)-1-methoxyethyl]-6-(propan-2-yl)imidazo[1,2-a]pyridin-2-yl}methanone | 477 |
| 59 | 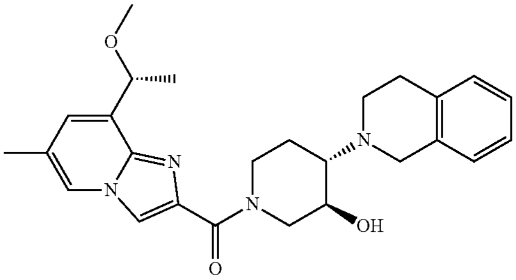 [SMILES: CO[C@H](C)c1cc(C)cn2cc(C(=O)N3CC[C@H](N4CCc5ccccc5C4)[C@@H](O)C3)nc12] | [(3S,4S)-4-(3,4-dihydroisoquinolin-2(1H)-yl)-3-hydroxypiperidin-1-yl]{8-[(1R)-1-methoxyethyl]-6-methylimidazo[1,2-a]pyridin-2-yl}methanone | 449 |

Example 60: (4-(1-cyclopropyl-1H-1,2,4-triazol-5-yl)phenyl)((3S,4S)-4-(3,4-dihydroisoquinolin-2(1H)-yl)-3-hydroxypiperidin-1-yl)methanone

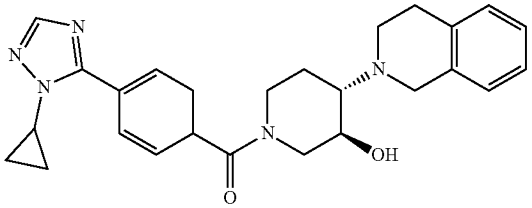 [SMILES: O=C(C1C=CC(c2ncnn2C2CC2)=CC1)N1CC[C@H](N2CCc3ccccc3C2)[C@@H](O)C1]

To a mixture of 4-(1-cyclopropyl-1H-1,2,4-triazol-5-yl)benzoic acid (50 mg, 0.218 mmol) in DMF (2 mL) was added 2-(3H-[1,2,3]triazolo[4,5-b]pyridin-3-yl)-1,1,3,3-tetramethylisouronium hexafluorophosphate(V) (100 mg, 0.262 mmol) and DIEA (114 μL, 0.654 mmol). The mixture stirred at 15° C. for 5 min. To the mixture was added (3S,4S)-4-(3,4-dihydroisoquinolin-2(1H)-yl)piperidin-3-ol (50.7 mg, 0.218 mmol) at 15° C., The resulting mixture stirred at 15° C. for 1 h. The mixture was concentrated under reduced pressure. The residue was purified by reverse phase HPLC (ACN/water with 0.10 $NH_4HCO_3$ modifier) to give (4-(1-cyclopropyl-1H-1,2,4-triazol-5-yl)phenyl)((3S,4S)-4-(3,4-dihydroisoquinolin-2(1H)-yl)-3-hydroxypiperidin-1-yl)methanone as a solid. MS: 444 (M+1). $^1$H NMR (400 MHz, $CD_3OD$) δ 8.03-8.01 (1, 2H), 7.96 (s, 1H), 7.70-7.68 (m, 2H), 7.29-7.26 (m, 3H), 7.22-7.20 (m, 1H), 4.91 (s, 2H), 3.88-3.85 (m, 3H), 3.65-3.58 (m, 3H), 3.31-3.21 (m, 3H), 2.99-2.85 (m, 1H), 2.45-2.18 (m, 2H), 2.01-1.76 (m, 1H), 1.15-1.10 (m, 4H).

TABLE 13

The following examples were prepared similarly as above example 60 using HATU as coupling reagent.

| Ex | Structure | Compound Name | Exact Mass (M + 1) |
|---|---|---|---|
| 61 | 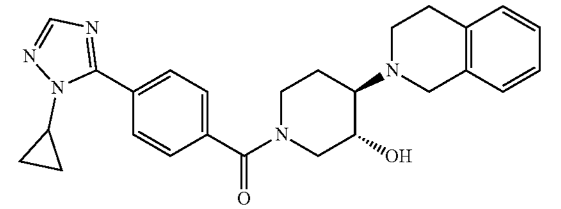 [SMILES: O=C(c1ccc(-c2ncnn2C2CC2)cc1)N1CC[C@@H](N2CCc3ccccc3C2)[C@H](O)C1] | (4-(1-cyclopropyl-1H-1,2,4-triazol-5-yl)phenyl)((3R,4R)-4-(3,4-dihydroisoquinolin-2(1H)-yl)-3-hydroxypiperidin-1-yl)methanone | 444 |
| 62 | 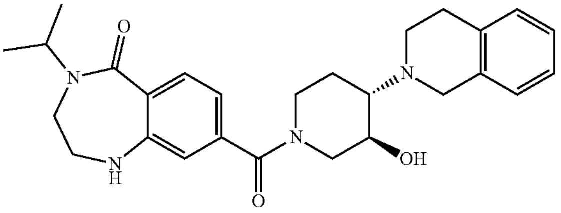 [SMILES: CC(C)N1CCNc2cc(C(=O)N3CC[C@H](N4CCc5ccccc5C4)[C@@H](O)C3)ccc2C1=O] | 8-((3S,4S)-4-(3,4-dihydroisoquinolin-2(1H)-yl)-3-hydroxypiperidine-1-carbonyl)-4-isopropyl-1,2,3,4-tetrahydro-5H-benzo[e][1,4]diazepin-5-one | 463 |
| 63 | 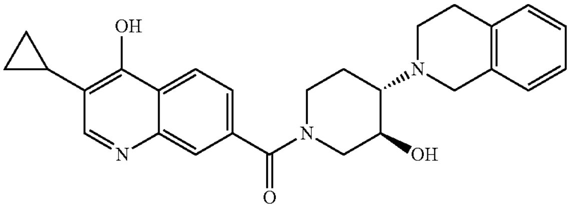 [SMILES: O=C(c1ccc2c(O)c(C3CC3)cnc2c1)N1CC[C@H](N2CCc3ccccc3C2)[C@@H](O)C1] | (3-cyclopropyl-4-hydroxyquinolin-7-yl)((3S,4S)-4-(3,4-dihydroisoquinolin-2(1H)-yl)-3-hydroxypiperidin-1-yl)methanone | 444 |
| 64 | 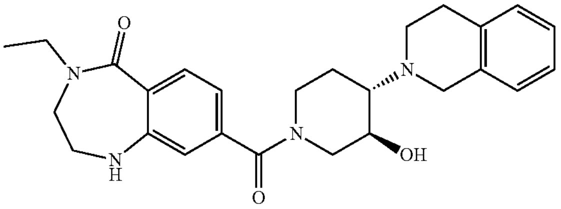 [SMILES: CCN1CCNc2cc(C(=O)N3CC[C@H](N4CCc5ccccc5C4)[C@@H](O)C3)ccc2C1=O] | 8-((3S,4S)-4-(3,4-dihydroisoquinolin-2(1H)-yl)-3-hydroxypiperidine-1-carbonyl)-4-ethyl-1,2,3,4-tetrahydro-5H-benzo[e][1,4]diazepin-5-one | 449 |
| 65 | 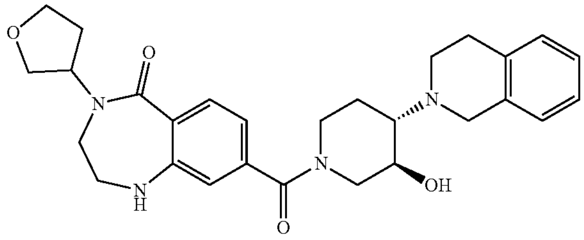 [SMILES: O=C(c1ccc2c(c1)NCCN(C1CCOC1)C2=O)N1CC[C@H](N2CCc3ccccc3C2)[C@@H](O)C1] | 8-((3S,4S)-4-(3,4-dihydroisoquinolin-2(1H)-yl)-3-hydroxypiperidine-1-carbonyl)-4-(tetrahydrofuran-3-yl)-1,2,3,4-tetrahydro-5H-benzo[e][1,4]diazepin-5-one | 491 |
| 66 | 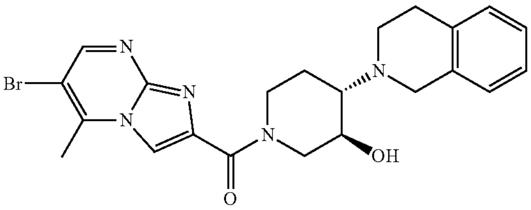 [SMILES: Cc1c(Br)cnc2nc(C(=O)N3CC[C@H](N4CCc5ccccc5C4)[C@@H](O)C3)cn12] | (6-bromo-5-methylimidazo[1,2-a]pyrimidin-2-yl)((3S,4S)-4-(3,4-dihydroisoquinolin-2(1H)-yl)-3-hydroxypiperidin-1-yl)methanone | 470, 472 |

TABLE 13-continued

The following examples were prepared similarly as above example 60 using HATU as coupling reagent.

| Ex | Structure | Compound Name | Exact Mass (M + 1) |
|---|---|---|---|
| 67 | 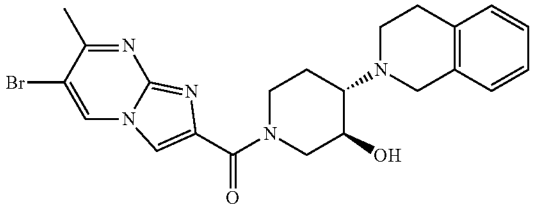 [SMILES: Cc1nc2nc(C(=O)N3CC[C@H](N4CCc5ccccc5C4)[C@@H](O)C3)cn2cc1Br] | (6-bromo-7-methylimidazo[1,2-a]pyrimidin-2-yl)((3S,4S)-4-(3,4-dihydroisoquinolin-2(1H)-yl)-3-hydroxypiperidin-1-yl)methanone | 470, 472 |
| 68 | 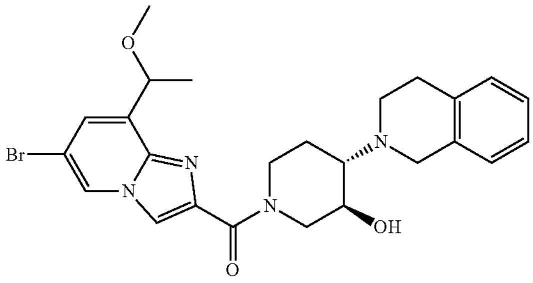 [SMILES: COC(C)c1cc(Br)cn2cc(C(=O)N3CC[C@H](N4CCc5ccccc5C4)[C@@H](O)C3)nc12] | (6-bromo-8-((R or S)-1-methoxyethyl)imidazo[1,2-a]pyridin-2-yl)((3S,4S)-4-(3,4-dihydroisoquinolin-2(1H)-yl)-3-hydroxypiperidin-1-yl)methanone | 513, 515 |
| 69 | 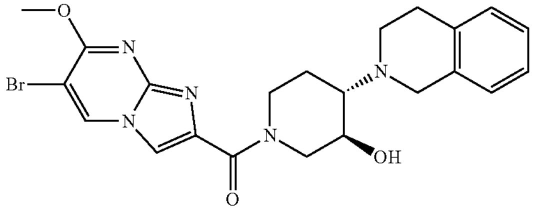 [SMILES: COc1nc2nc(C(=O)N3CC[C@H](N4CCc5ccccc5C4)[C@@H](O)C3)cn2cc1Br] | (6-bromo-7-methoxyimidazo[1,2-a]pyrimidin-2-yl)((3S,4S)-4-(3,4-dihydroisoquinolin-2(1H)-yl)-3-hydroxypiperidin-1-yl)methanone | 486, 488 |
| 70 | 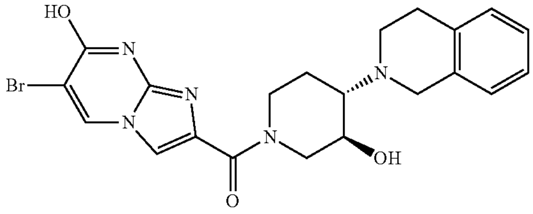 [SMILES: O=C(c1cn2cc(Br)c(O)nc2n1)N1CC[C@H](N2CCc3ccccc3C2)[C@@H](O)C1] | (6-bromo-7-hydroxyimidazo[1,2-a]pyrimidin-2-yl)((3S,4S)-4-(3,4-dihydroisoquinolin-2(1H)-yl)-3-hydroxypiperidin-1-yl)methanone | 472, 474 |
| 71 | 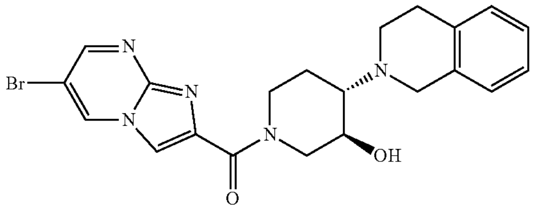 [SMILES: O=C(c1cn2cc(Br)cnc2n1)N1CC[C@H](N2CCc3ccccc3C2)[C@@H](O)C1] | (6-bromoimidazo[1,2-a]pyrimidin-2-yl)[(3S,4S)-4-(3,4-dihydroisoquinolin-2(1H)-yl)-3-hydroxypiperidin-1-yl]methanone | 456, 458 |
| 72 | 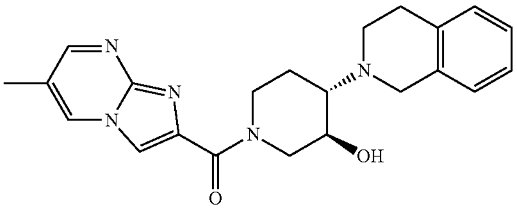 [SMILES: Cc1cnc2nc(C(=O)N3CC[C@H](N4CCc5ccccc5C4)[C@@H](O)C3)cn2c1] | [(3S,4S)-4-(3,4-dihydroisoquinolin-2(1H)-yl)-3-hydroxypiperidin-1-yl](6-methylimidazo[1,2-a]pyrimidin-2-yl)methanone | 392 |

TABLE 13-continued

The following examples were prepared similarly as above example 60 using HATU as coupling reagent.

| Ex | Structure | Compound Name | Exact Mass (M + 1) |
|---|---|---|---|
| 75 | 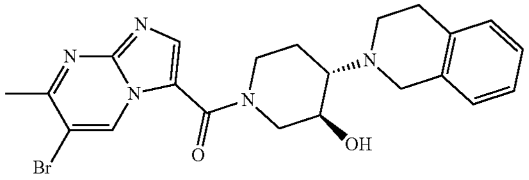 [SMILES: Cc1nc2ncc(C(=O)N3CC[C@H](N4CCc5ccccc5C4)[C@@H](O)C3)n2cc1Br] | (6-bromo-7-methylimidazo[1,2-a]pyrimidin-3-yl)[(3S,4S)-4-(3,4-dihydroisoquinolin-2(1H)-yl)-3-hydroxypiperidin-1-yl]methanone | 470 and 472 |
| 76 | 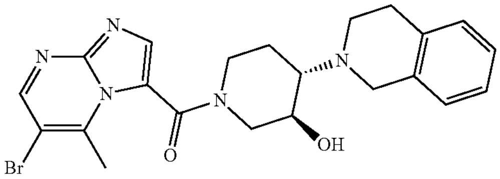 [SMILES: Cc1c(Br)cnc2ncc(C(=O)N3CC[C@H](N4CCc5ccccc5C4)[C@@H](O)C3)n12] | (6-bromo-5-methylimidazo[1,2-a]pyrimidin-3-yl)[(3S,4S)-4-(3,4-dihydroisoquinolin-2(1H)-yl)-3-hydroxypiperidin-1-yl]methanone | 470 and 472 |
| 77 | 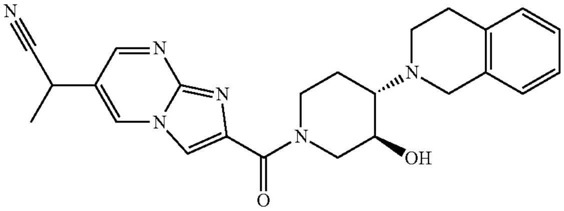 [SMILES: CC(C#N)c1cnc2nc(C(=O)N3CC[C@H](N4CCc5ccccc5C4)[C@@H](O)C3)cn2c1] | 2-{2-[(3S,4S)-4-(3,4-dihydroisoquinolin-2(1H)-yl)-3-hydroxypiperidine-1-carbonyl]imidazo[1,2-a]pyrimidin-6-yl}propanenitrile | 431 |
| 78 | 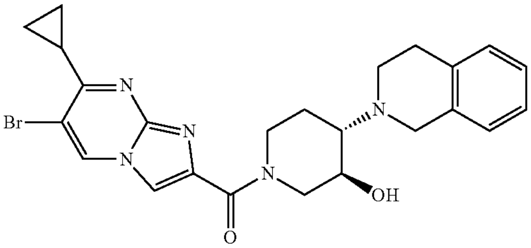 [SMILES: O=C(c1cn2cc(Br)c(C3CC3)nc2n1)N1CC[C@H](N2CCc3ccccc3C2)[C@@H](O)C1] | (6-bromo-7-cyclopropylimidazo[1,2-a]pyrimidin-2-yl)[(3S,4S)-4-(3,4-dihydroisoquinolin-2(1H)-yl)-3-hydroxypiperidin-1-yl]methanone | 496 and 498 |
| 79 | 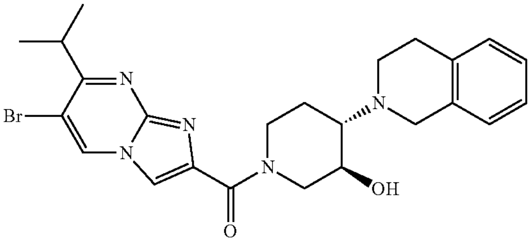 [SMILES: CC(C)c1nc2nc(C(=O)N3CC[C@H](N4CCc5ccccc5C4)[C@@H](O)C3)cn2cc1Br] | [6-bromo-7-(propan-2-yl)imidazo[1,2-a]pyrimidin-2-yl][(3S,4S)-4-(3,4-dihydroisoquinolin-2(1H)-yl)-3-hydroxypiperidin-1-yl]methanone | 498 and 500 |

Example 80: 2-cyclopropyl-6-((3S,4S)-4-(3,4-dihydroisoquinolin-2(1H)-yl)-3-hydroxypiperidine-1-carbonyl)-2H-benzo[b][1,4]oxazin-3(4H)-one Example 81: 2-cyclopropyl-6-((3S,4S)-4-(3,4-dihydroisoquinolin-2(1H)-yl)-3-hydroxypiperidine-1-carbonyl)-2H-benzo[b][1,4]oxazin-3(4H)-one

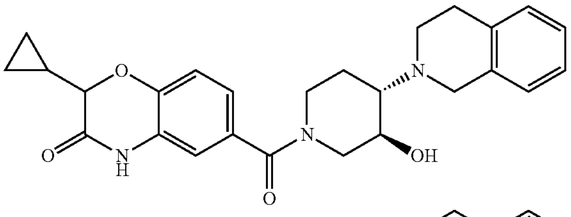

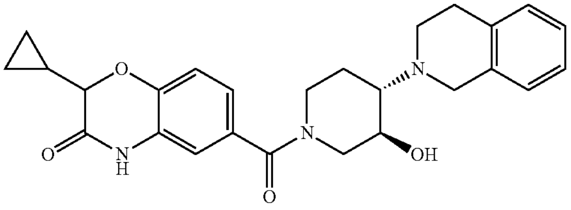

To a mixture of 2-cyclopropyl-3-oxo-3,4-dihydro-2H-benzo[b][1,4]oxazine-6-carboxylic acid (100 mg, 0.429 mmol) in DMF (2 mL) was added 1-propanephosphonic anhydride (819 mg, 1.29 mmol) and DIEA (0.225 mL, 1.29 mmol). The mixture was stirred at 13° C. for 5 min. Then (3S,4S)-4-(3,4-dihydroisoquinolin-2(1H)-yl)piperidin-3-ol (120 mg, 0.515 mmol) was added at 13° C. The resulting mixture was stirred at 13° C. for 1 h. The mixture was concentrated under reduced pressure. The residue was purified by reverse phase HPLC (ACN/water with 0.05% ammonia hydroxide modifier) to give 2-cyclopropyl-6-((3S,4S)-4-(3,4-dihydroisoquinolin-2(1H)-yl)-3-hydroxypiperidine-1-carbonyl)-2H-benzo[b][1,4]oxazin-3(4H)-one. The racemic mixture was purified by chiral SFC (AD column, ethanol/$CO_2$) to afford: 2-cyclopropyl-6-((3S,4S)-4-(3,4-dihydroisoquinolin-2(1H)-yl)-3-hydroxypiperidine-1-carbonyl)-2H-benzo[b][1,4]oxazin-3(4H)-one as a solid (Example 80, isomer 1, first eluting). MS: 448 (M+1). $^1H$ NMR (400 MHz, $CD_3OD$) δ 7.10-7.00 (m, 7H), 4.62-4.50 (m, 1H), 4.06-4.04 (m, 1H), 3.96-3.92 (m, 3H), 3.88-3.84 (m, 1H), 3.02-2.75 (m, 7H), 2.03-1.70 (m, 1H), 1.63-1.50 (m, 1H), 1.25-1.21 (m, 1H), 0.67-0.53 (m, 4H).

2-cyclopropyl-6-((3S,4S)-4-(3,4-dihydroisoquinolin-2(1H)-yl)-3-hydroxypiperidine-1-carbonyl)-2H-benzo[b][1,4]oxazin-3(4H)-one (Example 81, isomer 2, second eluting). MS: 448 (M+1). $^1H$ NMR (400 MHz, $CD_3OD$) δ 7.11-7.00 (m, 7H), 4.04-3.98 (m, 3H), 3.95-3.93 (m, 3H), 3.74-3.46 (m, 5H), 3.31-2.73 (m, 2H), 1.85-1.45 (m, 2H), 1.22-1.19 (m, 1H), 0.56-0.52 (m, 4H)

TABLE 14

The following examples were prepared as above examples 80 and 81 utilizing the appropriate carboxylic acid.

| Ex | Structure | Compound Name | Exact Mass (M + 1) |
|---|---|---|---|
| 82 | 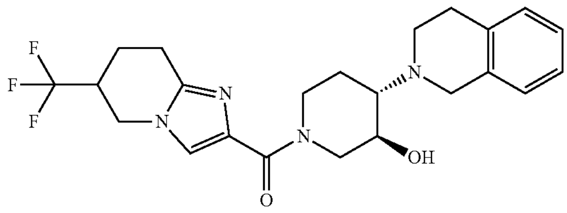 [SMILES: O=C(c1cn2c(n1)CCC(C(F)(F)F)C2)N1CC[C@H](N2CCc3ccccc3C2)[C@@H](O)C1] First eluting peak | ((3S,4S)-4-(3,4-dihydroisoquinolin-2(1H)-yl)-3-hydroxypiperidin-1-yl)(-6-(trifluoromethyl)-5,6,7,8-tetrahydroimidazo[1,2-a]pyridin-2-yl)methanone | 449 |
| 83 | 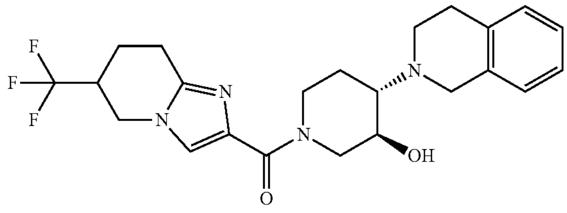 [SMILES: O=C(c1cn2c(n1)CCC(C(F)(F)F)C2)N1CC[C@H](N2CCc3ccccc3C2)[C@@H](O)C1] Second eluting peak | ((3S,4S)-4-(3,4-dihydroisoquinolin-2(1H)-yl)-3-hydroxypiperidin-1-yl)(-6-(trifluoromethyl)-5,6,7,8-tetrahydroimidazo[1,2-a]pyridin-2-yl)methanone | 449 |
| 84 | 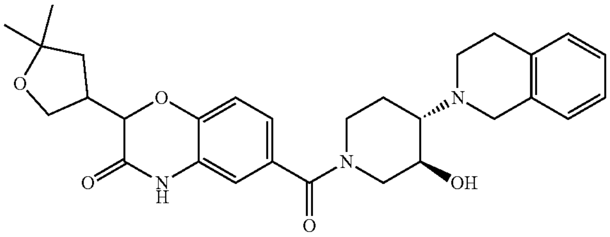 [SMILES: CC1(C)CC(C2Oc3ccc(C(=O)N4CC[C@H](N5CCc6ccccc6C5)[C@@H](O)C4)cc3NC2=O)CO1] First eluting peak | 6-((3S,4S)-4-(3,4-dihydroisoquinolin-2(1H)-yl)-3-hydroxypiperidine-1-carbonyl)-2-(-5,5-dimethyltetrahydrofuran-3-yl)-2H-benzo[b][1,4]oxazin-3(4H)-one | 506 |

TABLE 14-continued

| The following examples were prepared as above examples 80 and 81 utilizing the appropriate carboxylic acid. | | | |
|---|---|---|---|
| Ex | Structure | Compound Name | Exact Mass (M + 1) |
| 85 | 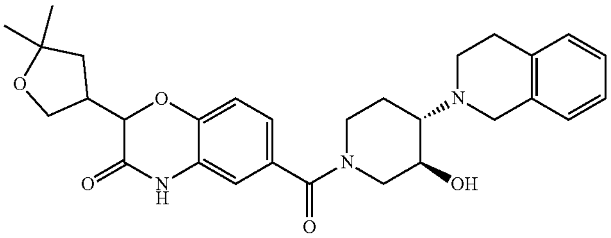 [SMILES: CC1(C)CC(C2Oc3ccc(C(=O)N4CC[C@H](N5CCc6ccccc6C5)[C@@H](O)C4)cc3NC2=O)CO1] Second eluting peak | 6-((3S,4S)-4-(3,4-dihydroisoquinolin-2(1H)-yl)-3-hydroxypiperidine-1-carbonyl)-2-(-5,5-dimethyltetrahydrofuran-3-yl)-2H-benzo[b][1,4]oxazin-3(4H)-one | 506 |
| 86 | 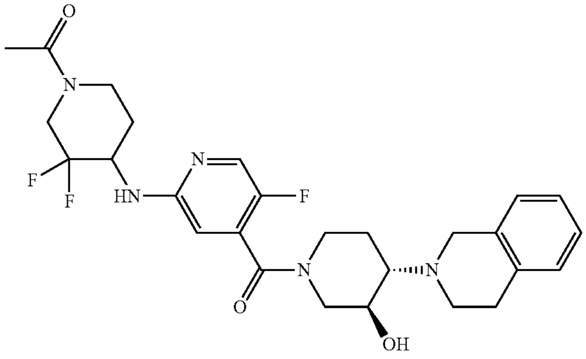 [SMILES: CC(=O)N1CCC(Nc2cc(C(=O)N3CC[C@H](N4CCc5ccccc5C4)[C@@H](O)C3)c(F)cn2)C(F)(F)C1] First eluting peak | 1-(4-((4-((3S,4S)-4-(3,4-dihydroisoquinolin-2(1H)-yl)-3-hydroxypiperidine-1-carbonyl)-5-fluoropyridin-2-yl)amino)-3,3-difluoropiperidin-1-yl)ethan-1-one | 532 |
| 87 | 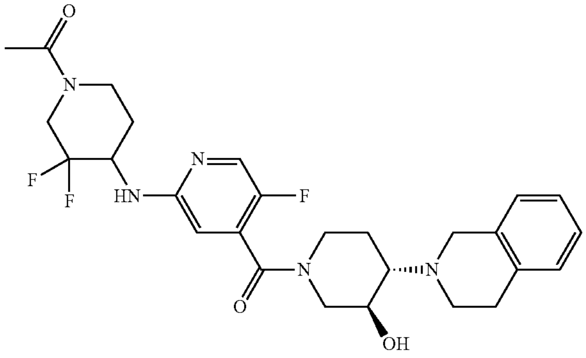 [SMILES: CC(=O)N1CCC(Nc2cc(C(=O)N3CC[C@H](N4CCc5ccccc5C4)[C@@H](O)C3)c(F)cn2)C(F)(F)C1] Second eluting peak | 1-(4-((4-((3S,4S)-4-(3,4-dihydroisoquinolin-2(1H)-yl)-3-hydroxypiperidine-1-carbonyl)-5-fluoropyridin-2-yl)amino)-3,3-difluoropiperidin-1-yl)ethan-1-one | 532 |
| 88 | 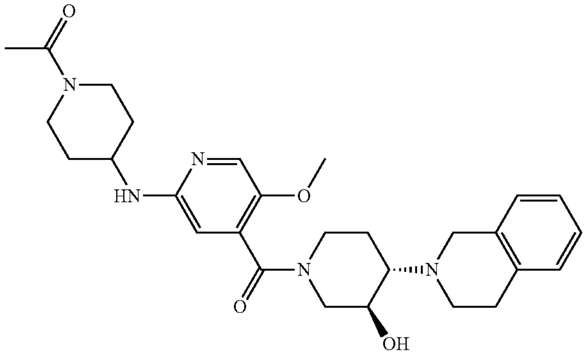 [SMILES: COc1cnc(NC2CCN(C(C)=O)CC2)cc1C(=O)N1CC[C@H](N2CCc3ccccc3C2)[C@@H](O)C1] | 1-(4-((4-((3S,4S)-4-(3,4-dihydroisoquinolin-2(1H)-yl)-3-hydroxypiperidine-1-carbonyl)-5-methoxypyridin-2-yl)amino)piperidin-1-yl)ethan-1-one | 508 |

Example 89: 2-(5-{[(3S,4S)-4-(3,4-dihydroisoquinolin-2(1H)-yl)-3-hydroxypiperidin-1-yl]carbonyl}pyridin-2-yl)-2-methylpropanenitrile Example 90: 2-(5-{[(3R,4R)-4-(3,4-dihydroisoquinolin-2(1H)-yl)-3-hydroxypiperidin-1-yl]carbonyl}pyridin-2-yl)-2-methylpropanenitrile

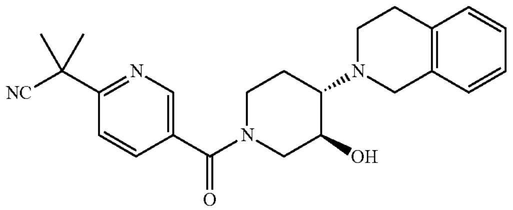

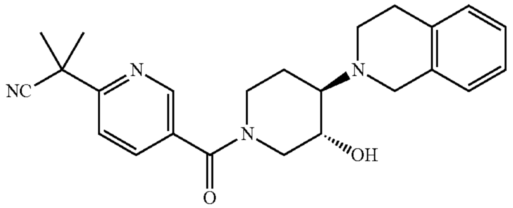

To a mixture of 2-(5-bromopyridin-2-yl)-2-methylpropanenitrile (100 mg, 0.444 mmol), triethylamine (62 μL, 0.44 mmol), and 4-(3,4-dihydroisoquinolin-2(1H)-yl)piperidin-3-ol (124 mg, 0.533 mmol) in acetonitrile (3 mL) was added [1,1'-bis(diphenylphosphino)ferrocene]dichloropalladium (II) (33 mg, 0.044 mmol) at room temperature under an argon atmosphere. The reaction was degassed and back filled with carbon monoxide (80 psi), and the reaction was stirred at 75° C. for 18 h. Another 0.1 eq of $PdCl_2$(dppf) was added, and the mixture was stirred at 75° C. for 18 h at 80 psi. The mixture was cooled to room temperature and diluted with water and EtOAc. The aqueous layer was extracted with EtOAc (2×), and the combined organic layers were dried over sodium sulfate, filtered, and concentrated under reduced pressure. The residue was purified by mass triggered reverse phase column chromatography (eluting with acetonitrile/water gradient with 0.1% TFA modifier) to afford desired product as a mixture of trans isomers, which were purified by chiral SFC (Lux column, MeOH/$CO_2$ with 0.25% DMEA modifier) to afford crude, chirally pure products.

Example 89, isomer 1, first eluting: Repurified by achiral SFC (ES Basic column, MeOH/$CO_2$) to afford 2-(5-{[(3S,4S)-4-(3,4-dihydroisoquinolin-2(1H)-yl)-3-hydroxypiperidin-1-yl]carbonyl}pyridin-2-yl)-2-methylpropanenitrile (Example 89) as a solid. MS: 405 (M+1). $^1$H NMR (600 MHz, DMSO-$d_6$) δ 8.64-8.60 (m, 1H), 7.94-7.89 (m, 1H), 7.67-7.61 (m, 1H), 7.07-7.01 (m, 2H), 7.01-6.96 (m, 1H), 4.86-4.69 (m, 1H), 4.52-4.23 (m, 1H), 3.82-3.73 (m, 2H), 3.68-3.60 (m, 1H), 3.55-3.40 (m, 2H), 2.94-2.84 (m, 2H), 2.81-2.70 (m, 2H), 2.64-2.55 (m, 1H), 1.88-1.78 (m, 1H), 1.69 (s, 6H), 1.59-1.46 (m, 2H), 1.33-1.15 (m, 1H).

Example 90, isomer 2, second eluting: Repurified by achiral SFC (ES Basic column, MeOH/$CO_2$) to afford 2-(5-{[(3R,4R)-4-(3,4-dihydroisoquinolin-2(1H)-yl)-3-hydroxypiperidin-1-yl]carbonyl}pyridin-2-yl)-2-methylpropanenitrile (Example 90) as a solid: MS: 405 (M+1). $^1$H NMR (600 MHz, DMSO-$d_6$) δ 8.64-8.60 (m, 1H), 7.94-7.89 (m, 1H), 7.67-7.61 (m, 1H), 7.07-7.01 (m, 2H), 7.01-6.96 (m, 1H), 4.86-4.69 (m, 1H), 4.52-4.23 (m, 1H), 3.82-3.73 (m, 2H), 3.68-3.60 (m, 1H), 3.55-3.40 (m, 2H), 2.94-2.84 (m, 2H), 2.81-2.70 (m, 2H), 2.64-2.55 (m, 1H), 1.88-1.78 (m, 1H), 1.69 (s, 6H), 1.59-1.46 (m, 2H), 1.33-1.15 (m, 1H).

TABLE 15

The following examples were prepared as above examples 89 and 90 from the corresponding aryl bromide.

| Ex | Structure | Compound Name | Exact Mass (M + 1) |
|---|---|---|---|
| 91 | 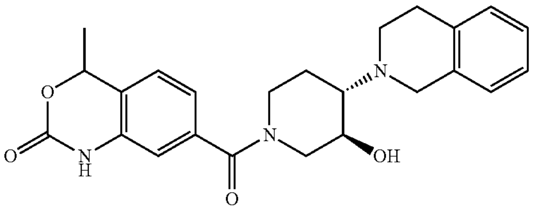 [SMILES: CC1OC(=O)Nc2cc(C(=O)N3CC[C@H](N4CCc5ccccc5C4)[C@@H](O)C3)ccc21] From Intermediate 42 | 7-((3R,4R)-4-(3,4-dihydroisoquinolin-2(1H)-yl)-3-hydroxypiperidine-1-carbonyl)-4-methyl-1,4-dihydro-2H-benzo[d][1,3]oxazin-2-one | 422 |
| 92 | 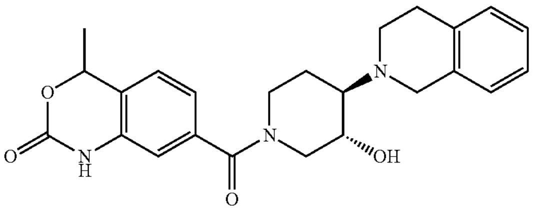 [SMILES: CC1OC(=O)Nc2cc(C(=O)N3CC[C@@H](N4CCc5ccccc5C4)[C@H](O)C3)ccc21] From Intermediate 42 | 7-((3S,4S)-4-(3,4-dihydroisoquinolin-2(1H)-yl)-3-hydroxypiperidine-1-carbonyl)-4-methyl-1,4-dihydro-2H-benzo[d][1,3]oxazin-2-one | 422 |

TABLE 15-continued

The following examples were prepared as above examples 89 and 90 from the corresponding aryl bromide.

| Ex | Structure | Compound Name | Exact Mass (M + 1) |
|---|---|---|---|
| 93 | 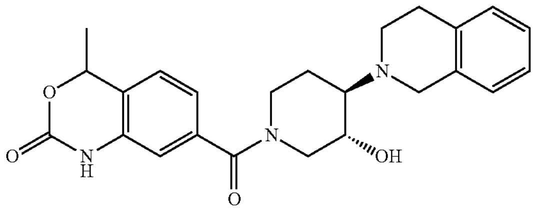 [SMILES: CC1OC(=O)Nc2cc(C(=O)N3CC[C@@H](N4CCc5ccccc5C4)[C@H](O)C3)ccc21] From Intermediate 41 | 7-((3S,4S)-4-(3,4-dihydroisoquinolin-2(1H)-yl)-3-hydroxypiperidine-1-carbonyl)-4-methyl-1,4-dihydro-2H-benzo[d][1,3]oxazin-2-one | 422 |
| 94 | 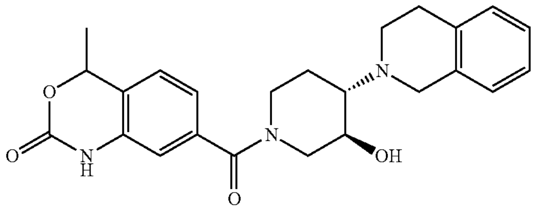 [SMILES: CC1OC(=O)Nc2cc(C(=O)N3CC[C@H](N4CCc5ccccc5C4)[C@@H](O)C3)ccc21] From Intermediate 41 | 7-((3R,4R)-4-(3,4-dihydroisoquinolin-2(1H)-yl)-3-hydroxypiperidine-1-carbonyl)-4-methyl-1,4-dihydro-2H-benzo[d][1,3]oxazin-2-one | 422 |
| 95 | 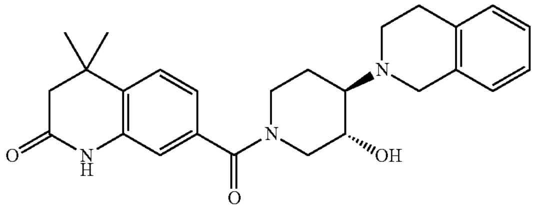 [SMILES: CC1(C)CC(=O)Nc2cc(C(=O)N3CC[C@@H](N4CCc5ccccc5C4)[C@H](O)C3)ccc21] | 7-((3R,4R)-4-(3,4-dihydroisoquinolin-2(1H)-yl)-3-hydroxypiperidine-1-carbonyl)-4,4-dimethyl-3,4-dihydroquinolin-2(1H)-one | 434 |
| 96 | 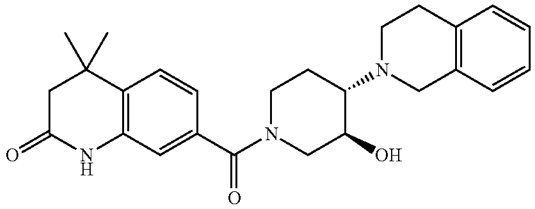 [SMILES: CC1(C)CC(=O)Nc2cc(C(=O)N3CC[C@H](N4CCc5ccccc5C4)[C@@H](O)C3)ccc21] | 7-((3S,4S)-4-(3,4-dihydroisoquinolin-2(1H)-yl)-3-hydroxypiperidine-1-carbonyl)-4,4-dimethyl-3,4-dihydroquinolin-2(1H)-one | 434 |
| 97 | 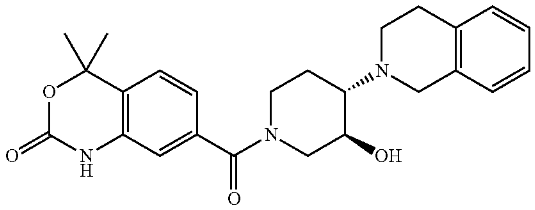 [SMILES: CC1(C)OC(=O)Nc2cc(C(=O)N3CC[C@H](N4CCc5ccccc5C4)[C@@H](O)C3)ccc21] | 7-((3S,4S)-4-(3,4-dihydroisoquinolin-2(1H)-yl)-3-hydroxypiperidine-1-carbonyl)-4,4-dimethyl-1,4-dihydro-2H-benzo[d][1,3]oxazin-2-one | 436 |
| 98 | 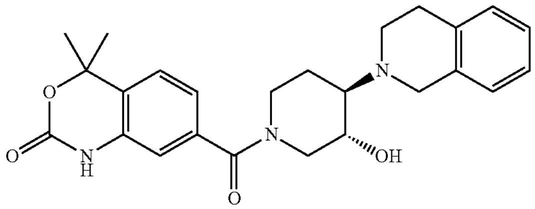 [SMILES: CC1(C)OC(=O)Nc2cc(C(=O)N3CC[C@@H](N4CCc5ccccc5C4)[C@H](O)C3)ccc21] | 7-((3R,4R)-4-(3,4-dihydroisoquinolin-2(1H)-yl)-3-hydroxypiperidine-1-carbonyl)-4,4-dimethyl-1,4-dihydro-2H-benzo[d][1,3]oxazin-2-one | 436 |

TABLE 15-continued

| Ex | Structure | Compound Name | Exact Mass (M + 1) |
|---|---|---|---|
| The following examples were prepared as above examples 89 and 90 from the corresponding aryl bromide. | | | |
| 99 | 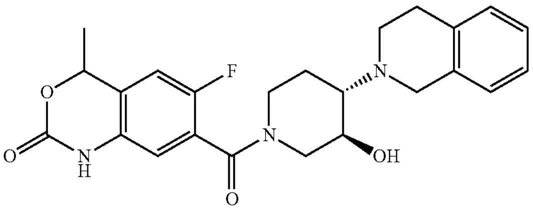 [SMILES: CC1OC(=O)Nc2cc(C(=O)N3CC[C@H](N4CCc5ccccc5C4)[C@@H](O)C3)c(F)cc21] First eluting peak | 7-((3S,4S)-4-(3,4-dihydroisoquinolin-2(1H)-yl)-3-hydroxypiperidine-1-carbonyl)-6-fluoro-4-methyl-1,4-dihydro-2H-benzo[d][1,3]oxazin-2-one | 440 |
| 100 | 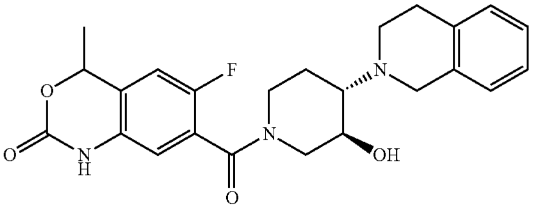 [SMILES: CC1OC(=O)Nc2cc(C(=O)N3CC[C@H](N4CCc5ccccc5C4)[C@@H](O)C3)c(F)cc21] Second eluting peak | 7-((3S,4S)-4-(3,4-dihydroisoquinolin-2(1H)-yl)-3-hydroxypiperidine-1-carbonyl)-6-fluoro-4-methyl-1,4-dihydro-2H-benzo[d][1,3]oxazin-2-one | 440 |
| 101 | 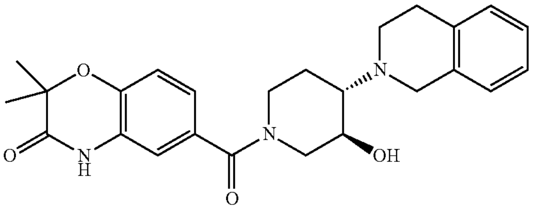 [SMILES: CC1(C)Oc2ccc(C(=O)N3CC[C@H](N4CCc5ccccc5C4)[C@@H](O)C3)cc2NC1=O] | 6-((3S,4S)-4-(3,4-dihydroisoquinolin-2(1H)-yl)-3-hydroxypiperidine-1-carbonyl)-2,2-dimethyl-2H-benzo[b][1,4]oxazin-3(4H)-one | 436 |
| 102 | 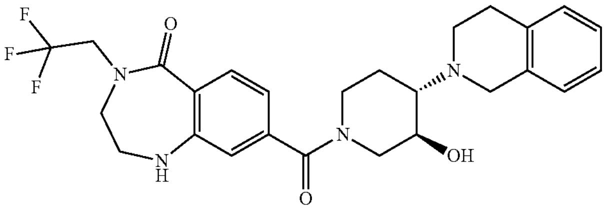 [SMILES: O=C(c1ccc2c(c1)NCCN(CC(F)(F)F)C2=O)N1CC[C@H](N2CCc3ccccc3C2)[C@@H](O)C1] | 8-((3S,4S)-4-(3,4-dihydroisoquinolin-2(1H)-yl)-3-hydroxypiperidine-1-carbonyl)-4-(2,2,2-trifluoroethyl)-1,2,3,4-tetrahydro-5H-benzo[e][1,4]diazepin-5-one | 503 |

Example 104: tert-butyl-3-((4-((3S,4S)-4-(3,4-dihydroisoquinolin-2(1H)-yl)-3-hydroxypiperidine-1-carbonyl)-5-fluoropyridin-2-yl)amino)-8-azabicyclo[3.2.1]octane-8-carboxylate

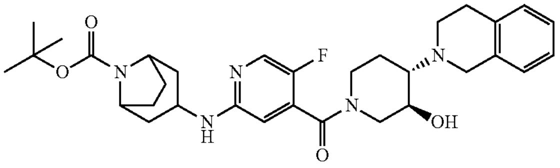 [SMILES: CC(C)(C)OC(=O)N1C2CCC1CC(Nc1cc(C(=O)N3CC[C@H](N4CCc5ccccc5C4)[C@@H](O)C3)c(F)cn1)C2]

(2-Bromo-5-fluoropyridin-4-yl)((3S,4S)-4-(3,4-dihydroisoquinolin-2(1H)-yl)-3-hydroxypiperidin-1-yl)methanone (350 mg, 0.81 mmol), tert-butyl 3-amino-8-azabicyclo[3.2.1]octane-8-carboxylate (182 mg, 0.806 mmol), cesium carbonate (525 mg, 1.61 mmol), and Ruphos Pd G3 (67.4 mg, 0.081 mmol) were added to a 20 mL microwave tube, evacuated under nitrogen, and charged with dioxane (5 mL). The mixture was heated to 140° C. for 3 h. The reaction was cooled to room temperature and then diluted with ethyl acetate, washed with water (×2), dried over anhydrous magnesium sulfate, filtered, and concentrated under reduced pressure. The residue was purified by column chromatography on silica (0 to 10% (7N Ammonia/Methanol in DCM)) followed by mass triggered reverse phase HPLC (ACN/water with 0.1% ammonia modifier) to afford tert-butyl-3-((4-((3S,4S)-4-(3,4-dihydroisoquinolin-2(1H)-yl)-3-hydroxypiperidine-1-carbonyl)-5-fluoropyridin-2-yl)amino)-8-azabicyclo[3.2.1]octane-8-carboxylate. MS: 580 (M+1). $^1$H NMR (600 MHz, $CD_3OD$) δ 7.91 (d, J=10.8 Hz, 1H), 7.04 (m, 7.08-6.99, 4H), 6.38 (d, J=10.2 Hz, 1H), 4.74-4.50 (m, 1H), 4.41-4.14 (m, 3H), 3.97-3.80 (m, 2H), 3.77-3.52 (m, 2H), 3.18-3.10 (m, 1H), 3.05-2.68 (m, 8H), 2.00-1.81 (m, 7H), 1.55-1.45 (m, 1H), 1.45 (s, 9H).

TABLE 16

The following examples were prepared as above example 104 using the appropriate amine.

| Ex | Structure | Compound Name | Exact Mass (M + 1) |
|---|---|---|---|
| 105 | 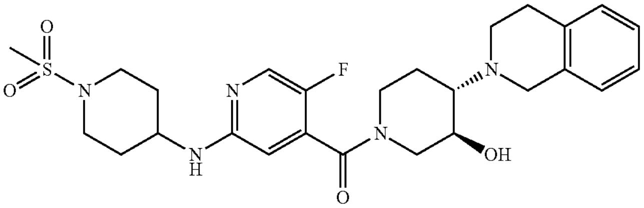 [SMILES: CS(=O)(=O)N1CCC(Nc2cc(C(=O)N3CC[C@H](N4CCc5ccccc5C4)[C@@H](O)C3)c(F)cn2)CC1] | ((3S,4S)-4-(3,4-dihydroisoquinolin-2(1H)-yl)-3-hydroxypiperidin-1-yl)(5-fluoro-2-((1-(methylsulfonyl)piperidin-4-yl)amino)pyridin-4-yl)methanone | 532 |
| 106 | 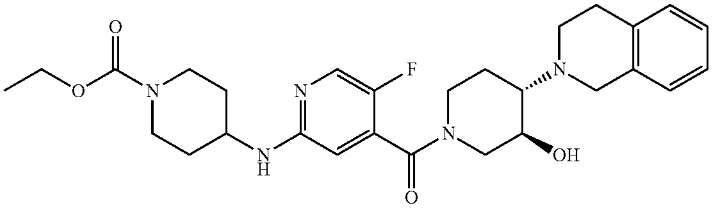 [SMILES: CCOC(=O)N1CCC(Nc2cc(C(=O)N3CC[C@H](N4CCc5ccccc5C4)[C@@H](O)C3)c(F)cn2)CC1] | ethyl 4-((4-((3S,4S)-4-(3,4-dihydroisoquinolin-2(1H)-yl)-3-hydroxypiperidine-1-carbonyl)-5-fluoropyridin-2-yl)amino)piperidine-1-carboxylate | 526 |
| 107 | 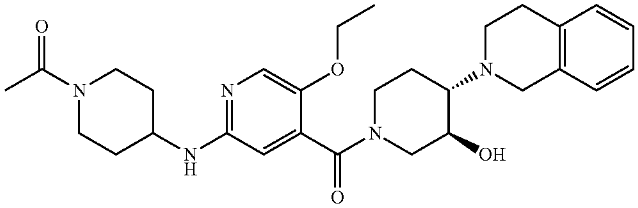 [SMILES: CCOc1cnc(NC2CCN(C(C)=O)CC2)cc1C(=O)N1CC[C@H](N2CCc3ccccc3C2)[C@@H](O)C1] | 1-(4-((4-((3S,4S)-4-(3,4-dihydroisoquinolin-2(1H)-yl)-3-hydroxypiperidine-1-carbonyl)-5-ethoxypyridin-2-yl)amino)piperidin-1-yl)ethan-1-one | 522 |
| 108 | 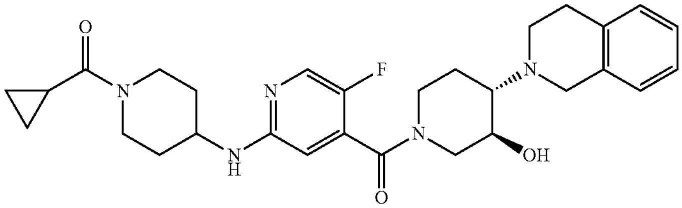 [SMILES: O=C(c1cc(NC2CCN(C(=O)C3CC3)CC2)ncc1F)N1CC[C@H](N2CCc3ccccc3C2)[C@@H](O)C1] | (2-((1-(cyclopropanecarbonyl)piperidin-4-yl)amino)-5-fluoropyridin-4-yl)((3S,4S)-4-(3,4-dihydroisoquinolin-2(1H)-yl)-3-hydroxypiperidin-1-yl)methanone | 522 |
| 109 | 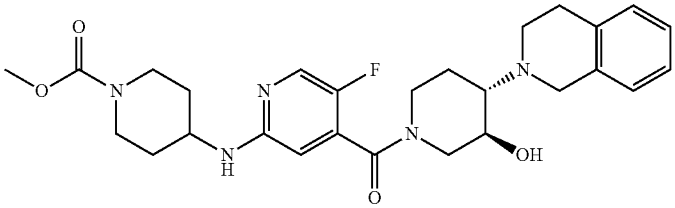 [SMILES: COC(=O)N1CCC(Nc2cc(C(=O)N3CC[C@H](N4CCc5ccccc5C4)[C@@H](O)C3)c(F)cn2)CC1] | methyl 4-((4-((3S,4S)-4-(3,4-dihydroisoquinolin-2(1H)-yl)-3-hydroxypiperidine-1-carbonyl)-5-fluoropyridin-2-yl)amino)piperidine-1-carboxylate | 512 |
| 110 | 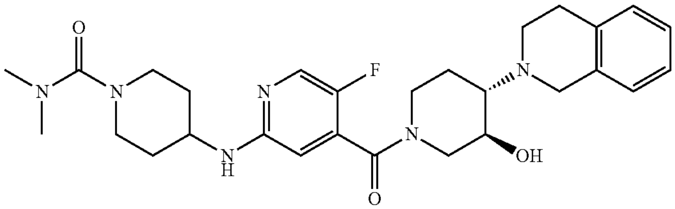 [SMILES: CN(C)C(=O)N1CCC(Nc2cc(C(=O)N3CC[C@H](N4CCc5ccccc5C4)[C@@H](O)C3)c(F)cn2)CC1] | 4-((4-((3S,4S)-4-(3,4-dihydroisoquinolin-2(1H)-yl)-3-hydroxypiperidine-1-carbonyl)-5-fluoropyridin-2-yl)amino)-N,N-dimethylpiperidine-1-carboxamide | 525 |
| 111 | 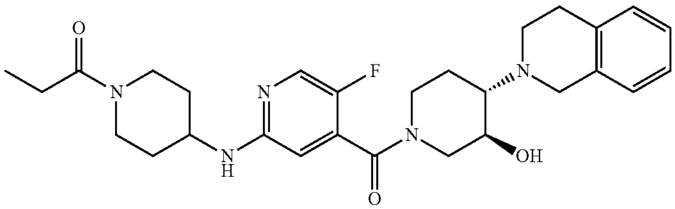 [SMILES: CCC(=O)N1CCC(Nc2cc(C(=O)N3CC[C@H](N4CCc5ccccc5C4)[C@@H](O)C3)c(F)cn2)CC1] | 1-(4-((4-((3S,4S)-4-(3,4-dihydroisoquinolin-2(1H)-yl)-3-hydroxypiperidine-1-carbonyl)-5-fluoropyridin-2-yl)amino)piperidin-1-yl)propan-1-one | 510 |

TABLE 16-continued

The following examples were prepared as above example 104 using the appropriate amine.

| Ex | Structure | Compound Name | Exact Mass (M + 1) |
|---|---|---|---|
| 112 | 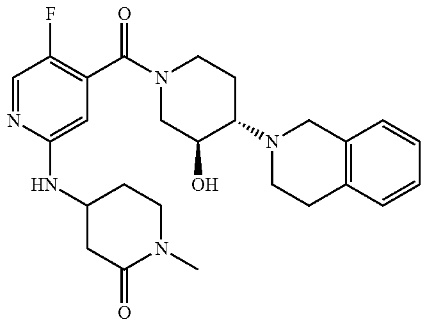 [SMILES: CN1CCC(Nc2cc(C(=O)N3CC[C@H](N4CCc5ccccc5C4)[C@@H](O)C3)c(F)cn2)CC1=O] | 4-((4-((3S,4S)-4-(3,4-dihydroisoquinolin-2(1H)-yl)-3-hydroxypiperidine-1-carbonyl)-5-fluoropyridin-2-yl)amino)-1-methylpiperidin-2-one | 482 |

Example 113: 1-(-3-((4-((3S,4S)-4-(3,4-dihydroisoquinolin-2(1H)-1)-3-hydroxypiperidine-1-carbonyl)-5-fluoropyridin-2-yl)amino)pyrrolidin-1-yl)ethan-1-one Example 114: 1-(-3-((4-((3S,4S)-4-(3,4-dihydroisoquinolin-2(1H)-1)-3-hydroxypiperidine-1-carbonyl)-5-fluoropyridin-2-yl)amino)pyrrolidin-1-yl)ethan-1-one

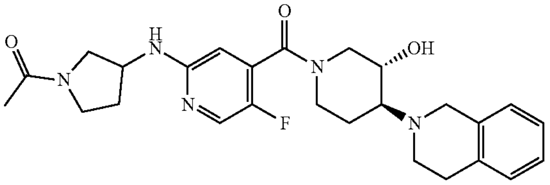

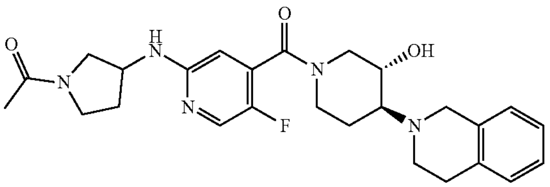

In a 20 mL vial charged with (2-bromo-5-fluoropyridin-4-yl)((3S,4S)-4-(3,4-dihydroisoquinolin-2(1H)-yl)-3-hydroxypiperidin-1-yl)methanone (240 mg, 0.55 mmol), 1-acetyl-3-aminopyrrolidine (85 mg, 0.66 mmol), cesium carbonate (360 mg, 1.11 mmol), and Ruphos Pd G3 (4.62 mg, 5.53 μmol) was added dioxane (5 mL) under nitrogen. The reaction mixture was allowed to stir at 100° C. for 2 h. The reaction mixture was diluted with ethyl acetate, washed with water (×2), dried over anhydrous magnesium sulfate, filtered, and concentrated under reduced pressure. The residue was purified by reverse phase HPLC (ACN/water with 0.1% TFA modifier) to afford 1-(3-((4-((3S,4S)-4-(3,4-dihydroisoquinolin-2(1H)-yl)-3-hydroxypiperidine-1-carbonyl)-5-fluoropyridin-2-yl)amino)pyrrolidin-1-yl)ethan-1-one.

The racemic mixture was purified by chiral SFC (AD-H column, IPA/$CO_2$ with 0.25% DMEA modifier) to give two isomers: 1-(-3-((4-((3S,4S)-4-(3,4-dihydroisoquinolin-2(1H)-yl)-3-hydroxypiperidine-1-carbonyl)-5-fluoropyridin-2-yl)amino)pyrrolidin-1-yl)ethan-1-one as a solid (Example 113, isomer 1, first eluting). MS: 482 (M+1). $^1$H NMR (600 MHz, $CD_3OD$) δ 8.03-7.92 (m, 1H), 7.16-7.04 (m, 4H), 6.46 (s, 1H), 4.79-4.30 (m, 1H), 4.15-3.97 (m, 1H), 3.90-3.33 (m, 4H), 3.19-2.68 (m, 6H), 2.37-2.14 (m, 1H), 2.12-1.88 (m, 1H), 2.03 (s, 3H), 1.77-1.49 (m, 2H), 1.37-1.10 (m, 3H), 0.91-0.78 (m, 2H).

1-(-3-((4-((3S,4S)-4-(3,4-dihydroisoquinolin-2(1H)-yl)-3-hydroxypiperidine-1-carbonyl)-5-fluoropyridin-2-yl)amino)pyrrolidin-1-yl)ethan-1-one as a solid (Example 114, isomer 2, second eluting). MS: 482 (M+1). $^1$H NMR (600 MHz, $CD_3OD$) δ 1H NMR (600 MHz, $CD_3OD$) δ 7.97 (dd, J=10.5, 3.7 Hz, 1H), 7.08-6.99 (m, 4H), 6.46 (s, 1H), 4.75-4.34 (m, 1H), 3.96-3.30 (m, 6H), 3.17-2.66 (m, 6H), 2.32-2.16 (m, 1H), 2.03 (s, 3H), 2.07-1.84 (m, 2H), 1.65-0.79 (m, 5H).

TABLE 17

| The following examples were prepared as above examples 113 and 114 using the corresponding amine. | | | |
|---|---|---|---|
| Ex | Structure | Compound Name | Exact Mass (M + 1) |
| 115 | 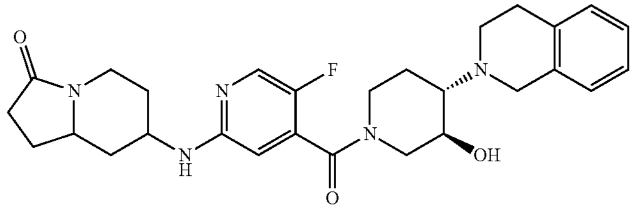 [SMILES: O=C(c1cc(NC2CCN3C(=O)CCC3C2)ncc1F)N1CC[C@H](N2CCc3ccccc3C2)[C@@H](O)C1] Second eluting peak HPLC, first eluting peak SFC | 7-[(4-{[(3S,4S)-4-(3,4-dihydroisoquinolin-2(1H)-yl)-3-hydroxypiperidin-1-yl]carbonyl}-5-fluoropyridin-2-yl)amino]hexahydroindolizin-3(2H)-one | 508 |
| 116 | 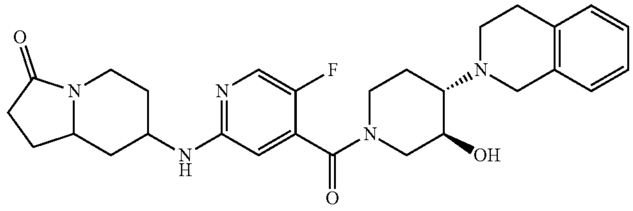 [SMILES: O=C(c1cc(NC2CCN3C(=O)CCC3C2)ncc1F)N1CC[C@H](N2CCc3ccccc3C2)[C@@H](O)C1] First eluting peak HPLC, first eluting peak SFC | 7-[(4-{[(3S,4S)-4-(3,4-dihydroisoquinolin-2(1H)-yl)-3-hydroxypiperidin-1-yl]carbonyl}-5-fluoropyridin-2-yl)amino]hexahydroindolizin-3(2H)-one | 508 |
| 117 | 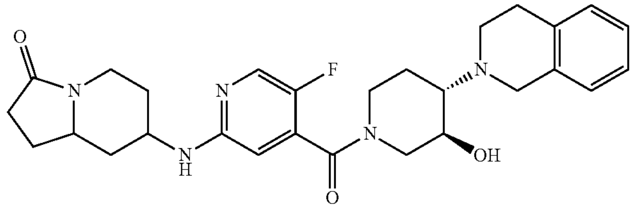 [SMILES: O=C(c1cc(NC2CCN3C(=O)CCC3C2)ncc1F)N1CC[C@H](N2CCc3ccccc3C2)[C@@H](O)C1] First eluting peak HPLC, second eluting peak SFC | 7-[(4-{[(3S,4S)-4-(3,4-dihydroisoquinolin-2(1H)-yl)-3-hydroxypiperidin-1-yl]carbonyl}-5-fluoropyridin-2-yl)amino]hexahydroindolizin-3(2H)-one | 508 |
| 118 | 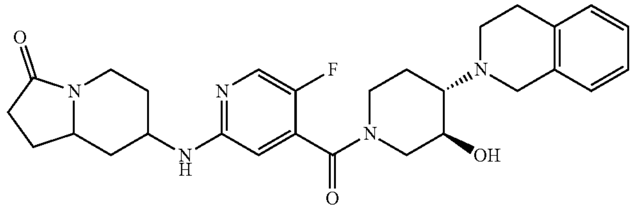 [SMILES: O=C(c1cc(NC2CCN3C(=O)CCC3C2)ncc1F)N1CC[C@H](N2CCc3ccccc3C2)[C@@H](O)C1] Second eluting peak HPLC, second eluting peak SFC | 7-[(4-{[(3S,4S)-4-(3,4-dihydroisoquinolin-2(1H)-yl)-3-hydroxypiperidin-1-yl]carbonyl}-5-fluoropyridin-2-yl)amino]hexahydroindolizin-3(2H)-one | 508 |

Example 119: 1-(5-((4-((3S,4S)-4-(3,4-dihydroisoquinolin-2(1H)-yl)-3-hydroxypiperidine-1-carbonyl)-5-fluoropyridin-2-yl)amino)-2-azabicyclo[2.2.1]heptan-2-yl)ethan-1-one Example 120: 1-(5-((4-((3S,4S)-4-(3,4-dihydroisoquinolin-2(1H)-1)-3-hydroxypiperidine-1-carbonyl)-5-fluoropyridin-2-yl)amino)-2-azabicyclo[2.2.1]heptan-2-yl)ethan-1-one

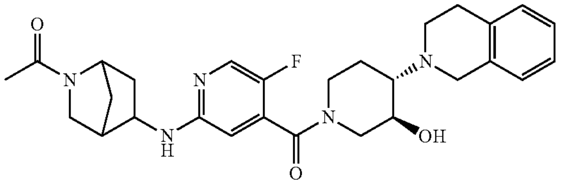

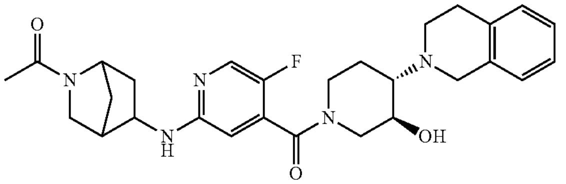

Step 1: To a flask charged with tert-butyl 5-((4-((3S,4S)-4-(3,4-dihydroisoquinolin-2(1H)-yl)-3-hydroxypiperidine-1-carbonyl)-5-fluoropyridin-2-yl)amino)-2-azabicyclo[12.2.1]heptane-2-carboxylate (478 mg, 0.85 mmol) was added HCl (4M in dioxane, 2.11 mL, 8.45 mmol). The reaction mixture was allowed to stir at room temperature for 2 h. The mixture was concentrated under reduced pressure. The residue was titrated with ether, and then filtered to give (2-((2-azabicyclo[2.2.1]heptan-5-yl)amino)-5-fluoropyridin-4-yl)((3S,4S)-4-(3,4-dihydroisoquinolin-2(1H)-yl)-3-hydroxypiperidin-1-yl)methanone HCl salt, which was used in the next step without further purification. MS: 466 (M+1).

Step 2: In a vial charged with 2-azabicyclo[2.2.1]heptan-5-ylamino)-5-fluoropyridin-4-yl)((3S,4S)-4-(3,4-dihydroisoquinolin-2(1H)-yl)-3-hydroxypiperidin-1-yl)methanone HCl salt (200 mg, 0.398 mmol) in DCM (4.3 mL) was added TEA (0.167 mL, 1.20 mmol). To the mixture was added acetic anhydride (0.045 mL, 0.478 mmol) dropwise. The reaction mixture was allowed to stir at room temperature for 1 h. The mixture was diluted with DCM. The organic layer was washed with brine, dried over anhydrous magnesium sulfate, filtered, and concentrated under reduced pressure. The residue was purified by column chromatography on silica (methanol/DCM). The residue was then purified by reverse phase HPLC (ACN/water with 0.1% TFA modifier) to give two isomers.

1-(-5-((4-((3S,4S)-4-(3,4-dihydroisoquinolin-2(1H)-yl)-3-hydroxypiperidine-1-carbonyl)-5-fluoropyridin-2-yl)amino)-2-azabicyclo[2.2.1]heptan-2-yl)ethan-1-one TFA salt as a solid (Example 119, isomer 1, first eluting). MS: 508 (M+1). $^1$H NMR (600 MHz, $CD_3OD$) δ 8.00 (d, J=15.0 Hz, 1H), 7.36-7.14 (m, 4H), 6.52 (s, 1H), 4.81-4.21 (m, 3H), 4.04-3.35 (m, 7H), 3.19-3.02 (m, 3H), 2.97-2.71 (m, 1H), 2.66-2.59 (m, 1H), 2.33-2.10 (m, 2H), 2.96-2.18 (m, 3H), 1.90-1.42 (m, 6H).

1-(-5-((4-((3S,4S)-4-(3,4-dihydroisoquinolin-2(1H)-yl)-3-hydroxypiperidine-1-carbonyl)-5-fluoropyridin-2-yl)amino)-2-azabicyclo[2.2.1]heptan-2-yl)ethan-1-one TFA salt as a solid (Example 120, isomer 2, second eluting). MS: 508 (M+1). $^1$H NMR (600 MHz, $CD_3OD$) δ 7.98 (d, J=13.5 Hz, 1H), 7.45-7.08 (m, 4H), 6.58 (s, 1H), 4.82-4.15 (m, 4H), 4.05-3.31 (m, 7H), 3.20-2.72 (m, 4H), 2.35-2.11 (m, 3H), 2.07-1.96 (m, 3H), 1.92-1.65 (m, 4H), 1.45-1.31 (m, 1H).

Example 121: (2-((8-azabicyclo[3.2.1]octan-3-yl)amino)-5-fluoropyridin-4-yl)((3S,4S)-4-(3,4-dihydroisoquinolin-2(1H)-yl)-3-hydroxypiperidin-1-yl)methanone Example 122: 1-(3-((4-((3S,4S)-4-(3,4-dihydroisoquinolin-2(1H)-yl)-3-hydroxypiperidine-1-carbonyl)-5-fluoropyridin-2-yl)amino)-8-azabicyclo[3.2.1]octan-8-yl)ethan-1-one

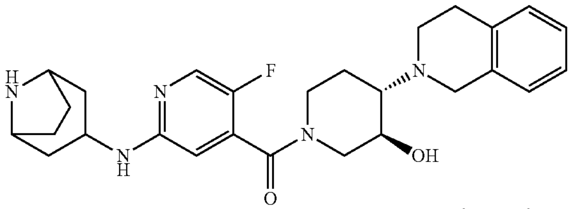

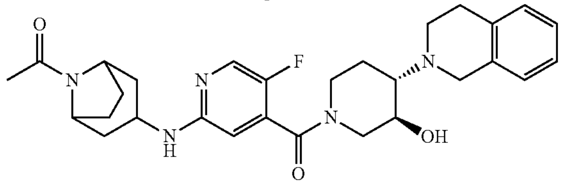

Step 1: To a flask containing tert-butyl-3-((4-((3S,4S)-4-(3,4-dihydroisoquinolin-2(1H)-yl)-3-hydroxypiperidine-1-carbonyl)-5-fluoropyridin-2-yl)amino)-8-azabicyclo[3.2.1]octane-8-carboxylate (25 mg, 0.043 mmol) was added HCl in dioxane (4M, 0.129 mL, 0.52 mmol). The mixture was allowed to stir at rt overnight. The reaction mixture was diluted with ether and filtered to collect (2-((8-azabicyclo[3.2.1]octan-3-yl)amino)-5-fluoropyridin-4-yl)((3S,4S)-4-(3,4-dihydroisoquinolin-2(1H)-yl)-3-hydroxypiperidin-1-yl)methanone (example 121) as solid HCl salt. MS: 480 (M+1). $^1$H NMR (600 MHz, $CD_3OD$) δ 8.06 (d, J=12.7 Hz, 1H), 7.34-7.15 (m, 5H), 4.80-4.63 (m, 2H), 4.56-4.33 (m, 1H), 4.35-4.18 (m, 1H), 4.15-4.02 (m, 2H), 3.87-3.42 (m, 8H), 3.16-3.07 (m, 2H), 2.99-2.76 (m, 1H), 2.34-1.83 (m, 8H).

Step 2: To a flask charged with (2-((8-azabicyclo[3.2.1]octan-3-yl)amino)-5-fluoropyridin-4-yl)((3S,4S)-4-(3,4-dihydroisoquinolin-2(1H)-yl)-3-hydroxypiperidin-1-yl)methanone HCl salt (62.8 mg, 0.12 mmol) in DCM (1.2 mL) was added triethylamine (0.051 mL, 0.365 mmol), then acetic anhydride (0.014 mL, 0.146 mmol) was added dropwise. The mixture was allowed to stir at room temperature for 2 h. The reaction was quenched with water, and the mixture was concentrated under reduced pressure. The residue was purified by reverse phase HPLC (ACN/water with 0.1% TFA modifier) to afford 1-(3-((4-((3S,4S)-4-(3,4-dihydroisoquinolin-2(1H)-yl)-3-hydroxypiperidine-1-carbonyl)-5-fluoropyridin-2-yl)amino)-8-azabicyclo[3.2.1]octan-8-yl)ethan-1-one (Example 122) as a solid. MS: 522 (M+1). $^1$H NMR (600 MHz, $CD_3OD$) δ 7.97 (d, J=14.0 Hz, 1H), 7.33-7.17 (m, 5H), 4.81-4.55 (m, 3H), 4.54-4.25 (m, 3H), 4.01-3.88 (m, 1H), 3.84-3.68 (m, 3H), 3.62-3.53 (m, 2H), 3.19-3.06 (m, 2H), 2.95-2.71 (m, 1H), 2.15-2.11 (m, 2H), 2.07 (s, 3H), 2.03-1.86 (m, 6H), 1.57-1.47 (m, 2H).

TABLE 18

The following examples were prepared as above example 121 using the appropriate amine, except for Example 124, which was purified by SFC instead of mass triggered reverse phase HPLC.

| Ex | Structure | Compound Name | Exact Mass (M + 1) |
| --- | --- | --- | --- |
| 123 | 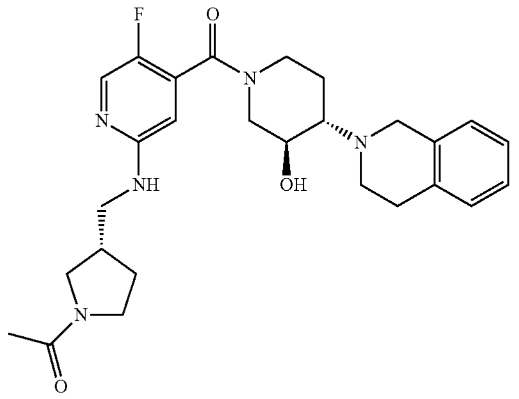 [SMILES: CC(=O)N1CC[C@@H](CNc2cc(C(=O)N3CC[C@H](N4CCc5ccccc5C4)[C@@H](O)C3)c(F)cn2)C1] | 1-((S)-3-(((4-((3S,4S)-4-(3,4-dihydroisoquinolin-2(1H)-yl)-3-hydroxypiperidine-1-carbonyl)-5-fluoropyridin-2-yl)amino)methyl)pyrrolidin-1-yl)ethan-1-one | 496 |
| 124 | 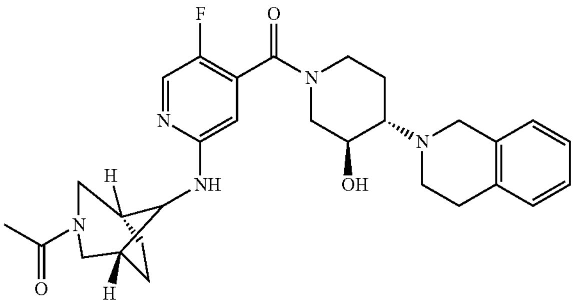 [SMILES: CC(=O)N1C[C@H]2CC[C@@H](C1)C2Nc1cc(C(=O)N2CC[C@H](N3CCc4ccccc4C3)[C@@H](O)C2)c(F)cn1] | 1-((1R,5S)-8-((4-((3S,4S)-4-(3,4-dihydroisoquinolin-2(1H)-yl)-3-hydroxypiperidine-1-carbonyl)-5-fluoropyridin-2-yl)amino)-3-azabicyclo[3.2.1]octan-3-yl)ethan-1-one | 522 |

Example 125: 1-(2-((3S,4S)-4-(3,4-dihydroisoquinolin-2(1H)-yl)-3-hydroxypiperidine-1-carbonyl)imidazo[1,2-a]pyridin-6-yl)cyclopropane-1-carbonitrile

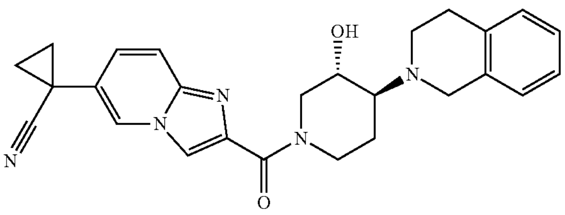 [SMILES: N#CC1(c2ccc3nc(C(=O)N4CC[C@H](N5CCc6ccccc6C5)[C@@H](O)C4)cn3c2)CC1]

Step 1: To a solution of 6-bromoimidazo[1,2-a]pyridine-2-carboxylic acid (1.0 g, 4.15 mmol), (3S,4S)-4-(3,4-dihydroisoquinolin-2(1H)-yl)piperidin-3-ol (1.01 g, 4.36 mmol), and 1-propanephosphonic anhydride (3.70 ml, 6.22 mmol) in DMF (41.5 ml) was added DIEA (2.17 ml, 12.4 mmol). The reaction was allowed to stir for 18 h at room temperature. Upon completion the reaction was diluted with water and extracted with EtOAc (3×), and the organic layer was dried over sodium sulfate. The mixture was filtered, and concentrated under reduced pressure to afford (6-bromoimidazo[1,2-a]pyridin-2-yl)((3S,4S)-4-(3,4-dihydroisoquinolin-2(1H)-yl)-3-hydroxypiperidin-1-yl)methanone as a solid. MS: 455 and 457 (M+1).

Step 2: Xantphos palladacycle G4 (10.6 mg, 10.9 μmol) was charged in a 20 mL microwave vial. The flask was backfilled with nitrogen gas (×3). THF (1.1 mL) was added to the flask and the mixture was stirred for 5 minutes at room temperature. A solution of cyclopropanecarbonitrile (0.012 mL, 0.165 mmol) and (6-bromoimidazo[1,2-a]pyridin-2-yl)((3S,4S)-4-(3,4-dihydroisoquinolin-2(1H)-yl)-3-hydroxypiperidin-1-yl)methanone (0.05 g, 0.110 mmol) in THF (1.1 mL) was added followed by the addition of lithium bis(trimethylsilyl)amide (1M in THF) (0.329 mL, 0.329 mmol) dropwise via syringe. The reaction mixture was stirred at room temperature for 2 h. Upon completion the reaction was quenched with sat aq $NH_4Cl$, extracted with DCM, dried over sodium sulfate, filtered, and concentrated under reduced pressure. The material was purified by reverse phase HPLC (ACN/water with 0.1% TFA for the modifier) to afford 1-(2-((3S,4S)-4-(3,4-dihydroisoquinolin-2(1H)-yl)-3-hydroxypiperidine-1-carbonyl)imidazo[1,2-a]pyridin-6-yl)cyclopropane-1-carbonitrile as the TFA salt. MS: 442 (M+1). $^1$H NMR (500 MHz, DMSO-$d_6$) δ 9.92 (s, 1H), 7.83-7.70 (m, 1H), 7.35-7.15 (m, 4H), 6.90-6.75 (m, 1H), 6.64-6.42 (m, 1H), 5.25 (s, 1H), 4.70-4.53 (m, 2H), 4.48-4.37 (m, 2H), 3.94-3.86 (m, 1H), 3.80-3.71 (m, 1H), 3.60-3.52 (m, 1H), 3.49-3.39 (m, 1H), 3.37-3.24 (m, 1H), 3.20-3.10 (m, 1H), 3.07-2.96 (m, 2H), 2.23-2.02 (m, 2H), 1.86-1.74 (m, 2H), 1.65-1.54 (m, 2H).

Example 126: ((3S,4S)-4-(3A-dihydroisoquinolin-2(1H)-yl)-3-hydroxypiperidin-1-yl)(4-hydroxy-3-(2,2,2-trifluoroethyl)quinolin-7-yl)methanone

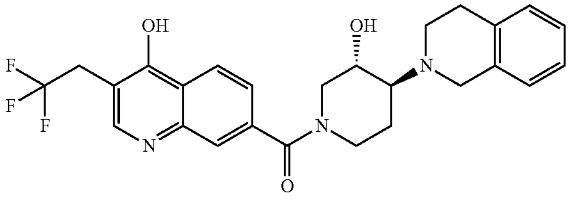 [SMILES: O=C(c1ccc2c(O)c(CC(F)(F)F)cnc2c1)N1CC[C@H](N2CCc3ccccc3C2)[C@@H](O)C1]

Step 1: To a solution of 4-butoxy-3-(2,2,2-trifluoroethyl)quinoline-7-carboxylic acid (30 mg, 0.092 mmol), (3S,4S)-4-(3,4-dihydroisoquinolin-2(1H)-yl)piperidin-3-ol (21.3 mg, 0.092 mmol) and DIEA (0.048 mL, 0.275 mmol) in DMF (2 mL) was added 2,4,6-tripropyl-1,3,5,2,4,6-trioxatriphosphinane 2,4,6-trioxide (117 mg, 0.183 mmol) (50% Wt in DMF) at 25° C. The mixture was stirred at 25° C. for 10 min. The mixture was quenched with water (20 mL). The mixture was extracted with EtOAc (10 mL×3). The combined organic layers were washed with brine (20 mL), dried over anhydrous sodium sulfate, filtered, and the filtrate was concentrated under reduced pressure to give the crude product (4-butoxy-3-(2,2,2-trifluoroethyl)quinolin-7-yl)((3S,4S)-4-(3,4-dihydroisoquinolin-2(1H)-yl)-3-hydroxypiperidin-1-yl)methanone as an oil, which was used directly in next step. MS: 542 (M+1).

Step 2: To a solution of (4-butoxy-3-(2,2,2-trifluoroethyl)quinolin-7-yl)((3S,4S)-4-(3,4-dihydroisoquinolin-2(1H)-yl)-3-hydroxypiperidin-1-yl)methanone (48 mg, 0.089 mmol) in DCM (20 mL) was added $BBr_3$ (3.35 mL, 35.5 mmol) at 25° C. The mixture was stirred at 25° C. for 30 min. The reaction was quenched with MeOH (20 mL) at 0° C. The mixture was concentrated under reduced pressure. The residue was purified by reverse phase HPLC (ACN/water with 0.05% $NH_4HCO_3$ modifier) to give ((3S,4S)-4-(3,4-dihydroisoquinolin-2(1H)-yl)-3-hydroxypiperidin-1-yl)(4-hydroxy-3-(2,2,2-trifluoroethyl)quinolin-7-yl)methanone as a solid. MS: 486 (M+1). $^1H$ NMR (400 MHz, $CD_3OD$) δ 8.35 (br s, 1H), 8.12 (s, 1H), 7.63 (br d, J=5.26 Hz, 1H), 7.50-7.42 (m, 1H), 7.12-7.01 (m, 4H), 4.65-4.54 (m, 1H), 4.01-3.65 (m, 4H), 3.52 (q, J=10.96 Hz, 2H), 3.20-2.95 (m, 3H), 2.91 (br s, 3H), 2.78 (br s, 1H), 2.12-1.83 (m, 1H), 1.80-1.57 (m, 1H).

Example 127: 1-(2-{[(3S,4S)-4-(3,4-dihydroisoquinolin-2(1H)-yl)-3-hydroxypiperidin-1-yl]carbonyl}imidazo[1,2-a]pyrimidin-6-yl)-2,2-dimethylcyclopropanecarbonitrile Example 128: 1-(2-{[(3S,4S)-4-(3,4-dihydroisoquinolin-2(1H)-yl)-3-hydroxypiperidin-1-yl]carbonyl}imidazo[1,2-a]pyrimidin-6-yl)-2,2-dimethylcyclopropanecarbonitrile

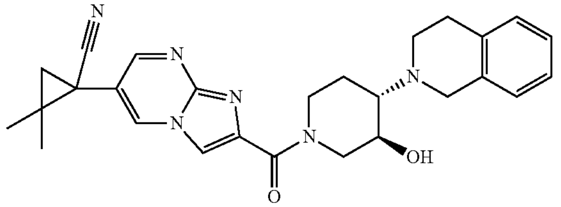

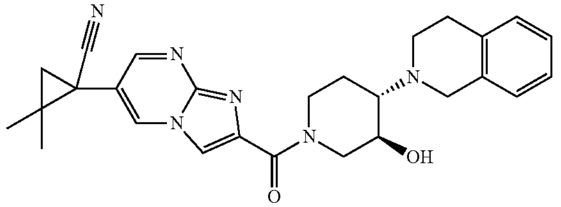

Step 1: To a mixture of 6-(1-cyano-2,2-dimethylcyclopropyl)imidazo[1,2-a]pyrimidine-2-carboxylic acid (300 mg, 1.17 mmol) in DMF (6 mL) was added HATU (534 mg, 1.41 mmol), DIEA (0.613 mL, 3.51 mmol) and (3S,4S)-4-(3,4-dihydroisoquinolin-2(1H)-yl)piperidin-3-ol (272 mg, 1.17 mmol). The mixture was stirred at 25° C. for 15 min. The mixture was purified by reverse phase HPLC (ACN/water with 0.05% $NH_4HCO_3$ modifier) to afford racemic 1-(2-{[(3S,4S)-4-(3,4-dihydroisoquinolin-2(1H)-yl)-3-hydroxypiperidin-1-yl]carbonyl}imidazo[1,2-a]pyrimidin-6-yl)-2,2-dimethylcyclopropanecarbonitrile as a solid. The racemic mixture was purified by chiral SFC (Daicel Chiralpak AD column, 50%/50% EtOH/$CO_2$ with 0.1% ammonia hydroxide modifier) to afford two isomers.

1-(2-{[(3S,4S)-4-(3,4-dihydroisoquinolin-2(1H)-yl)-3-hydroxypiperidin-1-yl]carbonyl}imidazo[1,2-a]pyrimidin-6-yl)-2,2-dimethylcyclopropanecarbonitrile (example 129, isomer 1, first eluting): MS: 471 (M+1); $^1H$ NMR (400 MHz, Methanol-$d_4$) δ 9.01-8.98 (m, 1H), 8.73 (d, J=1.75 Hz, 1H), 8.15 (s, 1H), 7.10-7.01 (m, 4H), 4.82 (br d, J=11.40 Hz, 1H), 4.67-4.56 (m, 1H), 4.00-3.76 (m, 3H), 3.25-2.98 (m, 2H), 2.97-2.68 (m, 5H), 2.08-1.89 (m, 1H), 1.78-1.66 (m, 2H), 1.62 (d, J=5.70 Hz, 1H), 1.58 (s, 3H), 0.98 (s, 3H).

1-(2-{[(3S,4S)-4-(3,4-dihydroisoquinolin-2(1H)-yl)-3-hydroxypiperidin-1-yl]carbonyl}imidazo[1,2-a]pyrimidin-6-yl)-2,2-dimethylcyclopropanecarbonitrile as a solid (example 130, isomer 2, second eluting peak): MS: 471 (M+1); $^1H$ NMR (400 MHz, Methanol-$d_4$) δ 9.01-8.98 (m, 1H), 8.73 (d, J=2.19 Hz, 1H), 8.15 (s, 1H), 7.10-7.01 (m, 4H), 4.84-4.74 (m, 1H), 4.61 (br d, J=11.40 Hz, 1H), 4.01-3.77 (m, 3H), 3.27-3.00 (m, 2H), 2.99-2.71 (m, 5H), 2.10-1.89 (m, 1H), 1.79-1.67 (m, 2H), 1.62 (d, J=5.70 Hz, 1H), 1.58 (s, 3H), 0.98 (s, 3H).

TABLE 19

The following examples were prepared as above examples 127 & 128 using the appropriate carboxylic acid

| Ex | Structure | Compound Name | Exact Mass (M + 1) |
|---|---|---|---|
| 129 | 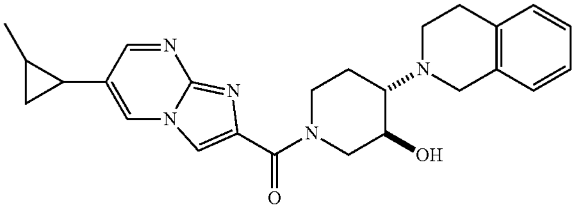 First eluting peak (mix of two isomers) | ((3S,4S)-4-(3,4-dihydroisoquinolin-2(1H)-yl)-3-hydroxypiperidin-1-yl)(6-(2-methylcyclopropyl)imidazo[1,2-a]pyrimidin-2-yl)methanone | 432 |
| 130 | 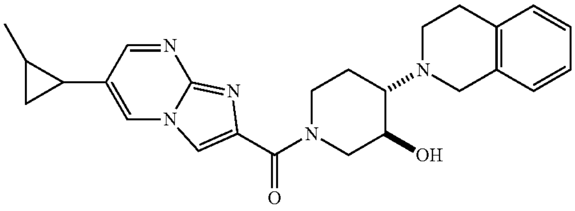 Second eluting peak | ((3S,4S)-4-(3,4-dihydroisoquinolin-2(1H)-yl)-3-hydroxypiperidin-1-yl)(6-(2-methylcyclopropyl)imidazo[1,2-a]pyrimidin-2-yl)methanone | 432 |
| 131 | 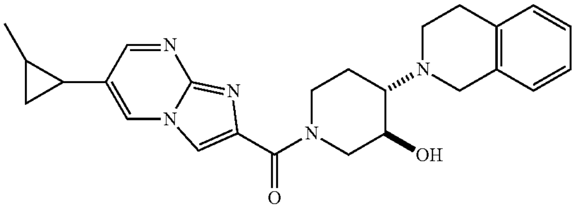 Third eluting peak | ((3S,4S)-4-(3,4-dihydroisoquinolin-2(1H)-yl)-3-hydroxypiperidin-1-yl)(6-(2-methylcyclopropyl)imidazo[1,2-a]pyrimidin-2-yl)methanone | 432 |

Example 132: (6-chloroimidazo[1,2-a]pyridin-2-yl)[(3S,4S)-4-(3,4-dihydroisoquinolin-2(1H)-yl)-3-hydroxypiperidin-1-yl]methanone

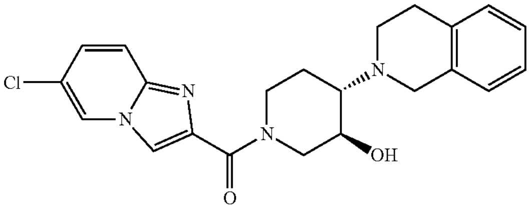 [SMILES: O=C(c1cn2cc(Cl)ccc2n1)N1CC[C@H](N2CCc3ccccc3C2)[C@@H](O)C1]

To 6-chloroimidazo[1,2-a]pyridine-2-carboxylic acid (19.7 mg, 0.1 mmol) was added 1 mL of a 0.1 M (3S,4S)-4-(3,4-dihydroisoquinolin-2(1H)-yl)piperidin-3-ol solution in NMP (0.1 mmol), 1 mL of a 0.1 M PyAOP solution in NMP (0.1 mmol), and DIEA (52 uL, 0.3 mmol). The resulting solution was stirred at room temperature for 24 h. The reaction was diluted with DMSO, filtered, and purified by reverse phase HPLC (ACN/water with 0.10% TFA modifier) to afford (6-chloroimidazo[1,2-a]pyridin-2-yl)[(3S,4S)-4-(3,4-dihydroisoquinolin-2(1H)-yl)-3-hydroxypiperidin-1-yl] methanone, TFA. MS: 411 (M+1). $^1$H NMR (500 MHz, DMSO-$d_6$) δ 8.87 (s, 1H), 8.35 (s, 1H), 7.68 (d, J=9.6 Hz, 1H), 7.42 (s, 1H), 7.38-7.22 (m, 3H), 7.20 (d, J=6.9 Hz, 1H), 5.41 (s, 1H), 4.82-4.52 (m, 1H), 4.43 (s, 1H), 3.92 (s, 1H), 3.77-3.52 (m, 1H), 3.25-3.10 (m, 1H), 3.11-2.95 (m, 1H), 2.89-2.76 (m, 1H), 2.74-2.65 (m, 1H), 2.30-2.03 (m, 1H), 1.90-1.66 (m, 1H). Note additional $^1$H peaks overlap with residual solvent.

TABLE 20

The following examples were prepared using a similar procedure as described in Example 132.

| Ex | Structure | Compound Name | Exact Mass (M + 1) |
|---|---|---|---|
| 133 | 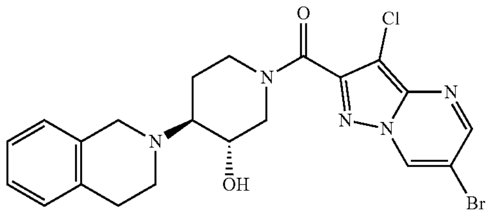 [SMILES: O=C(c1nn2cc(Br)cnc2c1Cl)N1CC[C@H](N2CCc3ccccc3C2)[C@@H](O)C1] | (6-bromo-3-chloropyrazolo[1,5-a]pyrimidin-2-yl)[(3S,4S)-4-(3,4-dihydroisoquinolin-2(1H)-yl)-3-hydroxypiperidin-1-yl]methanone | 490 and 492 |
| 134 | 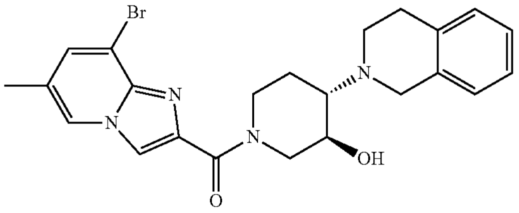 [SMILES: Cc1cc(Br)c2nc(C(=O)N3CC[C@H](N4CCc5ccccc5C4)[C@@H](O)C3)cn2c1] | (8-bromo-6-methylimidazo[1,2-a]pyridin-2-yl)[(3S,4S)-4-(3,4-dihydroisoquinolin-2(1H)-yl)-3-hydroxypiperidin-1-yl]methanone | 469 and 471 |
| 135 | 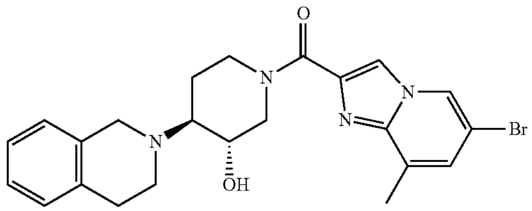 [SMILES: Cc1cc(Br)cn2cc(C(=O)N3CC[C@H](N4CCc5ccccc5C4)[C@@H](O)C3)nc12] | (6-bromo-8-methylimidazo[1,2-a]pyridin-2-yl)[(3S,4S)-4-(3,4-dihydroisoquinolin-2(1H)-yl)-3-hydroxypiperidin-1-yl]methanone | 469 and 471 |
| 136 | 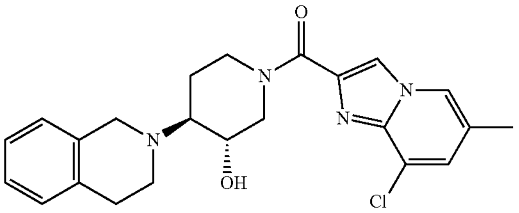 [SMILES: Cc1cc(Cl)c2nc(C(=O)N3CC[C@H](N4CCc5ccccc5C4)[C@@H](O)C3)cn2c1] | (8-chloro-6-methylimidazo[1,2-a]pyridin-2-yl)[(3S,4S)-4-(3,4-dihydroisoquinolin-2(1H)-yl)-3-hydroxypiperidin-1-yl]methanone | 425 |
| 137 | 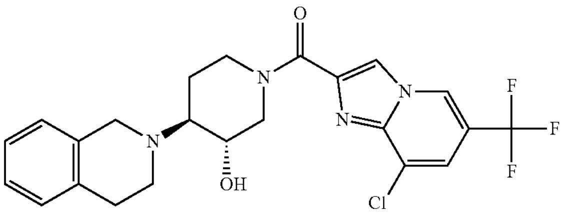 [SMILES: O=C(c1cn2cc(C(F)(F)F)cc(Cl)c2n1)N1CC[C@H](N2CCc3ccccc3C2)[C@@H](O)C1] | [8-chloro-6-(trifluoromethyl)imidazo[1,2-a]pyridin-2-yl][(3S,4S)-4-(3,4-dihydroisoquinolin-2(1H)-yl)-3-hydroxypiperidin-1-yl]methanone | 479 |
| 138 | 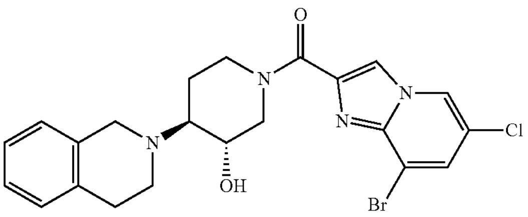 [SMILES: O=C(c1cn2cc(Cl)cc(Br)c2n1)N1CC[C@H](N2CCc3ccccc3C2)[C@@H](O)C1] | (8-bromo-6-chloroimidazo[1,2-a]pyridin-2-yl)[(3S,4S)-4-(3,4-dihydroisoquinolin-2(1H)-yl)-3-hydroxypiperidin-1-yl]methanone | 489 and 491 |

TABLE 20-continued

The following examples were prepared using a similar procedure as described in Example 132.

| Ex | Structure | Compound Name | Exact Mass (M + 1) |
|---|---|---|---|
| 139 | 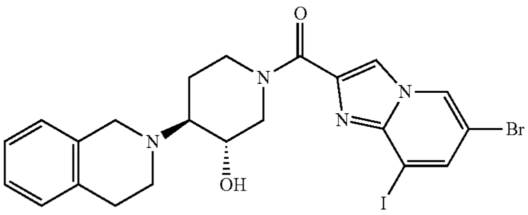 [SMILES: O=C(c1cn2cc(Br)cc(I)c2n1)N1CC[C@H](N2CCc3ccccc3C2)[C@@H](O)C1] | (6-bromo-8-iodoimidazo[1,2-a]pyridin-2-yl)[(3S,4S)-4-(3,4-dihydroisoquinolin-2(1H)-yl)-3-hydroxypiperidin-1-yl]methanone | 581 and 583 |
| 140 | 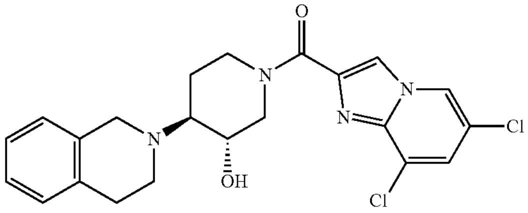 [SMILES: O=C(c1cn2cc(Cl)cc(Cl)c2n1)N1CC[C@H](N2CCc3ccccc3C2)[C@@H](O)C1] | (6,8-dichloroimidazo[1,2-a]pyridin-2-yl)[(3S,4S)-4-(3,4-dihydroisoquinolin-2(1H)-yl)-3-hydroxypiperidin-1-yl]methanone | 445 |
| 141 | 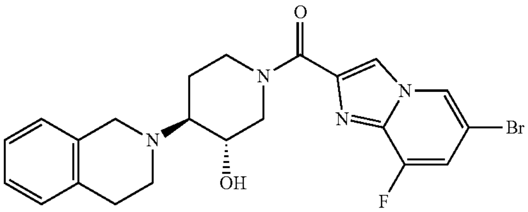 [SMILES: O=C(c1cn2cc(Br)cc(F)c2n1)N1CC[C@H](N2CCc3ccccc3C2)[C@@H](O)C1] | (6-bromo-8-fluoroimidazo[1,2-a]pyridin-2-yl)[(3S,4S)-4-(3,4-dihydroisoquinolin-2(1H)-yl)-3-hydroxypiperidin-1-yl]methanone | 473 and 475 |
| 142 | 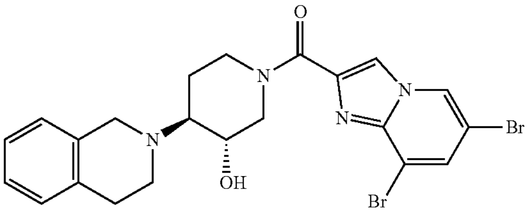 [SMILES: O=C(c1cn2cc(Br)cc(Br)c2n1)N1CC[C@H](N2CCc3ccccc3C2)[C@@H](O)C1] | (6,8-dibromoimidazo[1,2-a]pyridin-2-yl)[(3S,4S)-4-(3,4-dihydroisoquinolin-2(1H)-yl)-3-hydroxypiperidin-1-yl]methanone | 533 and 535 |
| 143 | 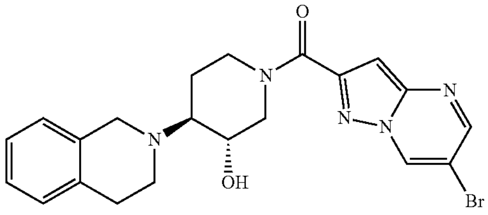 [SMILES: O=C(c1cc2ncc(Br)cn2n1)N1CC[C@H](N2CCc3ccccc3C2)[C@@H](O)C1] | (6-bromopyrazolo[1,5-a]pyrimidin-2-yl)[(3S,4S)-4-(3,4-dihydroisoquinolin-2(1H)-yl)-3-hydroxypiperidin-1-yl]methanone | 456 and 458 |

PRMT5-MEP50 Enzyme Methylation Assay (Version A)

PRMT5-MEP50 biochemical assay is a direct measurement of the methylation activity of the enzyme complex on a short peptide substrate derived from the N-terminus of H4 histone. Methylation experiment was performed with recombinant PRMT5-MEP50 protein complex. The assessment of inhibitory effect of small molecules was measured by the effectiveness of the compounds to inhibit this reaction ($EC_{50}$).

In this assay, the potency ($EC_{50}$) of each compound was determined from a twenty-point (1:2 serial dilution; top compound concentration of 100000 nM) titration curve using the following outlined procedure. To each well of a white ProxiPlus 384 well-plate, 100 nL of compound (1% DMSO in final assay volume of 10 μL) was dispensed, followed by the addition of 8 μL of 1× assay buffer (50 mM Bicine pH 8.0, 1 mM DTT, 0.004% Tween20, 0.01% BSA) containing 1.25 nM of Full-length (FL)-PRMT5-MEP50 enzyme complex (recombinant proteins from baculovirus-transfected Sf21 cells: FL-PRMT5; MW=73837 kDa and FL-MEP50; MW=38614) and 1 μL of 150 μM S-(5'-Adenosyl)-L-Methionine Chloride (SAM). A plate was sealed and placed in a 37° C. humidified chamber for a 60 minutes pre-incubation with compound. Subsequently, each reaction was initiated by the addition of 1 μL 1× assay buffer containing 750 nM biotinylated H4R3 (MeI) peptide. The final reaction in each well of 10 μL consists of 1.0 nM PRMT5-MEP50, 75 nM biotinylated-peptide, and 15 μM SAM. Methylation reactions were allowed to proceed for 150 minutes in a sealed plate at 37° C. Reactions were immediately quenched by the addition of 1 μL of 5% formic acid. A plate was then frozen and shipped to SAMDI™ Tech Inc. to determine the percent conversion from H4R3 (MeI) to H4R3 (Me2). Dose-response curves were generated by plotting percent effect (% product conversion; Y-axis) vs. Log 10 compound concentrations (X-axis). $EC_{50}$ values were determined by non-linear regression according to models for either sigmoidal (4 parameters) or biphasic (7 parameters) dose-response curves.

PRMT5-MEP50 Enzyme Methylation Assay (Version B)

PRMT5-MEP50 biochemical assay is a direct measurement of the methylation activity of the enzyme complex on a short peptide substrate derived from the N-terminus of H4 histone. Methylation experiment was performed with recombinant PRMT5-MEP50 protein complex. The assessment of inhibitory effect ($EC_{50}$) of small molecules was measured by the effectiveness of the compounds to inhibit this reaction.

In this assay, the potency ($EC_{50}$) of each compound was determined from a twenty-point (1:2 serial dilution; top compound concentration of 100000 nM) titration curve using the following outlined procedure. To each well of a white ProxiPlus 384 well-plate, 100 nL of compound (1% DMSO in final assay volume of 10 μL) was dispensed, followed by the addition of 8 μL of 1× assay buffer (50 mM Bicine pH 8.0, 1 mM DTT, 0.004% Tween20, 0.01% BSA) containing 0.625 nM of Full-length (FL)-PRMT5-MEP50 enzyme complex (recombinant proteins from baculovirus-transfected Sf21 cells: FL-PRMT5; MW=73837 kDa and FL-MEP50; MW=38614). Plates were sealed and placed in a 37° C. humidified chamber for 30 minutes pre-incubation with compounds. Subsequently, each reaction was initiated by the addition of 2 μL 1× assay buffer containing 375 nM biotinylated H4R3 (MeI) peptide, and 75 μM S-(5'-Adenosyl)-L-Methionine Chloride (SAM). The final reaction in each well of 10 μL consists of 0.5 nM PRMT5-MEP50, 75 nM biotinylated-peptide, and 15 μM SAM. Methylation reactions were allowed to proceed for 150 minutes in a sealed plate at 37° C. Reactions were immediately quenched by the addition of 1 μL of 10% formic acid. Plates were then frozen and shipped to SAMDI™ Tech Inc. to determine the percent conversion from K4R3 (MeI) to K4R3 (Me2). Dose-response curves were generated by plotting percent effect (% product conversion; Y-axis) vs. Log 10 compound concentrations (X-axis). $EC_{50}$ values were determined by non-linear regression according to models for either sigmoidal (4 parameters) or biphasic (7 parameters) dose-response curves.

PRMT5 Cell Target Engagement (TE) Assay

The PRMT5 TE assay is a biomarker assay for identifying compounds that inhibit symmetric dimethylation of arginine (SDMA) of PRMT5 substrates. The following substrates have been reported for PRMT5: histone H2A and H4 R3, Histone H3 R2, Histone H3 R8, spliceosome Sm proteins, ribosomal protein RPS10, p53, FEN1, nucleoplasmin, nucleolin, EGFR and EBNA. The assay focuses on detecting symmetrically dimethylated nuclear proteins using high content imaging technology. Detection of the expression of symmetrically dimethylated nuclear proteins is through a mixture of primary rabbit monoclonal antibodies to SDMA (CST 13222), which in turn recognized by an Alexafluor 488 dye-conjugated anti-rabbit IgG secondary antibody. The IN Cell Analyzer 2200 or Opera-Phenix measures nuclear Alexafluor 488 fluorescent dye intensity that is directly related to the level of expression of symmetrically dimethylated nuclear proteins at the single cell level. Nuclear AF488 dye intensities are compared to the mean value for DMSO treated cells (MIN) to report percent of inhibition for each compound-treated well.

In this assay, the cell potency ($EC_{50}$) of each compound was determined from a ten point (1:3 serial dilution; top compound concentration of 10000 nM) titration curve using the following outlined procedure. Each well of a BD falcon collagen coated black/clear bottom 384-well plate was seeded with 4000 MCF-7 cells in 30 μl media and allowed to attach for 5 h. Media is ATCC-formulated Eagle's Minimum Essential Medium, Catalog No. 30-2003. To make the complete growth medium, the following components were added to the base medium: 0.01 mg/mL human recombinant insulin; fetal bovine serum to a final concentration of 10%. Additional 30 μl of media containing 2× compounds were added to each well. Cells were treated for 3 days in 37° C. $CO_2$ incubator. On day 3, cells were fixed with Cytofix, permeabilized with 0.4% Triton-X-100/Cytofix, and washed with D-PBS without Ca/Mg. Cells were blocked with Licor Odessey blocking reagent for 1 h at room temperature, followed by incubation with anti-SDMA (1:1000) antibody at 4° C. overnight. 1° antibody was removed, followed by three washings with DPBS without Ca/Mg and 0.05% Tween20. Hoechst (5 μg/mL), Cell Mask deep stain (1:2000) and Alexa488-conjugated goat anti-rabbit IgG (2 μg/mL) was added for 1 h at room temperature. A final washing step (three washes) was performed before sealing plate for imaging on In Cell Analyzer 2200 or Opera-Phenix. Images from analyzer were uploaded to Columbus (at WP or BOS) for image analysis. $IC_{50}$ values were determined by 4 parameters robust fit of percent fluorescence units vs. ($Log_{10}$) compound concentrations.

Representative compounds of the present invention were tested using the assay protocol described in this example. Results are provided in Table 21.

TABLE 21

When only one $EC_{50}$ is shown, the data was fit to a 4 parameters single site sigmodal model. When two EC50s are shown, the data was fit to a 7 parameters biphasic model

| Ex. No. | Enzyme Methylation Assay Version A ($EC_{50}$, nM or $EC_{50}$_1, nM; $EC_{50}$_2, nM) | Enzyme Methylation Assay Version B ($EC_{50}$, nM or $EC_{50}$_1, nM; $EC_{50}$_2, nM) | TE Assay ($EC_{50}$, nM) |
|---|---|---|---|
| 1 | 1.1 | N/A | 9.8 |
| 2 | N/A | 13; 5888 | 509 |
| 3 | N/A | 75; 37580 | 3094 |
| 4 | N/A | 10; 29170 | >10000 |
| 5 | N/A | 1407 | >10000 |
| 6 | N/A | 4.8; 2690 | 24 |
| 7 | N/A | 16; 8565 | 326 |
| 8 | N/A | 571; >100000 | 9290 |
| 9 | N/A | 61; 8786 | 1677 |
| 10 | N/A | 6.4; 4624 | 119 |
| 11 | N/A | 1.8; 1072 | 4.9 |
| 12 | N/A | 106; 45710 | 6068 |
| 13 | N/A | 14; 17580 | 641 |
| 14 | N/A | 20; 17180 | 275 |
| 15 | N/A | 6.8; 3715 | 57 |
| 16 | N/A | 160; 83180 | 5727 |
| 17 | N/A | 191; >100000 | 8418 |
| 18 | 3; 6761 | N/A | 54 |
| 19 | 507 | N/A | 9795 |
| 20 | N/A | 4.4; 1496 | 12 |
| 21 | N/A | 56; 25410 | 1584 |
| 22 | 159; 58880 | N/A | >10000 |
| 23 | 36; 31620 | N/A | 4692 |
| 24 | N/A | 5564 | >10000 |
| 25 | N/A | 841; 33880 | >10000 |
| 26 | N/A | 15200 | >10000 |

TABLE 21-continued

When only one $EC_{50}$ is shown, the data was fit to a 4 parameters single site sigmodal model. When two EC50s are shown, the data was fit to a 7 parameters biphasic model

| Ex. No. | Enzyme Methylation Assay Version A ($EC_{50}$, nM or $EC_{50}$_1, nM; $EC_{50}$_2, nM) | Enzyme Methylation Assay Version B ($EC_{50}$, nM or $EC_{50}$_1, nM; $EC_{50}$_2, nM) | TE Assay ($EC_{50}$, nM) |
|---|---|---|---|
| 27 | N/A | 809 | >10000 |
| 28 | N/A | 1274; 45190 | 1662 |
| 29 | N/A | 1336 | >10000 |
| 30 | N/A | 4833 | >10000 |
| 31 | N/A | 30; 34280 | 405 |
| 32 | N/A | 2163 | >10000 |
| 33 | N/A | 23; 4653 | 27 |
| 34 | N/A | 38; 20580 | 2224 |
| 35 | N/A | 6.6; 2576 | 68 |
| 36 | N/A | 552; >100000 | >10000 |
| 37 | N/A | 87; 28610 | 1854 |
| 38 | N/A | 402; >100000 | >10000 |
| 39 | N/A | 31250; >100000 | >10000 |
| 40 | N/A | 45130; >100000 | >10000 |
| 41 | N/A | 19; 8110 | 1492 |
| 42 | N/A | 12400; >100000 | >10000 |
| 43 | N/A | 3.7; 3199 | 441 |
| 44 | N/A | 312; >100000 | >10000 |
| 47 | N/A | 1184 | >10000 |
| 48 | N/A | 17760 | >10000 |
| 49 | N/A | 11; 8913 | 7.8 |
| 50 | N/A | 76; 33500 | 4257 |
| 51 | 0.4; 120 | N/A | 6.3 |
| 52 | 580 | N/A | >10000 |
| 53 | 28; >10000 | N/A | >10000 |
| 56 | 0.4 | N/A | 1.8 |
| 57 | 1.1 | N/A | 8.7 |
| 58 | 0.3 | N/A | 0.6 |
| 59 | 0.5 | N/A | 4.4 |
| 60 | N/A | 14; 4677 | 435 |
| 61 | N/A | 2549 | >10000 |
| 62 | 3.6 | N/A | 21 |
| 63 | 0.7; 3311 | N/A | 140 |
| 64 | 1.9; 1660 | N/A | 45 |
| 65 | 3.5 | N/A | 9.6 |
| 66 | 5.2; 861 | N/A | 1808 |
| 67 | 0.6; 53 | N/A | 49 |
| 68 | 0.4 | N/A | 2.2 |
| 69 | 1.2; 733 | N/A | 55 |
| 70 | 45; 86100 | N/A | >10000 |
| 71 | 1.1 | N/A | 10 |
| 72 | 0.9; 248 | N/A | 37 |
| 75 | 41; 1549 | N/A | 647 |
| 76 | 3.1; 1679 | N/A | 2227 |
| 77 | 2.1 | N/A | 13 |
| 78 | 0.7 | N/A | 21 |
| 79 | 0.7 | N/A | 4.9 |
| 80 | 0.7 | N/A | 2.5 |
| 81 | 1.6; 5012 | N/A | 59 |
| 82 | N/A | 8; 6166 | 100 |
| 83 | N/A | 12; 9550 | 365 |
| 84 | 0.9 | N/A | 5.6 |
| 85 | 1.3 | N/A | 6.4 |
| 86 | N/A | 5.3; 3758 | 4.4 |
| 87 | N/A | 8.6; 7244 | 59 |
| 88 | N/A | 9.3; 2042 | 14 |
| 89 | N/A | 110; >100000 | 3947 |
| 90 | N/A | 1537 | >10000 |
| 91 | N/A | 127; 70790 | 7525 |
| 92 | N/A | 4.4; 2455 | 32 |
| 93 | N/A | 18; 11750 | 182 |
| 94 | N/A | 291; >100000 | 4560 |
| 95 | N/A | 62; 39360 | 2712 |
| 96 | N/A | 14; 15140 | 331 |
| 97 | N/A | 5.4; 2851 | 59 |
| 98 | N/A | 118; >100000 | 5834 |
| 99 | N/A | 8.2; 8710 | 131 |
| 100 | N/A | 4.8; 1718 | 15 |
| 101 | 0.9; 2884 | N/A | 16 |
| 102 | 1.5; 905 | N/A | 10 |
| 104 | 1.7 | N/A | 42 |
| 105 | N/A | 3.2; 1035 | 15 |
| 106 | N/A | 1.9; 496 | 6.2 |
| 107 | 2.1 | N/A | 7.9 |
| 108 | 1.3 | N/A | 3.8 |
| 109 | 1.2 | N/A | 3.5 |
| 110 | 1.4 | N/A | 8.1 |
| 111 | 1.4 | N/A | 6.1 |
| 112 | 4.5; 4416 | N/A | 50 |
| 113 | 3.1; 9550 | N/A | 50 |
| 114 | 3.3; 3126 | N/A | 28 |
| 115 | 6.5 | N/A | 140 |
| 116 | 3.9 | N/A | 6.6 |
| 117 | 1.8 | N/A | 3.3 |
| 118 | 2.9; 10590 | N/A | 55 |
| 119 | 3.5 | N/A | 15 |
| 120 | 20; 5495 | N/A | 316 |
| 121 | 14; 2884 | N/A | 1587 |
| 122 | 3.4 | N/A | 5.9 |
| 123 | 4.1 | N/A | 17 |
| 124 | 5.2; 4266 | N/A | 33 |
| 125 | 58; 13650 | N/A | 1747 |
| 126 | 1.1; 1334 | N/A | 69 |
| 127 | 0.4 | N/A | 12 |
| 128 | 0.3 | N/A | 1.1 |
| 129 | 1.4 | N/A | 6.4 |
| 130 | 0.7 | N/A | 3.8 |
| 131 | 0.5 | N/A | 4.6 |
| 132 | 3.2 | N/A | 32 |
| 133 | 3.2; 569 | N/A | 140 |
| 134 | 1.8; 202 | N/A | 43 |
| 135 | 1.7 | N/A | 12 |
| 136 | 1.2; 79 | N/A | 50 |
| 137 | 1.1 | N/A | 9.2 |
| 138 | 1.1; 39 | N/A | 17 |
| 139 | 1.3 | N/A | 7.6 |
| 140 | 0.8; 65 | N/A | 28 |
| 141 | 1.1 | N/A | 21 |
| 142 | 1.1 | N/A | 8.6 |
| 143 | 2.8; 1820 | N/A | 806 |

What is claimed is:

1. A compound of formula I,

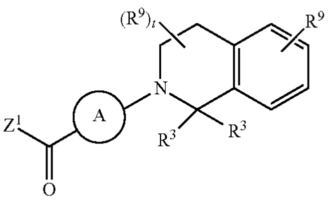

or a pharmaceutically acceptable salt thereof, wherein

A is a 6 membered heterocycle containing 1 nitrogen ring atom and 5 carbon ring atoms, wherein A is substituted with OH and optionally substituted with 0-2 $R^2$;

$z^1$ is

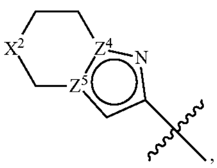,
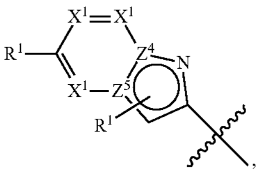,
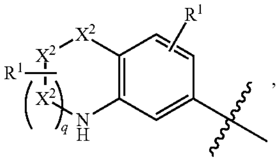,
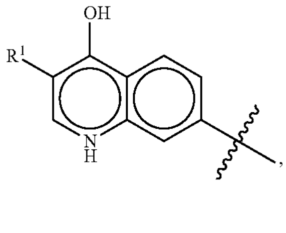,
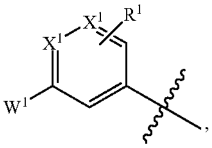,
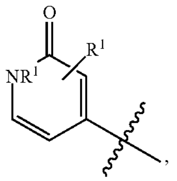, or
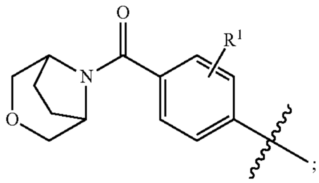;

when present, $W^1$ is H, $CHF_2$, $NHW^2$, or $OCHF_2$;

when present, $W^2$ is

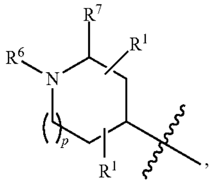,
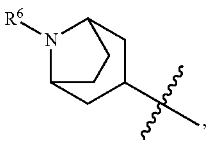,
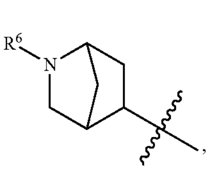,
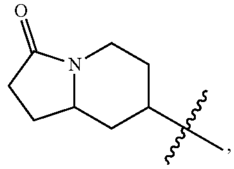,
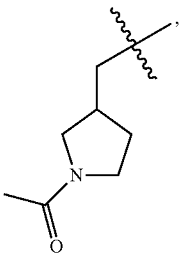,
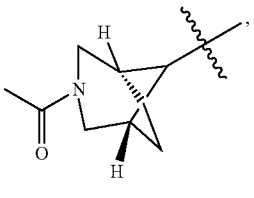,

-continued

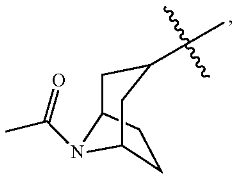,
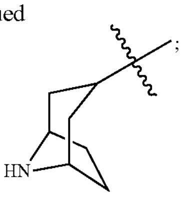;

when present, $R^1$ is independently selected from hydrogen, halogen, =O, $C_{1-6}$alkyl, $OC_{0-6}$alkyl, $C_{1-6}$alkylOC$_{1-6}$alkyl, tetrahydrofuran, cyclopropyl, triazole, thiazole or pyrazole, wherein the $C_{1-6}$alkyl, $OC_{0-6}$alkyl, $C_{1-6}$alkylOC$_{1-6}$alkyl, tetrahydrofuran, or cyclopropyl are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN, or cyclopropyl;

when present, $R^2$ is selected from H or $CH_3$;

each $R^3$ is selected from hydrogen or deuterium;

when present, $R^6$ is H, $C_{1-6}$alkyl, C(O)$C_{1-6}$alkyl, C(O)O$C_{1-6}$alkyl, C(O)$C_{1-6}$cycloalkyl, C(O)N($C_{1-6}$alkyl)$_2$, or S(O)$_2$$C_{1-6}$alkyl;

when present, $R^7$ is H or =O;

when present, $R^9$ is H, halogen or $CH_3$;

when present, $Z^4$ is N while $Z^5$ is C, or $Z^4$ is C while $Z^5$ is N;

when present, each $X^1$ is selected from N or $CR^1$, provided no more than one $X^1$ is N;

when present, $X^2$ is independently selected from O, C=O, $CHR^1$, C($R^1$)$_2$, or $NR^1$, where two $X^2$ in the same ring cannot both be $NR^1$;

when present, t is 1 or 2;

when present, p is 0 or 1; and when present, q is 1 or 2, provided that the compound of formula (I) is not:

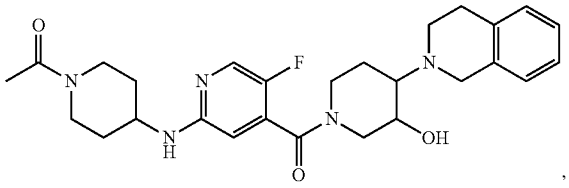,
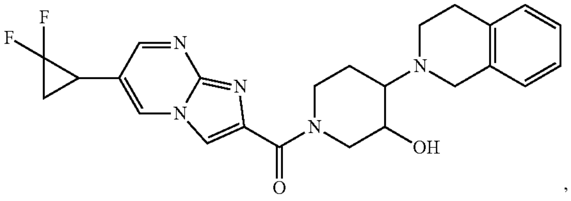,
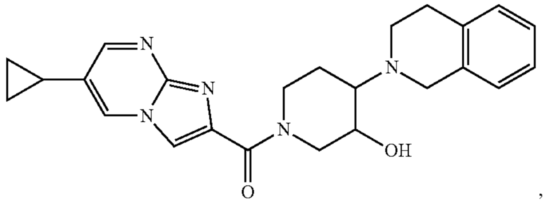, or

-continued

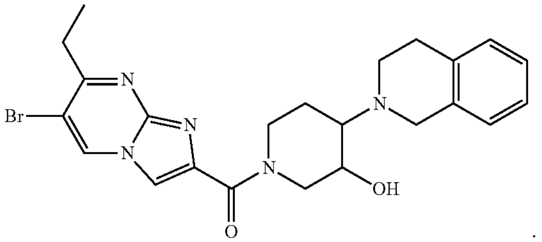

.

2. A compound of Formula Ii,

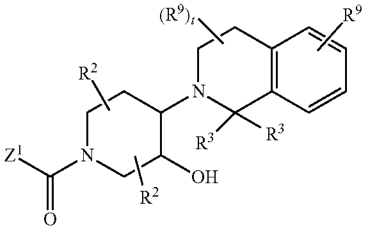

or a pharmaceutically acceptable salt thereof, wherein $Z^1$ is

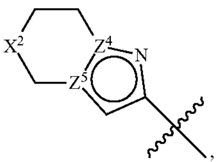

,

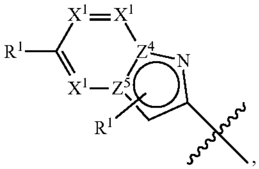

,

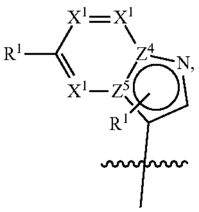

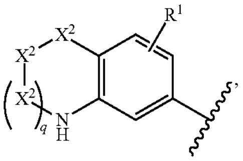

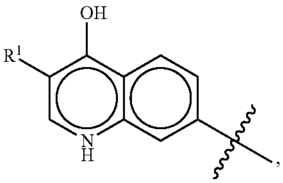

,

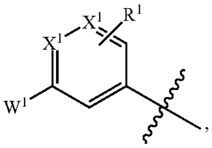

,

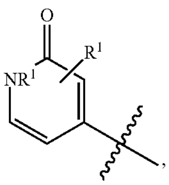

, or

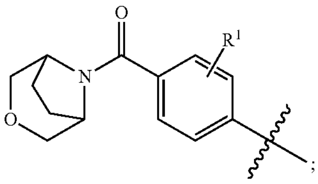

;

when present, $W^1$ is H, $CHF_2$, $NHW^2$, or $OCHF_2$;

when present, $W^2$ is

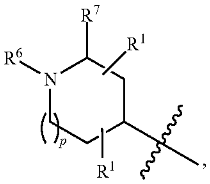

,

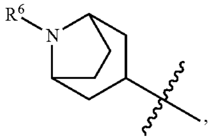

,

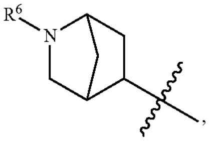

,

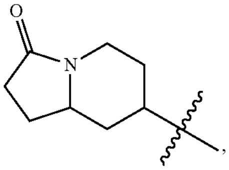

,

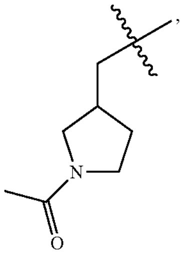

, or

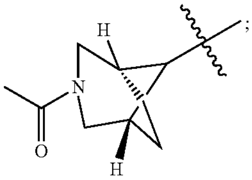

;

when present, $R^1$ is independently selected from H, halogen, =O, $C_{1-6}$alkyl, $OC_{0-6}$alkyl, $C_{1-6}$alkyl$OC_{1-6}$alkyl, tetrahydrofuran, cyclopropyl, triazole, thiazole or pyrazole, wherein the $C_{1-6}$alkyl, $OC_{0-6}$alkyl, $C_{1-6}$alkyl$OC_{1-6}$alkyl, tetrahydrofuran, or cyclopropyl are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN, or cyclopropyl, when present, $R^2$ is independently selected from H or $CH_3$;

each $R^3$ is selected from hydrogen or deuterium;

when present, $R^6$ is H, $C_{1-6}$alkyl, $C(O)C_{1-6}$alkyl, $C(O)C_{1-6}$cycloalkyl, $C(O)OC_{1-6}$alkyl, $C(O)N(C_{1-6}alkyl)_2$, or $S(O)_2C_{1-6}$alkyl;

when present, $R^7$ is H or =O;

when present $R^9$ is H, halogen, or $CH_3$;

when present, $Z^4$ is N while $Z^5$ is C, or $Z^4$ is C while $Z^5$ is N;

when present, $X^1$ is selected from N or $CR^1$, provided no more than one $X^1$ is N;

when present, $X^2$ is independently selected from O, C=O, $CHR^1$, $C(R^1)_2$, or $NR^1$, where two $X^2$ in the same ring cannot both be $NR^1$;

when present, p is 0 or 1;

when present, t is 1 or 2; and when present, q is 1 or 2.

3. The compound of claim 2, of formula Ia:

Ia

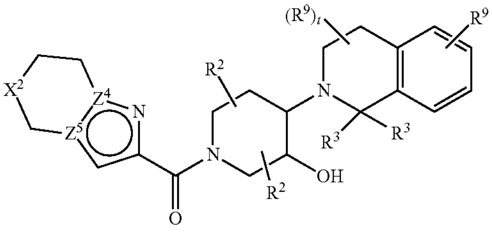

or a pharmaceutically acceptable salt thereof, wherein $X^2$ is $NR^1$ or $C(R^1)_2$;

$R^1$ is independently selected from H, halogen, =O, OH, $CH_3$, $CF_3$, $OCH_3$, $CH_2CH_3$, $CH(CH_3)CN$, $CH_2CF_3$, $OCH_2CF_3$, $OCH_2CH_3$, $OCH_2CF_3$, $CH(CH_3)OCH_3$, $CH(CH_3)_2$, $C(CH_3)_2CN$, cyclopropyl, tetrahydrofuran, triazole, thiazole or pyrazole, wherein the cyclopropyl or tetrahydrofuran are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN or cyclopropyl;

$Z^4$ is N while $Z^5$ is C, or $Z^4$ is C while $Z^5$ is N; and $R^9$ is H, halogen or $CH_3$.

4. The compound of claim 3, or a pharmaceutically acceptable salt thereof, wherein $X^2$ is $NR^1$ or $C(R^1)_2$.

5. The compound of claim 3, or a pharmaceutically acceptable salt thereof, wherein $Z^4$ is N and $Z^5$ is C, or $Z^4$ is C and $Z^5$ is N.

6. The compound of claim 2, of formula Ib:

Ib

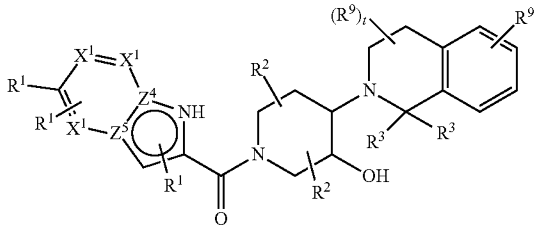

or a pharmaceutically acceptable salt thereof, wherein $R^1$ is independently selected from H, halogen, OH, $CH_3$, $CF_3$, $OCH_3$, $CH_2CH_3$, $CH(CH_3)CN$, $CH_2CF_3$, $OCH_2CH_3$, $OCH_2CF_3$, $CH(CH_3)OCH_3$, $CH(CH_3)_2$, $C(CH_3)_2CN$, cyclopropyl, tetrahydrofuran, triazole, thiazole or pyrazole, wherein the cyclopropyl or tetrahydrofuran are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN or cyclopropyl; and $X^1$ is independently selected from N or $CR^1$, provided no more than one $X^1$ is N.

7. The compound of claim 6, or a pharmaceutically acceptable salt thereof, wherein one $X^1$ is N and two $X^1$'s are $CR^1$, or wherein all three $X^1$'s are $CR^1$.

8. The compound of claim 2 of formula Ic:

Ic

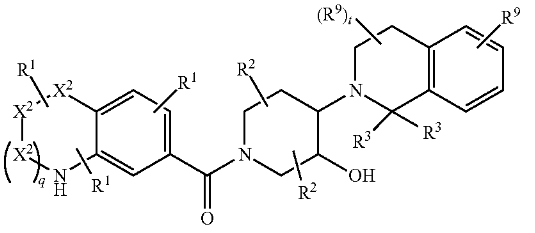

or a pharmaceutically acceptable salt thereof, wherein $R^1$ is independently selected from H, halogen, =O, OH, $CH_3$, $CF_3$, $OCH_3$, $CH_2CH_3$, $CH(CH_3)CN$, $CH_2CF_3$, $OCH_2CF_3$, $OCH_2CH_3$, $OCH_2CF_3$, $CH(CH_3)OCH_3$, $CH(CH_3)_2$, $C(CH_3)_2CN$, or cyclopropyl, tetrahydrofuran, triazole, thiazole or pyrazole, wherein the cyclopropyl or tetrahydrofuran are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN or cyclopropyl;

q is 1, or 2; and $X^2$ is independently selected from O, C=O, $NR^1$, $CHR^1$ or $C(R^1)_2$.

9. The compound of claim 8, or a pharmaceutically acceptable salt thereof, wherein at least one $X^2$ is O.

10. The compound of claim 8, or a pharmaceutically acceptable salt thereof, wherein at least one $X^2$ is $NR^1$.

11. The compound of claim 8, or a pharmaceutically acceptable salt thereof, wherein at least one $X^2$ is $C(R^1)_2$.

12. The compound of claim 8, or a pharmaceutically acceptable salt thereof, wherein at least one $X^2$ is $CHR^1$.

13. The compound of claim 8, or a pharmaceutically acceptable salt thereof, wherein $R^1$ is independently selected from H, $CH_3$, $CF_3$, $CH_2CH_3$, $CH_2CF_3$, =O, or $CH(CH_3)_2$.

14. The compound of claim 8, or a pharmaceutically acceptable salt thereof, wherein q is 1.

15. The compound of claim 2, of formula Id:

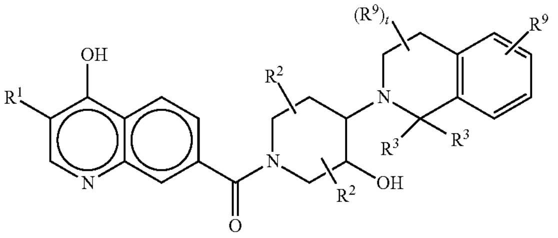

or a pharmaceutically acceptable salt thereof, wherein $R^1$ is independently selected from H, halogen, =O, OH, $CH_3$, $CF_3$, $OCH_3$, $CH_2CH_3$, $CH(CH_3)CN$, $CH_2CF_3$, $OCH_2CF_3$, $OCH_2CH_3$, $OCH_2CF_3$, $CH(CH_3)OCH_3$, $CH(CH_3)_2$, $C(CH_3)_2CN$, cyclopropyl, tetrahydrofuran, triazole, thiazole or pyrazole, wherein the cyclopropyl or tetrahydrofuran are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN or cyclopropyl.

16. The compound of claim 15, or a pharmaceutically acceptable salt thereof, wherein $R^1$ is H, cyclopropyl, or $CH_2CF_3$.

17. The compound of claim 2, of formula Ie:

Ie

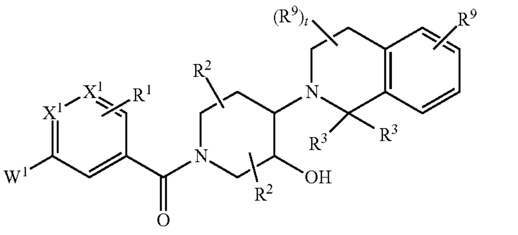

or a pharmaceutically acceptable salt thereof, wherein $W^1$ is H, $CHF_2$, $NHW^2$, or $OCHF_2$;

$W^2$ is

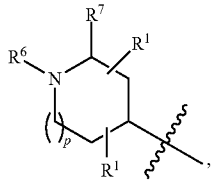,
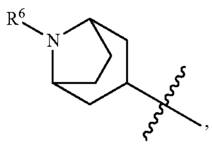,
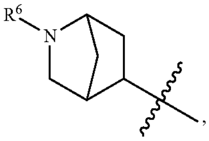,
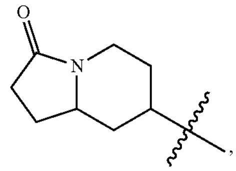,
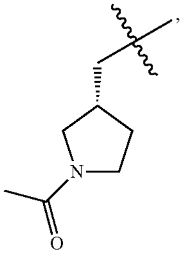, or
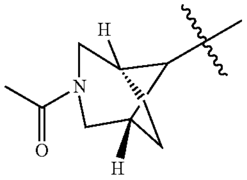,
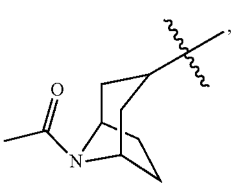, or
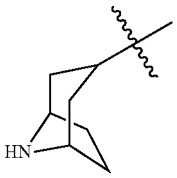

$X^1$ is independently selected from N or $CR^1$, provided no more than one $X^1$ is N;

$R^1$ is independently selected from H, halogen, =O, OH, $CH_3$, $CF_3$, $OCH_3$, $CH_2CH_3$, $CH(CH_3)CN$, $CH_2CF_3$, $OCH_2CF_3$, $OCH_2CH_3$, $OCH_2CF_3$, $CH(CH_3)OCH_3$, $CH(CH_3)_2$, $C(CH_3)_2CN$, cyclopropyl, tetrahydrofuran, triazole, thiazole or pyrazole, wherein the cyclopropyl or tetrahydrofuran are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN or cyclopropyl, $R^6$ is H, $C_{1-6}$alkyl, $C(O)C_{1-6}$alkyl, $C(O)C_{1-6}$cycloalkyl, $C(O)OC_{1-6}$alkyl, $C(O)N(C_{1-6}alkyl)_2$, or $S(O)_2C_{1-6}$alkyl;

$R^7$ is H or =O;

$R^9$ is H, halogen or $CH_3$; and $R^2$ is independently selected from H or $CH_3$.

18. The compound of claim 17, or a pharmaceutically acceptable salt thereof, wherein $W^2$ is

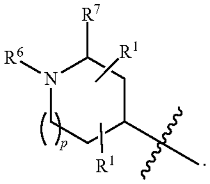.

19. The compound of claim 17, or a pharmaceutically acceptable salt thereof, wherein $R^1$ is independently selected from H, F, Cl, =O, $OCH_2CF_3$, $OCH_3$, $OCH_2CH_3$, $C(CH_3)_2CN$, tetrahydrofuran optionally substituted with cyclopropyl.

20. The compound of claim 17, or a pharmaceutically acceptable salt thereof, wherein $R^6$ is H, $CH_3$, $C(O)CH_2CH_3$, $C(O)N(CH_3)_2$, $C(O)CH_3$, $C(O)OC(CH_3)_3$, $S(O)_2CH_3$, $C(O)OCH_2CH_3$, $C(O)OCH_2CH_3$, C(O)cyclopropyl, or $C(O)OCH_3$.

21. The compound of claim 2, of formula Ie:

If

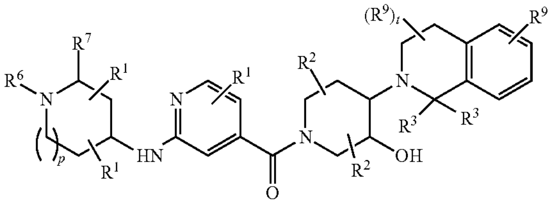

or a pharmaceutically acceptable salt thereof, wherein $R^1$ is independently selected from H, halogen, =O, OH, $CH_3$, $CF_3$, $OCH_3$, $CH_2CH_3$, $CH(CH_3)CN$, $CH_2CF_3$, $OCH_2CF_3$, $OCH_2CH_3$, $OCH_2CF_3$, $CH(CH_3)OCH_3$, $CH(CH_3)_2$, $C(CH_3)_2CN$, cyclopropyl, tetrahydrofuran, triazole, thiazole or pyrazole, wherein the cyclopropyl or tetrahydrofuran are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN or cyclopropyl;

p is 0 or 1;

$R^6$ is H, $C_{1-6}$alkyl, $C(O)C_{1-6}$alkyl, $C(O)C_{1-6}$cycloalkyl, $C(O)OC_{1-6}$alkyl, $C(O)N(C_{1-6}alkyl)_2$, or $S(O)_2C_{1-6}$alkyl;

$R^7$ is H or =O;

$R^9$ is H, halogen or $CH_3$; and $R^2$ is independently selected from H or $CH_3$.

22. The compound of claim 21, or a pharmaceutically acceptable salt thereof, wherein $R^1$ is independently selected from H, F, CI, $OCH_2CF_3$, $CHF_2$, $OCHF_2$, $OCH_3$, $OCH_2CH_3$, or $C(CH_3)_2CN$, $R^7$ is H, p is 1, and $R^6$ is H, $CH_3$, $C(O)CH_2CH_3$, $C(O)N(CH_3)_2$, $C(O)CH_3$, $C(O)OC(CH_3)_3$, $S(O)_2CH_3$, $C(O)OCH_2CH_3$, $C(O)OCH_2CH_3$, C(O)cyclopropyl, or $C(O)OCH_3$.

23. The compound of claim 2, of formula Ig:

Ig

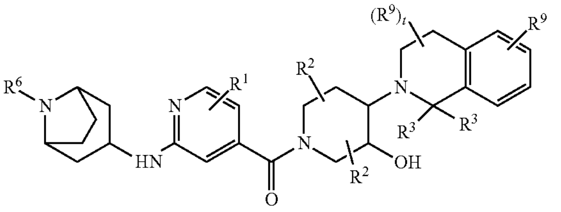

or a pharmaceutically acceptable salt thereof, wherein $R^6$ is H, $C(O)CH_3$ or $C(O)OC(CH_3)_3$.

24. The compound of claim 2, of formula Ih:

Ih

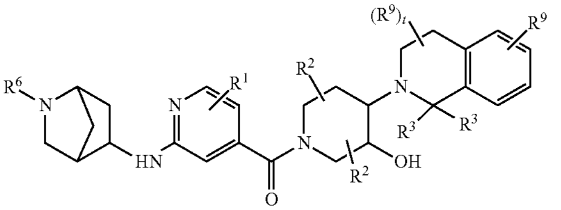

or a pharmaceutically acceptable salt thereof, wherein $R^1$ is H or F;

$R^6$ is H or $C(O)CH_3$.

25. The compound of claim 2, of formula Ij:

(Ij)

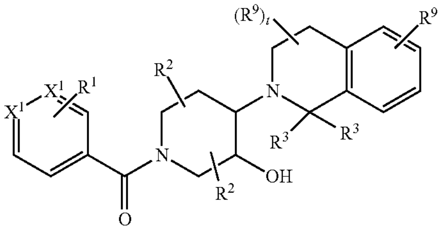

or a pharmaceutically acceptable salt thereof, wherein $X^1$ is independently selected from N or $CR^1$, provided no more than one $X^1$ is N;

$R^1$ is independently selected from H, halogen, =O, OH, $CH_3$, $CF_3$, $OCH_3$, $CH_2CH_3$, $CH(CH_3)CN$, $CH_2CF_3$, $OCH_2CF_3$, $OCH_2CH_3$, $OCH_2CF_3$, $CH(CH_3)OCH_3$, $CH(CH_3)_2$, $C(CH_3)_2CN$, cyclopropyl, tetrahydrofuran, triazole, thiazole or pyrazole, wherein the cyclopropyl or tetrahydrofuran are optionally substituted with one to three substituents independently selected from halogen, $CH_3$, CN, cyclopropyl, or =O, or wherein the triazole, thiazole or pyrazole are optionally substituted with one to three substituents independently selected from halogen, $CH_3$, CN or cyclopropyl; and $R^2$ is independently selected from H or $CH_3$.

26. The compound of claim 25, or a pharmaceutically acceptable salt thereof, wherein $R^1$ is independently selected from H, F, Cl, =O, $OCH_2CF_3$, $OCHF_2$, $OCH_3$, $OCH_2CH_3$, $C(CH_3)_2CN$, or tetrahydrofuran optionally substituted with cyclopropyl.

27. The compound of claim 2, of formula Ik:

(Ik)

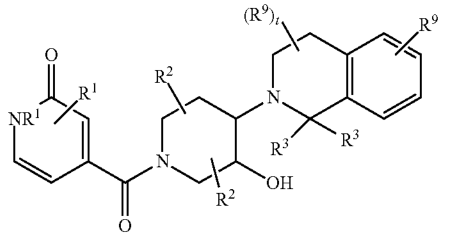

or a pharmaceutically acceptable salt thereof, wherein $R^1$ is H or $CH_2CF_3$;

$R^9$ is H, halogen or $CH_3$; and $R^2$ is independently selected from H or $CH_3$.

28. The compound of claim 2, of formula Im:

(Im)

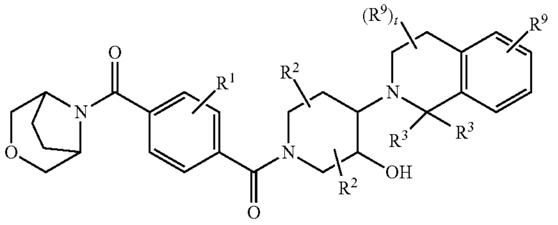

or a pharmaceutically acceptable salt thereof, wherein $R^1$ is H or $OCH_2CH_3$, $R^2$ is H, $R^3$ is H or deuterium, and $R^9$ is H, halogen, or $CH_3$.

29. The compound of claim 2, of formula In:

(In)

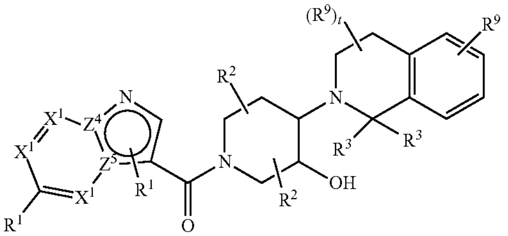

or a pharmaceutically acceptable salt thereof, wherein $X^1$ is independently selected from N or $CR^1$, provided no more than one $X^1$ is N, and $R^1$ is H or halogen.

30. A compound or a pharmaceutically acceptable salt thereof, which is:

(6-Bromoimidazo [1,2-a]pyridin-2-yl)((3S,4S)-4-(3,4-dihydroisoquinolin-2 (1H)-yl)-3-hydroxypiperidin-1-yl) methanone, (6-Bromoimidazo [1,2-a]pyridin-2-yl)((3R,4R)-4-(3,4-dihydroisoquinolin-2 (1H)-yl)-3-hydroxypiperidin-1-yl) methanone, ((3S,4S)-3-hydroxy-4-(6-methyl-3,4-dihydroisoquinolin-2 (1H)-yl)piperidin-1-yl)(6-(2,2,2-trifluoroethoxy) pyridin-3-yl)methanone, ((3R,4R)-3-hydroxy-4-(6-methyl-3,4-dihydroisoquinolin-2 (1H)-yl)piperidin-1-yl)(6-(2,2,2-trifluoroethoxy)pyridin-3-yl)methanone, 1-(-4-((4-((3S,4S)-4-(3,4-dihydroisoquinolin-2 (1H)-yl)-3-hydroxypiperidine-1-carbonyl)pyridin-2-yl)amino)-3,3-difluoropiperidin-1-yl)ethan-1-one, 1-(-4-((4-((3S,4S)-4-(3,4-dihydroisoquinolin-2 (1H)-yl)-3-hydroxypiperidine-1-carbonyl)pyridin-2-yl)amino)-3,3-difluoropiperidin-1-yl)ethan-1-one, 1-(-4-((4-((3R,4R)-4-(3,4-dihydroisoquinolin-2 (1H)-yl)-3-hydroxypiperidine-1-carbonyl)pyridin-2-yl)amino)-3,3-difluoropiperidin-1-yl)ethan-1-one, 1-(-4-((4-((3R,4R)-4-(3,4-dihydroisoquinolin-2 (1H)-yl)-3-hydroxypiperidine-1-carbonyl)pyridin-2-yl)amino)-3,3-difluoropiperidin-1-yl)ethan-1-one, 6-((3S,4S)-4-(3,4-dihydroisoquinolin-2 (1H)-yl)-3-hydroxypiperidine-1-carbonyl)-2-ethyl-2H-benzo[b][1,4]oxazin-3 (4H)-one, 6-((3S,4S)-4-(3,4-dihydroisoquinolin-2 (1H)-yl)-3-hydroxypiperidine-1-carbonyl)-2-ethyl-2H-benzo[b][1,4]oxazin-3 (4H)-one, 6-((3R,4R)-4-(3,4-dihydroisoquinolin-2 (1H)-yl)-3-hydroxypiperidine-1-carbonyl)-2-ethyl-2H-benzo[b][1,4]oxazin-3 (4H)-one, 6-((3R,4R)-4-(3,4-dihydroisoquinolin-2 (1H)-yl)-3-hydroxypiperidine-1-carbonyl)-2-ethyl-2H-benzo[b][1,4]oxazin-3 (4H)-one, 1-(-4-((4-((3S,4S)-4-(3,4-dihydroisoquinolin-2 (1H)-yl)-3-hydroxypiperidine-1-carbonyl)-3-fluoropyridin-2-yl)amino)-3,3-difluoropiperidin-1-yl)ethan-1-one, 1-(-4-((4-((3S,4S)-4-(3,4-dihydroisoquinolin-2 (1H)-yl)-3-hydroxypiperidine-1-carbonyl)-3-fluoropyridin-2-yl)amino)-3,3-difluoropiperidin-1-yl)ethan-1-one, 1-(-4-((4-((3R,4R)-4-(3,4-dihydroisoquinolin-2 (1H)-yl)-3-hydroxypiperidine-1-carbonyl)-3-fluoropyridin-2-yl)amino)-3,3-difluoropiperidin-1-yl)ethan-1-one, 1-(-4-((4-((3R,4R)-4-(3,4-dihydroisoquinolin-2 (1H)-yl)-3-hydroxypiperidine-1-carbonyl)-3-fluoropyridin-2-yl)amino)-3,3-difluoropiperidin-1-yl)ethan-1-one, 1-(4-((4-((3S,4S)-4-(3,4-dihydroisoquinolin-2 (1H)-yl)-3-hydroxypiperidine-1-carbonyl)-3-fluoropyridin-2-yl)amino)piperidin-1-yl)ethan-1-one, 1-(4-((4-((3R,4R)-4-(3,4-dihydroisoquinolin-2 (1H)-yl)-3-hydroxypiperidine-1-carbonyl)-3-fluoropyridin-2-yl)amino)piperidin-1-yl)ethan-1-one, 1-(4-((4-(4-(3,4-dihydroisoquinolin-2 (1H)-yl)-3-hydroxy-2-methylpiperidine-1-carbonyl)pyridin-2-yl)amino)piperidin-1-yl)ethan-1-one, 1-(4-((4-(4-(3,4-dihydroisoquinolin-2 (1H)-yl)-3-hydroxy-2-methylpiperidine-1-carbonyl)pyridin-2-yl)amino)piperidin-1-yl)ethan-1-one, 1-(4-((4-(4-(3,4-dihydroisoquinolin-2 (1H)-yl)-3-hydroxy-2,2-dimethylpiperidine-1-carbonyl)pyridin-2-yl)amino)piperidin-1-yl)ethan-1-one, 1-(4-((4-(4-(3,4-dihydroisoquinolin-2 (1H)-yl)-3-hydroxy-2,2-dimethylpiperidine-1-carbonyl)pyridin-2-yl)amino)piperidin-1-yl)ethan-1-one, 1-(4-((4-(-4-(4,4-difluoro-3,4-dihydroisoquinolin-2 (1H)-yl)-3-hydroxypiperidine-1-carbonyl)-5-fluoropyridin-2-yl)amino)piperidin-1-yl)ethan-1-one, 1-(4-((5-chloro-4-(-4-(4,4-difluoro-3,4-dihydroisoquinolin-2 (1H)-yl)-3-hydroxypiperidine-1-carbonyl)pyridin-2-yl)amino)piperidin-1-yl)ethan-1-one, (-4-(4,4-difluoro-3,4-dihydroisoquinolin-2 (1H)-yl)-3-hydroxypiperidin-1-yl)(6-(2,2,2-trifluoroethoxy)pyridin-3-yl)methanone, 1-(4-((5-fluoro-4-(-4-(4,4-difluoro-3,4-dihydroisoquinolin-2 (1H)-yl)-3-hydroxypiperidine-1-carbonyl)pyridin-2-yl)amino)piperidin-1-yl)ethan-1-one, 1-(4-((5-chloro-4-(-4-(4,4-difluoro-3,4-dihydroisoquinolin-2 (1H)-yl)-3-hydroxypiperidine-1-carbonyl)pyridin-2-yl)amino)piperidin-1-yl)ethan-1-one, (-4-(4,4-difluoro-3,4-dihydroisoquinolin-2 (1H)-yl)-3-hydroxypiperidin-1-yl)(6-(2,2,2-trifluoroethoxy)pyridin-3-yl)methanone, 1-{4-[(4-{[(1R,4R)-5-(3,4-dihydroisoquinolin-2 (1H)-yl)-6-hydroxy-2-azabicyclo[2.2.1]hept-2-yl]carbonyl}-5-fluoropyridin-2-yl)amino]piperidin-1-yl}ethenone, 4-((3S,4S)-4-(3,4-dihydroisoquinolin-2 (1H)-yl)-3-hydroxypiperidine-1-carbonyl)-1-(2,2,2-trifluoroethyl)pyridin-2(1H)-one, 4-((3R,4R)-4-(3,4-dihydroisoquinolin-2 (1H)-yl)-3-hydroxypiperidine-1-carbonyl)-1-(2,2,2-trifluoroethyl)pyridin-2(1H)-one, (4-(3-oxa-8-azabicyclo[3.2.1]octane-8-carbonyl)-2-ethoxyphenyl)((3S,4S)-4-(3,4-dihydroisoquinolin-2 (1H)-yl)-3-hydroxypiperidin-1-yl)methanone, (4-(3-oxa-8-azabicyclo[3.2.1]octane-8-carbonyl)-2-ethoxyphenyl)((3R,4R)-4-(3,4-dihydroisoquinolin-2 (1H)-yl)-3-hydroxypiperidin-1-yl)methanone, (4-(3-oxa-8-azabicyclo[3.2.1]octane-8-carbonyl)phenyl)((3S,4S)-4-(3,4-dihydroisoquinolin-2 (1H)-yl)-3-hydroxypiperidin-1-yl)methanone, (4-(3-oxa-8-azabicyclo[3.2.1]octane-8-carbonyl)phenyl)((3R,4R)-4-(3,4-dihydroisoquinolin-2 (1H)-yl)-3-hydroxypiperidin-1-yl)methanone, (4-(3-oxa-8-azabicyclo[3.2.1]octane-8-carbonyl)phenyl)((3S,4S)-4-(5-fluoro-3,4-dihydroisoquinolin-2 (1H)-yl)-3-hydroxypiperidin-1-yl)methanone, (4-(3-oxa-8-azabicyclo[3.2.1]octane-8-carbonyl)phenyl)((3R,4R)-4-(5-fluoro-3,4-dihydroisoquinolin-2 (1H)-yl)-3-hydroxypiperidin-1-yl)methanone, (4-(3-oxa-8-azabicyclo[3.2.1]octane-8-carbonyl)phenyl)((3S,4S)-4-(6-fluoro-3,4-dihydroisoquinolin-2 (1H)-yl)-3-hydroxypiperidin-1-yl)methanone, (4-(3-oxa-8-azabicyclo[3.2.1]octane-8-carbonyl)phenyl)((3R,4R)-4-(6-fluoro-3,4-dihydroisoquinolin-2 (1H)-yl)-3-hydroxypiperidin-1-yl)methanone, (4-(3-oxa-8-azabicyclo[3.2.1]octane-8-carbonyl)phenyl)((3S,4S)-4-(7-fluoro-3,4-dihydroisoquinolin-2 (1H)-yl)-3-hydroxypiperidin-1-yl)methanone, (4-(3-oxa-8-azabicyclo[3.2.1]octane-8-carbonyl)phenyl)((3R,4R)-4-(7-fluoro-3,4-dihydroisoquinolin-2 (1H)-yl)-3-hydroxypiperidin-1-yl)methanone, ((3S,4S)-4-(3,4-dihydroisoquinolin-2 (1H)-yl)-3-hydroxypiperidin-1-yl)(6-(2,2,2-trifluoroethoxy)pyridin-3-yl)methanone, ((3R,4R)-4-(3,4-dihydroisoquinolin-2 (1H)-yl)-3-hydroxypiperidin-1-yl)(6-(2,2,2-trifluoroethoxy)pyridin-3-yl)methanone, ((3R,4R or 3S,4S)-3-hydroxy-4-(7-methyl-3,4-dihydroisoquinolin-2 (1H)-yl)piperidin-1-yl)(6-(2,2,2-trifluoroethoxy)pyridin-3-yl)methanone, ((3S,4S or 3R,4R)-3-hydroxy-4-(7-methyl-3,4-dihydroisoquinolin-2 (1H)-yl)piperidin-1-yl)(6-(2,2,2-trifluoroethoxy)pyridin-3-yl)methanone, 1-{4-[(5-chloro-4-{[(3S,4S)-4-(3,4-dihydroisoquinolin-2 (1H)-yl)-3-hydroxypiperidin-1-yl]carbonyl}pyridin-2-yl)amino]piperidin-1-yl}ethenone, ((3S,4S)-4-(3,4-dihydroisoquinolin-2 (1H)-yl)-3-hydroxypiperidin-1-yl)(5-(2,2,2-trifluoroethyl)-4,5,6,7-tetrahydropyrazolo[1,5-a]pyrazin-2-yl)methanone, (6-bromo-8-ethoxyimidazo [1,2-a]pyrazin-2-yl)((3S,4S)-4-(3,4-dihydroisoquinolin-2 (1H)-yl)-3-hydroxypiperidin-1-yl)methanone, (2-(difluoromethyl)pyridin-4-yl)((3S,4S)-4-(3,4-dihydroisoquinolin-2 (1H)-yl)-3-hydroxypiperidin-1-yl) methanone, (2-(difluoromethoxy)pyridin-4-yl)((3S,4S)-4-(3,4-dihydroisoquinolin-2 (1H)-yl)-3-hydroxypiperidin-1-yl) methanone,

[(3S,4S)-4-(3,4-dihydroisoquinolin-2 (1H)-yl)-3-hydroxypiperidin-1-yl][6-(2,4-dimethyl-1,3-thiazol-5-yl) imidazo [1,2-a]pyrimidin-2-yl]methanone,

[(3S,4S)-4-(3,4-dihydroisoquinolin-2 (1H)-yl)-3-hydroxypiperidin-1-yl][6-(1-methyl-1H-pyrazol-5-yl) imidazo [1,2-a]pyrimidin-2-yl]methanone,

[(3S,4S)-4-(3,4-dihydroisoquinolin-2 (1H)-yl)-3-hydroxypiperidin-1-yl]{8-[(1R)-1-methoxyethyl]-6-(propan-2-yl)imidazo [1,2-a]pyridin-2-yl}methanone,

[(3S,4S)-4-(3,4-dihydroisoquinolin-2 (1H)-yl)-3-hydroxypiperidin-1-yl]{8-[(1R)-1-methoxyethyl]-6-methylimidazo [1,2-a]pyridin-2-yl}methanone, (4-(1-cyclopropyl-1H-1,2,4-triazol-5-yl)phenyl)((3S,4S)-4-(3,4-dihydroisoquinolin-2 (1H)-yl)-3-hydroxypiperidin-1-yl)methanone, (4-(1-cyclopropyl-1H-1,2,4-triazol-5-yl)phenyl)((3R,4R)-4-(3,4-dihydroisoquinolin-2 (1H)-yl)-3-hydroxypiperidin-1-yl)methanone, 8-((3S,4S)-4-(3,4-dihydroisoquinolin-2 (1H)-yl)-3-hydroxypiperidine-1-carbonyl)-4-isopropyl-1,2,3,4-tetrahydro-5H-benzo[e][1,4]diazepin-5-one, (3-cyclopropyl-4-hydroxyquinolin-7-yl)((3S,4S)-4-(3,4-dihydroisoquinolin-2 (1H)-yl)-3-hydroxypiperidin-1-yl)methanone, 8-((3S,4S)-4-(3,4-dihydroisoquinolin-2 (1H)-yl)-3-hydroxypiperidine-1-carbonyl)-4-ethyl-1,2,3,4-tetrahydro-5H-benzo[e][1,4]diazepin-5-one, 8-((3S,4S)-4-(3,4-dihydroisoquinolin-2 (1H)-yl)-3-hydroxypiperidine-1-carbonyl)-4-(tetrahydrofuran-3-yl)-1,2,3,4-tetrahydro-5H-benzo[e][1,4]diazepin-5-one, (6-bromo-5-methylimidazo [1,2-a]pyrimidin-2-yl)((3S,4S)-4-(3,4-dihydroisoquinolin-2 (1H)-yl)-3-hydroxypiperidin-1-yl)methanone, (6-bromo-7-methylimidazo [1,2-a]pyrimidin-2-yl)((3S,4S)-4-(3,4-dihydroisoquinolin-2 (1H)-yl)-3-hydroxypiperidin-1-yl)methanone, (6-bromo-8-((R or S)-1-methoxyethyl)imidazo [1,2-a] pyridin-2-yl)((3S,4S)-4-(3,4-dihydroisoquinolin-2 (1H)-yl)-3-hydroxypiperidin-1-yl)methanone, (6-bromo-7-methoxyimidazo [1,2-a]pyrimidin-2-yl)((3S,4S)-4-(3,4-dihydroisoquinolin-2 (1H)-yl)-3-hydroxypiperidin-1-yl)methanone, (6-bromo-7-hydroxyimidazo [1,2-a]pyrimidin-2-yl)((3S,4S)-4-(3,4-dihydroisoquinolin-2 (1H)-yl)-3-hydroxypiperidin-1-yl)methanone, (6-bromoimidazo [1,2-a]pyrimidin-2-yl)[(3S,4S)-4-(3,4-dihydroisoquinolin-2 (1H)-yl)-3-hydroxypiperidin-1-yl]methanone,

[(3S,4S)-4-(3,4-dihydroisoquinolin-2 (1H)-yl)-3-hydroxypiperidin-1-yl](6-methylimidazo [1,2-a]pyrimidin-2-yl)methanone, (6-bromo-7-methylimidazo [1,2-a]pyrimidin-3-yl)[(3S,4S)-4-(3,4-dihydroisoquinolin-2 (1H)-yl)-3-hydroxypiperidin-1-yl]methanone, (6-bromo-5-methylimidazo [1,2-a]pyrimidin-3-yl)[(3S,4S)-4-(3,4-dihydroisoquinolin-2 (1H)-yl)-3-hydroxypiperidin-1-yl]methanone, 2-{2-[(3S,4S)-4-(3,4-dihydroisoquinolin-2 (1H)-yl)-3-hydroxypiperidine-1-carbonyl]imidazo [1,2-a]pyrimidin-6-yl}propanenitrile, (6-bromo-7-cyclopropylimidazo [1,2-a]pyrimidin-2-yl)[(3S,4S)-4-(3,4-dihydroisoquinolin-2 (1H)-yl)-3-hydroxypiperidin-1-yl]methanone,

[6-bromo-7-(propan-2-yl)imidazo [1,2-a]pyrimidin-2-yl][(3S,4S)-4-(3,4-dihydroisoquinolin-2 (1H)-yl)-3-hydroxypiperidin-1-yl]methanone, 2-cyclopropyl-6-((3S,4S)-4-(3,4-dihydroisoquinolin-2 (1H)-yl)-3-hydroxypiperidine-1-carbonyl)-2H-benzo [b][1,4]oxazin-3 (4H)-one, 2-cyclopropyl-6-((3S,4S)-4-(3,4-dihydroisoquinolin-2 (1H)-yl)-3-hydroxypiperidine-1-carbonyl)-2H-benzo [b][1,4]oxazin-3 (4H)-one, ((3S,4S)-4-(3,4-dihydroisoquinolin-2 (1H)-yl)-3-hydroxypiperidin-1-yl) (-6-(trifluoromethyl)-5,6,7,8-tetrahydroimidazo [1,2-a]pyridin-2-yl)methanone, ((3S,4S)-4-(3,4-dihydroisoquinolin-2 (1H)-yl)-3-hydroxypiperidin-1-yl) (-6-(trifluoromethyl)-5,6,7,8-tetrahydroimidazo [1,2-a]pyridin-2-yl)methanone, 6-((3S,4S)-4-(3,4-dihydroisoquinolin-2 (1H)-yl)-3-hydroxypiperidine-1-carbonyl)-2-(-5,5-dimethyltetrahydrofuran-3-yl)-2H-benzo[b][1,4]oxazin-3 (4H)-one, 6-((3S,4S)-4-(3,4-dihydroisoquinolin-2 (1H)-yl)-3-hydroxypiperidine-1-carbonyl)-2-(-5,5-dimethyltetrahydrofuran-3-yl)-2H-benzo[b][1,4]oxazin-3 (4H)-one, 1-(4-((4-((3S,4S)-4-(3,4-dihydroisoquinolin-2 (1H)-yl)-3-hydroxypiperidine-1-carbonyl)-5-fluoropyridin-2-yl) amino)-3,3-difluoropiperidin-1-yl)ethan-1-one, 1-(4-((4-((3S,4S)-4-(3,4-dihydroisoquinolin-2 (1H)-yl)-3-hydroxypiperidine-1-carbonyl)-5-fluoropyridin-2-yl) amino)-3,3-difluoropiperidin-1-yl)ethan-1-one, 1-(4-((4-((3S,4S)-4-(3,4-dihydroisoquinolin-2 (1H)-yl)-3-hydroxypiperidine-1-carbonyl)-5-methoxypyridin-2-yl)amino)piperidin-1-yl)ethan-1-one, 2-(5-{[(3S,4S)-4-(3,4-dihydroisoquinolin-2 (1H)-yl)-3-hydroxypiperidin-1-yl]carbonyl}pyridin-2-yl)-2-methylpropanenitrile, 2-(5-{[(3R,4R)-4-(3,4-dihydroisoquinolin-2 (1H)-yl)-3-hydroxypiperidin-1-yl]carbonyl}pyridin-2-yl)-2-methylpropanenitrile, 7-((3R,4R)-4-(3,4-dihydroisoquinolin-2 (1H)-yl)-3-hydroxypiperidine-1-carbonyl)-4-methyl-1,4-dihydro-2H-benzo[d][1,3]oxazin-2-one, 7-((3S,4S)-4-(3,4-dihydroisoquinolin-2 (1H)-yl)-3-hydroxypiperidine-1-carbonyl)-4-methyl-1,4-dihydro-2H-benzo[d][1,3]oxazin-2-one, 7-((3S,4S)-4-(3,4-dihydroisoquinolin-2 (1H)-yl)-3-hydroxypiperidine-1-carbonyl)-4-methyl-1,4-dihydro-2H-benzo[d][1,3]oxazin-2-one, 7-((3R,4R)-4-(3,4-dihydroisoquinolin-2 (1H)-yl)-3-hydroxypiperidine-1-carbonyl)-4-methyl-1,4-dihydro-2H-benzo[d][1,3]oxazin-2-one, 7-((3R,4R)-4-(3,4-dihydroisoquinolin-2 (1H)-yl)-3-hydroxypiperidine-1-carbonyl)-4,4-dimethyl-3,4-dihydroquinolin-2 (1H)-one, 7-((3S,4S)-4-(3,4-dihydroisoquinolin-2 (1H)-yl)-3-hydroxypiperidine-1-carbonyl)-4,4-dimethyl-3,4-dihydroquinolin-2 (1H)-one, 7-((3S,4S)-4-(3,4-dihydroisoquinolin-2 (1H)-yl)-3-hydroxypiperidine-1-carbonyl)-4,4-dimethyl-1,4-dihydro-2H-benzo[d][1,3]oxazin-2-one, 7-((3R,4R)-4-(3,4-dihydroisoquinolin-2 (1H)-yl)-3-hydroxypiperidine-1-carbonyl)-4,4-dimethyl-1,4-dihydro-2H-benzo[d][1,3]oxazin-2-one, 7-((3S,4S)-4-(3,4-dihydroisoquinolin-2 (1H)-yl)-3-hydroxypiperidine-1-carbonyl)-6-fluoro-4-methyl-1,4-dihydro-2H-benzo[d][1,3]oxazin-2-one, 7-((3S,4S)-4-(3,4-dihydroisoquinolin-2 (1H)-yl)-3-hydroxypiperidine-1-carbonyl)-6-fluoro-4-methyl-1,4-dihydro-2H-benzo[d][1,3]oxazin-2-one, 6-((3S,4S)-4-(3,4-dihydroisoquinolin-2 (1H)-yl)-3-hydroxypiperidine-1-carbonyl)-2,2-dimethyl-2H-benzo[b][1,4]oxazin-3 (4H)-one, 8-((3S,4S)-4-(3,4-dihydroisoquinolin-2 (1H)-yl)-3-hydroxypiperidine-1-carbonyl)-4-(2,2,2-trifluoroethyl)-1,2,3,4-tetrahydro-5H-benzo[e][1,4]diazepin-5-one, tert-butyl-3-((4-((3S,4S)-4-(3,4-dihydroisoquinolin-2 (1H)-yl)-3-hydroxypiperidine-1-carbonyl)-5-fluoropyridin-2-yl)amino)-8-azabicyclo[3.2.1]octane-8-carboxylate, ((3S,4S)-4-(3,4-dihydroisoquinolin-2 (1H)-yl)-3-hydroxypiperidin-1-yl)(5-fluoro-2-((1-(methylsulfonyl)piperidin-4-yl)amino)pyridin-4-yl)methanone, ethyl 4-((4-((3S,4S)-4-(3,4-dihydroisoquinolin-2 (1H)-yl)-3-hydroxypiperidine-1-carbonyl)-5-fluoropyridin-2-yl)amino)piperidine-1-carboxylate, 1-(4-((4-((3S,4S)-4-(3,4-dihydroisoquinolin-2 (1H)-yl)-3-hydroxypiperidine-1-carbonyl)-5-ethoxypyridin-2-yl)amino)piperidin-1-yl)ethan-1-one, (2-((1-(cyclopropanecarbonyl)piperidin-4-yl)amino)-5-fluoropyridin-4-yl)((3S,4S)-4-(3,4-dihydroisoquinolin-2 (1H)-yl)-3-hydroxypiperidin-1-yl)methanone, methyl 4-((4-((3S,4S)-4-(3,4-dihydroisoquinolin-2 (1H)-yl)-3-hydroxypiperidine-1-carbonyl)-5-fluoropyridin-2-yl)amino)piperidine-1-carboxylate, 4-((4-((3S,4S)-4-(3,4-dihydroisoquinolin-2 (1H)-yl)-3-hydroxypiperidine-1-carbonyl)-5-fluoropyridin-2-yl)amino)-N,N-dimethylpiperidine-1-carboxamide, 1-(4-((4-((3S,4S)-4-(3,4-dihydroisoquinolin-2 (1H)-yl)-3-hydroxypiperidine-1-carbonyl)-5-fluoropyridin-2-yl)amino)piperidin-1-yl) propan-1-one, 4-((4-((3S,4S)-4-(3,4-dihydroisoquinolin-2 (1H)-yl)-3-hydroxypiperidine-1-carbonyl)-5-fluoropyridin-2-yl)amino)-1-methylpiperidin-2-one, 1-(-3-((4-((3S,4S)-4-(3,4-dihydroisoquinolin-2 (1H)-yl)-3-hydroxypiperidine-1-carbonyl)-5-fluoropyridin-2-yl)amino) pyrrolidin-1-yl)ethan-1-one, 1-(-3-((4-((3S,4S)-4-(3,4-dihydroisoquinolin-2 (1H)-yl)-3-hydroxypiperidine-1-carbonyl)-5-fluoropyridin-2-yl)amino) pyrrolidin-1-yl)ethan-1-one, 7-[(4-{[(3S,4S)-4-(3,4-dihydroisoquinolin-2 (1H)-yl)-3-hydroxypiperidin-1-yl]carbonyl}-5-fluoropyridin-2-yl)amino]hexahydroindolizin-3 (2H)-one, 7-[(4-{[(3S,4S)-4-(3,4-dihydroisoquinolin-2 (1H)-yl)-3-hydroxypiperidin-1-yl]carbonyl}-5-fluoropyridin-2-yl)amino]hexahydroindolizin-3 (2H)-one, 7-[(4-{[(3S,4S)-4-(3,4-dihydroisoquinolin-2 (1H)-yl)-3-hydroxypiperidin-1-yl]carbonyl}-5-fluoropyridin-2-yl)amino]hexahydroindolizin-3 (2H)-one, 7-[(4-{[(3S,4S)-4-(3,4-dihydroisoquinolin-2 (1H)-yl)-3-hydroxypiperidin-1-yl]carbonyl}-5-fluoropyridin-2-yl)amino]hexahydroindolizin-3 (2H)-one, 1-(5-((4-((3S,4S)-4-(3,4-dihydroisoquinolin-2 (1H)-yl)-3-hydroxypiperidine-1-carbonyl)-5-fluoropyridin-2-yl)amino)-2-azabicyclo[2.2.1]heptan-2-yl)ethan-1-one, 1-(5-((4-((3S,4S)-4-(3,4-dihydroisoquinolin-2 (1H)-yl)-3-hydroxypiperidine-1-carbonyl)-5-fluoropyridin-2-yl)amino)-2-azabicyclo[2.2.1]heptan-2-yl)ethan-1-one, (2-((8-azabicyclo[3.2.1]octan-3-yl)amino)-5-fluoropyridin-4-yl)((3S,4S)-4-(3,4-dihydroisoquinolin-2 (1H)-yl)-3-hydroxypiperidin-1-yl)methanone, 1-(3-((4-((3S,4S)-4-(3,4-dihydroisoquinolin-2 (1H)-yl)-3-hydroxypiperidine-1-carbonyl)-5-fluoropyridin-2-yl)amino)-8-azabicyclo[3.2.1]octan-8-yl)ethan-1-one, 1-((S)-3-(((4-((3S,4S)-4-(3,4-dihydroisoquinolin-2 (1H)-yl)-3-hydroxypiperidine-1-carbonyl)-5-fluoropyridin-2-yl)amino)methyl) pyrrolidin-1-yl)ethan-1-one, 1-((1R,5S)-8-((4-((3S,4S)-4-(3,4-dihydroisoquinolin-2 (1H)-yl)-3-hydroxypiperidine-1-carbonyl)-5-fluoropyridin-2-yl)amino)-3-azabicyclo[3.2.1]octan-3-yl)ethan-1-one, 1-(2-((3S,4S)-4-(3,4-dihydroisoquinolin-2 (1H)-yl)-3-hydroxypiperidine-1-carbonyl)imidazo [1,2-a]pyridin-6-yl) cyclopropane-1-carbonitrile, ((3S,4S)-4-(3,4-dihydroisoquinolin-2 (1H)-yl)-3-hydroxypiperidin-1-yl)(4-hydroxy-3-(2,2,2-trifluoroethyl) quinolin-7-yl)methanone, 1-(2-{[(3S,4S)-4-(3,4-dihydroisoquinolin-2 (1H)-yl)-3-hydroxypiperidin-1-yl]carbonyl}imidazo [1,2-a]pyrimidin-6-yl)-2,2-dimethylcyclopropanecarbonitrile, 1-(2-{[(3S,4S)-4-(3,4-dihydroisoquinolin-2 (1H)-yl)-3-hydroxypiperidin-1-yl]carbonyl}imidazo [1,2-a]pyrimidin-6-yl)-2,2-dimethylcyclopropanecarbonitrile, ((3S,4S)-4-(3,4-dihydroisoquinolin-2 (1H)-yl)-3-hydroxypiperidin-1-yl)(6-(2-methylcyclopropyl)imidazo [1,2-a]pyrimidin-2-yl)methanone, ((3S,4S)-4-(3,4-dihydroisoquinolin-2 (1H)-yl)-3-hydroxypiperidin-1-yl)(6-(2-methylcyclopropyl)imidazo [1,2-a]pyrimidin-2-yl)methanone, ((3S,4S)-4-(3,4-dihydroisoquinolin-2 (1H)-yl)-3-hydroxypiperidin-1-yl)(6-(2-methylcyclopropyl)imidazo [1,2-a]pyrimidin-2-yl)methanone, (6-chloroimidazo [1,2-a]pyridin-2-yl)[(3S,4S)-4-(3,4-dihydroisoquinolin-2 (1H)-yl)-3-hydroxypiperidin-1-yl] methanone, (6-bromo-3-chloropyrazolo[1,5-a]pyrimidin-2-yl)[(3S,4S)-4-(3,4-dihydroisoquinolin-2 (1H)-yl)-3-hydroxypiperidin-1-yl]methanone, (8-bromo-6-methylimidazo [1,2-a]pyridin-2-yl)[(3S,4S)-4-(3,4-dihydroisoquinolin-2 (1H)-yl)-3-hydroxypiperidin-1-yl]methanone, (6-bromo-8-methylimidazo [1,2-a]pyridin-2-yl)[(3S,4S)-4-(3,4-dihydroisoquinolin-2 (1H)-yl)-3-hydroxypiperidin-1-yl]methanone, (8-chloro-6-methylimidazo [1,2-a]pyridin-2-yl)[(3S,4S)-4-(3,4-dihydroisoquinolin-2 (1H)-yl)-3-hydroxypiperidin-1-yl]methanone,

[8-chloro-6-(trifluoromethyl)imidazo [1,2-a]pyridin-2-yl][(3S,4S)-4-(3,4-dihydroisoquinolin-2 (1H)-yl)-3-hydroxypiperidin-1-yl]methanone, (8-bromo-6-chloroimidazo [1,2-a]pyridin-2-yl)[(3S,4S)-4-(3,4-dihydroisoquinolin-2 (1H)-yl)-3-hydroxypiperidin-1-yl]methanone, (6-bromo-8-iodoimidazo [1,2-a]pyridin-2-yl)[(3S,4S)-4-(3,4-dihydroisoquinolin-2 (1H)-yl)-3-hydroxypiperidin-1-yl]methanone, (6,8-dichloroimidazo [1,2-a]pyridin-2-yl)[(3S,4S)-4-(3,4-dihydroisoquinolin-2 (1H)-yl)-3-hydroxypiperidin-1-yl]methanone, (6-bromo-8-fluoroimidazo [1,2-a]pyridin-2-yl)[(3S,4S)-4-(3,4-dihydroisoquinolin-2 (1H)-yl)-3-hydroxypiperidin-1-yl]methanone, (6,8-dibromoimidazo [1,2-a]pyridin-2-yl)[(3S,4S)-4-(3,4-dihydroisoquinolin-2 (1H)-yl)-3-hydroxypiperidin-1-yl]methanone, or (6-bromopyrazolo[1,5-a]pyrimidin-2-yl)[(3S,4S)-4-(3,4-dihydroisoquinolin-2 (1H)-yl)-3-hydroxypiperidin-1-yl]methanone.

31. A composition for treating cancer comprising a compound of claim 1, or a pharmaceutically acceptable salt thereof, and a pharmaceutically carrier.

32. A method for treating a PRMT5 mediated cancer comprising administering to a patient in need thereof a compound of claim 1, or a pharmaceutically acceptable salt thereof.

* * * * *